United States Patent
Indorf et al.

(10) Patent No.: US 10,856,750 B2
(45) Date of Patent: Dec. 8, 2020

(54) SPOT CHECK MEASUREMENT SYSTEM

(71) Applicant: MASIMO CORPORATION, Irvine, CA (US)

(72) Inventors: Keith Ward Indorf, Riverside, CA (US); Sebastian T. Frey, Laguna Niguel, CA (US); Bilal Muhsin, San Clemente, CA (US); Prashanth Rengaswamy Chandran, Irvine, CA (US); Mihir Chinchalkar, Irvine, CA (US); Prashanth Iyengar, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 164 days.

(21) Appl. No.: 15/965,364

(22) Filed: Apr. 27, 2018

(65) Prior Publication Data
US 2018/0310822 A1    Nov. 1, 2018

Related U.S. Application Data

(60) Provisional application No. 62/535,168, filed on Jul. 20, 2017, provisional application No. 62/564,879, (Continued)

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0015* (2013.01); *A61B 5/02055* (2013.01);
(Continued)

(58) Field of Classification Search
CPC . A61B 5/0015; A61B 5/02416; A61B 5/7282; A61B 5/7275; A61B 5/742;
(Continued)

(56) References Cited

U.S. PATENT DOCUMENTS

| | | | |
|---|---|---|---|
| 4,815,469 | A | 3/1989 | Cohen et al. |
| 4,858,615 | A | 8/1989 | Meinema |

(Continued)

FOREIGN PATENT DOCUMENTS

| | | |
|---|---|---|
| JP | H08-315919 | 11/1996 |
| JP | H11-156657 | 11/1997 |

(Continued)

OTHER PUBLICATIONS

US 8,845,543 B2, 09/2014, Diab et al. (withdrawn)

(Continued)

*Primary Examiner* — Catherine M Voorhees
(74) *Attorney, Agent, or Firm* — Knobbe, Martens, Olson & Bear, LLP

(57) ABSTRACT

A portable spot-check system configured to assess the validity of a measured physiological parameter. The spot-check device can take into consideration a variety of factors to determine whether a valid measurement exists. For instance, the considerations can include signal stability, interference, signal IQ, patient movement, sensor position, timing of that measurement, comparison to previous or acceptable measurements, cancellation of measurement by the patient, confidence of the measurement, etc. The spot-check device can track a number of valid measurements. In some instances, the spot-check device is configured to provide a specified number of available measurements. If a valid measurement is recorded, the spot-check device can decrement the remaining number of available measurements.

15 Claims, 85 Drawing Sheets

Related U.S. Application Data filed on Sep. 28, 2017, provisional application No. 62/575,231, filed on Oct. 20, 2017, provisional application No. 62/492,083, filed on Apr. 28, 2017.

(51) Int. Cl.
    *G16H 50/30*     (2018.01)
    *A61B 5/1455*     (2006.01)
    *A61B 5/0205*     (2006.01)
    *A61B 5/145*     (2006.01)

(52) U.S. Cl.
    CPC ...... *A61B 5/02438* (2013.01); *A61B 5/14542* (2013.01); *A61B 5/14551* (2013.01); *A61B 5/4842* (2013.01); *A61B 5/6826* (2013.01); *A61B 5/7221* (2013.01); *A61B 5/7275* (2013.01); *A61B 5/7282* (2013.01); *A61B 5/742* (2013.01); *A61B 5/7405* (2013.01); *A61B 5/746* (2013.01); *A61B 5/6802* (2013.01); *A61B 5/6838* (2013.01); *A61B 5/72* (2013.01); *G16H 50/30* (2018.01)

(58) Field of Classification Search
    CPC ... A61B 5/7405; A61B 5/7221; A61B 5/4842; A61B 5/746; A61B 5/14542; A61B 5/14551; A61B 5/6826; A61B 5/02055; A61B 5/02438; A61B 5/6838; A61B 5/72; A61B 5/6802; G16H 50/30
See application file for complete search history.

(56) References Cited

U.S. PATENT DOCUMENTS

| | | |
|---|---|---|
| 4,900,904 A | 2/1990 | Wright et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,317,269 A | 5/1994 | Mills et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,991,355 A | 11/1999 | Dahlke |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,069,955 A | 5/2000 | Coppersmith et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,330,468 B1 | 12/2001 | Scharf |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,419,636 B1 | 7/2002 | Young et al. |
| 6,430,437 B1 | 8/2002 | Marro |
| 6,430,525 B1 | 8/2002 | Weber et al. |
| 6,433,696 B1 | 8/2002 | Deiterman et al. |

(56) References Cited

U.S. PATENT DOCUMENTS

| | | |
|---|---|---|
| 6,463,310 B1 | 10/2002 | Swedlow et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,499,843 B1 | 12/2002 | Cox et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,553,241 B2 | 4/2003 | Mannheimer et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,587,945 B1 | 7/2003 | Pasieka |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,631,353 B1 | 10/2003 | Davis et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,704,786 B1 | 3/2004 | Gupta et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,997,879 B1 | 2/2006 | Turcott |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| 7,349,856 B2 | 3/2008 | Ackermann et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,390,299 B2 | 6/2008 | Weiner et al. |
| 7,394,370 B2 | 7/2008 | Chan |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,444,436 B2 | 10/2008 | Wille |
| 7,450,927 B1 | 11/2008 | Creswell et al. |
| 7,454,240 B2 | 11/2008 | Diab et al. |

(56) References Cited

U.S. PATENT DOCUMENTS

| | | |
|---|---|---|
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| 7,660,616 B1 | 2/2010 | Poore |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,797,248 B1 | 9/2010 | Bierbaum et al. |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,881,761 B2 | 2/2011 | Mannheimer et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| D663,421 S | 7/2012 | Steiner |
| 8,219,172 B2 | 7/2012 | Schurman et al. |
| 8,222,166 B2 | 7/2012 | Chu et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,234,126 B1 | 7/2012 | Estes |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |

(56) References Cited

U.S. PATENT DOCUMENTS

| | | |
|---|---|---|
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,725,645 B1 | 5/2014 | Montini |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| D729,939 S | 5/2015 | Moon |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,069,069 B2 | 6/2015 | Freund et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| D741,497 S | 10/2015 | Aber |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| D745,167 S | 12/2015 | Canas et al. |
| D745,497 S | 12/2015 | Canas |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |

(56) References Cited

U.S. PATENT DOCUMENTS

| | | |
|---|---|---|
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| D794,803 S | 8/2017 | Thom |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,039,482 B2 | 8/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |

(56) References Cited

U.S. PATENT DOCUMENTS

| | | |
|---|---|---|
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,621,571 B2 | 4/2020 | Martinez de Velasco Cortina et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0013517 A1 | 1/2002 | West et al. |
| 2002/0013538 A1 | 1/2002 | Teller |
| 2002/0058864 A1 | 5/2002 | Mansfield et al. |
| 2002/0120467 A1 | 8/2002 | Buanes |
| 2002/0133080 A1 | 9/2002 | Apruzzese et al. |
| 2002/0138336 A1 | 9/2002 | Bakes et al. |
| 2002/0147693 A1 | 10/2002 | Banerjee et al. |
| 2002/0178126 A1 | 11/2002 | Beck et al. |
| 2002/0184224 A1 | 12/2002 | Haff et al. |
| 2002/0198740 A1 | 12/2002 | Roman et al. |
| 2003/0013975 A1 | 1/2003 | Kiani |
| 2003/0018243 A1 | 1/2003 | Gerhardt et al. |
| 2003/0055794 A1 | 3/2003 | Johnson et al. |
| 2003/0063913 A1 | 4/2003 | Yamazaki |
| 2003/0093301 A1 | 5/2003 | Chesney et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0068436 A1 | 4/2004 | Boubek et al. |
| 2004/0106163 A1 | 6/2004 | Workman, Jr. et al. |
| 2004/0146328 A1 | 7/2004 | Sasayama |
| 2004/0162035 A1 | 8/2004 | Petersen et al. |
| 2004/0236699 A1 | 11/2004 | Beenau et al. |
| 2004/0245330 A1 | 12/2004 | Swift et al. |
| 2004/0267103 A1 | 12/2004 | Li et al. |
| 2004/0267552 A1 | 12/2004 | Gilliam et al. |
| 2005/0055276 A1 | 3/2005 | Kiani et al. |
| 2005/0108060 A1 | 5/2005 | Sasano |
| 2005/0125317 A1 | 6/2005 | Winkelman, III |
| 2005/0131810 A1 | 6/2005 | Garrett |
| 2005/0135306 A1 | 6/2005 | McAllen et al. |
| 2005/0165693 A1 | 7/2005 | Moritzen |
| 2005/0221276 A1 | 10/2005 | Rozakis et al. |
| 2005/0228242 A1 | 10/2005 | Kawamura et al. |
| 2005/0234317 A1 | 10/2005 | Kiani |
| 2005/0247778 A1 | 11/2005 | Roberts |
| 2006/0073719 A1 | 4/2006 | Kiani |
| 2006/0087407 A1 | 4/2006 | Stewart et al. |
| 2006/0149594 A1 | 7/2006 | Hilligoss et al. |
| 2006/0161054 A1* | 7/2006 | Reuss ............ A61B 5/00 600/300 |
| 2006/0167351 A1 | 7/2006 | Isaacson et al. |
| 2006/0189871 A1 | 8/2006 | Al-Ali et al. |
| 2006/0224059 A1 | 10/2006 | Swedlow et al. |
| 2006/0258917 A1 | 11/2006 | Burd et al. |
| 2006/0259328 A1 | 11/2006 | Burd et al. |
| 2007/0021843 A1 | 1/2007 | Neill et al. |
| 2007/0022015 A1 | 1/2007 | Tarinelli et al. |
| 2007/0073116 A1 | 3/2007 | Kiani et al. |
| 2007/0133767 A1 | 6/2007 | Hahn et al. |
| 2007/0180140 A1 | 8/2007 | Welch et al. |
| 2007/0197881 A1 | 8/2007 | Wolf et al. |
| 2007/0213658 A1 | 9/2007 | Hickle |
| 2007/0226013 A1 | 9/2007 | Elletson et al. |
| 2007/0244377 A1 | 10/2007 | Cozad et al. |
| 2007/0282478 A1 | 12/2007 | Al-Ali et al. |
| 2007/0293745 A1 | 12/2007 | McCutcheon et al. |
| 2007/0299318 A1 | 12/2007 | Chen et al. |
| 2008/0000479 A1 | 1/2008 | Elaz et al. |
| 2008/0015423 A1 | 1/2008 | Lam et al. |
| 2008/0046286 A1 | 2/2008 | Halsted |
| 2008/0064965 A1 | 3/2008 | Jay et al. |
| 2008/0071155 A1 | 3/2008 | Kiani |
| 2008/0089499 A1 | 4/2008 | Hahn et al. |
| 2008/0094228 A1 | 4/2008 | Welch et al. |
| 2008/0097908 A1 | 4/2008 | Dicks et al. |
| 2008/0103375 A1 | 5/2008 | Kiani |
| 2008/0179401 A1 | 7/2008 | Hart et al. |
| 2008/0221418 A1 | 9/2008 | Al-Ali et al. |
| 2008/0242945 A1 | 10/2008 | Gugliotti et al. |
| 2008/0251579 A1 | 10/2008 | Larsen |
| 2008/0281168 A1 | 11/2008 | Gibson et al. |
| 2008/0300572 A1 | 12/2008 | Rankers et al. |
| 2008/0319510 A1 | 12/2008 | Simpson et al. |
| 2009/0036759 A1 | 2/2009 | Ault et al. |
| 2009/0047926 A1 | 2/2009 | Mastrantuono |
| 2009/0076844 A1 | 3/2009 | Koegen |
| 2009/0093687 A1 | 4/2009 | Telfort et al. |
| 2009/0095926 A1 | 4/2009 | MacNeish, III |
| 2009/0112769 A1 | 4/2009 | Dicks et al. |
| 2009/0119062 A1 | 5/2009 | Owens et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0056875 A1 | 3/2010 | Schoenberg et al. |
| 2010/0057556 A1 | 3/2010 | Rousso et al. |
| 2010/0094951 A1 | 4/2010 | Furuta |
| 2010/0099964 A1 | 4/2010 | O'Reilly et al. |
| 2010/0145833 A1 | 6/2010 | Hamilton, II et al. |
| 2010/0204557 A1 | 8/2010 | Kiaie et al. |
| 2010/0234718 A1 | 9/2010 | Sampath et al. |
| 2010/0254581 A1 | 10/2010 | Nesser |
| 2010/0268120 A1 | 10/2010 | Eriksen |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0073644 A1 | 3/2011 | Sarkis et al. |
| 2011/0077484 A1 | 3/2011 | Van Slyke et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tani et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0179405 A1 | 7/2011 | Dicks et al. |
| 2011/0208015 A1 | 8/2011 | Welch et al. |
| 2011/0208568 A1 | 8/2011 | Deitiker et al. |
| 2011/0230733 A1 | 9/2011 | Al-Ali |
| 2011/0235792 A1 | 9/2011 | Foster |
| 2012/0109685 A1 | 5/2012 | Carter et al. |
| 2012/0123231 A1 | 5/2012 | O'Reilly |
| 2012/0143754 A1 | 6/2012 | Patel |
| 2012/0143772 A1 | 6/2012 | Abadir |
| 2012/0156337 A1 | 6/2012 | Studor |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |

(56) References Cited

U.S. PATENT DOCUMENTS

| | | |
|---|---|---|
| 2013/0041591 A1 | 2/2013 | Lamego |
| 2013/0060147 A1 | 3/2013 | Welch et al. |
| 2013/0066644 A1 | 3/2013 | Dicks et al. |
| 2013/0096405 A1 | 4/2013 | Garfio |
| 2013/0096936 A1 | 4/2013 | Sampath et al. |
| 2013/0097085 A1 | 4/2013 | Peckover |
| 2013/0117155 A1 | 5/2013 | Glasgo |
| 2013/0159456 A1 | 6/2013 | Daoud et al. |
| 2013/0160082 A1 | 6/2013 | Miller |
| 2013/0212381 A1 | 8/2013 | Bousarnra et al. |
| 2013/0243021 A1 | 9/2013 | Siskavich |
| 2013/0246132 A1 | 9/2013 | Buie |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0312066 A1 | 11/2013 | Suarez et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0012981 A1 | 1/2014 | Samuell et al. |
| 2014/0037089 A1 | 2/2014 | Itoh et al. |
| 2014/0038545 A1 | 2/2014 | Ramprasad et al. |
| 2014/0051953 A1 | 2/2014 | Lamego et al. |
| 2014/0106706 A1 | 4/2014 | Tan et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0129702 A1 | 5/2014 | Lamego |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0181524 A1 | 6/2014 | Itoh et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330993 A1 | 11/2014 | Raz |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0048159 A1 | 2/2015 | Martinez de Velasco Cortina et al. |
| 2015/0073241 A1 | 3/2015 | Lamego |
| 2015/0073925 A1 | 3/2015 | Renfroe |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0165312 A1 | 6/2015 | Kiani |
| 2015/0196249 A1 | 7/2015 | Brown et al. |
| 2015/0207626 A1 | 7/2015 | Neftel |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |

(56) References Cited

U.S. PATENT DOCUMENTS

| | | |
|---|---|---|
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192953 A1 | 7/2018 | Shreim et al. |
| 2018/0199871 A1 | 7/2018 | Pauley et al. |
| 2018/0213583 A1 | 7/2018 | Al-Ali |
| 2018/0214090 A1 | 8/2018 | Al-Ali et al. |
| 2018/0218792 A1 | 8/2018 | Muhsin et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0034775 A1 | 1/2019 | Martinez de Velasco Cortina et al. |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |

FOREIGN PATENT DOCUMENTS

| | | | |
|---|---|---|---|
| JP | H10-314149 | 12/1998 | |
| JP | 2002-268764 | 9/2002 | |
| JP | 2002/351564 | 12/2002 | |
| JP | 2003/502092 | 1/2003 | |
| JP | 2003-521985 | 7/2003 | |
| JP | 2003/296114 | 10/2003 | |
| JP | 2004/164597 | 6/2004 | |
| JP | 2009/528909 | 8/2009 | |
| JP | 2013-504827 | 2/2013 | |
| WO | WO 01/17450 | 3/2001 | |
| WO | WO 02/17779 | 3/2002 | |
| WO | WO 2006/051461 | 5/2006 | |
| WO | WO 2007/108513 | 9/2007 | |
| WO | WO 2007/143626 | 12/2007 | |
| WO | WO 2011/032177 | 3/2011 | |
| WO | WO-2011032177 A2 * | 3/2011 | ............ G06Q 50/22 |
| WO | WO 2018/201078 | 4/2018 | |

OTHER PUBLICATIONS

US 9,579,050 B2, 02/2017, Al-Ali (withdrawn)
"E-ZPass Quick Guide" (https://web.archive.org/web/20121217041418/https://www.e-zpassny.com/en/about/i_guide.pdf). Archived on Jan. 6, 2012.
"E-ZPass User's Manual" (https://web.archive.org/web/20120417132149/http://www.paturnpike.com/ezpass/pdf/EZPass_User_Manual.pdf). Archived on Apr. 17, 2012.
International Search Report and Written Opinion, re PCT Application No. PCT/US2018/030004, dated Sep. 27, 2018.
Office Action in European Application No. 10763906.4 dated Mar. 31, 2017.
Office Action in Japanese Application No. 2012-529002 dated Feb. 12, 2014.
Office Action in Japanese Application No. 2012-529002 dated Jan. 27, 2015.
Partial International Search Report for PCT Application No. PCT/US2010/048825, dated Feb. 20, 2012 in 7 pages.

* cited by examiner

CEWT

*CEWT Score*

| SpO₂ | PR | RR | TEMP | SYS |
|------|----|----|------|-----|
| --- | --- | --- | --- | --- |

| LOC | Sup. O₂ | Resp. Distr. | Capil. Refill | |
|-----|---------|--------------|---------------|--|
| --- | --- | --- | --- | Actions |

*MANUAL*

- Supplmental O2: ---
- Sup. O2 Mode: ---
- LOC: ---
- Capillary Refill Time: ---
- Respiratory Distress: ---

*Temperature*

Please remove the probe from the well to begin.

| ORAL | PED AX | ADULT AX |

*NIBP*

Please press start once blood pressure cuff is fastened.

| LYING | STANDING | SITTING | LEFT ARM | LEFT LEG | RIGHT ARM | RIGHT LEG | rainbow

Please attach pulse oximeter.
Paul Heaton, 237

Cancel | Approve

FIG. 12

CEWT

CEWT Score

| [0] | [2] | [1] | -- | -- | |
|---|---|---|---|---|---|
| SpO₂ | PR | RR | TEMP | SYS | 5 |
| [3] | [0] | [0] | -- | | |
| LOC | Sup. O₂ | Resp. Distr. | Capil. Refill | | Actions |

*MANUAL*

| | |
|---|---|
| Supplmental O2 | < 1L/min |
| Sup. O2 Mode | Face Mask |
| LOC | verbal |
| Capillary Refill Time | >2 sec |
| Respiratory Distress | nil |

*Temperature* — Measuring

| ORAL | PED AX | ADULT AX |

*NIBP* — Measuring

| LYING | STANDING | SITTING | LEFT ARM | LEFT LEG | RIGHT ARM | RIGHT LEG | rainbow

97 SpO₂ | 110 bpm | Paul Heaton, 237 | 11 RRa rpm | 13.4 SpHB mmol/L

[Cancel]  [Approve]

CEWT

CEWT Score

| [0] | [2] | [1] | [2] | [0] | |
|---|---|---|---|---|---|
| SpO₂ | PR | RR | TEMP | SYS | 7 |
| [3] | [0] | [0] | [1] | | Actions |
| LOC | Sup. O₂ | Resp. Distr. | Capil. Refill | | Actions |

- Obtain a full CEWT score
- Registrar to review patient within 15 minutes
- Notify team leader
- Carry out and document appropriate interventions as prescribed
- If no review within 15 minutes, or if clinically concerned, initiate emergency call
- Obtain a full CEWT score after interventions
- Record observations at least once every 30 seconds
- Registrar to ensure consultant is notified
- Ward doctor to attend 39.2 °C

| ORAL | PED AX | ADULT AX |

NIBP

| 100 MAP mmHg | 112 PR bpm | 129/84 SYS/DIA mmHg | |
|---|---|---|---|
| LYING | STANDING | SITTING | LEFT ARM | LEFT LEG | RIGHT ARM | RIGHT LEG | rainbow

| 97 SpO₂ % | 110 PR bpm | 11 RRa rpm | 13.4 SpHB mmol/L |

Paul Heaton, 237

| Cancel | Approve |

CEWT

CEWT Score     Emergency call required

| [0] SpO₂ | [2] PR | [0] RR | [2] TEMP | [0] SYS |
|---|---|---|---|---|
| [E] LOC | [0] Sup. O₂ | [0] Resp. Distr. | [1] Capil. Refill | |

*1610* → E Actions

*MANUAL*

| | |
|---|---|
| Supplmental O2 | < 1L/min |
| Sup. O2 Mode | Face Mask |
| LOC | verbal |
| Capillary Refill Time | >2 sec |
| Respiratory Distress | nil |

*Temperature*

39.2 °C

*NIBP*

100 MAP mmHg    112 PR bpm    129/84 SYS/DIA mmHg

*rainbow*

97 SpO₂ %    110 PR bpm    11 RRa rpm    13.4 SpHB mmol/L

Paul Heaton, 237

[ Cancel ]    [ Approve ]

SPOT CHECK MEASUREMENT SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Physiological monitoring systems often measure a patient's physiological parameters, such as oxygen saturation, respiration rate, and pulse rate, and output these parameters on a display. When a parameter exceeds a threshold, an alarm can be triggered to request aid from a clinician. Alarms can be audible or visual.

SUMMARY

The present disclosure describes example medical devices for performing spot check measurements, among other features. In general, the spot check measurements can involve applying a sensor or sensors to a patient, obtaining measurements, automatically sending the measurements to the patient's electronic chart, and/or optionally outputting some or all measurements audibly. Spot check measurements can be performed automatically in response to a sensor being removed or upon a button press—which can free clinicians to focus on patients. Automatically saving measurements to patients' charts instead of entering measurements manually can permit clinicians to focus on patients' needs. Further, audibly outputting parameter measurements can free clinicians to focus on patients rather than looking at measurements on a display.

In addition to or instead of calculating spot checks, a medical device can calculate an early warning score (EWS). The EWS can represent an aggregation of vital signs and/or clinical observations and may represent the potential degree of patient deterioration. The EWS may be a sum of contributor scores for each of a plurality of physiological parameters (such as oxygen saturation, respiration rate, pulse rate, level of consciousness, temperature, blood pressure, or others). Each of the contributor scores and the EWS itself may be grouped together in a single area of the display, instead of being spread about the display as in some currently-available devices. A trend graph of EWS scores over time may also be displayed instead of or together with the contributor scores.

For purposes of summarizing the disclosure, certain aspects, advantages, and novel features of the inventions have been described herein. It is to be understood that not necessarily all such advantages can be achieved in accordance with any particular embodiment. Thus, the features described herein can be embodied or carried out in a manner that achieves or optimizes one advantage or group of advantages as taught herein without necessarily achieving other advantages as can be taught or suggested herein.

BRIEF DESCRIPTION OF THE DRAWINGS

The features disclosed herein can be described below with reference to the drawings. Throughout the drawings, reference numbers are re-used to indicate correspondence between referenced elements. The drawings are provided to illustrate examples of the inventions described herein and not to limit the scope thereof.

FIGS. 12 through 16 depict example patient monitor displays that provide functionality for inputting physiological parameters manually and calculating physiological parameters automatically.

FIG. 59 depicts an example patient lookup user interface.

DETAILED DESCRIPTION

Introduction

The present disclosure describes example medical devices with a display that can output (1) an early warning score and/or (2) spot check measurements.

An early warning score (EWS) can represent an aggregation of vital signs and/or clinical observations and may represent the potential degree of patient deterioration. The EWS may be a convenient aid to clinical assessment and may facilitate rapid response to patient deterioration. The EWS may be a sum of contributor scores for each of a plurality of physiological parameters (such as oxygen saturation, respiration rate, pulse rate, level of consciousness, temperature, blood pressure, or others). For example, the medical device can compute a contributor score for each physiological parameter measured based on predefined ranges, or user-configurable ranges.

Each of the contributor scores and the EWS itself may be grouped together in a single area of the display, instead of being spread about the display as in some currently-available devices. That way, a clinician can more easily see the contributor scores together with the EWS in a single area on the display, speeding up visual recognition of the patient's condition. As a result, the clinician may more readily apprehend the nature of the patient's condition and more quickly provide life-saving care when needed. The medical device can also output a user interface that enables a clinician to define a list of one or more actions to be taken if an EWS has a certain value. These actions can be based on hospital policies. Later, when the medical device is monitoring a patient and a certain EWS is reached, the medical device can output the list of one or more actions to instruct a clinician to perform those actions (for example, to perform certain lifesaving actions to protect the patient).

The EWS features are described initially with respect to FIGS. 1-18. Additional features related to spot check monitoring examples are also discussed in detail below, primarily with respect to FIGS. 18-82. Many of the spot check monitoring examples also include calculations of an EWS based on spot check measurements.

Example Patient Monitoring Environments

Figure 1:
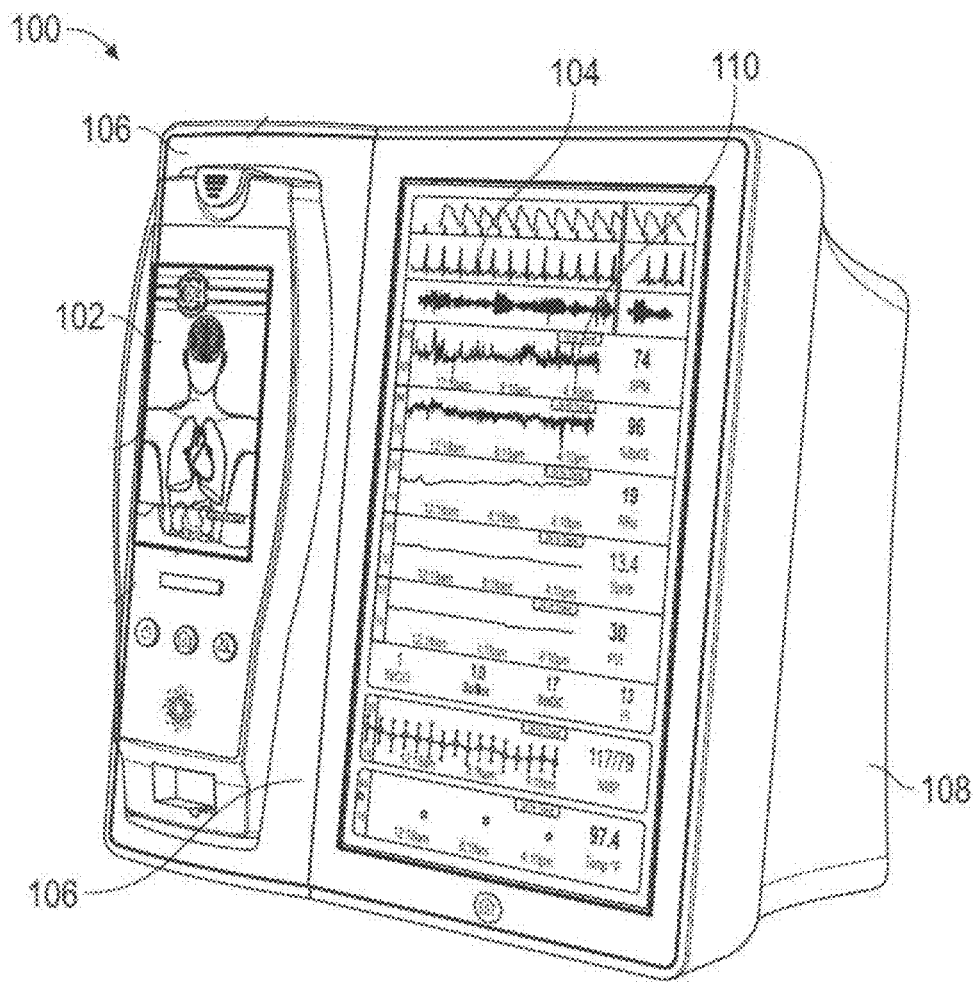
FIG. 1 depicts an example a patient monitor.

FIG. 1 illustrates an example monitoring environment including a perspective view of an example patient monitor 100 that can implement the various EWS features described herein. The patient monitor 100 can be a pulse oximeter or pulse oximetry monitor. For example, the patient monitor 100 can be an example of the Root™ product available from Masimo Corporation™ of Irvine, Calif. The Root™ patient monitor can work in conjunction with other Masimo™ devices, including Radical-7™ or Radius-7 Pulse™ CO-Oximeters and Masimo Open Connect™ (MOC-9™) measurements, and can feature Masimo SET Measure-through Motion and Low Perfusion™ pulse oximetry, rainbow SET™ pulse CO-Oximetry, Nomoline™ capnography and gas monitoring, SedLine brain function monitoring, O3™ regional oximetry, SunTech™ blood pressure, and Welch Allyn™ temperature monitoring. Of course, these are example features of an example patient monitor, and other patient monitors can be used to perform the functions described herein.

The patient monitor 100 is shown with an optional docked portable patient monitor (PPM) 102. The patient monitor 100 includes a display 104 and a docking station 106, which can mechanically and electrically mate with the portable patient monitor 102, each housed in a movable, mountable and portable housing 108. The housing 108 includes a generally upright inclined shape configured to rest on a horizontal flat surface, although the housing 108 can be affixed in a wide variety of positions and mountings and comprise a wide variety of shapes and sizes. Patient monitors without docked portable patient monitors may be used in other examples.

The display 104 may present a wide variety of measurement and/or treatment data in numerical, graphical, waveform, or other display indicia 110. The display 104 can occupy much of a front face of the housing 108, although the display 104 may comprise a tablet or tabletop horizontal configuration, a laptop-like configuration or the like. Other implementations may include communicating display information and data to a table computer, smartphone, television, or any display system currently available. The upright inclined configuration of FIG. 1 presents display information to a caregiver in an easily viewable manner.

The patient monitor 100 can display an EWS. As mentioned above, the EWS can represent an aggregation of vital signs and/or clinical observations and may represent the potential degree of patient deterioration. There are several EWS protocols or scoring systems currently studied, such as Pediatric EWS (PEWS), Modified EWS (MEWS), and National EWS (NEWS). The EWS output by the patient monitor 100 can be based on any of these publicly-available scoring systems or a customized scoring system, as will be discussed below. The publicly-available scoring systems can use vital signs contributors—such as oxygen saturation, pulse rate, respiration rate, body temperature, and systolic blood pressure—and contributors input by clinicians, such as level of consciousness, use of supplemental oxygen, and urine output. The weighting and number of contributors may differ depending upon which EWS protocol is used. The patient monitor 100 can be customized for various predefined EWS protocols, or hospitals can configure their own set of required contributors, and optionally their relative weights, to create an EWS protocol or scoring system unique to their care environments.

By way of overview, the EWS may be initiated by a clinician (using, for example, a display option of the patient monitor 100), and then may be automatically calculated by the patient monitor 100. The patient monitor 100 may calculate contributor scores using measured values and/or clinician input, then combine these contributor scores into an aggregated EWS. The patient monitor 100 can output the EWS and associated contributor scores in a readily interpretable, high-visibility display with intuitive, optional multi-touchscreen navigation for easy and adaptable use in hospital environments.

Clinicians can choose to have the patient monitor 100 act as a stand-alone device (not connected to a network) perform EWS calculations, helping assist spot-check-based nursing workflows. Or, clinicians can use the patient monitor 100 as a network-connected device that performs EWS calculations and transmits these calculations to an electronic medical record database (see, for example, FIG. 17, discussed below).

Figure 1A:
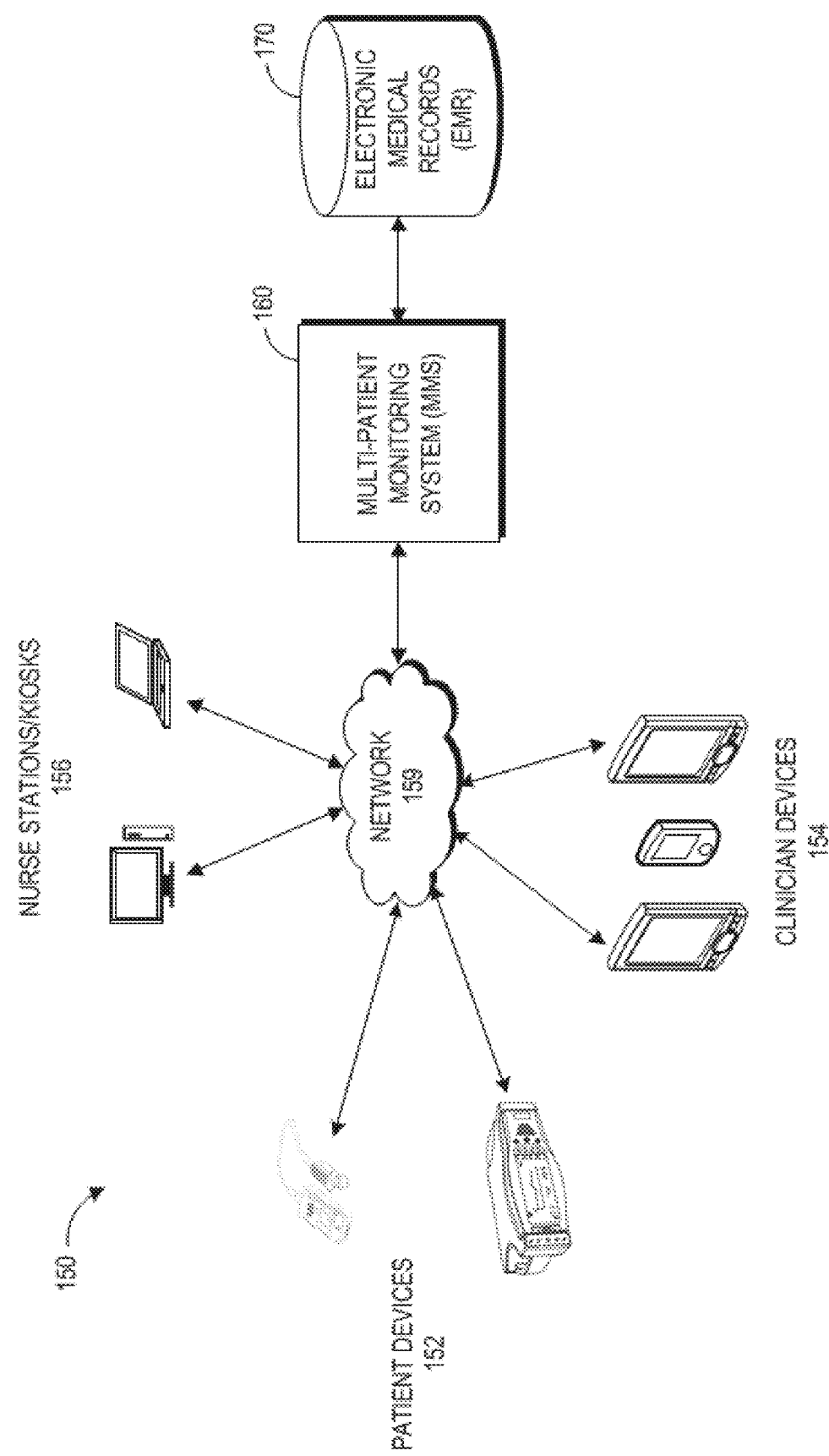
FIG. 1A depicts an example clinical computing environment that includes a multi-patient monitoring system.

Turning to FIG. 1A, an example of a clinical computing environment 150 is shown. The clinical computing environment 150 may be implemented in one or more hospitals or other clinical facilities. Further, the clinical computing environment 150 can facilitate monitoring patients within their homes if such patients are using network-enabled monitoring equipment. Additional details of the example environment 150 are described in U.S. Pub. No. 2015/0106121, titled "Alarm Notification System," filed Oct. 10, 2014 ("the '121 publication"), the disclosure of which is hereby incorporated by reference in its entirety. Any of the features described in the '121 publication can be implemented together with any of the features described herein.

In the clinical computing environment 150, various patient devices 152, clinician devices 154, and nurse's station systems or kiosks 156 can communicate over a network 159 with a multi-patient monitoring system (MMS) 160. The MMS 160 is an example of a remote server that can communicate with patient devices and clinician devices. The network 159 may include a local area network (LAN), a wide area network (WAN), a public network (such as the Internet), a private network, or any combination of the same. For instance, the network 159 can include a wireless and/or wired hospital network or a network that connects multiple clinical facilities.

The patient devices 152 may be any of the patient monitors or monitoring devices described herein and may include bedside monitors, ambulatory or mobile monitors, in-home monitors, and the like. The patient devices 152 can be point-of-care devices, such as bedside devices or patient-worn devices. The patient devices 152 can receive input from physiological sensors coupled with a patient and may measure parameters such as oxygen saturation or SpO2, respiratory rate, blood pressure, heart rate or pulse rate, perfusion, other blood gas parameters, brain activity, brain oxygen saturation, any of the other parameters described herein, and the like. The patient devices 102 can provide information about a patient's status, including current values of physiological parameters, waveforms, trend values, and historical values of physiological parameters over the network 159 to the MMS 160. The MMS 160 can in turn store this data in an electronic medical records (EMR) system 170.

In addition, the MMS 160 can provide this data to the nurse's station systems 156. The nurse's station systems 156 can include any type of computing device including, but not limited to, a desktop, laptop, tablet, phone or the like. The nurse's station systems 156 may also include clinical facility kiosks such as computers on wheels (COWs) (which may use laptop or tablet computers), which may be dispersed throughout a clinical facility. The nurse's station systems 156 can communicate with a plurality of patient devices 152 to receive information of a plurality of patients so that the nurse's station systems 156 can provide clinicians with the ability to monitor physiological parameter data for a plurality of patients.

The clinician devices 104 can include any mobile device, such as a laptop, tablet, cell phone, smartphone, personal digital assistant (PDA), or any other device. In some cases, the clinician devices can include desktop systems. In turn, the MMS 160 can send alarms or messages representing alarms to the nurse's station systems 156 and/or the clinician devices 154. Further, the patient devices 152 may have network capability that enables the patient devices 102 to send the alarm notifications over the network 109 to the MMS 160, the nurse's station systems 156 and/or to the clinician devices 154. Some alarms can include nonclinical alarms that may not represent that a physiological parameter has exceeded a threshold but instead may include information about a sensor that has been disconnected or otherwise has fallen off (often referred to as a probe-off condition), or a low battery of a patient device 152. Sensor disconnection or probe-off can be detected using any of a variety of techniques, some examples of which are described in U.S. Pat. No. 6,360,114, filed Mar. 21, 2000, titled "Pulse Oximeter Probe-off Detector," and U.S. Pat. No. 9,750,461, filed Dec. 20, 2013, titled "Acoustic Respiratory Monitoring Sensor with Probe-off Detection," the disclosures of which are hereby incorporated by reference in their entirety.

Example Patient Monitor User Interfaces

Figure 2A:
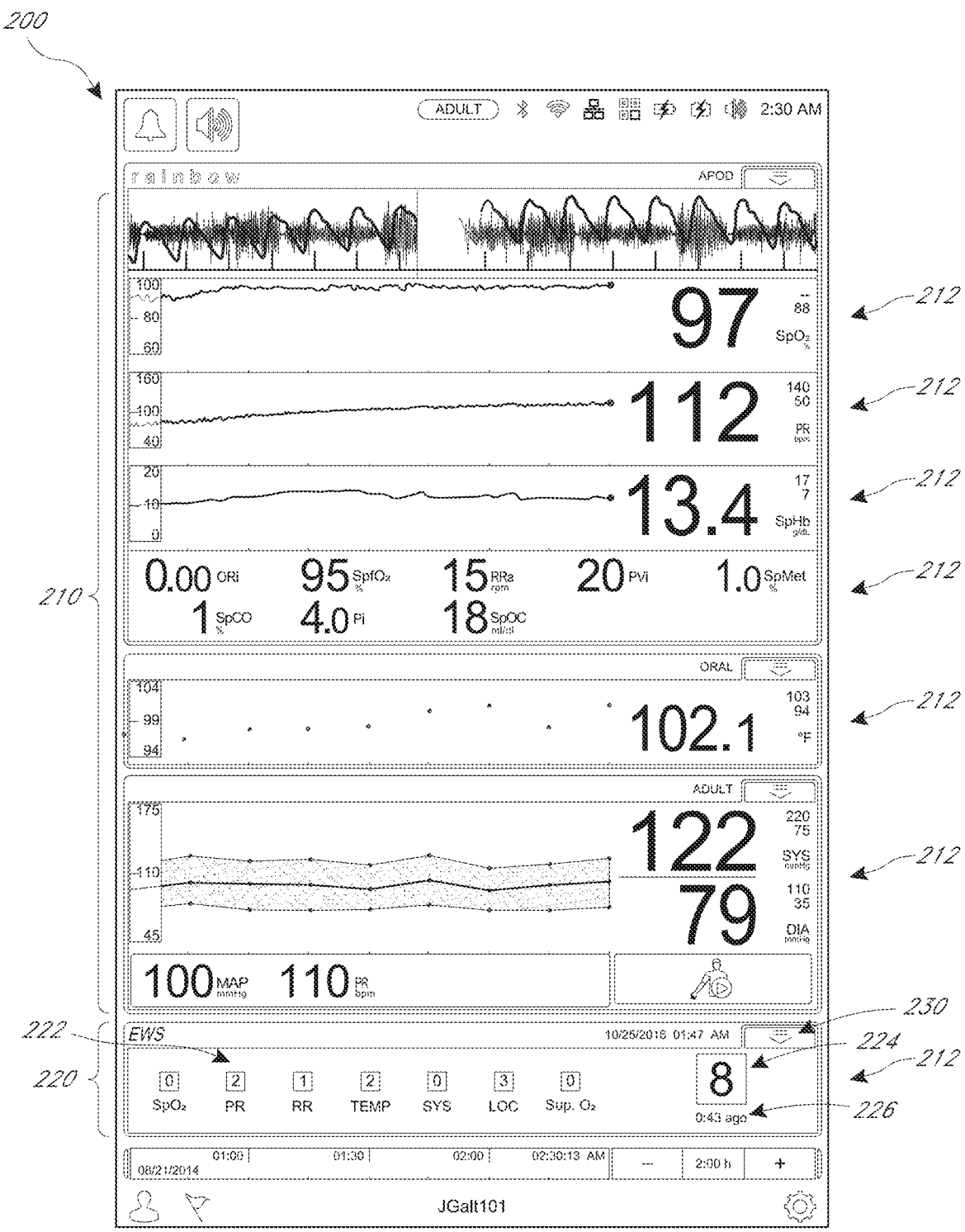
FIG. 2A depicts an example patient monitor display including an early warning score channel or group.

FIG. 2A depicts an example patient monitor display 200 including an EWS region 220, which can be a separate channel or group from other channels of physiological data on the display 200. The patient monitor display 200 can be implemented in the patient monitor 100 of FIG. 1. The display 200 is a user interface that outputs values of physiological parameters for presentation to a clinician so that clinicians can make informed decisions about patients by knowing the status of patients' health.

Figure 2B:
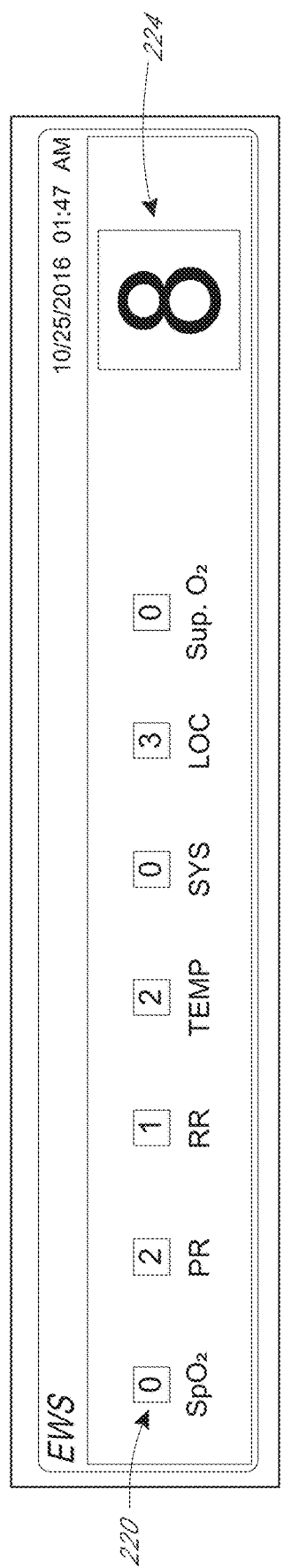
FIG. 2B depicts an example early warning score channel or group of FIG. 2A.

The display 200 includes two general regions, a first region 210 and a second (EWS) region 220. The first region 210 can include the majority of the display 200, and the second (EWS) region 220 includes a small horizontal section of the display below the region 210. The relative location of these two regions 210, 220 is unimportant and can be varied. The region 210 includes several horizontal rows 212. Each row 212 can represent a channel of data obtained by calculating a physiological parameter from a physiological signal, for example, received from a sensor coupled to a patient. Several rows 212 include numbers representing physiological parameter values (such as 97 for $SpO_2$ percentage and 112 for pulse rate). In addition, the rows 212 include graphs that depict trend lines corresponding to those parameters over time. FIG. 2B depicts an example close-up of the second region 220 (with different scores, explained below, shown for illustration purposes).

In contrast to the rows 212 in the first region 210, the second region 220, also referred to as an EWS region, depicts a plurality of boxes 220 with numbers inside the boxes. Each box 220 is above the name of one of the parameters listed in the first region 210. For instance, a first box 222 is above the parameter $SpO_2$ and has the number 0 in it. The next box is above the PR, or pulse rate, parameter and has the number 2 in it, and so on. To the right of these boxes (although optionally may be located to the left or elsewhere) is a larger box 224 that includes the EWS—here, having a value 8. The EWS value of 8 is the sum of the numbers in the boxes 222 in this example.

Each of the numbers in the smaller boxes 222 can be considered a contributor score which contributes to the EWS in the box 224. Each contributor score can represent a severity level of the physiological parameters depicted in the region 210. Some of the contributor scores correspond to parameters that are not shown in the region 210, such as LOC or level of consciousness and supplemental oxygen (Sup.O$_2$). The input of these scores may be performed by clinicians manually and will be discussed in greater detail below. The contributor scores can range from 0 to 3, with 0 representing the least severe and 3 representing the most severe. This scale is somewhat arbitrary and may be changed in other implementations.

In general, the higher the contributor scores in any given box 222 represents a higher severity level for the corresponding physiological parameter. For pulse rate, for instance, a very high or a very low pulse rate may represent a greater degree of severity than an average pulse rate. Thus, the higher or lower the extreme of the pulse rate, the higher the pulse rate contributor score might be. Other physiological parameters may have different scales, but in general, the worse the parameter value (for example, corresponding to worse health status of the patient), the more severe the contributor score may be. The resulting EWS, which may be an aggregation of the contributor scores, can therefore directly reflect the severity of multiple measured physiological parameters.

Thus, the EWS can represent a rough indication of the health status of the patient. The lower the EWS, the greater the likelihood that the patient is in better health than with a higher score. A higher score reflects that, likely, multiple of the contributor scores are relatively high. Thus, for instance, in this example, pulse rate has a score of 2, respiratory rate 1, temperature 2, and level of consciousness 3, resulting in an EWS of 8. This EWS indicates that greater attention may be needed for the patient than if the EWS were lower.

The boxes 222 and 224 around the scores are of course optional but help to draw visual attention to the individual contributor scores in their EWS. In fact, the color of the boxes 222 may correspond directly to the values of the contributor scores within the boxes 222. Likewise, the color of the EWS box 224 may correspond to the value of the EWS in the box 224. For example, one color scheme may be represented with green as a low score, yellow as a slightly higher score, orange as a higher score than yellow, and red as a most severe score. With colors and numbers representing the values of the physiological parameters in the box or region 210, an easy and readily understandable display method can be provided for conveying the health status of the patient to a clinician. Thus, a clinician can look at the EWS region 220 of the display and readily grasp whether or not the patient is likely in need of greater medical assistance than he or she is currently receiving.

Viewing the EWS region 220 may be easier than looking at the region 210 and deciphering several different physiological parameter values, many of which may be on different scales and thus hard to interpret together. In fact, because the physiological parameters have different scales—for instance SpO$_2$ goes from 0 to 100% while pulse rate may range from approximately 40 or lower to well over 200—a clinician may need greater training to understand and interpret the physiological parameter values than a clinician may need to interpret the contributor scores and the EWS. Thus, a clinician with perhaps less training may be able to glean more information about the health status of the patient than the clinician might have been able to otherwise, merely by looking at the EWS region 220. Even clinicians with more training can more quickly glean information about patient health by reviewing the EWS region 220.

The region 210 and the region 220 can be two separate regions that may or may not overlap. The region 220 can be in a horizontal line or horizontal section and can group together some or all of the contributor scores and the EWS in that section. By doing so, a clinician can readily visually perceive the various contributor scores and EWS together. In contrast, if the contributor score or EWS were distributed amongst the region 210, for example, with each contributor score next to the physiological parameter value, then a clinician would have to hunt and peck to find the different contributor scores and EWS. Of course this would take longer to identify the different contributor scores. Thus, by grouping the contributor scores and the EWS together in a horizontal row (or in some other area grouped together), the clinician can more quickly ascertain the health status of the patient and therefore more quickly react to the needs of the patient.

The horizontal row of contributor scores and EWS value may instead be vertical, but nevertheless grouped together. Or, the contributor scores may be grouped together in multiple rows in some type of rectangular or square matrix or the like. Essentially, any combination of the contributor scores and EWS graphically may be provided so long as they are grouped together in some fashion so that they are readily visually perceptible to a clinician. The EWS may be in a separate area of the display from the grouped together contributor scores or may be grouped together with the contributor scores as shown.

The EWS can be calculated or derived using any of a variety of currently available warning score systems, as discussed above (such as MEWS or NEWS). Further, as will be described in greater detail, the hospital or administrative staff may be provided functionality through the medical device or patient monitor 100 or a separate device in communication thereof, to customize the parameters used in the EWS as well as optionally other aspects of the EWS.

In addition to the features shown, a last time calculated value 226 is shown underneath the EWS 224. The last time calculated value 226 depicts when the last time the EWS was calculated and may be used when the EWS is calculated in a spot check fashion, on demand at the request of a clinician. Instead of calculating the EWS as a spot check, the EWS can be calculated continuously, which can include calculating the EWS automatically along with changes in the physiological data. Continuous does not necessarily mean in an analog sense, where it would always be changing, but rather, may be performed using discrete calculations that are rapid enough (such as once a second or once a minute) to be relatively more continuous than infrequent spot checks. The continuous version of the EWS calculation may be useful to give the clinician a moment-by-moment indication of changing health status of the patient. A spot check of the EWS may also be calculated periodically in an automatic fashion, where the EWS is calculated for instance every hour or every two hours or upon clinician request.

More generally, each of the user interfaces shown in FIGS. 2A and 2B, as well as in other user interface figures described below, includes one or more user interface controls that can be selected by a user, for example. Thus, each of the user interfaces shown may be output for presentation by electronic hardware as graphical user interfaces. The user interface controls shown are merely illustrative examples and can be varied. For instance, any of the user interface controls shown may be substituted with other types of user interface controls that provide the same or similar functionality. Some examples of user interface controls that may be used include buttons, dropdown boxes, select boxes, text boxes or text fields, checkboxes, radio buttons, toggles, breadcrumbs (for example, identifying a page or interface that is displayed), sliders, search fields, pagination controls, tags, icons, tooltips, progress bars, notifications, message boxes, image carousels, modal windows (such as pop-ups), date and/or time pickers, accordions (for example, a vertically stacked list with show/hide functionality), and the like. Additional user interface controls not listed here may be used.

Further, user interface controls may be combined or divided into other sets of user interface controls such that similar functionality or the same functionality may be provided with very different looking user interfaces. Moreover, each of the user interface controls may be selected by a user using one or more input options, such as a mouse, touch screen input (for example, finger or pen), or keyboard input, among other user interface input options.

Example EWS Calculation Process

Figure 3:
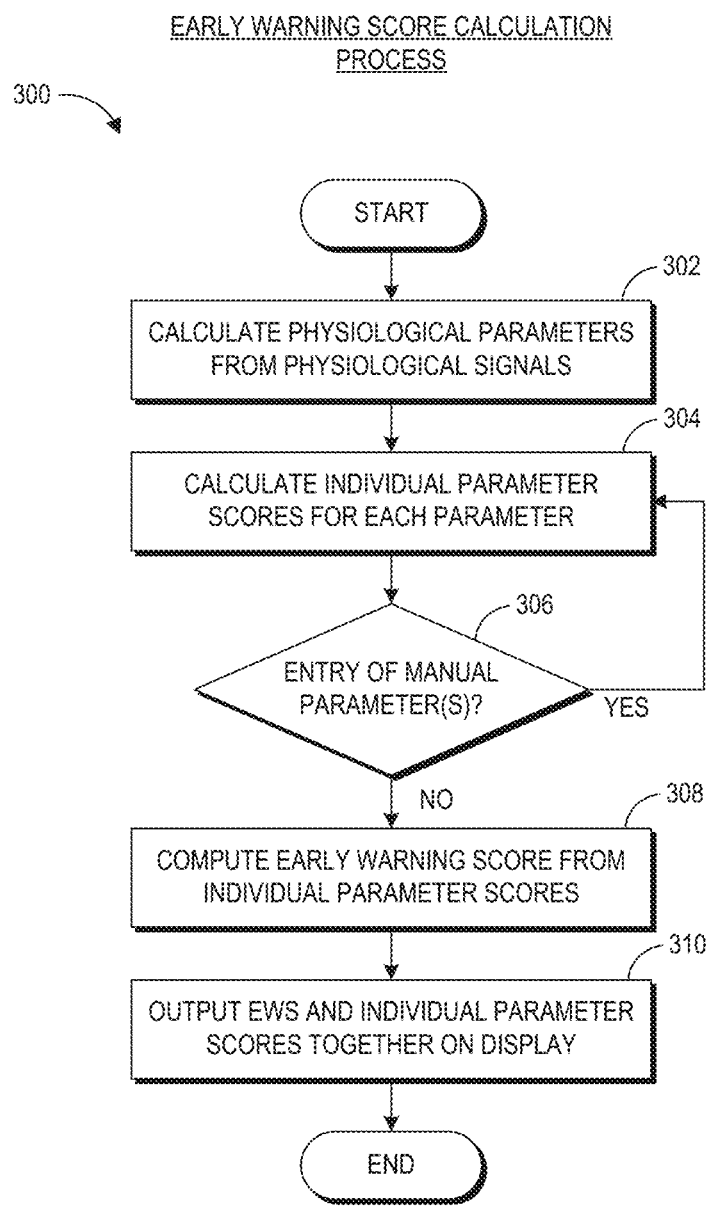
FIG. 3 depicts an example early warning calculation process.

Turning to FIG. 3, an example EWS calculation process 300 is shown. The EWS calculation process may be implemented by a patient monitor such as the patient monitor 100. More generally, the EWS calculation process 300 can be implemented by any processor or computer system that can perform processing calculations. For instance, the EWS calculation process 300 may be implemented by a remote system, whether in the cloud or in a dedicated server in a hospital, which is in communication with the patient monitor such that the EWS is calculated remotely and then potentially transmitted locally to a patient monitor, nurse's station or the like (see, for example, FIG. 17). Or, the process 300 could be implemented by a mobile phone, tablet, laptop, or other computing device having a processor. Thus, the process 300 will be generally referred to as implemented by a processor.

At block 302, a processor calculates physiological parameters from physiological signals obtained from the patient. The physiological signals may be obtained from any of a number of sensors including optical sensors, piezoelectric sensors, electrical sensors, biomechanical sensors, or combinations of the same. For instance, optical sensors may provide parameters such as oxygen saturation or $SpO_2$, pulse rate, pleth variability index (PVI), perfusion index (PI), total hemoglobin or SpHb, methemoglobin or SpMet, carboxyhemoglobin or SpCO, among others. A piezoelectric sensor may be used to calculate parameters such as respiratory rate and pulse rate. Electrical sensors can be used to calculate parameters such as respiratory rate, heart rate, and other ECG-related parameters obtained from the electrocardiogram. Biomechanical sensors, such as bioimpedance sensors, can be also used to capture parameters like respiratory rate.

Other example parameters may be calculated using any of a variety of sensors, such as blood glucose level (using an optical sensor or finger prick sensor), blood pressure (using a biomechanical sensor such as an oscillatory cuff or an optical sensor), and temperature (using a temperature probe or the like), among others. Any number of physiological parameters may be selected to be calculated as a basis for inclusion in an EWS. Seven parameters, nine parameters, or 14 parameters can be selected in various implementations. More or fewer parameters may instead be selected. Further, the number and type of parameter selected may be chosen by a clinician or the hospital.

Referring again to FIG. 3, at block 304, the processor calculates contributor scores for each parameter. Contributor scores may have a variety of values as discussed above. With respect to FIG. 2 in one example, these values can be integers ranging from 0 to 3. They need not be integer values, although integer values may be easier to see and interpret on a display than fractional values. Furthermore, the contributor scores (or EWS itself) need not be numbers, but instead could be alpha values or alphanumerical values, or even symbols (such as red, yellow, and green filled circles ranging from most severe to least severe contributor scores). The contributor scores may be calculated for each parameter by looking up the value of the parameter in a lookup table or the like, where different values fall within a range that maps to a specific contributor value. For instance, an oxygen saturation value from 95% to 100% may correspond to a low risk score such as 0, whereas an oxygen saturation value of below 85% may correspond to a very high risk value such as a 3, with other values of oxygen saturation falling in-between those two extremes of contributor scores. The ranges of physiological parameter values that correspond to the different scores may also be configured by a user, such as a clinician or hospital staff as discussed in greater detail below (see FIG. 10).

At block 306, it is determined by the processor whether any manual parameters are entered. Manual parameters can include parameters entered manually by a clinician, which may be measured using other instruments such as a temperature probe or parameters that are observed by a clinician without using an instrument (such as LOC, which may correspond to the degree to which a patient is aware of their surroundings). If any manual parameters are entered at block 306, then the process 300 loops back to block 304, where parameter scores or contributor scores are calculated for each of those manual parameters in a similar fashion to the automatic parameters.

Otherwise (and eventually), the process 300 proceeds to block 308, where the processor computes an EWS from the contributor scores. This may include a simple summation or a more complex aggregation. The aggregation may be a summation or may be a weighted summation where different weights are applied to different parameters. Some parameters may be considered more important for assessing the overall health status of the patient than others, and thus, greater weights may be applied to these parameters, for example, in the form of a coefficient. Other scales may of course be used, and weighting schemes may be linear or exponential.

At block 310, the processor outputs the EWS and the contributor scores together on the display, such as in the manner discussed above with respect to FIG. 2 or other examples discussed herein. Generally, the processor can output the EWS and the contributor scores together but apart in some way from the actual parameter values. Thus, for instance, parameter values may be in one region of the display—which may but need not be demarcated as such—which is separate from a region including the contributor scores and the EWS score (which also may but need not be demarcated). Further, the contributor scores can be together but separate from the EWS score on the display.

Additional Example Patient Monitor User Interfaces

Figure 4:
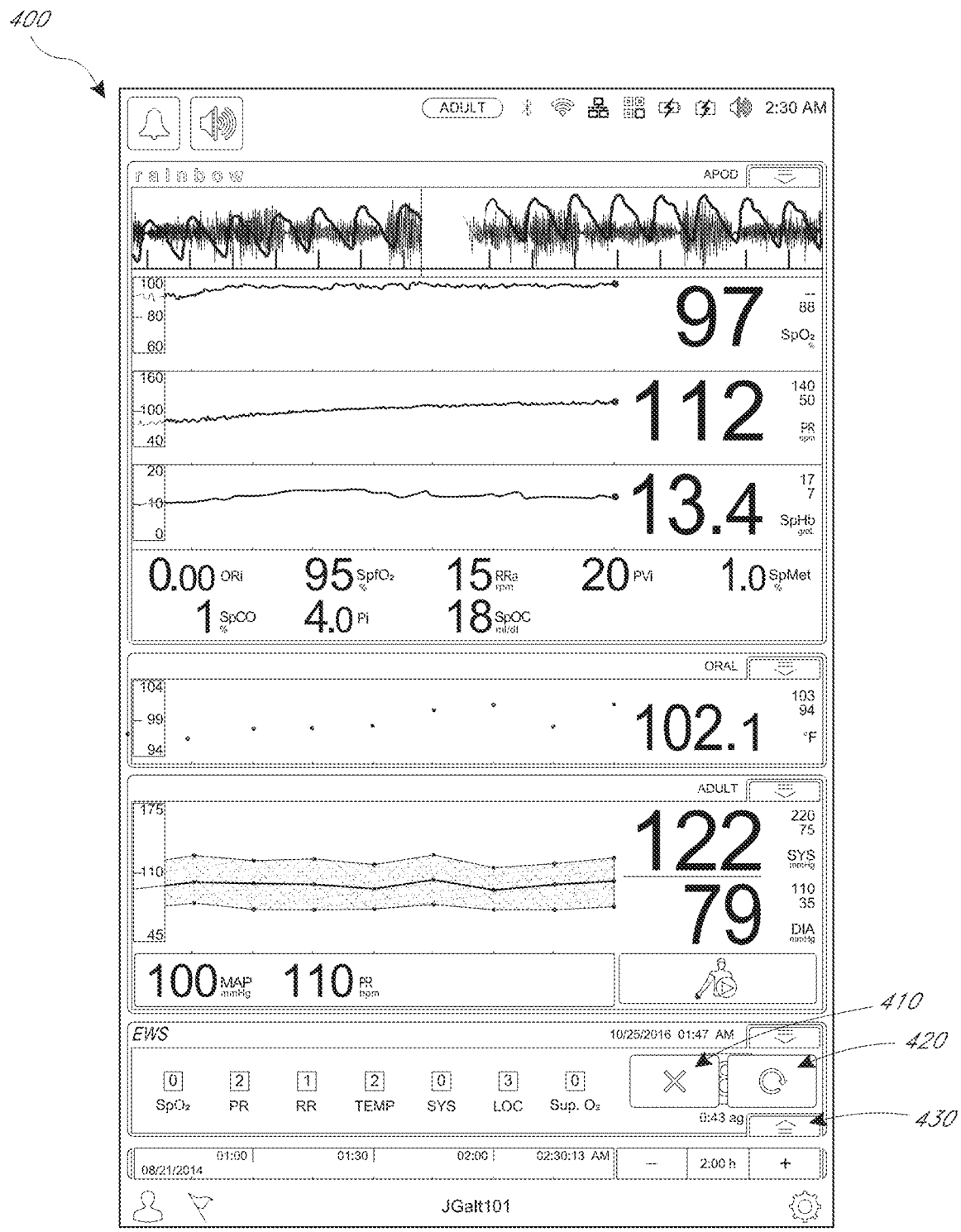
FIGS. 4 and 5 depict additional example patient monitor displays.
Figure 5:
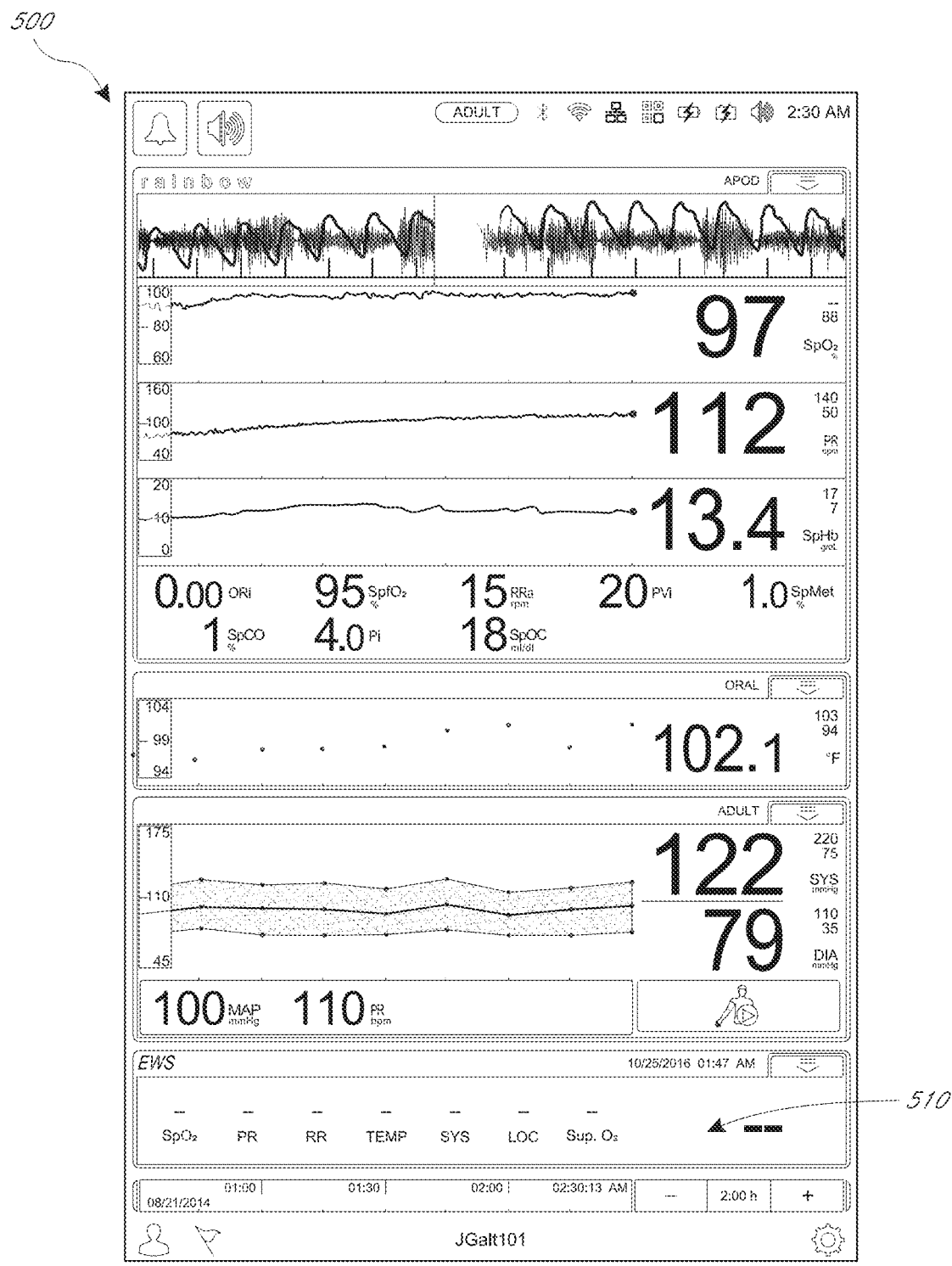

FIGS. 4 and 5 depict additional example patient monitor displays 400, 500. Each of the patient monitor displays 400, 500 may be implemented by a patient monitor such as the patient monitor 100 of FIG. 1. Each of the patient monitor displays 400, 500 are similar to the patient monitor display 200 of FIG. 2. However, in FIG. 4, the example patient monitor display 400 includes two buttons, 410, 420, which provide additional functionality. These buttons 410, 420 may be accessed by selecting the button 230 (see FIG. 2). The buttons 410, 420 may be dismissed by selecting the button 430 in FIG. 4.

The button 410 can be a clear button which can be used to clear the EWS and contributor scores shown in FIG. 4.

Selection of the clear button 410 can result in these scores being reset as shown in FIG. 5 in the region 510. Turning to FIG. 5, the region 510 includes a horizontal display as in FIG. 4 and FIG. 2, where the EWS and contributor scores would be, but in their places are lines indicating that these scores have been reset and are blank.

Turning back to FIG. 4, the button 420 can be used to calculate a new set of contributor scores and/or EWS. Selection of the button 420 can cause the contributor scores to update automatically and the EWS to update automatically directly on the display 400. After selection of the button 420, the buttons 410 and 420 can disappear to reveal the full set of contributor scores and EWS (for example, as in FIG. 2). However, selecting the button 420 can cause another menu to be displayed, from which the EWS can be calculated (as in, for example, FIG. 6). More generally, selecting the button 420 can cause a spot check calculation ultimately to be made.

Instead of providing the button 420, continuous calculations or updates of EWSs and contributor scores may be made without requests from a clinician to do so. Although the buttons 410 and 420 are displayed in the same horizontal row as the EWS and contributor scores, they need not be, but instead could be displayed elsewhere on the display 400.

Figure 6:
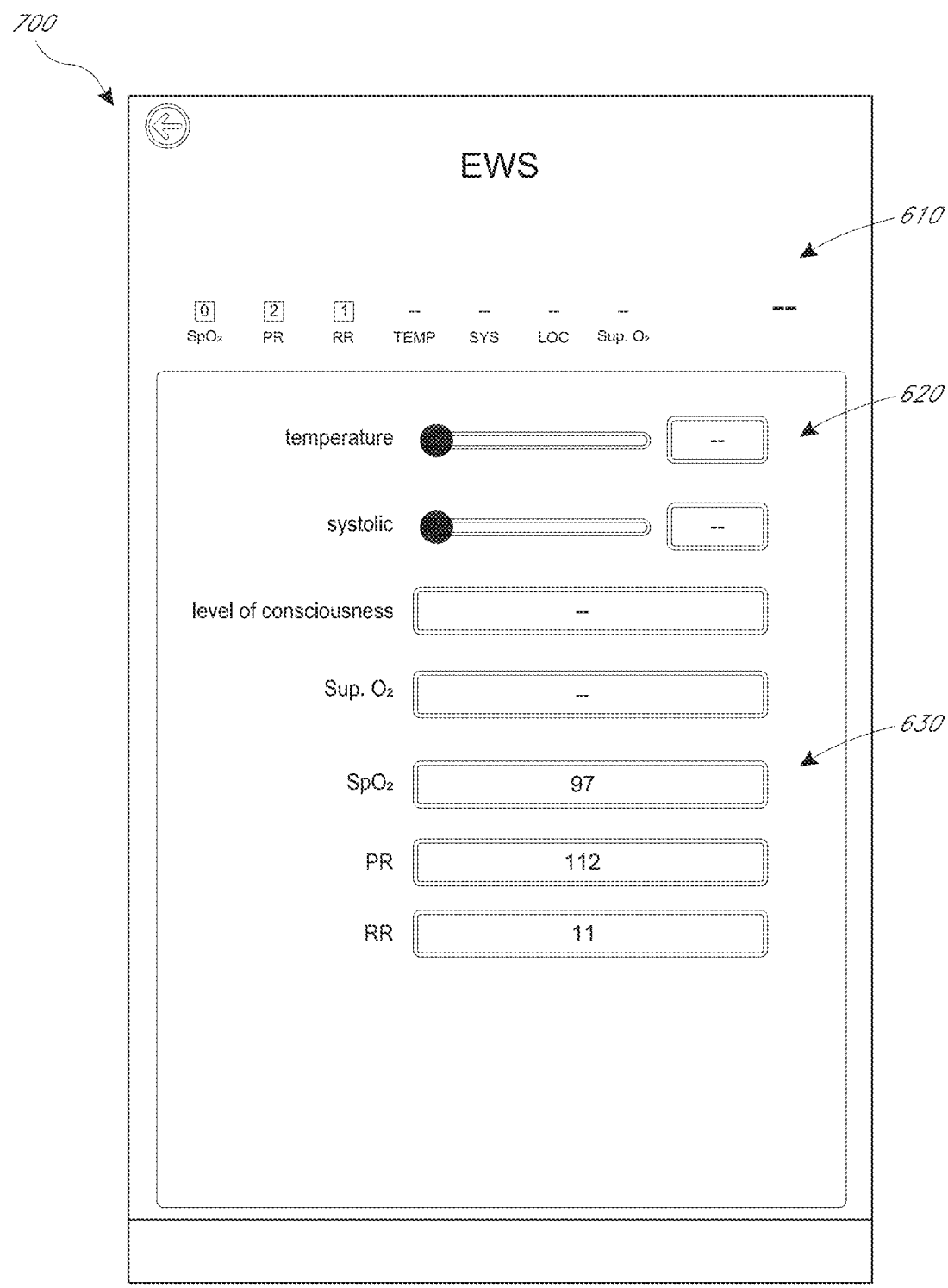
FIGS. 6 and 7 depict example patient monitor displays that provide functionality for inputting manual parameters used to calculate an early warning score.
Figure 7:
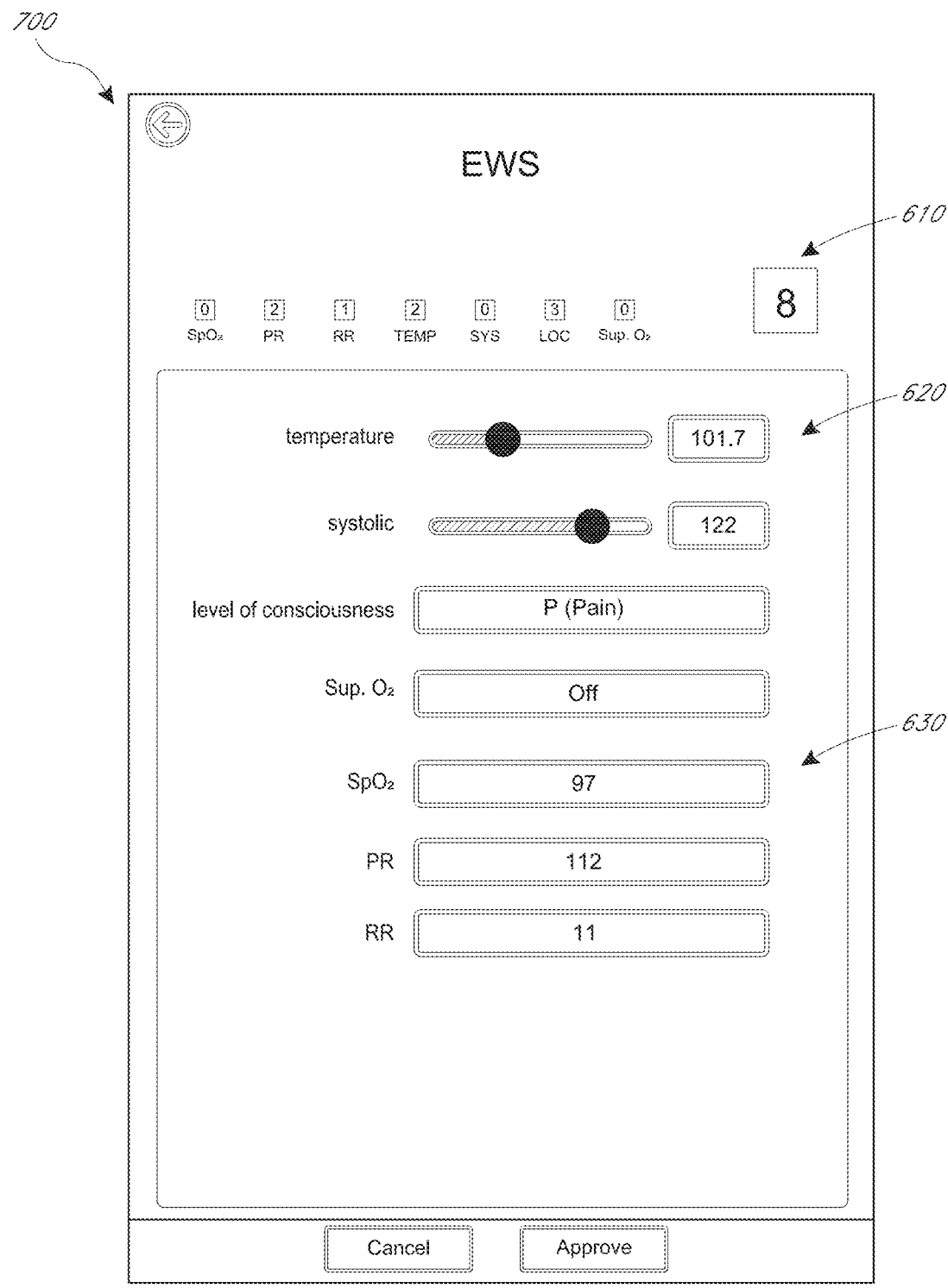

FIGS. 6 and 7 depict additional example patient monitor displays 600, 700 that can provide functionality for inputting manual parameters used to calculate an EWS. Referring specifically to FIG. 6, the display 600 may be reached by selecting the button 420 to calculate an EWS from the display 400. The example display 600 shown includes three general regions, a region 610, a region 620 and a region 630. (Viewed another way, there are two regions—a region 610 and a region defined by elements 620 and 630.) The region 610 includes a list of parameters for which contributor scores may be calculated as well as a blank spot for an EWS (populated in FIG. 7, discussed below). Some of these parameters have contributor scores already calculated, including $SpO_2$, pulse rate, and respiratory rate. These scores are shown as already calculated because the parameter values can be measured from sensors and therefore may be calculated without manual intervention from a clinician. The values of these physiological parameters are listed below in the region 630.

The region 620 includes user interface controls for specifying various parameters measured manually or independent of the physiological sensors connected to the patient or with other physiological sensors that the clinician may directly use with the patient. Examples of these parameters include temperature, blood pressure (systolic or otherwise), level of consciousness and supplemental $O_2$, among others. Slider controls allow temperature and blood pressure to be set by moving the slider from left to right, and dropdown box controls allow the level of consciousness and supplemental $O_2$ settings to be computed or selected. The region 630 can also allow manual editing of the physiological parameters shown. For instance, if a clinician manually measures a patient's pulse rate (PR) and identifies a different pulse rate than was obtained automatically from a sensor, the clinician can enter the manual measurement in the region 630.

Turning to FIG. 7, the display 700 shows an example of the parameters in the region 620 of FIG. 6 now inputted by a clinician. Because these parameters have been inputted in this example, contributor scores have been calculated for them in the region 610, and an EWS has been calculated based on the contributor scores.

Figure 8:
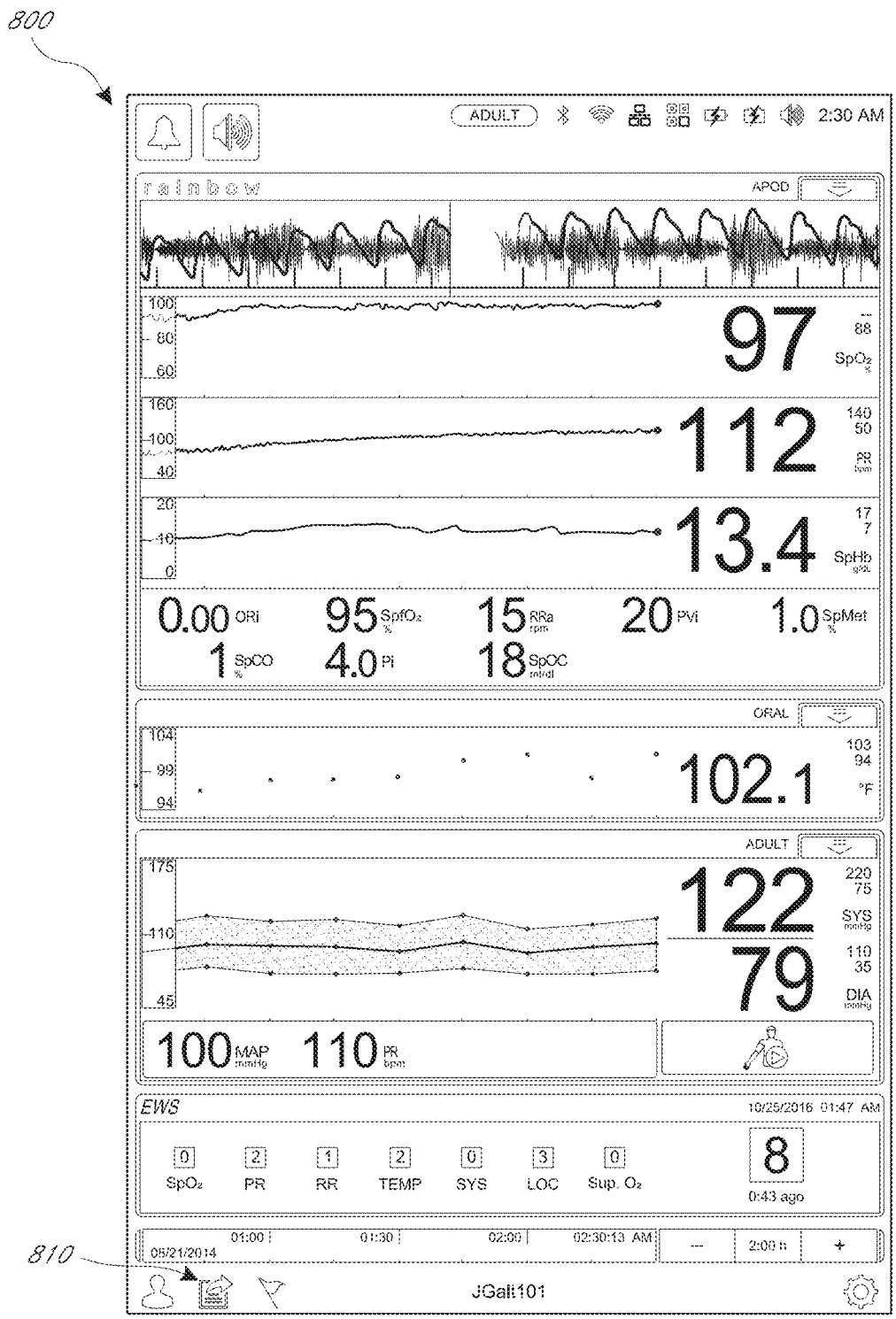
FIG. 8 depicts another example patient monitor display, which includes a user interface control for sending early warning score data to an electronic medical record database.

FIG. 8 depicts another example patient monitor display 800. This display 800 is similar to the displays shown in FIGS. 2 and 4 described previously. Unlike those displays, however, the display 800 includes a user interface control 810 for sending EWS data (including the EWS, contributor scores, parameter values, or combinations of the same) to an electronic medical record database (see FIG. 17). As shown in this example, the user interface control 810 is a button. Selecting the control 810 can cause any of the EWS data shown in this display 800 to be sent to the EMR database.

Figure 9A:
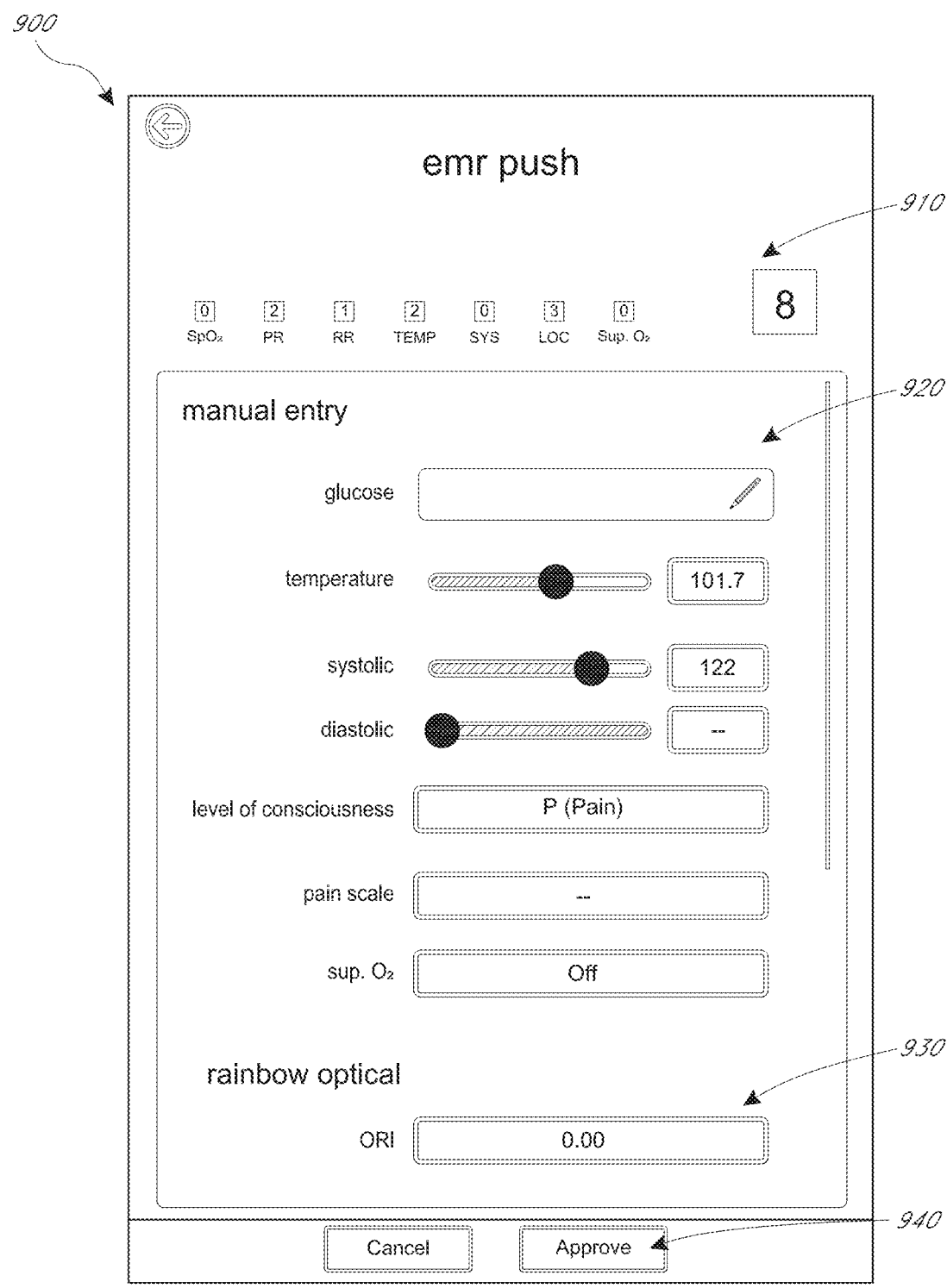
FIGS. 9A and 9B depict example patient monitor displays that provide functionality for inputting physiological parameters manually, which can be used to calculate an early warning score, as well as functionality for approving early warning score data for transmission to an electronic medical record database.

Turning to FIG. 9A, another example patient monitor display 900 is shown that can be output in response to the user interface control 810 of the display 800 being selected by a clinician. This display is much like the displays 600, 700 of FIGS. 6 and 7. For example, the display 900 includes three regions—910, 920, and 930—that have similar functionality as the regions 610, 620, and 630 of FIG. 6. For conciseness, these regions are shown populated with scores, parameter values and the like, whereas they may start off by having at least some fields or scores empty (as in FIG. 6). In addition, another example parameter, glucose, is shown to illustrate that the manual entry parameters may differ from those shown in FIG. 6. Another difference in the display 900 is that an approve button 940 is provided for approving these parameters for submission to the EMR. Upon selection of this button, data shown can be sent to the EMR database (see, for example, FIG. 17).

Figure 9B:
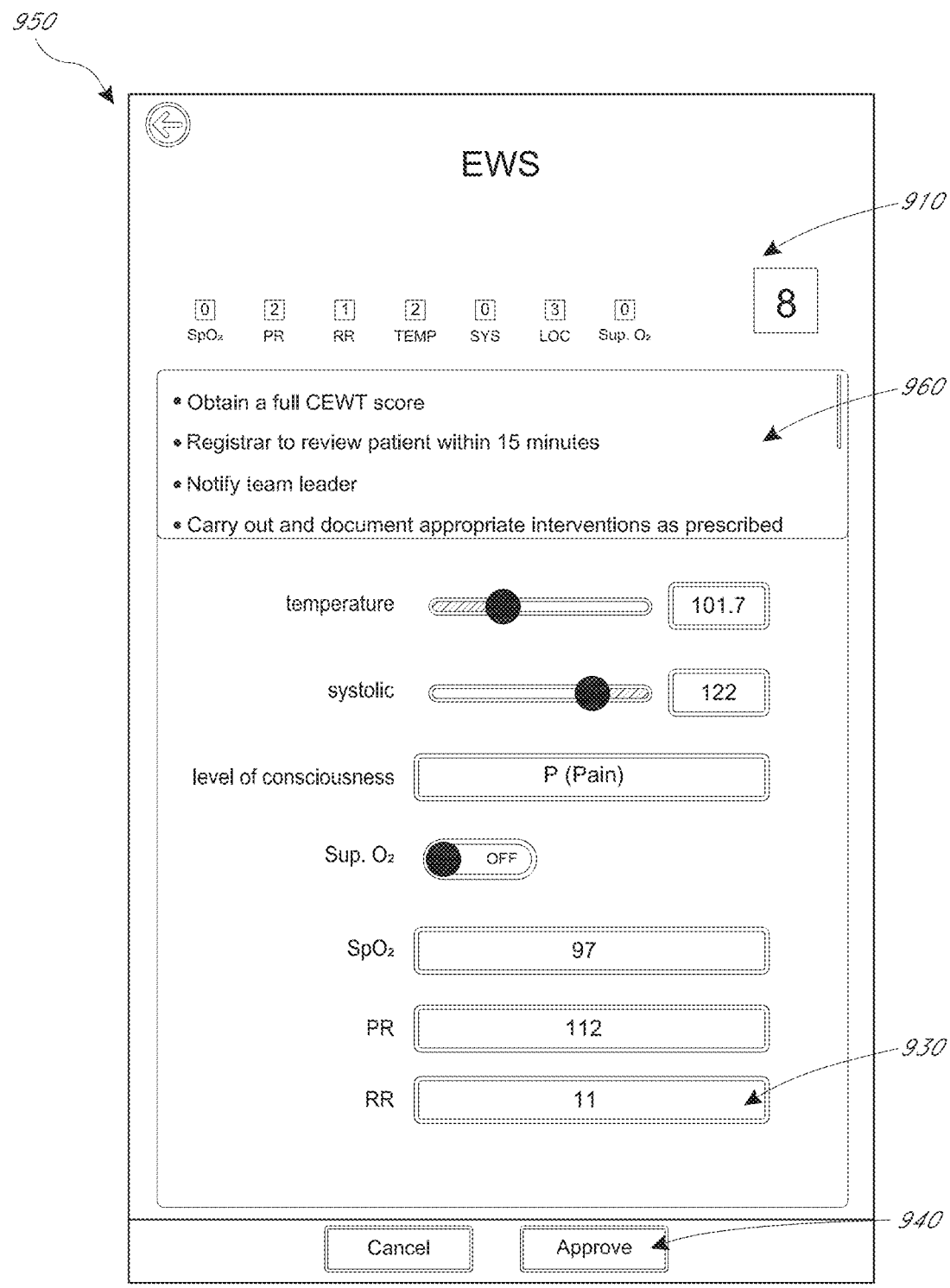

FIG. 9B shows essentially the same interface of FIG. 9A, except this interface 950 includes an action list 960 that includes instructions. The text of these instructions may be based on a severity level of the EWS displayed or may instead be general instructions to the clinician. Either way, the instructions may be customized or defined by the hospital (for example, by administrative staff). The action list 960 can be displayed by selecting a button or performing some action (such as swiping) in the interface 900 of FIG. 9A.

Figure 10:
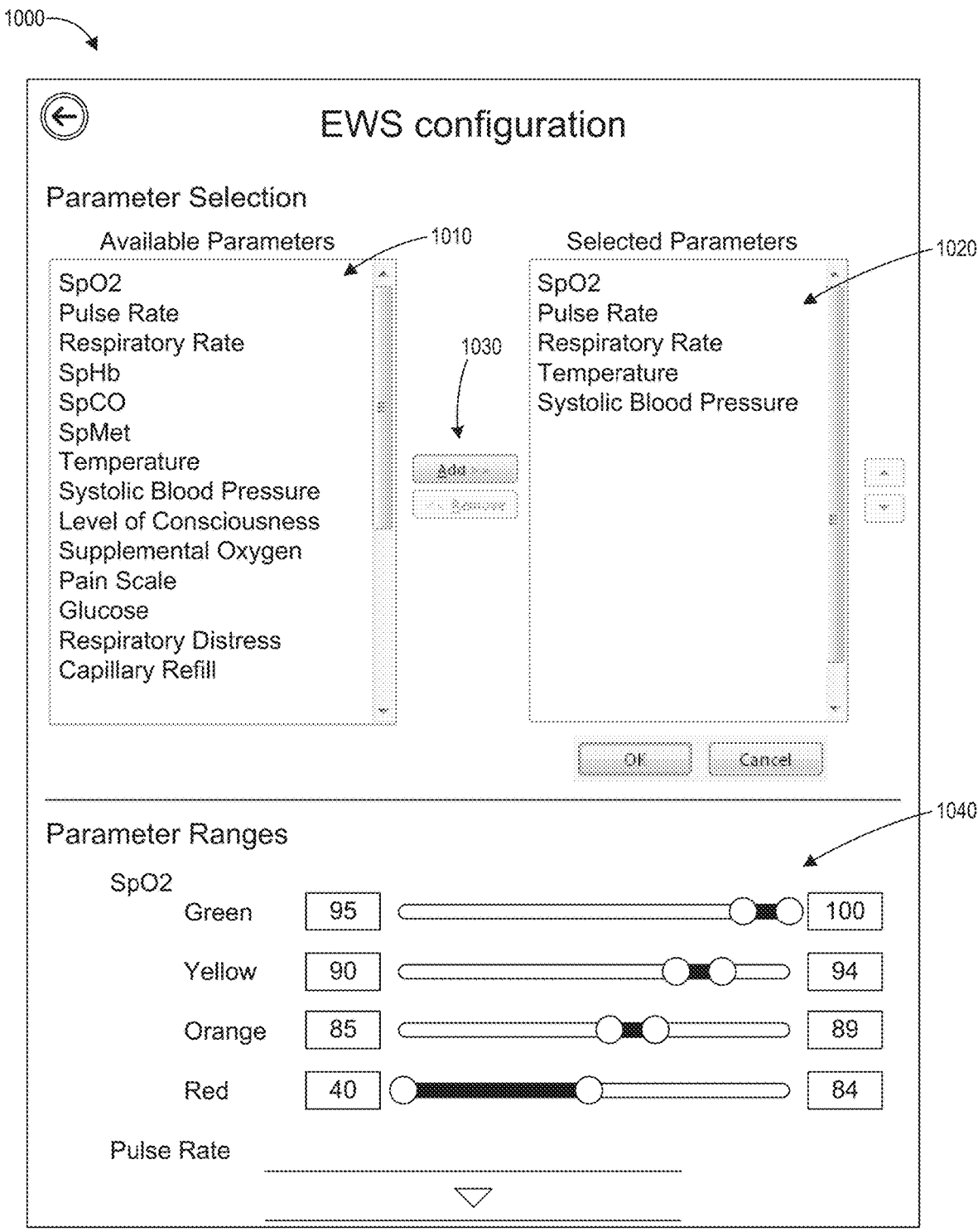
FIG. 10 depicts an example patient monitor display providing functionality for configuring early warning score parameters.

FIG. 10 depicts another example patient monitor display 1000 providing functionality for configuring EWS parameters. Like all the preceding displays, the display 1000 can be implemented in a patient monitor such as patient monitor 100. More generally, the display 1000 can be implemented on any computing device and need not be implemented on a patient monitor.

The patient monitor display 1000 can provide clinicians or hospital staff with the functionality to specify which parameters should be included in calculating an EWS. For example, the display 1000 can enable selecting which parameters should be used to compute contributor scores. Further, the display 1000 can enable a user to specify what ranges of those parameters result in certain contributor scores.

The display 1000 is divided into two example sections: parameter selection (for selecting parameters to be contributors to EWS) and parameter ranges (for specifying ranges corresponding to contributor scores). In the parameter selection section, a box 1010 lists available parameters which may be selected, for example, by selecting any of the available parameters (for example, via touch or other input) and then selecting an add button 1030 to add those parameters to a selected parameters box 1020. Parameters in the selected parameters box 1020 can be used to compute the EWS. Any number of parameters may be selected for addition to the box 1020 from the available parameters. Available parameters may also be defined by the hospital and may include parameters that are measured continuously using physiological sensors, parameters measured with spot checks using physiological sensors such as temperature or blood pressure, and/or parameters measured by observation of a clinician such as level of consciousness. The selected parameters in this example include SpO2, pulse rate, respiratory rate, temperature, and systolic blood pressure. With this selection made, a patient monitor can use each of these parameters to compute contributor scores and an EWS.

In the parameter ranges section of the display 1000, an example set of user interface controls 1040, which are sliders in this example, are shown for the $SpO_2$ parameter. The slider controls 1040 can enable a user, such as a clinician or hospital staff, to specify ranges for various severity levels corresponding to contributor scores. These ranges are shown having been selected corresponding to different severity levels: green, yellow, orange and red. These levels may correspond to contributor scores 0, 1, 2 and 3 discussed above. The number of ranges and the actual colors or scores may vary. Some parameters do not lend themselves directly to ranges but rather have a series of values that could be mapped one-to-one to contributor scores by a user using the display 1000. For example, level of consciousness may have single values that users can select from the display to correspond to different contributor score severity values.

Further, although not shown, the display 1000 could be adapted to provide functionality for a user to specify weights to apply to contributor scores. The weights can reflect the relative importance of contributor scores and may be used to combine the contributor scores into a single EWS using a weighted combination. Conceptually, a default weight of 1 can be effectively applied to each contributor score such that adding each contributor score results in the EWS. However, it could be desired to create a normalized scale for EWSs such as 0 to 1, 1 to 10, 0 to 100, or some other range. The parameters contributing to the EWS could be weighted to produce a normalized score. If additional parameters are added, the weights may be automatically adjusted by the patient monitor to preserve normalization.

The weightings could be selected by users (for example, clinicians or staff) to emphasize which parameters reflect a greater indication of patient health. For instance, vital signs may be prioritized above non-vital signs as being more indicative of the patient's health status. But any number of parameters may be weighted higher than others to meet a hospital's needs and goals for measuring patients' health. Further, weights and ranges may be set differently for different segments of the patient population. For example, different weights may be selected based on age (such as adult versus neonate), gender, and based on different co-morbidities or diseases. A patient who has a particular disease may have a different set of ranges or weights applied to that patient, which may be defined in a user interface such as the display 1000.

Figure 11:
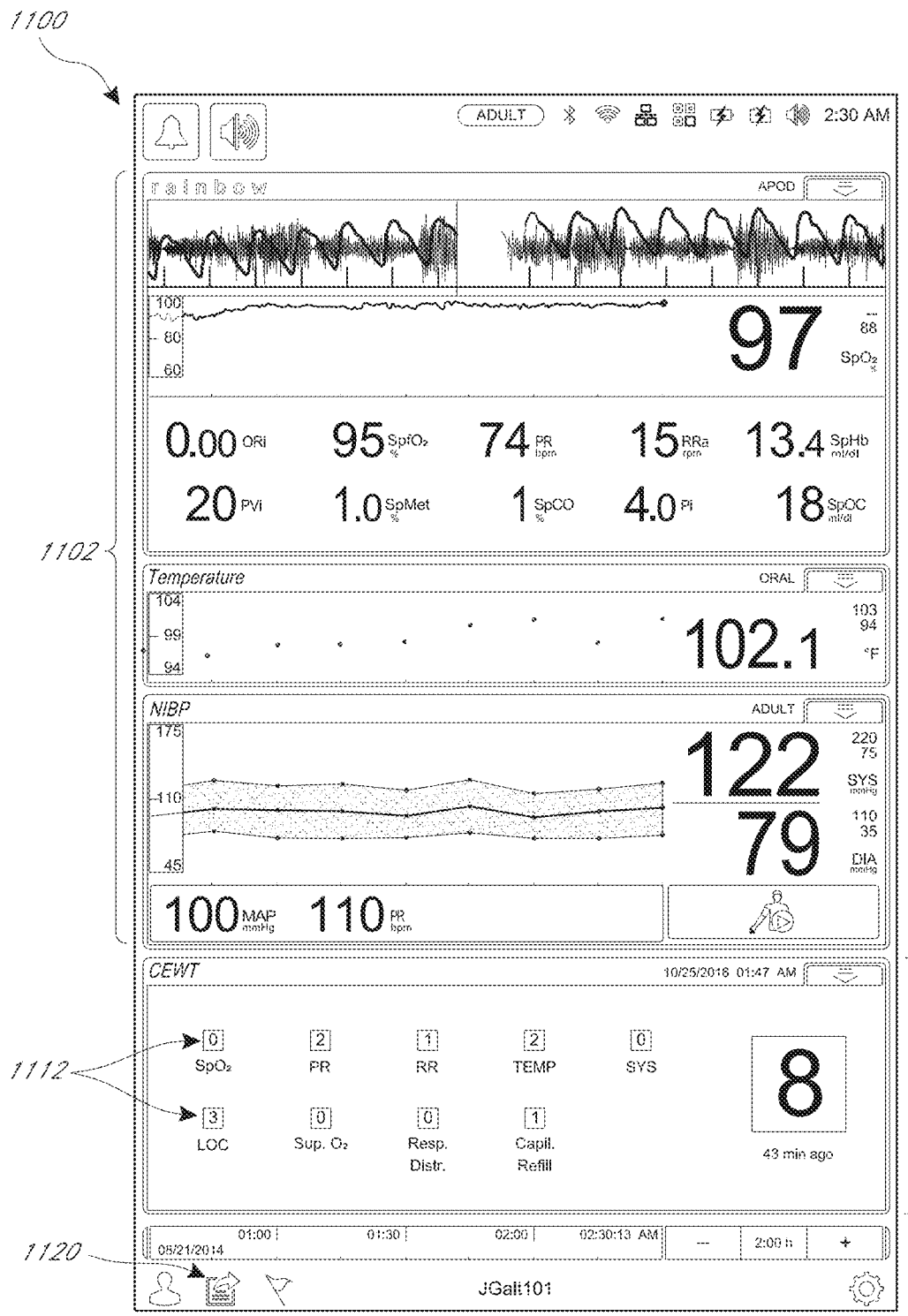
FIG. 11 depicts another example patient monitor display including another example early warning score channel or group.

FIG. 11 depicts another example patient monitor display 1100 including an example EWS region, channel, or group 1110 that differs from the previous examples discussed above. Like the other displays, such as display 200 in FIG. 2, the display 1100 depicts numerous physiological parameter values in a first region 1102 and depicts EWSs in a second region 1110. The difference here with FIG. 2 is that the EWSs in the region 1110 includes two rows 1112 of contributor scores. Like the display 200, the contributor scores shown may be represented vertically in multiple columns instead of horizontally in multiple rows.

Turning to FIG. 12, another display 1200 is shown that may be accessed by selecting the EMR push button 1120 of FIG. 11. The display 1200 is also similar to the displays 600 and 900 discussed above with respect to FIGS. 6 and 9A. The display 1200 includes two regions, 1210 and 1220, which can correspond to the regions 610, 910 and 620 and 920 (respectively). The region 1210 can represent contributor scores and an EWS. The region 1220 includes dropdown boxes for manual input of various parameters.

The new regions 1230 and 1240 can provide instructions for performing a spot check of different parameters using separate sensors—temperature and noninvasive blood pressure (NIBP) in this example. Following the instructions in those regions, measurements may be taken. Then, a display such as in FIG. 13 (the display 1300) may be shown, which can indicate that two measurements are in the process of being taken in the regions 1230 and 1240. In addition, the regions 1210 and 1220 in the display 1300 include contributor scores and an EWS that have been populated.

Figure 14:
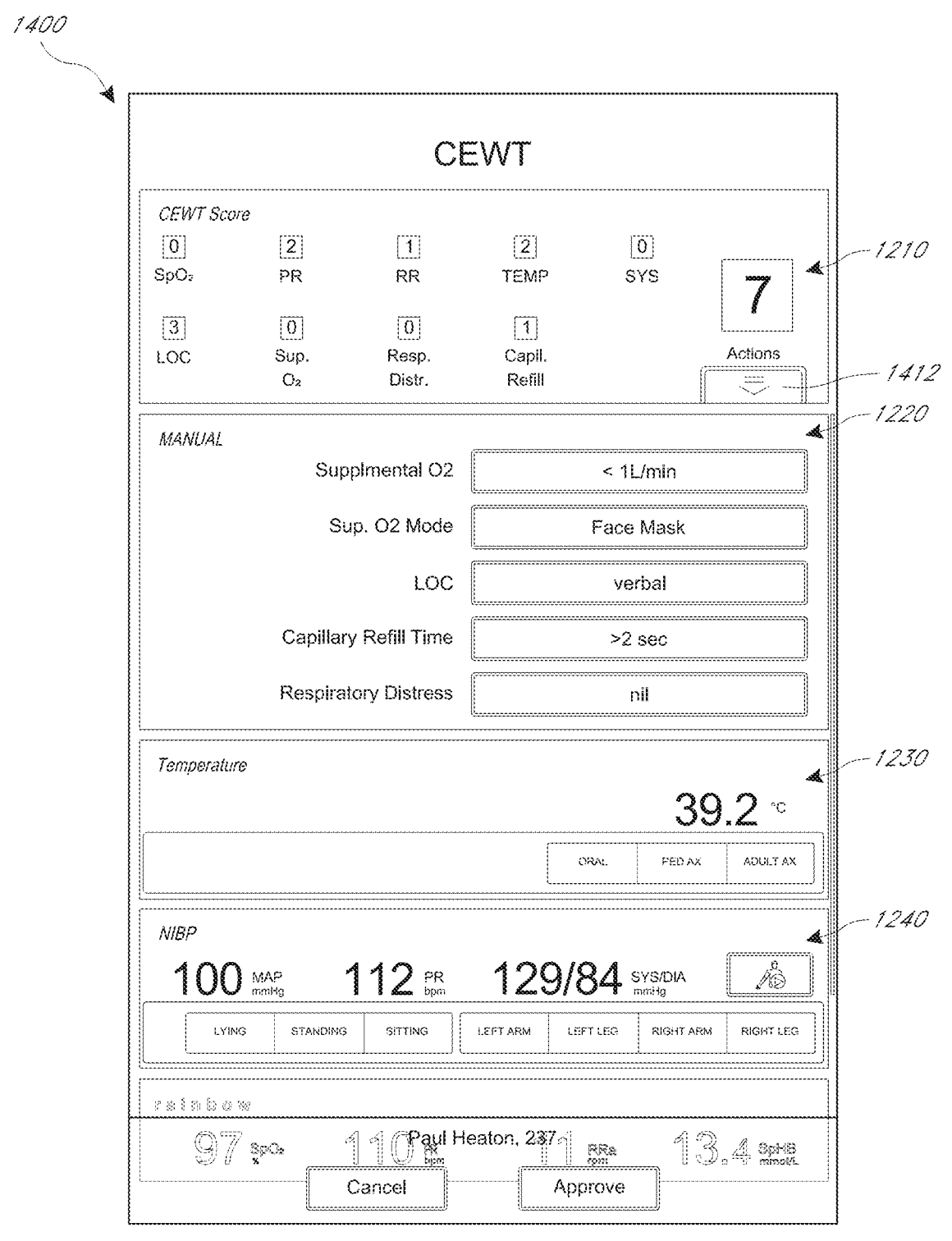

Turning to FIG. 14, another example patient monitor display 1400 is shown that depicts the regions 1230 and 1240 now with populated measurements that have been obtained by the temperature and NIBP sensors. The blood pressure measurements in this example include a mean arterial pressure (MAP), pulse rate derived from the blood pressure, and systolic and diastolic blood pressure measurements. Any of these measurements may be used to represent blood pressure measurements used to calculate the contributor score for blood pressure. Further, the pulse rate measurement derived from the blood pressure sensor can be used in place in, or in combination with, the pulse rate derived from another sensor (such as an optical or ECG sensor) when calculating a contributor score for pulse rate.

The display 1400 also includes a user interface control 1412 that may be selected (for example, by swiping) to display an action list as shown in FIG. 15, which depicts a similar display 1500 as shown in FIG. 14, except that an action list 1560 is shown. The action list 1560 may have the same functionality as the action list described above with respect to FIG. 9B, and the user interface control 1562 can be selected (for example, by swiping) to allow a user to dismiss the action list.

Turning to FIG. 16, another example patient monitor display 1600 is shown that is nearly identical to a patient display 1400 of FIG. 14, except that one of the contributor scores 1602 has an emergency value represented with the letter E. This contributor score can correspond to the level of consciousness parameter. As entered in the manual region 1220, the level of consciousness value in this example is "pain," which in this example is an emergency value. The emergency value essentially exceeds the highest contributor score numerical value that is typically used. An emergency score for any one contributor score can cause the patient monitor to assign an emergency value to the EWS, as noted in box 1610. In some implementations, an emergency score for one contributor score may not override the EWS but is merely shown separately from the EWS, which can be calculated as usual.

Example Hospital Environment

Figure 17:
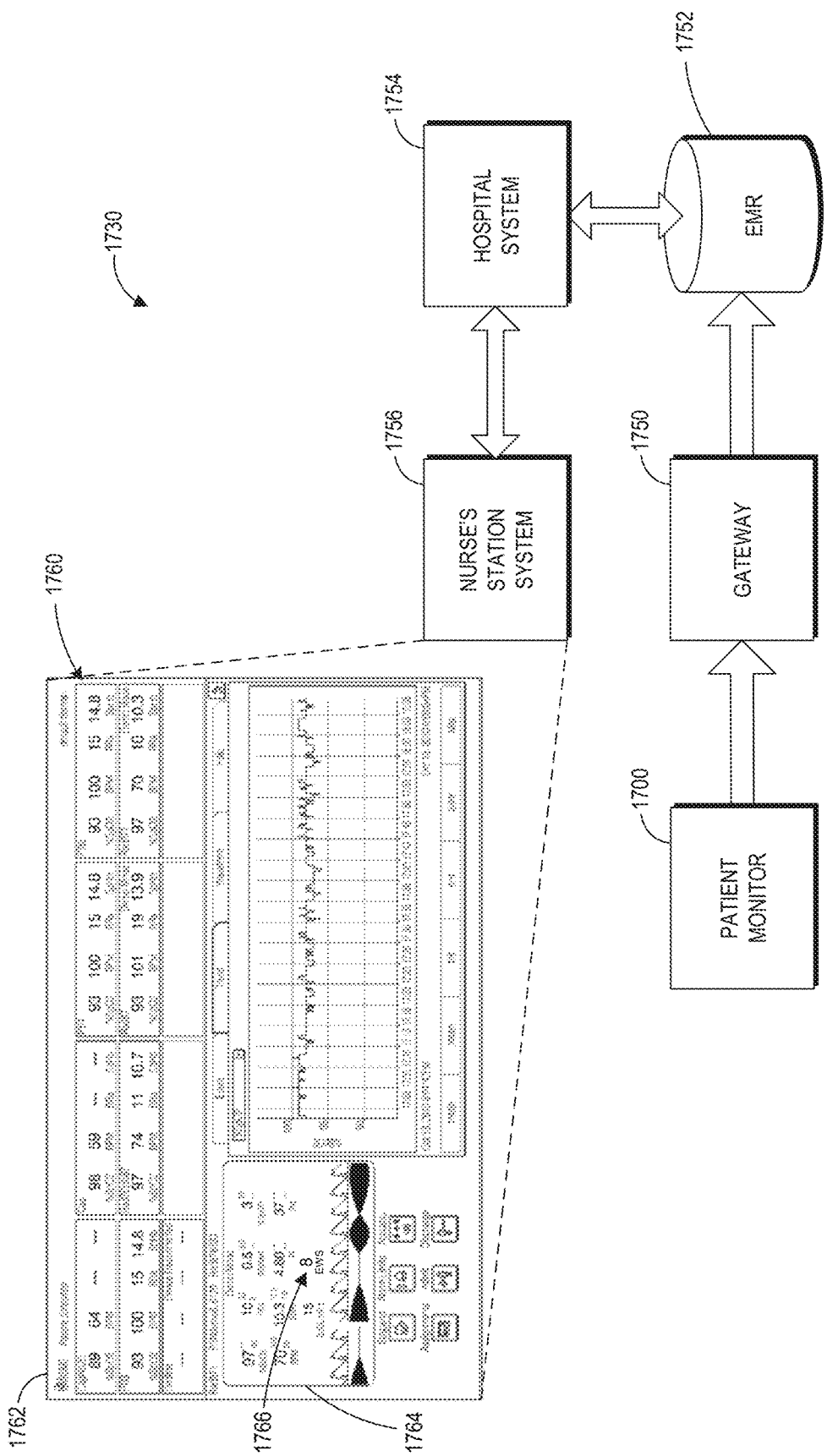
FIG. 17 depicts an example system for communicating early warning score data to an electronic medical record database and to a nurse's station system.

FIG. 17 depicts an example environment 1730 for communicating EWS data to an electronic medical record database and to a nurse's station system. The example environment 1730 of FIG. 17 includes a patient monitor 1700 in communication with a gateway 1750, which can be in communication with an EMR 1752. The EMR 1752 is in communication with a hospital system 1754, which is in communication with a nurse's station system 1756.

The patient monitor 1700 is an example representation of any of the patient monitors discussed herein, such as the patient monitor 100. The patient monitor 1700 can be used to implement any of the features described herein, just like the patient monitor 100.

The gateway 1750 may be a server or appliance that collects data from multiple patient monitors and forwards that data to the EMR 1752. The EMR 1752 is an example electronic medical record database that stores patient medical data. The hospital system 1754 may be a server or set of servers in communication with the nurse's station system 1756 as well as in communication with other nurse's station systems throughout the hospital. The hospital system 1754 may manage electronic scheduling for clinicians as well as paging or other features. The gateway 1750 and the hospital system 1754 may be part of the same system. The gateway 1750 and/or the hospital system 1754 may be examples of the MMS 160 described above with respect to FIG. 1A. Although not shown, the various devices and systems shown can communicate across a network, such as a hospital network, the Internet, or combinations of the same.

The patient monitor 1700 can be in communication with one or more non-invasive sensors coupled to a patient (not shown). The patient monitor 1700 can be used for continuous or spot check monitoring of one or more physiological parameters. The patient monitor 1700 may include hardware and software that processes physiological signals received from the one or more non-invasive sensors to compute contributor scores and early warning scores, for example, based on the process 300.

The patient monitor 1700 can communicate EWS data (including, for example, both contributor scores and an EWS) to the gateway 1750 across the network, which can format the data for storage in the EMR 1752 (for example, according to an HL7 data specification). The hospital system 1754 can access the EWS data and can forward this data to the nurse's station system 1756, so that clinicians not close to the patient monitor can be informed. The patient monitor 1700 may also communicate the EWS data directly to clinician devices (not shown, such as mobile phones, tablets, laptops, or desktops) over the network.

The nurse's station system 1756 can receive the EWS data from the hospital system 1754 and output the data on a display 1762. The display 1762 can include data 1760 corresponding to a plurality of patients as well as detailed data 1764 corresponding to a specific patient. The EWS data can be shown as data 1766 in the detailed data 1766 and may include just the EWS score (this example) or the entire set of EWS data (including contributor scores), which may be formatted as shown in FIG. 2B or in some other manner as discussed above.

Example Hardware Description of a Patient Device

Figure 18:
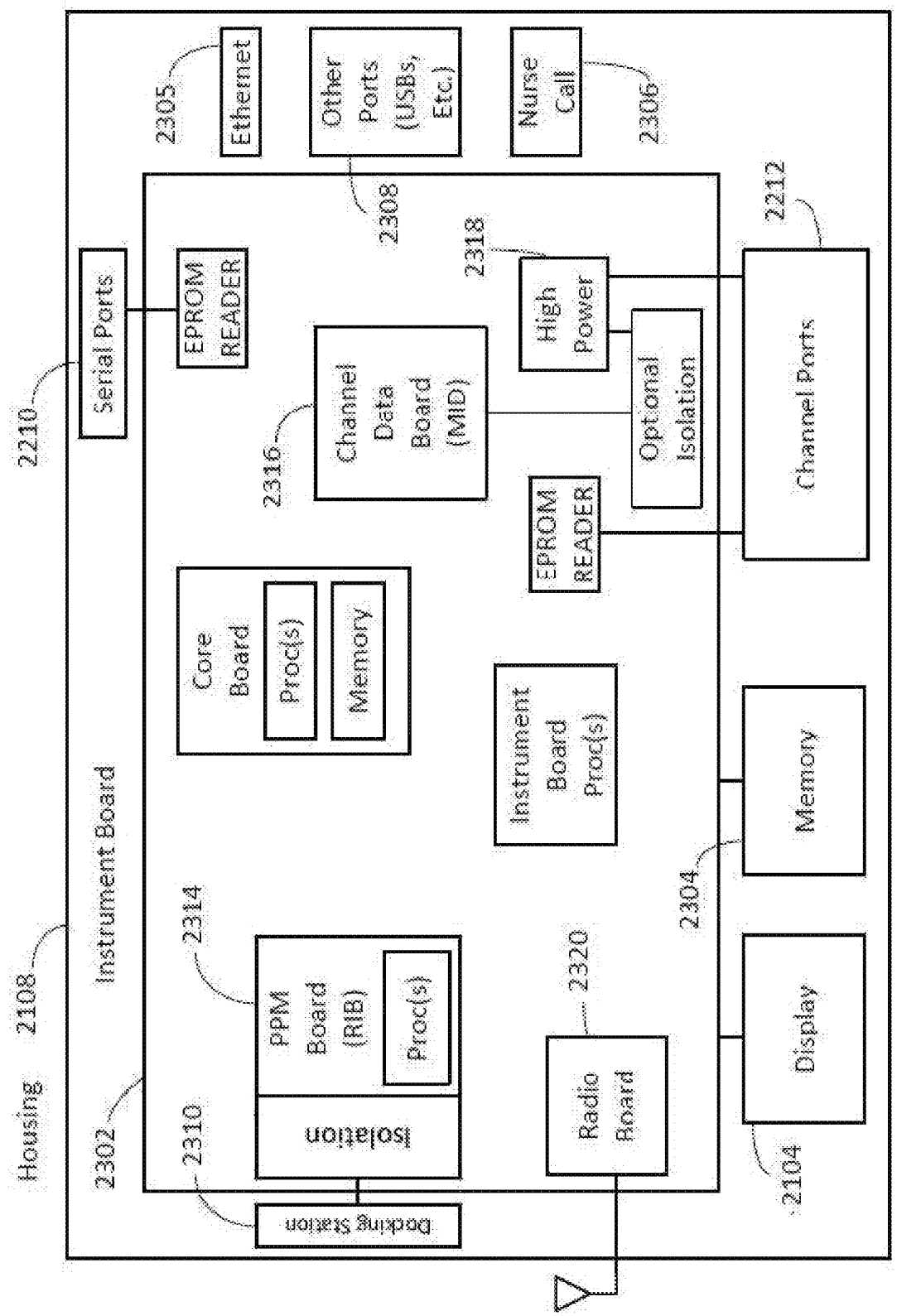
FIG. 18 depicts an example schematic block diagram corresponding to the patient monitor of FIG. 1.

FIG. 18 illustrates a simplified example hardware block diagram of the patient device 100 of FIG. 1. As shown in FIG. 18, the housing 2108 of the patient device 100 can position and/or encompass an instrument board 2302 (which may be a circuit board), the display 2104 (corresponding to the display 104), memory 2304, and the various communication connections, including serial ports 2210, channel ports 2212, Ethernet ports 2305, a nurse call port 2306, other communication ports 2308 including USB ports or the like, and a docking station interface 2310. Various of these ports can communicate with one or more physiological sensors or other medical devices and are described in more detail in U.S. Pat. No. 9,436,645, titled "Medical Monitoring Hub," filed Oct. 12, 2012, the disclosure of which is hereby incorporated by reference in its entirety. The instrument board 2302 comprises one or more substrates including communication interconnects, wiring, ports and the like to enable the communications and functions described herein, including inter-board communications.

An example core board 2312 includes the main parameter, signal, and other processor(s) and memory, a portable monitor board ("RIB") 2314 includes patient electrical isolation for the monitor 2102 and one or more processors, a channel board ("MID") 2316 controls the communication with the channel ports 2212 including optional patient electrical isolation and power supply 2318, and a radio board 2320 includes components configured for wireless communications. Additionally, the instrument board 2302 may include one or more processors and controllers, busses, all manner of communication connectivity and electronics, memory, memory readers including EPROM readers, and other electronics recognizable to an artisan from the disclosure herein. Each board comprises substrates for positioning and support, interconnect for communications, electronic components including controllers, logic devices, hardware/software combinations and the like to accomplish the tasks designated above and others.

The instrument board 2302 may comprise a large number of electronic components organized in a large number of ways. Using different boards such as those disclosed above may provide organization and compartmentalization to the complex system. Of course, using different boards for different functions is optional.

Detailed Spot-Check Measurement Examples

Generally speaking, there can be at least two ways to obtain physiological parameter measurements. These include continuous monitoring and spot check measuring. A third approach is a hybrid of these two where a patient is monitored continuously for a short period of time to obtain a snapshot of physiological information. Continuous monitoring can involve taking measurements of a patient continuously or at least approximately continuously over an extended period of time. This type of monitoring is commonly done on hospital floors, in emergency rooms, and in other settings where a patient's vital signs or other physiological parameters need to be observed over a period of time. In continuous monitoring, measured values are frequently compared with predetermined criteria to identify any changes in the measured values that might warrant clinician attention. It is common, for instance, in continuous monitoring to alarm if a patient's measurements have exceeded bounds of safety such that attention from a clinician (for example doctor or a nurse) may be warranted.

Spot check measurements, on the other hand, are typically performed as a single measurement at one point in time, instead of several measurements over a period of time as in continuous monitoring. A clinician may perform a spot check measurement by placing a sensor on a patient (or by manually observing some characteristic of the patient) and recording a measured physiological parameter value on the patient's chart (paper or electronic). Like continuous measurements, spot check measurements (sometimes referred to herein simply as "spot checks") may be performed in a hospital or in any other setting.

Clinicians may input spot check measurements into a paper chart or into a computing device, such as a computer on wheels (COW), tablet, or other mobile device. One problem with manually inputting spot check measurements in this manner is that it can take a clinician's focus away from the patient. While the clinician is inputting patient data, the clinician typically is not directly observing the patient and is instead focused on manual entry. Patients may perceive clinicians as ignoring them or less attentive to them while clinicians input parameters. Further, manual entry of spot check values can be cumbersome and time intensive for clinicians. Thus, both patients and clinicians could benefit from reducing or eliminating manual entry of spot checks. Some benefits of avoiding or reducing manual charting can include better patient care due to more attentive clinicians, more time for clinicians to spend with patients, and less time on mundane tasks and fewer clerical errors.

Example systems and methods for performing spot check measurements described herein can reduce or alleviate some or all of the problems with existing spot check measurement approaches. These spot check measurements may be performed anywhere, including in a hospital, home, or other care setting. In general, the spot check measurements can involve applying a sensor or sensors to a patient, obtaining measurements, automatically sending the measurements to the patient's electronic chart (for example, in an EMR database), and/or optionally outputting some or all measurements audibly. Spot check measurements can be performed automatically in response to a sensor being removed or upon a button press—which can free clinicians to focus on patients. Automatically saving measurements to patients' charts instead of entering measurements manually can permit clinicians to focus on patients' needs. Further, audibly outputting parameter measurements can free clinicians to focus on patients rather than looking at measurements on a display.

FIGS. 19 through 34 depict example user interfaces that can implement the spot check features described above (further, additional examples are discussed below with respect to subsequent figures). These useful interfaces are capable of being displayed on any computing device, for example, the patient device 100 described above with respect to FIG. 1 or any of the other devices described herein. Further, each of the user interfaces shown in FIGS. 19 through 34 may be implemented with any of the user interface features described above. Thus, although specific example user interfaces are shown, having specific user interface controls, different user interface controls, designs, and features may be used to implement the spot check techniques described herein.

Figure 19:
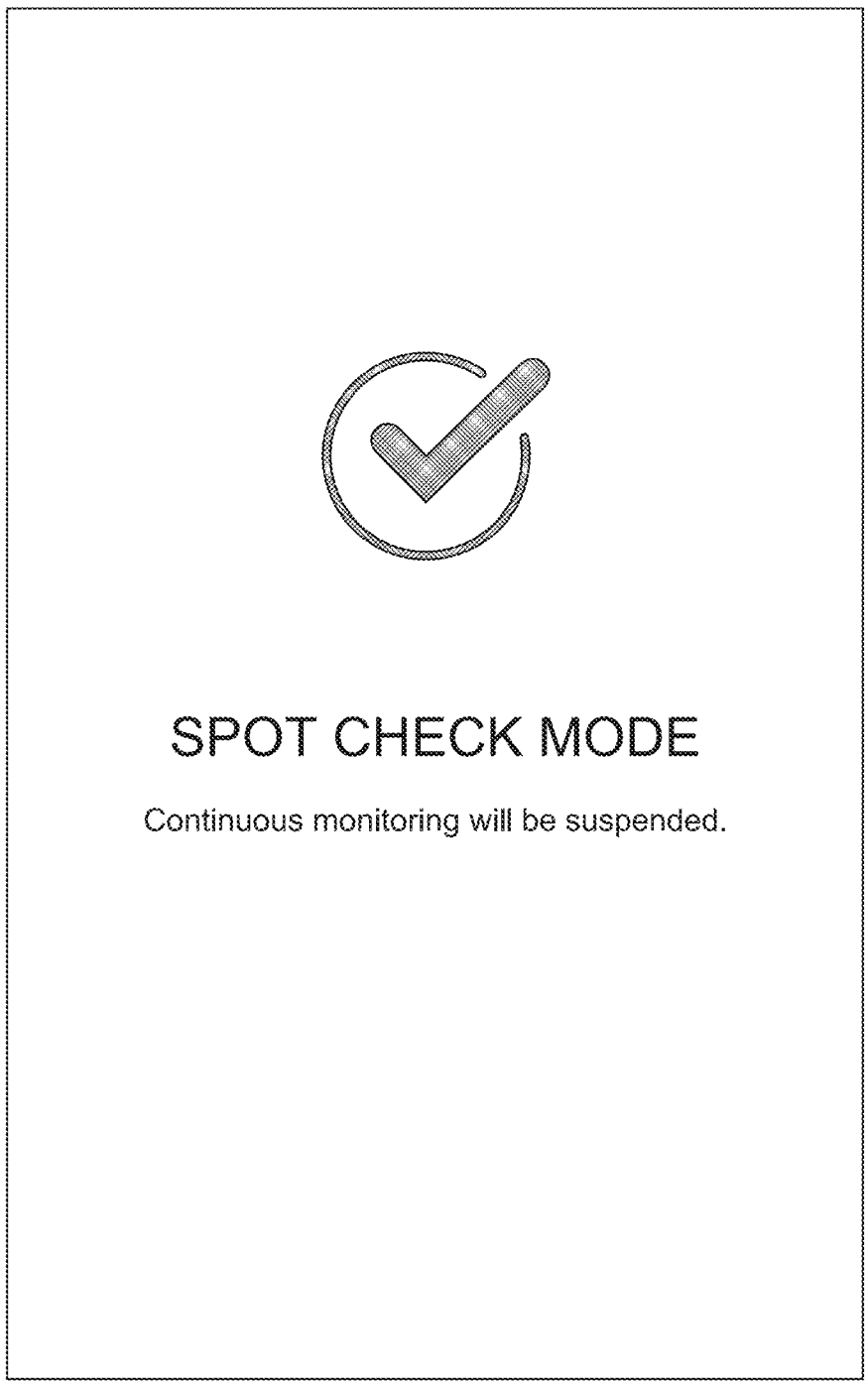
FIGS. 19-34 depict example spot check measurement user interfaces.

Referring specifically to FIG. 19, a user interface 1900 is shown, which is an example splash screen that may be displayed on reboot or boot up of the patient device 100. The user interface 1900 indicates that the device is in spot check mode and that continuous monitoring will be suspended. This splash screen 1900 may be displayed when the patient monitor 100 is selected to be in spot check mode instead of continuous monitoring mode. The user interface 1900 is optional.

A menu option (not shown) can be accessible from any of the displays described above, which can be selected to cause the patient device 100 to reboot into a locked spot check mode. It can be advantageous to have a device dedicated to spot check mode or otherwise locked into spot check mode so that it may be used for this purpose and not confused with devices that are used for continuous monitoring. A spot-check dedicated monitor may be put on a wheeled cart or may be carried from room to room in a hospital or other clinical setting, where it can be used to measure spot check parameters of several different patients. Thus, unlike continuous mode where a monitor is assigned to a single patient for an extended period of time, a monitor or patient device in spot-check mode may be used with many patients over a short period of time.

The spot check mode may be changed back to continuous mode by a clinician selecting another menu option (not shown). If a clinician were to select continuous mode, the patient device 100 may be rebooted into that continuous mode.

Figure 20:
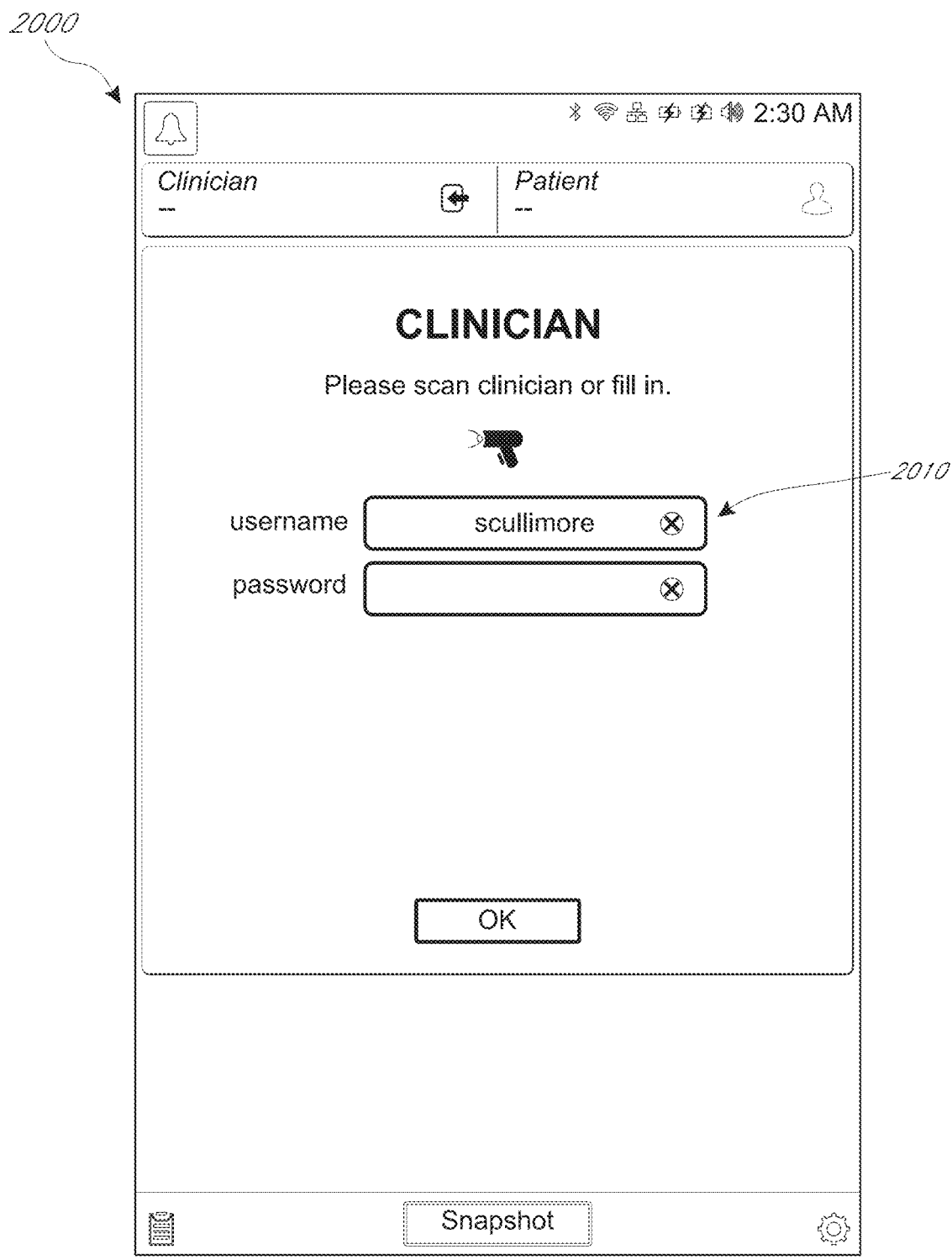

Turning to FIG. 20, another example user interface 2000 is shown. The user interface 2000 is an example of a clinician login screen and depicts an indication or a message for a clinician to scan or type the clinician's username and password in fields 2010. The clinician can scan his or her employee badge. By scanning the badge, the clinician's username may be automatically populated in the user interface 2000. Scanning of the badge may be performed using an optical scanner, such as the scanning technology described in U.S. Pub. No. 2015/0106121, filed Oct. 10, 2014, titled "Alarm Notification System", the disclosure of which is hereby incorporated by reference in its entirety. Alternatively, the clinician's badge may include a wireless chip (such as a radiofrequency identification or RFID chip), which when in proximity to the patient device 100, can be read by the patient device 100 so as to automatically log in the clinician. Examples for performing this RFID-based login are described in greater detail in U.S. Pub. No. 2014/0135588, filed Sep. 19, 2013, titled "Medical Monitoring System", the disclosure of which is hereby incorporated by reference in its entirety.

Figure 21:
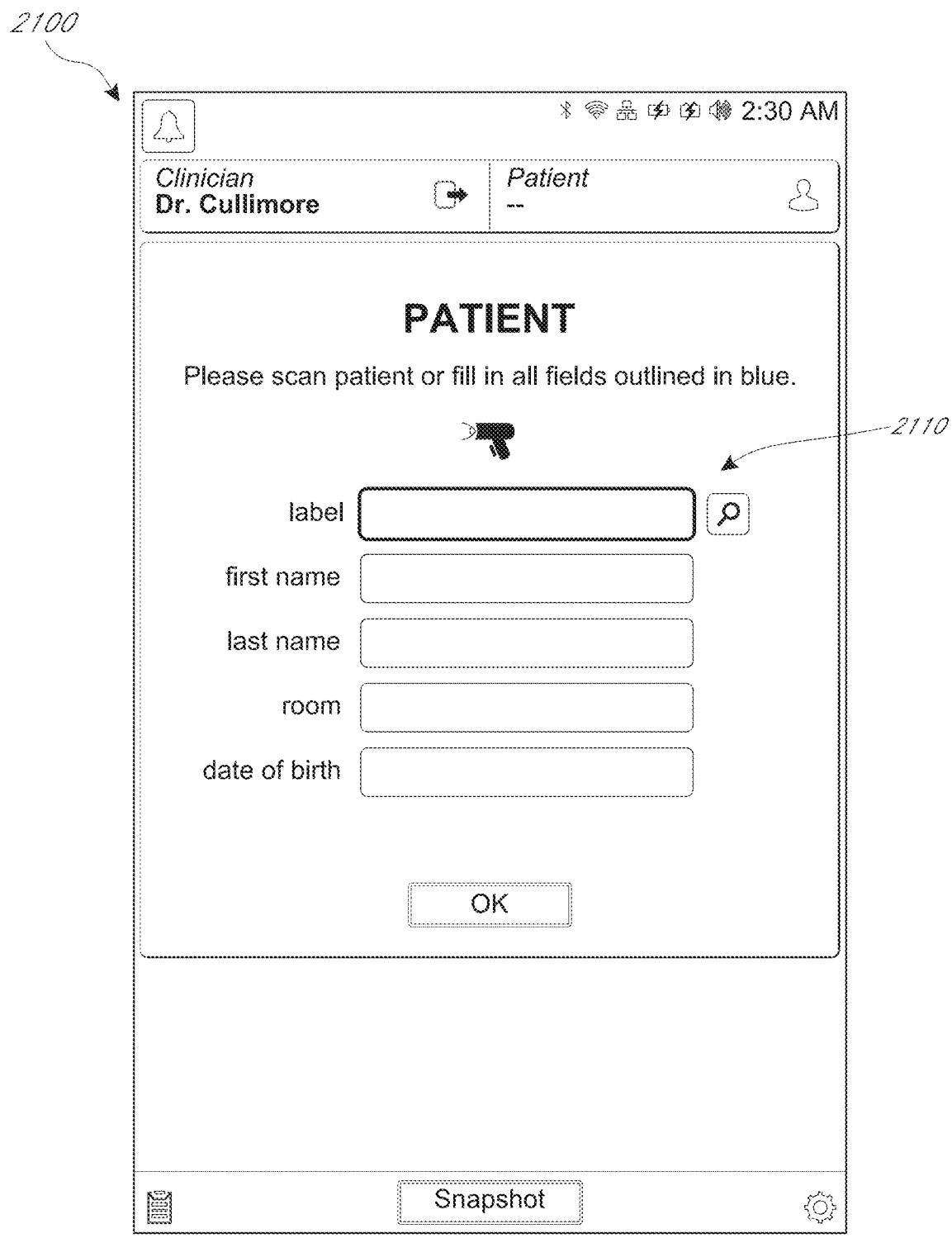
Figure 22:
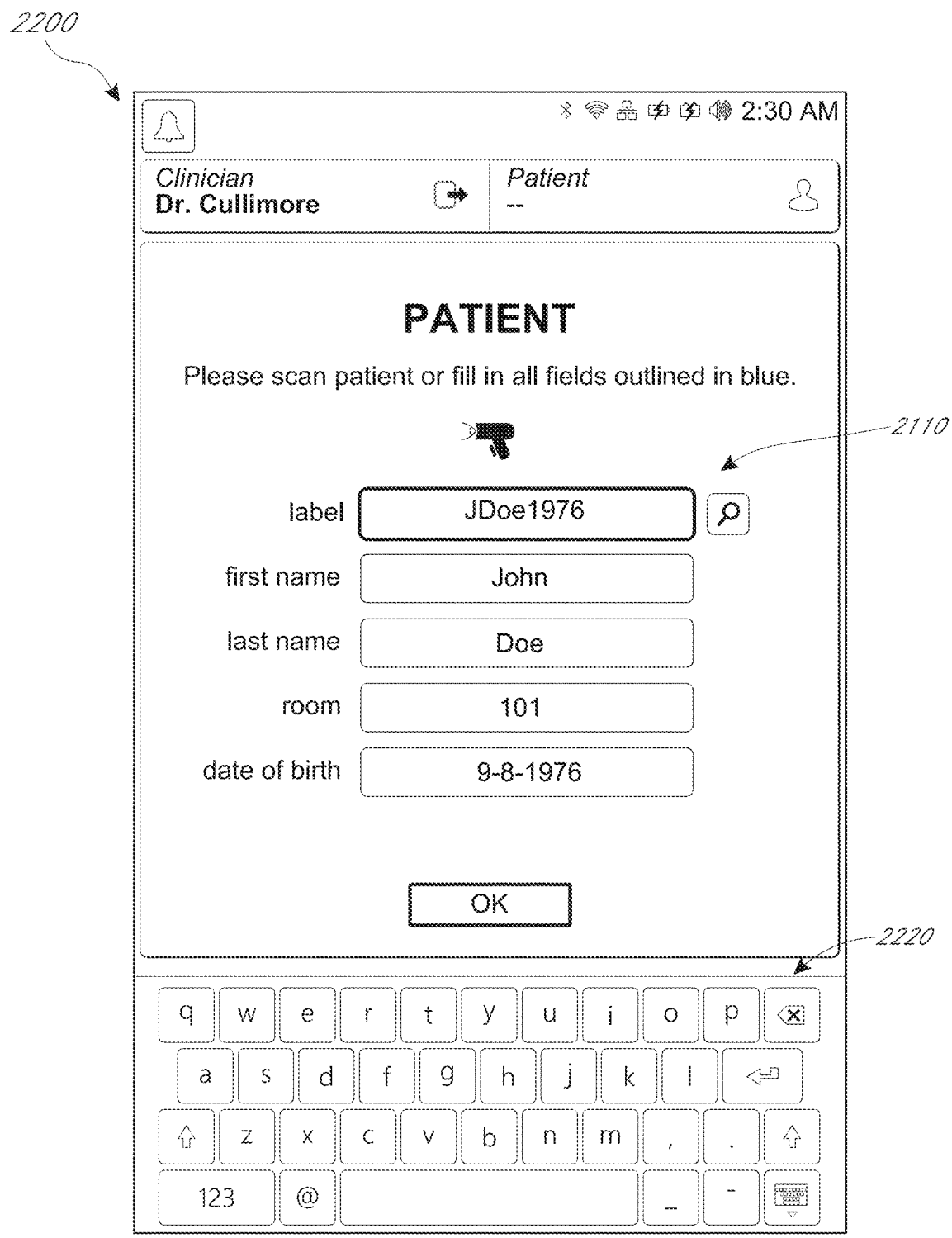

Turning to FIG. 21, another example user interface 2100 is shown. This user interface 2100 is an example patient login screen like the clinician login screen described above with respect to FIG. 20. The patient login screen 2100 provides fields 2110 to enter patient information. It also permits scanning of a patient bracelet to automatically populate those fields 2110, using, for example, the scanning technology described in U.S. Pub. No. 2015/0106121, referred to above, or the wireless technology described in U.S. Pub. No. 2014/0135588, referred to above. FIG. 22 depicts another example user interface 2200 that is identical to the user interface 2100 except that the fields 2110 are populated with patient information. A keyboard 2220 is shown, which is an example of a software (soft) keyboard that can be used to manually enter patient information.

Figure 23:
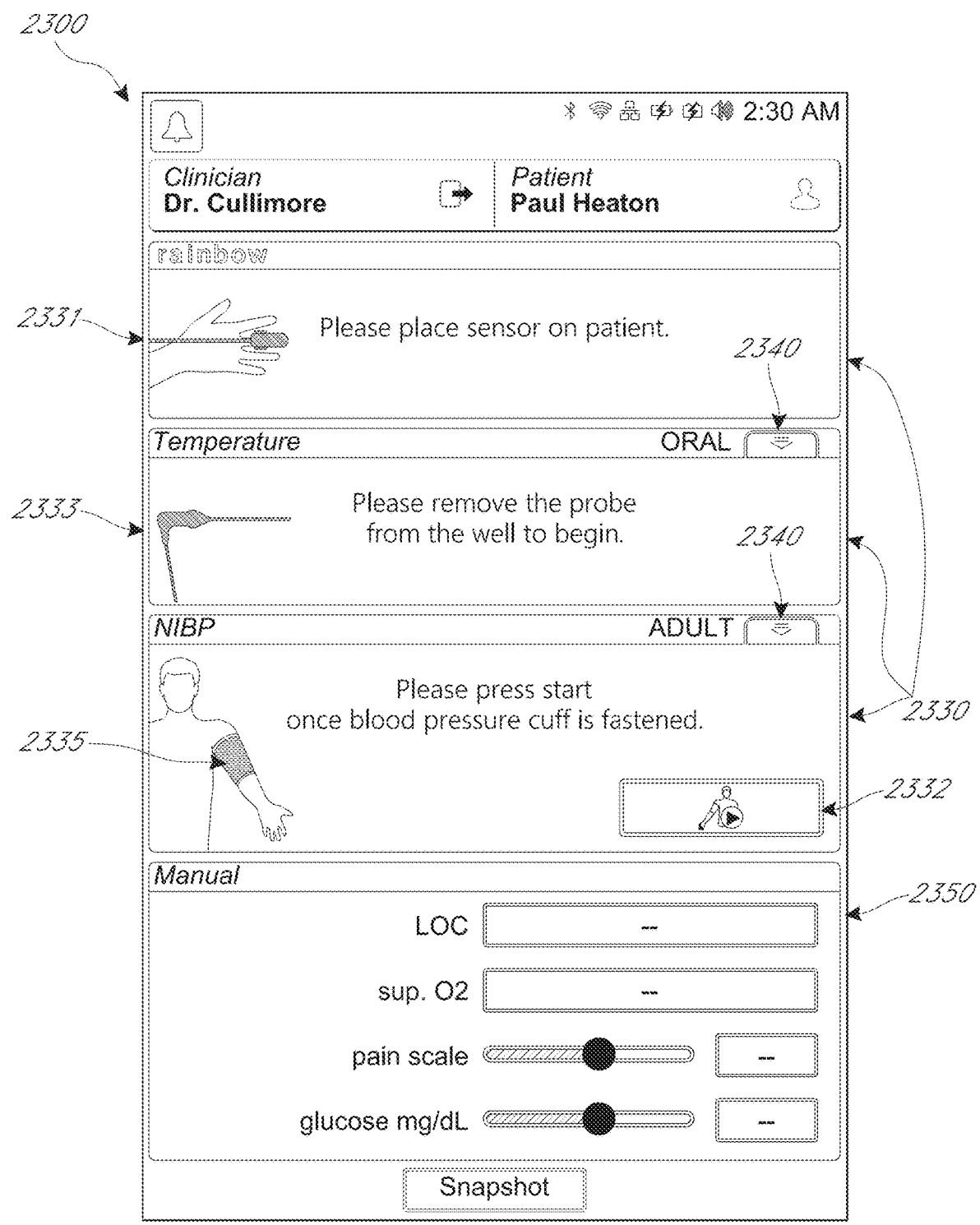

FIG. 23 depicts another example user interface 2300. The user interface 2300 is an example measurement initiation screen. The measurement initiation screen 2300 can provide instructions to the clinician for attaching sensors to patients and beginning measurements. These instructions are provided in areas 2330 of the display, which include instructions for application of an optical sensor 2331, application of a temperature sensor 2333, and an application of a blood pressure sensor 2335. The blood pressure sensor 2335 instructions are also accompanied with a button 2332 which, when pressed, can cause blood pressure cuff inflation to begin. Below the areas 2330 is a manual entry area 2350 that permits entry of some manual parameters, which can include parameters observed by a clinician without use of sensors (or optionally with the use of sensors). Some examples of such manual parameters are shown, which are described above, such as level of consciousness (LOC), supplemental oxygen (sup. $O_2$), pain scale, and glucose. Of course, these manual entry options may be omitted, and the types of parameters and measurements obtained may differ from those shown.

Figure 24:
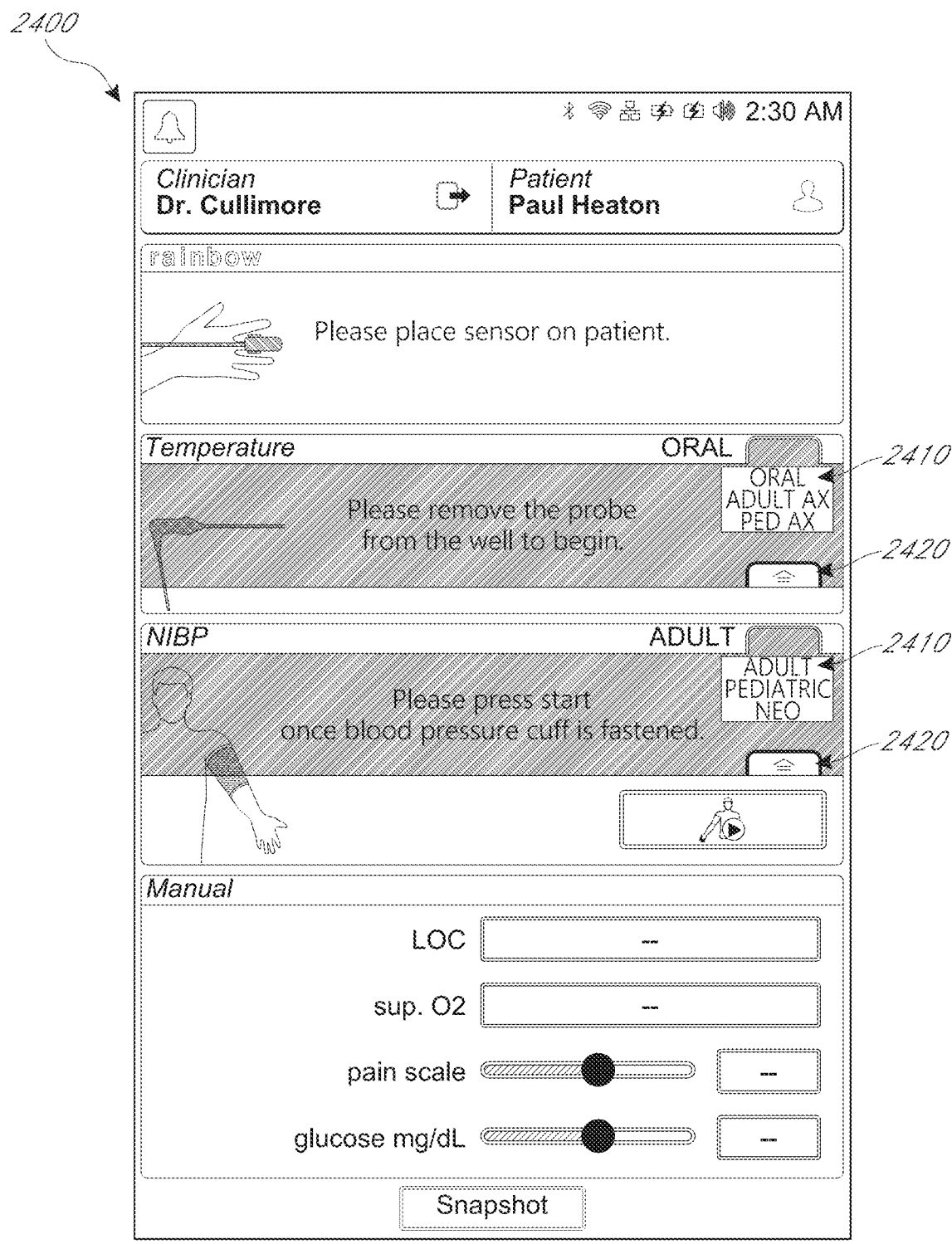

In addition, action menus 2340 may be selected if desired to cause action menus to be displayed. In FIG. 24, a nearly identical example user interface 2400 is shown as the user interface 2300 except that the action menus 2340 have been expanded to show options 2410 for selecting adult, pediatric, or neo (short for neonate) options for measurement. These different options 2410 may cause different measurement algorithms or the like to be performed for different age ranges of patients. User interface controls 2420 permit the action menus to be closed.

Figure 25:
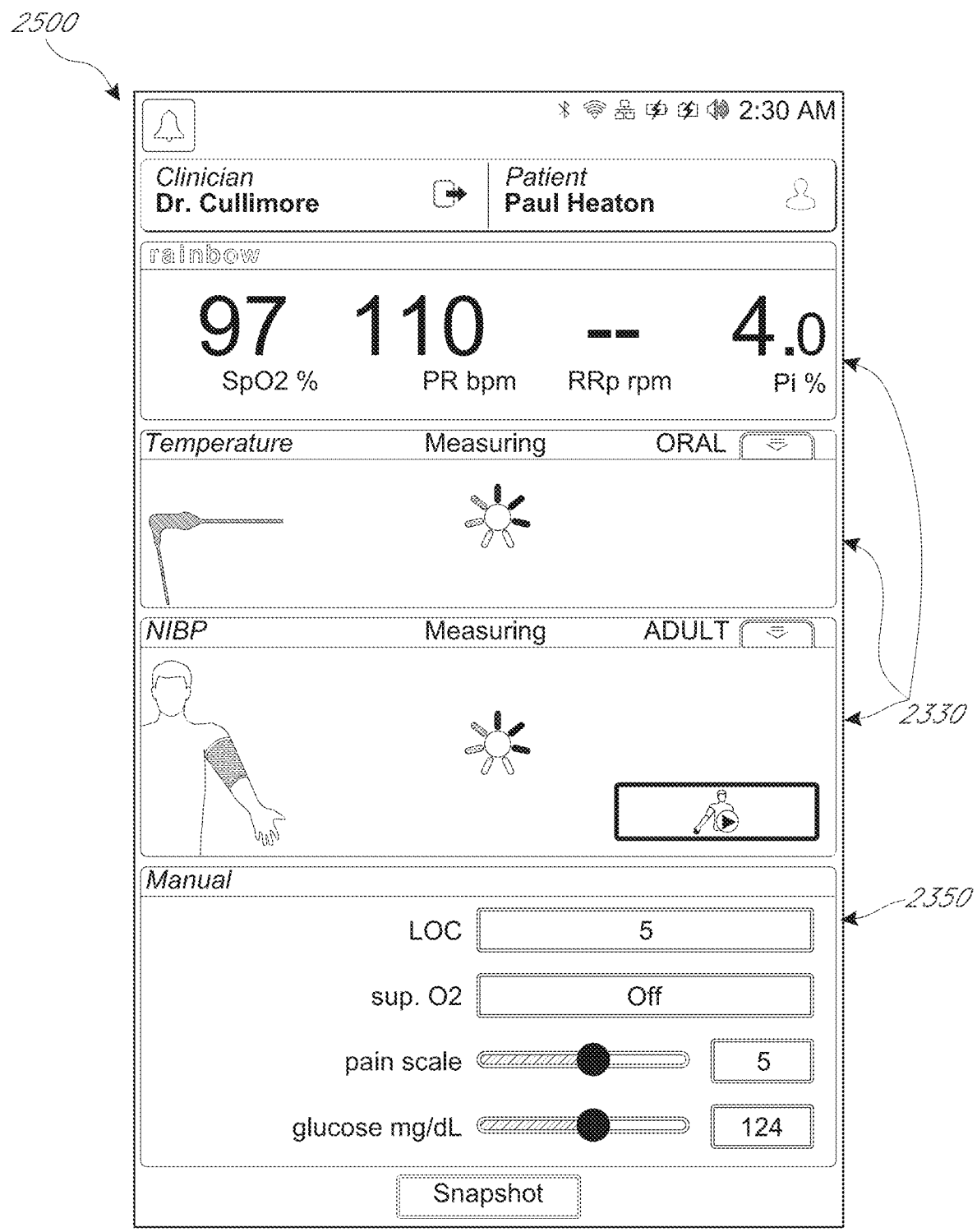

Turning to FIG. 25, another example user interface 2500 is shown, which is a continuation of the user interfaces 2300 and 2400. The user interface 2500 indicates that measurements are in process. The areas 2330 show different information depending on the type of sensor employed. For the optical sensor area 2330, measurements are displayed for at least some parameters including SpO$_2$, pulse rate, and perfusion index (PI). Although respiratory rate is also shown as an available measurement, it is not yet calculated in this example. This respiratory rate may be taken based on the photoplethysmograph (or photopleth, or simply pleth) obtained from the optical sensor. In contrast, the temperature and blood pressure measurements in the areas 2330 have not yet been completed and thus are shown as "measuring" in the depicted example user interface 2500. In the manual entry area 2350, each of the different parameters has been populated by a clinician.

Figure 26:
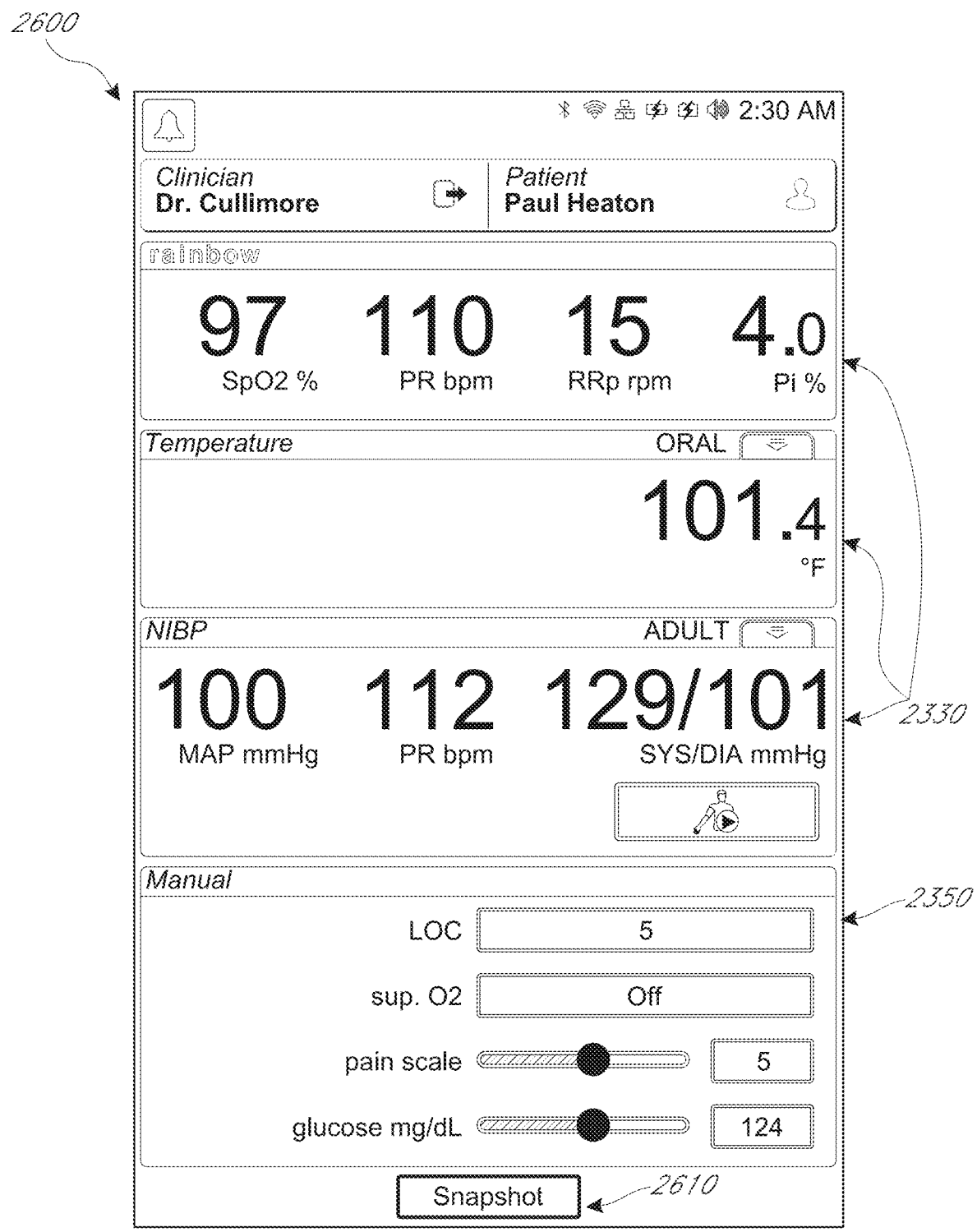

Turning to FIG. 26, another example user interface 2600 is shown that is a continuation of the interface 2500 and shows measurements for temperature and blood pressure populated in addition to the optical measurements discussed previously. Likewise, the respiratory rate based on the pleth measurement is now also populated.

With all these measurements populated, a snapshot may now be taken by selecting a snapshot button 2610 at the bottom of the screen. Selection of this button can cause the particular parameter values shown to be saved as snapshot parameters. Further, the optical parameters may also be frozen and stop measuring continuously once the snapshot button 2610 is selected or when the optical sensor is removed from the patient, as will be discussed in greater detail below.

Figure 27:
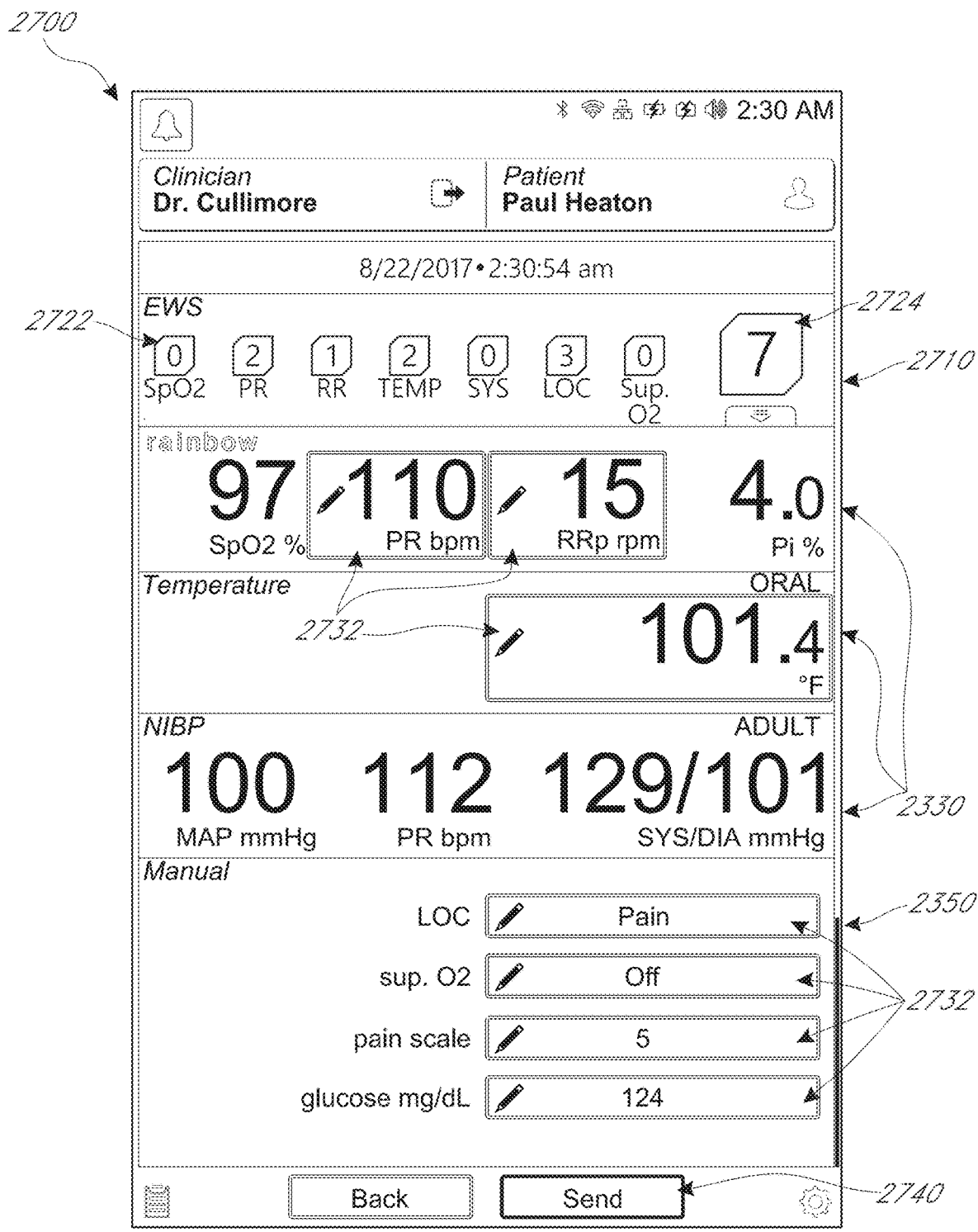
Figure 28:
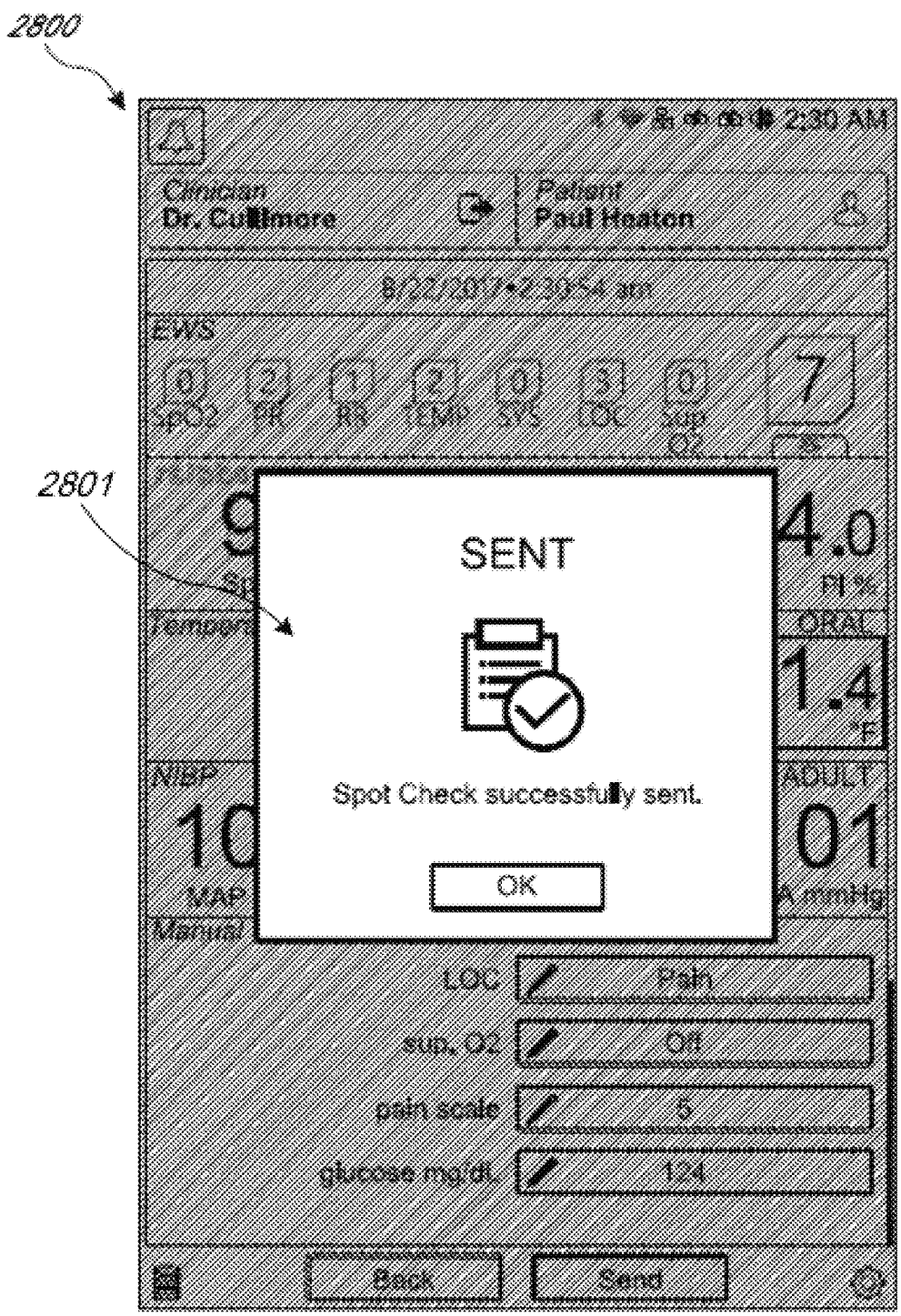

Turning to FIG. 27, another example user interface 2700 is shown. This user interface 2700 is an example snapshot screen, which shows the results of selecting the snapshot button 2610 in FIG. 26 or the result of removing the optical sensor. The snapshot screen includes measurements in the areas 2330 that are also shown in FIG. 26. In addition, another area 2710 is shown that presents an early warning score 2724 as well as individual contributor scores 2722 as described in greater detail above. Of note, the shapes around the contributor scores 2722 and the early warning score 2724—which differ from those in earlier figures—suggest an appearance of three-dimensional boxes. Of course, any kind of shapes or indicators may be used to indicate the severity of the contributor scores and early warning scores. The shapes can even be omitted in favor of coloring the contributor scores 2722 and or early warning score 2724 themselves according to severity level. A menu 2726 is also provided for depicting EWS actions as discussed above (see, for example, FIG. 15).

Some of the measurements in FIG. 27 are highlighted with buttons 2732 that may be selected to manually change the data. It may be desirable for a clinician to change a measured parameter if the clinician believes that the measured parameter does not accurately reflect a physiological parameter of the patient. The clinician may, for instance, decide to do an independent manual measurement. For example, the clinician may do a traditional pulse rate measurement at the patient's wrist or carotid artery and may determine to use that measurement instead of the measurement obtained from the optical sensor.

Figure 29:
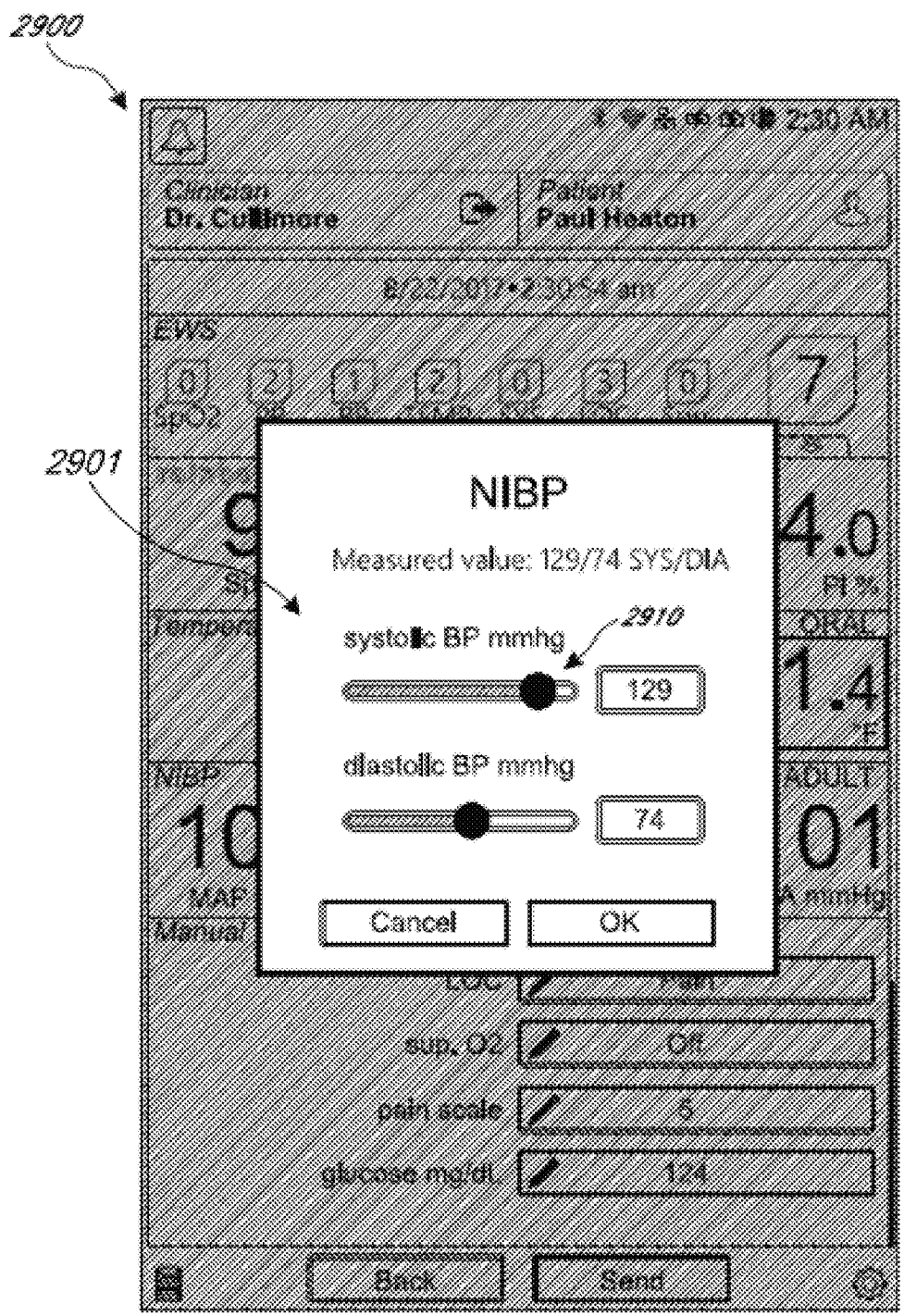

Although not all the measurements are shown editable with the buttons 2732, any number of measurements may be so editable. Further, the measurements that may be editable may be selected by the hospital or clinical staff prior to deploying the patient device 100, for example, according to hospital policies. Pulse rate, respiratory rate, and temperature are some examples of parameters that can be overwritten manually using the user interface 2700 (in addition to the manual parameters in the area 2350 below). An example selection of one of the buttons 2732 to perform manual entry can cause an example user interface 2900 or the like to be shown as depicted in FIG. 29. In the user interface 2900, an overlay 2901 including user interface controls 2910 can permit manual change of the data (blood pressure in this example).

Referring again to FIG. 27, a send button 2740 is also shown. This button 2740 may be selected to cause a snapshot of the measurements shown to be sent as spot check measurements to the patient's chart stored, for example, in the electronic medical record database (see, for example, FIG. 17). Selection of the button 2740 can cause a user interface such as the example user interface 2800 of FIG. 28 to be shown. An overlay 2801 in the user interface 2800 indicates that the spot check data was successfully sent to the EMR.

Figure 30:
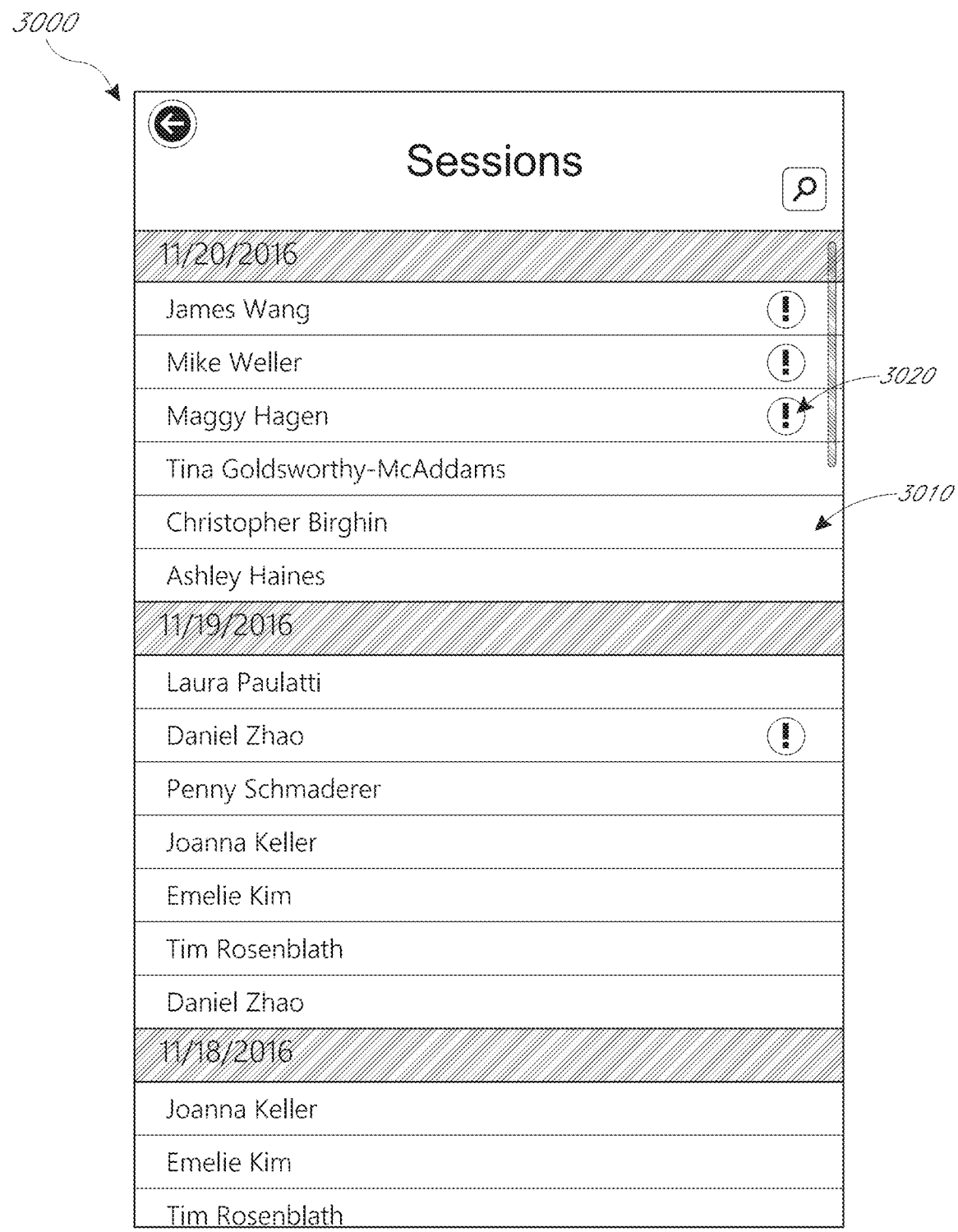

Turning to FIG. 30, an example previous spot check list user interface 3000 is shown. The previous spot check list 3000 depicts a plurality of patient names 3010 organized by date, which may be selected to view spot checks for a particular patient. Alert icons 3020 are shown next to some patients whose parameters or early warning scores may be outside of an acceptable or safe range and therefore perhaps warrant particular attention by a clinician. Alternatively, the alert icons 3020 can be used to indicate that a patient's spot check measurements have been saved to the patient monitor but have not yet been sent to the EMR, for example, due to the patient monitor being out of wireless network range.

Figure 31:
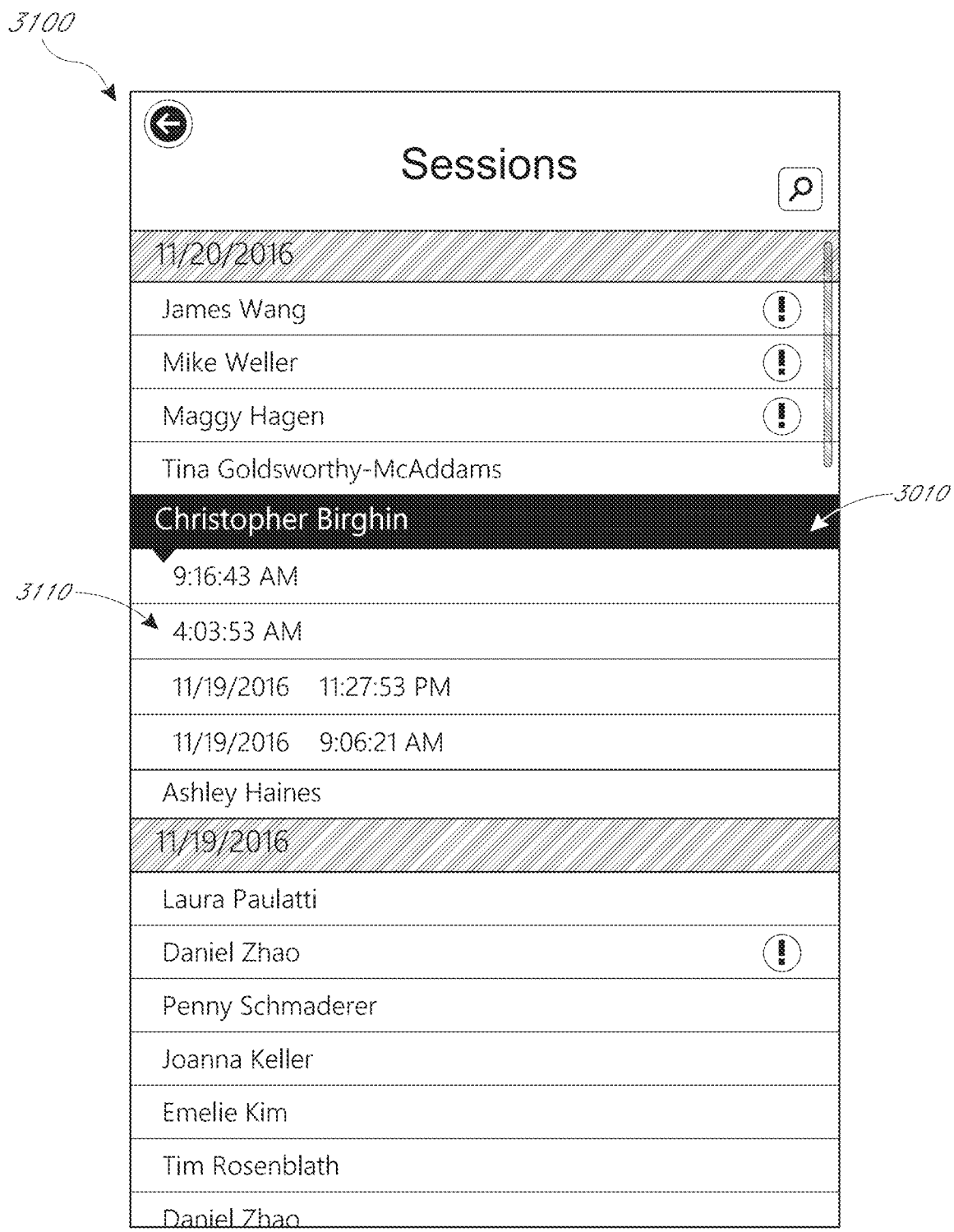

User selection of one of the patient names 3010 may cause a user interface 3100 of FIG. 31 to be shown. The user interface 3100 is similar to the previous spot checks interface 3000 of FIG. 30 except that one of the patients 3010 has been expanded to show this patient's previous spot checks 3110, organized by date and time. Those listings showing times may only represent spot checks taken the current day. Selection of any of these spot checks can result in a user interface being displayed such as any of the interfaces shown in FIGS. 32 through 34.

Figure 32:
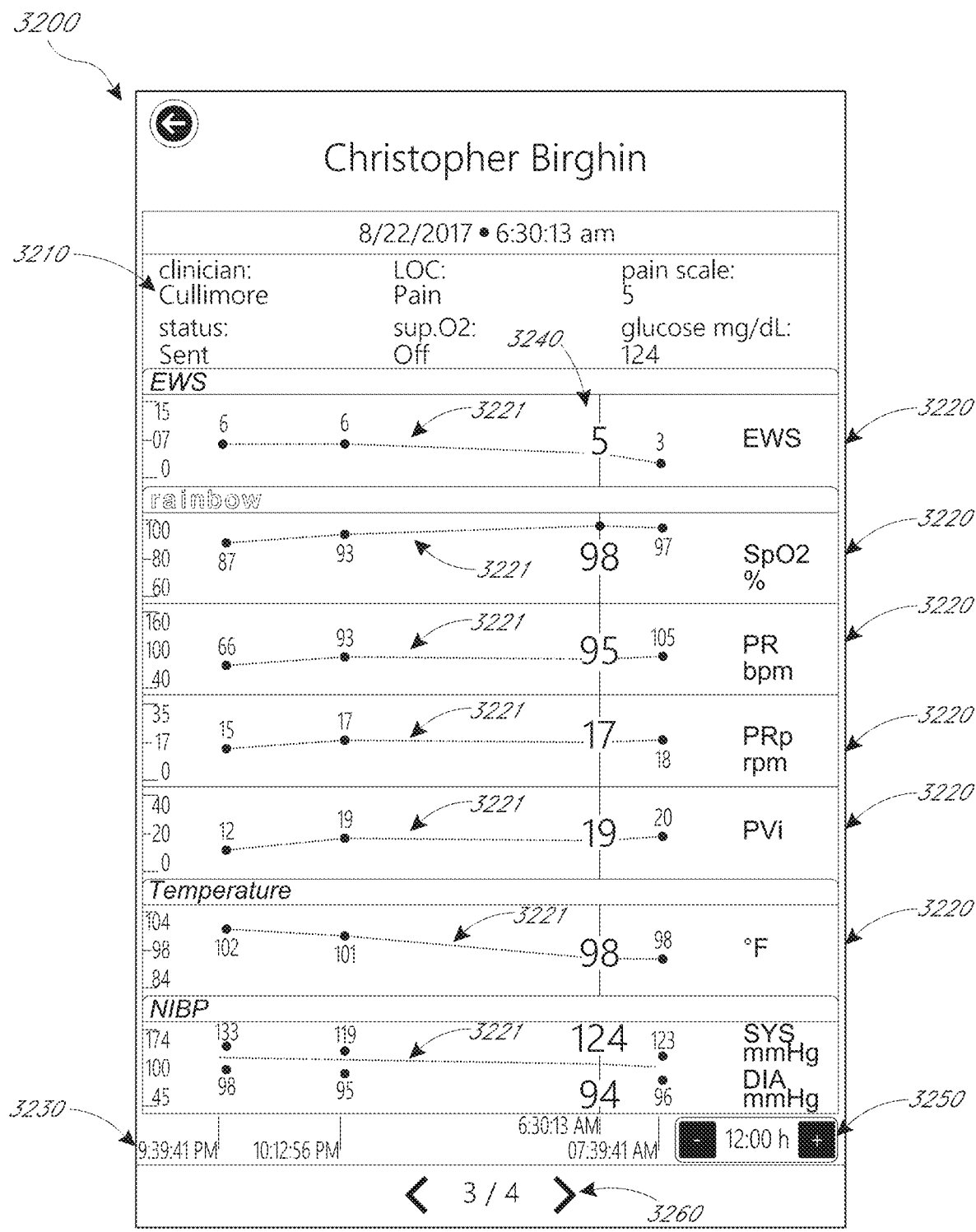
Figure 33:
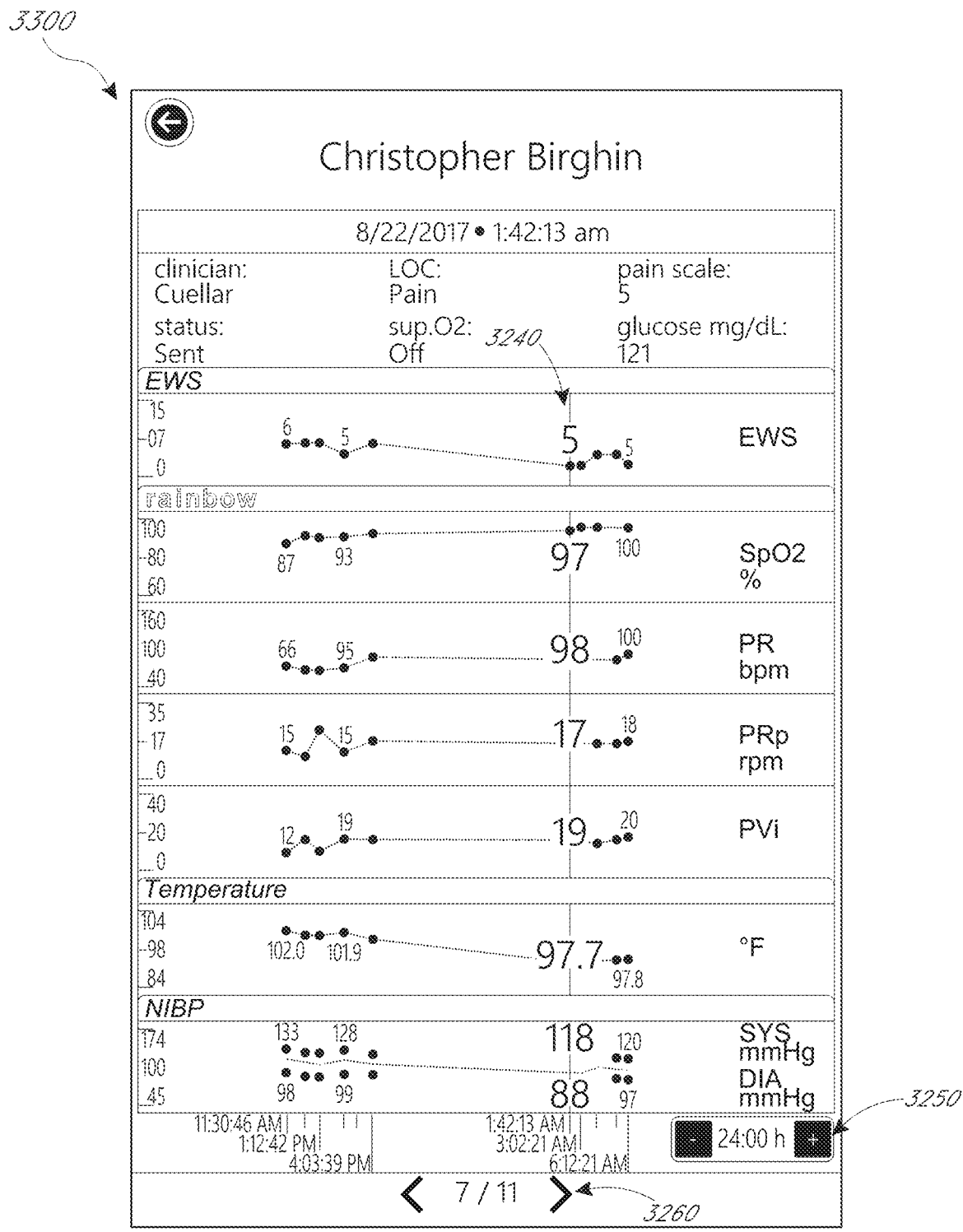
Figure 34:
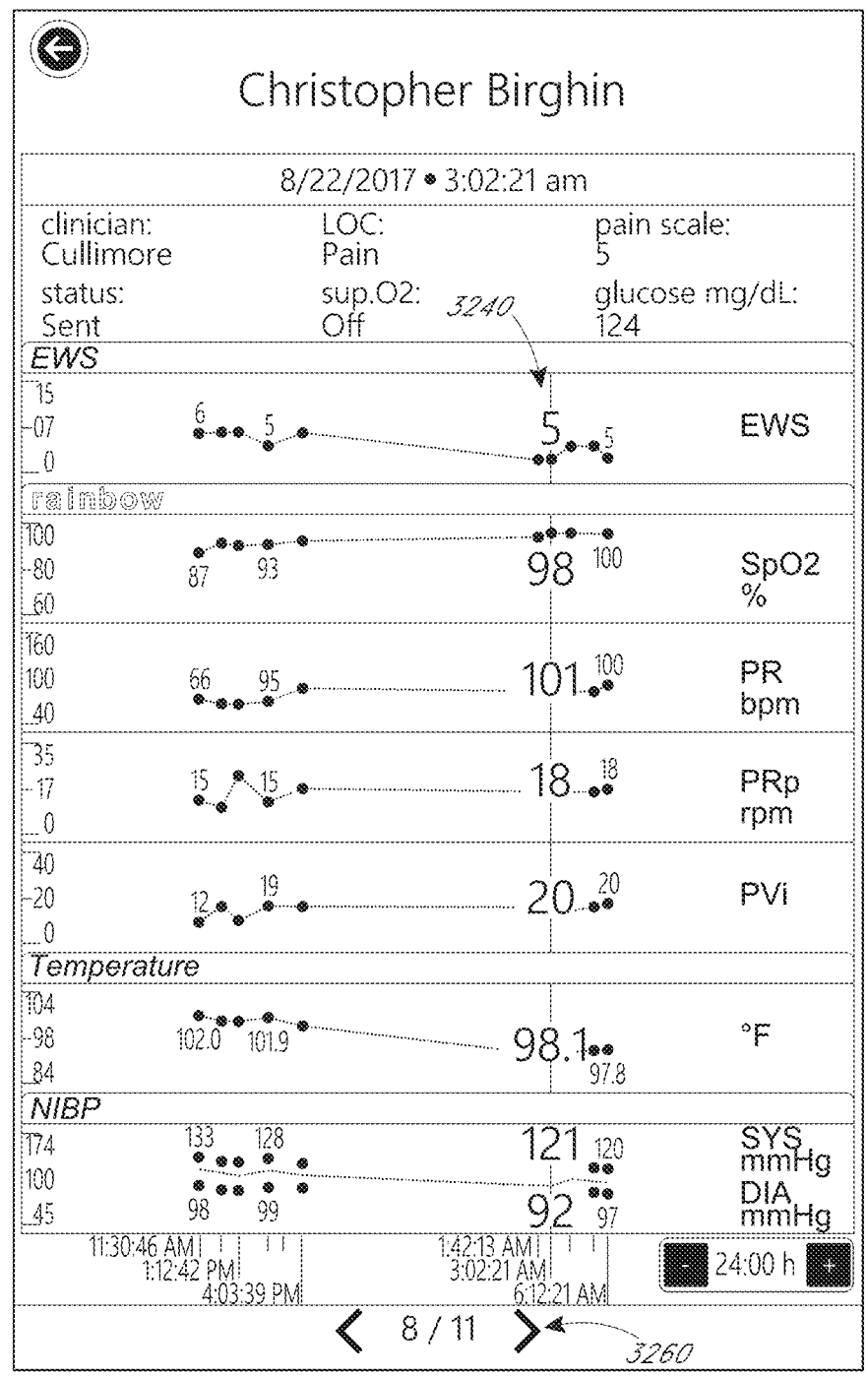

FIGS. 32 through 34 illustrate additional example interfaces 3200 through 3400 that depict various trend views of previous spot checks. These interfaces 3200 depict patient information 3210, including manual parameters entered as described above, as well as rows 3220 of spot check trend data. The spot check trend data in the rows 3220 is organized in this example as a series of dots, with each dot having a number beneath it representing a particular measurement taken at a particular time. The measurement times correspond to a timeline 3230 shown at the bottom of the display. The dots representing parameter measurements can be connected with other dots to represent trends over time. A trend line 3221, drawn through the dots, depicts an approximate trend for each parameter (including EWS in this example).

In the example user interface 3200, a line 3240 is drawn vertically across each row 3220 and intersects several dots representing spot checks performed at one time for a plurality of parameters. The values of those parameters along the line 3240 is shown larger than surrounding parameter values to indicate that this particular set of spot checks is currently selected by a user. Arrow buttons 3260 at the bottom of the display permit a user to cause the line 3240 to be moved from left to right to different spot check sets to change the focus on a different set of spot checks. This feature may be useful when the cluster of spot checks (see FIG. 33) a group close together so that selection of dots may be difficult via the fingers. When a touchscreen is used, the dots may be selected by the finger of the clinician.

Buttons 3250 at the bottom of the display can permit the time scale of the trends to be manipulated. In FIG. 32, the time scale is shown as 12 hours whereas in FIGS. 33 and 34, the time scale is shown as 24 hours, so selecting a longer time scale can show additional sets of spot checks occurring in the past (if available).

Figure 35:
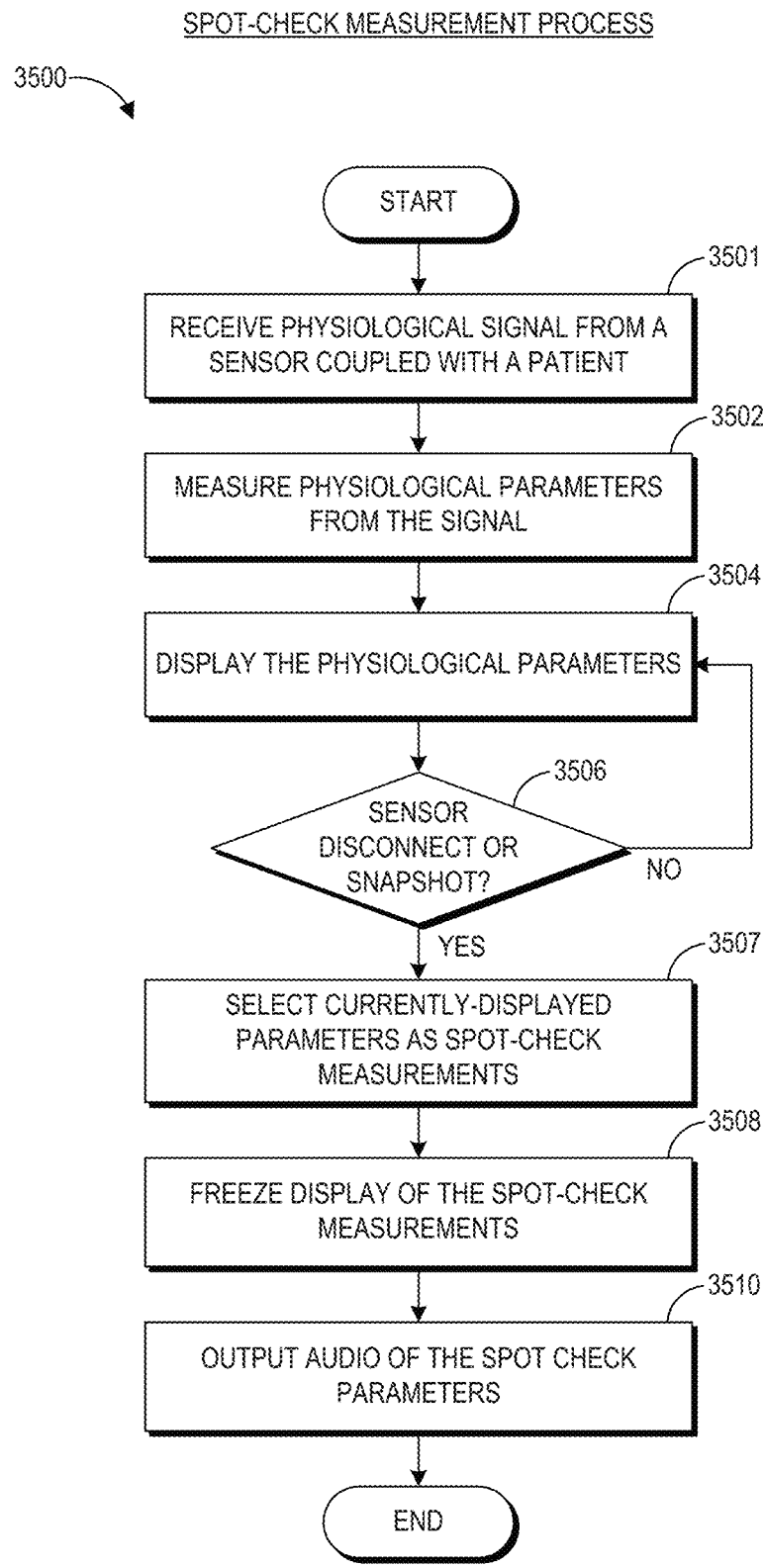
FIGS. 35 and 36 depict example spot check measurement processes.

Turning to FIG. 35, an example spot check measurement process 3500 is shown. The spot check measurement process 3500 may be implemented by the patient device 100 or by any other suitable computing device. The spot check measurement process may be implemented using at least some of the user interfaces described above (including at least some of the user interfaces in FIGS. 19-34). Further, the spot check measurement process 3500 may be particularly used with sensors that are traditionally used for continuous measurement, such as optical sensors or acoustic sensors, although the process 3500 may also be used with any type of sensor.

At block 3501, the patient device receives a physiological signal from a sensor coupled with a patient. At block 3502, the patient device measures one or more physiological parameters from the signal. These parameters might include, for example, oxygen saturation, pulse rate, respiratory rate (optical-, acoustic-, or electrocardiogram-based), perfusion index, pleth variability index (PVI), oxygen reserve index (ORI), carboxyhemoglobin concentration (SpCO), methemoglobin concentration (SpMet), and total hemoglobin concentration (SpHb), to name a few. Many other parameters may be measured in other implementations.

Figure 36:
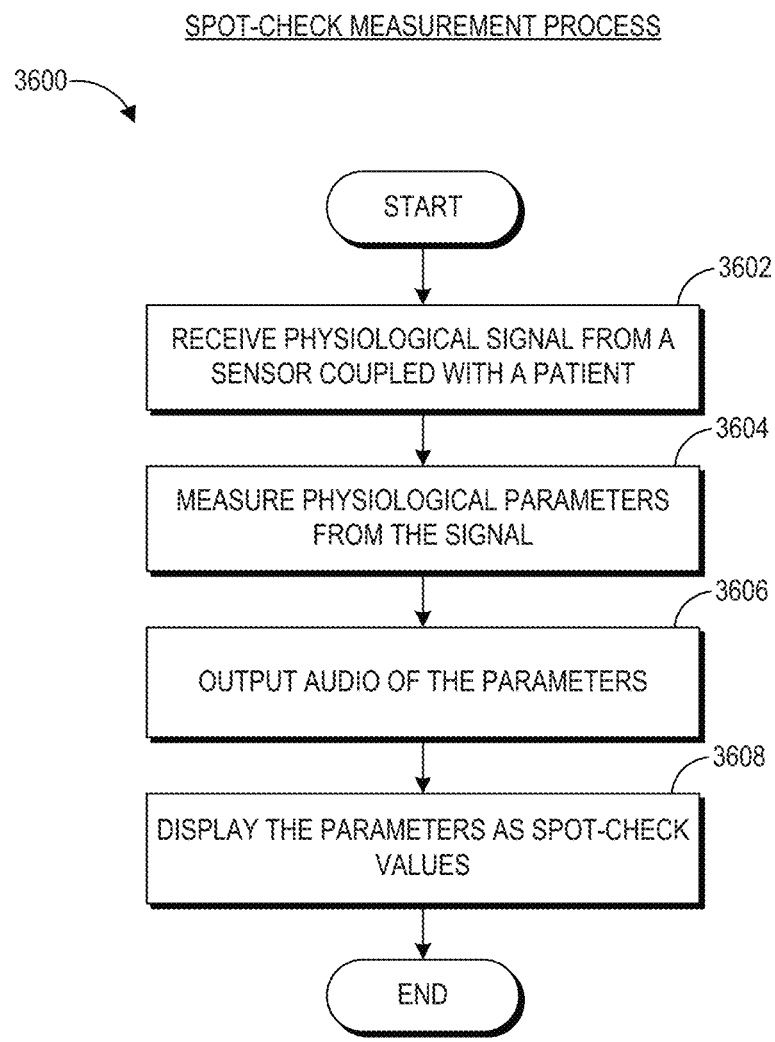

At block 3504, the patient device displays the physiological parameters (see, for example, FIG. 25; for temperature and blood pressure, see, for example, FIG. 36). The patient device then determines at block 3506 whether the sensor has been disconnected or a snapshot has been selected. If the sensor has been disconnected or a snapshot option (for example, FIG. 26 element 2610) has been selected, then the process 3500 proceeds on to block 3507. Otherwise, the process 3500 proceeds back to block 3504, effectively continuing to measure until an indication of a request for spot check measurement has been received, either by removing a sensor from a patient or by selecting a snapshot option in the user interface. A spot check measurement may be taken by removing the sensor or by selecting a snapshot button (or similar button).

At block 3507, once the snapshot option or sensor has been disconnected, the patient device selects the currently displayed parameters as spot check measurements, freezes the display of the spot check measurements in block 3508, and outputs audio of the spot check parameters at block 3510. The audio is optional. However, audio can be beneficial because if the parameter values are output audibly, then a clinician does not need to look at a display to determine what those measurements are. For example, the patient device might audibly output the following: "97 percent SpO$_2$," "65 beats per minute pulse rate," or the like.

Turning to FIG. 36, another example spot check measurement process 3600 is shown. The spot check measurement process 3600 may likewise be implemented using the patient device 100 or any other suitable computing device. The spot check measurement process 3600 may also be implemented using any of the figures described above, such as at least some of FIGS. 19-34. Further, the spot check measurement process 3600 can be implemented using any sensor or parameter, but may be particularly applicable to parameters that are traditionally spot check parameters as opposed to continuously-monitored parameters, such as temperature and blood pressure. Of course, blood pressure may be monitored more frequently, or even continuously, but blood pressure can also be considered to be a spot-check parameter.

At block 3602, the patient device receives a physiological signal from a sensor coupled with a patient. At block 3604, the patient device measures the physiological parameters from the signal (see, for example, FIG. 25). At block 3606, the patient device outputs audio of the parameters and outputs the parameters as spot check values on the display at block 3608 (see, for example, FIG. 26). Thus, in contrast to the process 3500, the process 3600 takes a single measurement for each of the traditional spot check parameters and outputs that measurement audibly as well as to the display. Although the process 3500 may be used to perform spot-check measurements of temperature and blood pressure (including by removal of the sensor(s)), removal of a sensor is not used in the process 3600 to measure a spot-check value.

ADDITIONAL EXAMPLES

The following description provides additional examples of the EWS features and spot check features described above, as well as a new example feature—vital signs check mode. Any of the features described above can be implemented together with any of the features described below. Further, any of the patient monitors or other patient devices described herein can implement the features described below.

Figure 37:
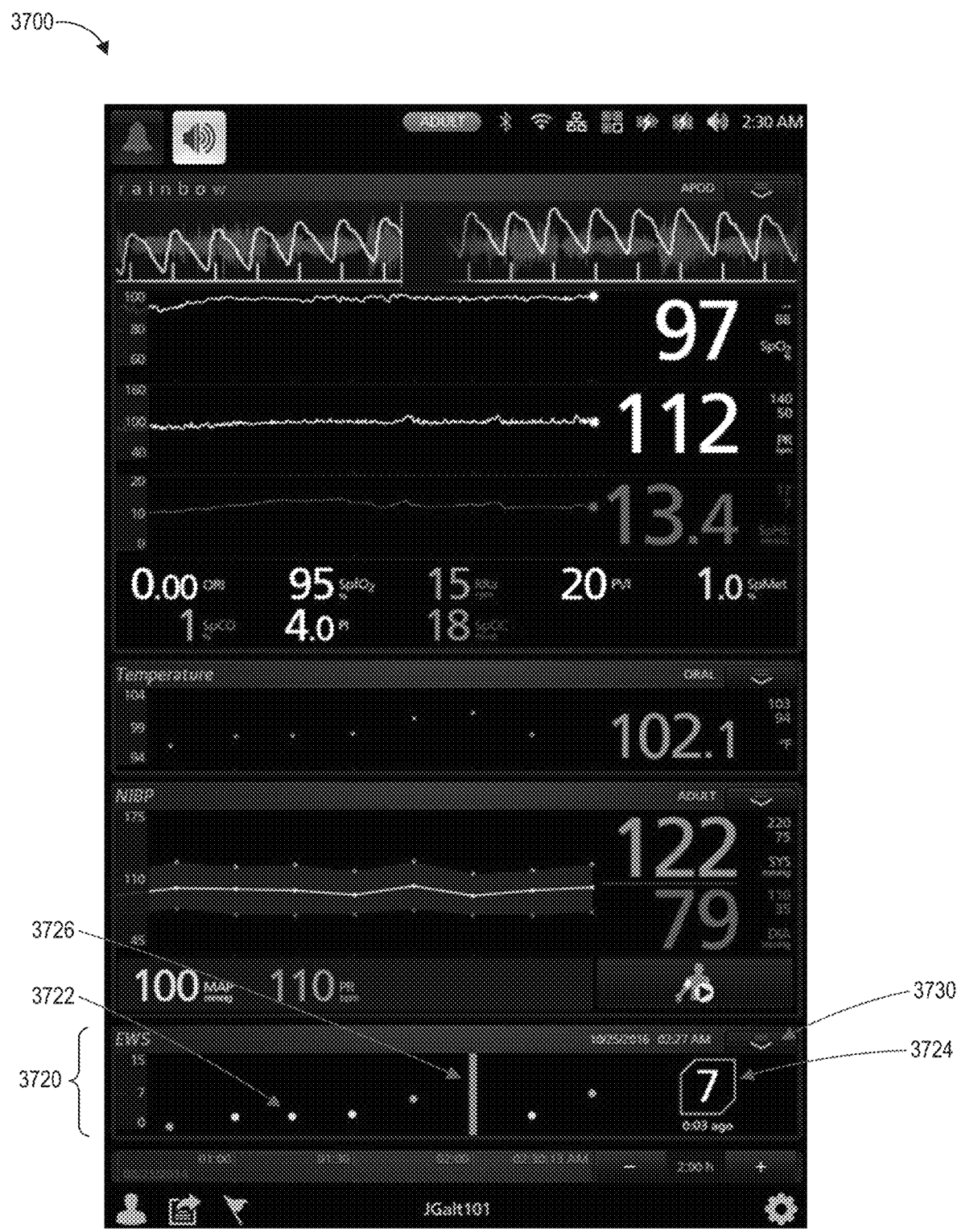
FIGS. 37-40 depict additional example patient monitor displays.

FIG. 37 depicts another example patient monitor display 3700. The patient monitor display 3700 can be generated in a similar manner as the other patient monitor displays described here in. For instance, the display 3700 can be generated and output on a display of the patient monitor 100 of FIG. 1. The patient monitor display 3700 is very similar to the patient monitor display 200 of FIG. 2A as well as other displays described herein (see, for example, FIG. 4).

One difference between the patient monitor display 200 of FIG. 2A and the display 3700 of FIG. 37 is that the EWS region 220 of FIG. 2A includes boxes 222 that depict numerical contributor scores that contribute to the EWS score shown in the box 224. In contrast, in FIG. 37 an EWS region 3720 is provided in a similar location to the EWS region 220 of FIG. 2A but instead of showing contributor scores, the EWS region 3720 depicts EWS trend values 3722 in a trend graph. Next to the EWS trend values 3722 is an EWS box 3724 that includes the EWS corresponding to the current parameters measured for the patient. In contrast, the EWS trend values 3722 depict a graph of dots with each dot corresponding to the previous EWS value occurring in time. Also, the EWS trend values 3722 may be colored in the same or similar manner as the contributor scores boxes 222 and the EWS box 224 described above.

The early warning score shown in the box 3724 may be calculated as described above. Although the appearance of the box 3724 is that of a 3-dimensional (3D) box, this is optional, and the box 3724 may be similar to a two-dimensional box as shown in FIG. 2A or any other suitable shape.

Another example feature of the EWS region 3720 is a vertical emergency bar 3726. The vertical emergency bar 3726 can cover an entire vertical portion of the EWS graph. The EWS region 3720 essentially includes a graph ranging from EWS scores of 0 to 15. The vertical emergency bar 3726 extends from 0 to 15 (the entire vertical range of the trend graph) in this example, representing that an emergency has occurred. Thus, the vertical emergency bar 3726 can be very visible. The emergency bar 3726 can correspond to when one of the contributor scores and hence the EWS has an emergency value, as described above with respect to FIG. 16.

Also shown is an example EWS menu button 3730. Selection of this button can perform a similar action as described above with respect to the button 230 of FIG. 2A. For example, an action menu or EWS menu may be shown that includes functionality for selecting different EWS region views and recalculating EWS values, among other possible options. For instance, the selection of the EWS menu button 3730 can provide an option that enables a user to switch between the trend view in the EWS region 3720 as shown here and a numeric view such as is shown in previous figures (for example, FIG. 2A). An example EWS menu is described below with respect to FIG. 39.

Figure 38:
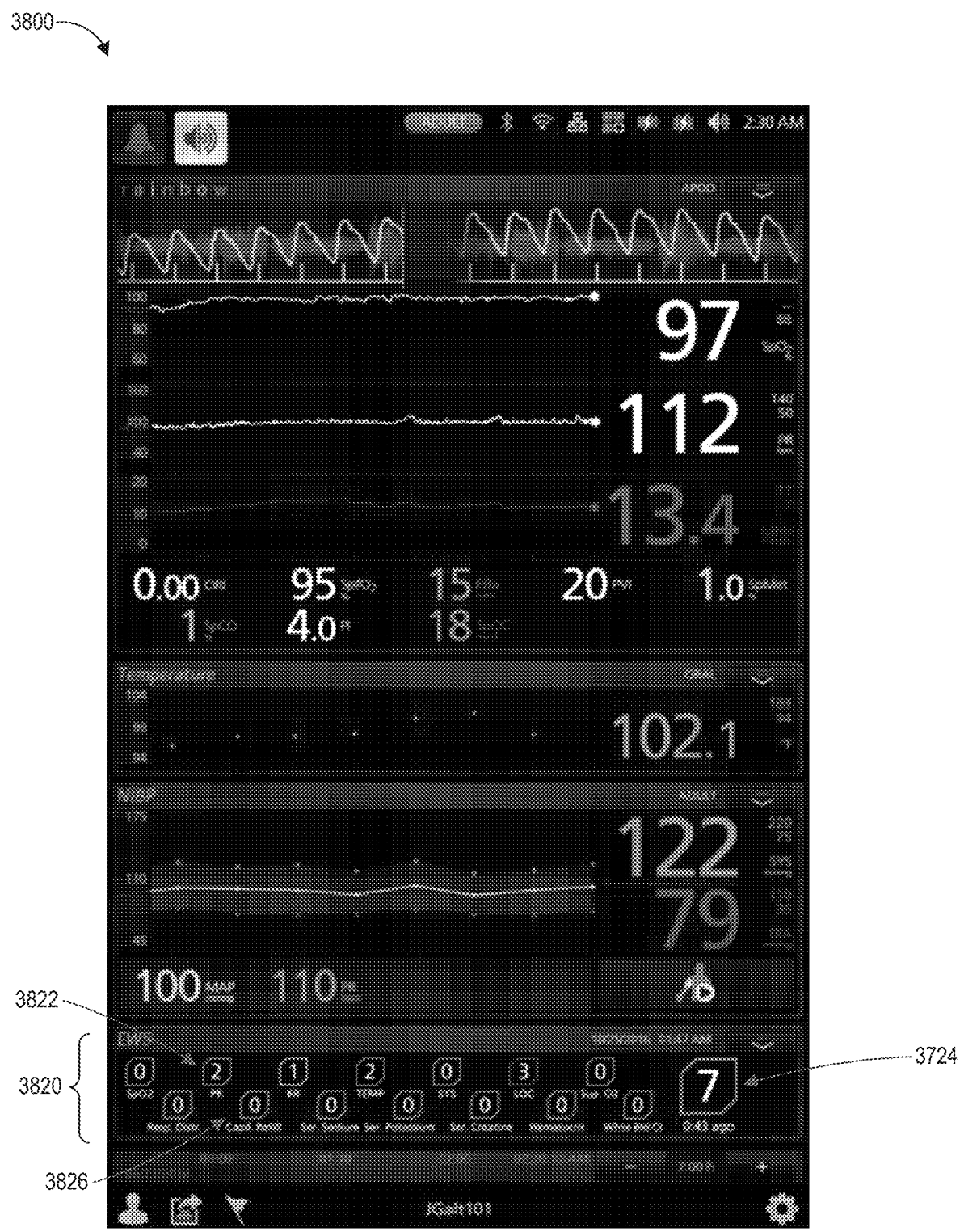

Turning to FIG. 38, another example patient monitor display 3800 is shown. The patient monitor display 3800 is similar in many respects to the display 3700 and may likewise be generated by a patient monitor such as the patient monitor 100 or any other patient monitor disclosed herein. For convenience, each of the remaining figures may be generated by the patient monitor 100 or another suitable patient monitor. The patient monitor display 3800 depicts another example EWS region 3820. In the region 3820, there are two rows 3822, 3826 of contributor scores. Each of these rows depicts a plurality of contributor scores. The upper row 3822 is offset from a lower row 3826 in this example. Offsetting the rows 3822, 3826 can cause the contributor score boxes to not line up vertically but instead to be instead offset vertically. This offset configuration can provide a more compact, easier-to-read alternative to the dual row configuration of FIG. 11. This compactness may arise because offsetting the contributor scores in each row 3822, 3826 can provide more room for the labels underneath the boxes in the upper row 3822. A similar configuration can also be used vertically to reduce space usage.

Figure 39:
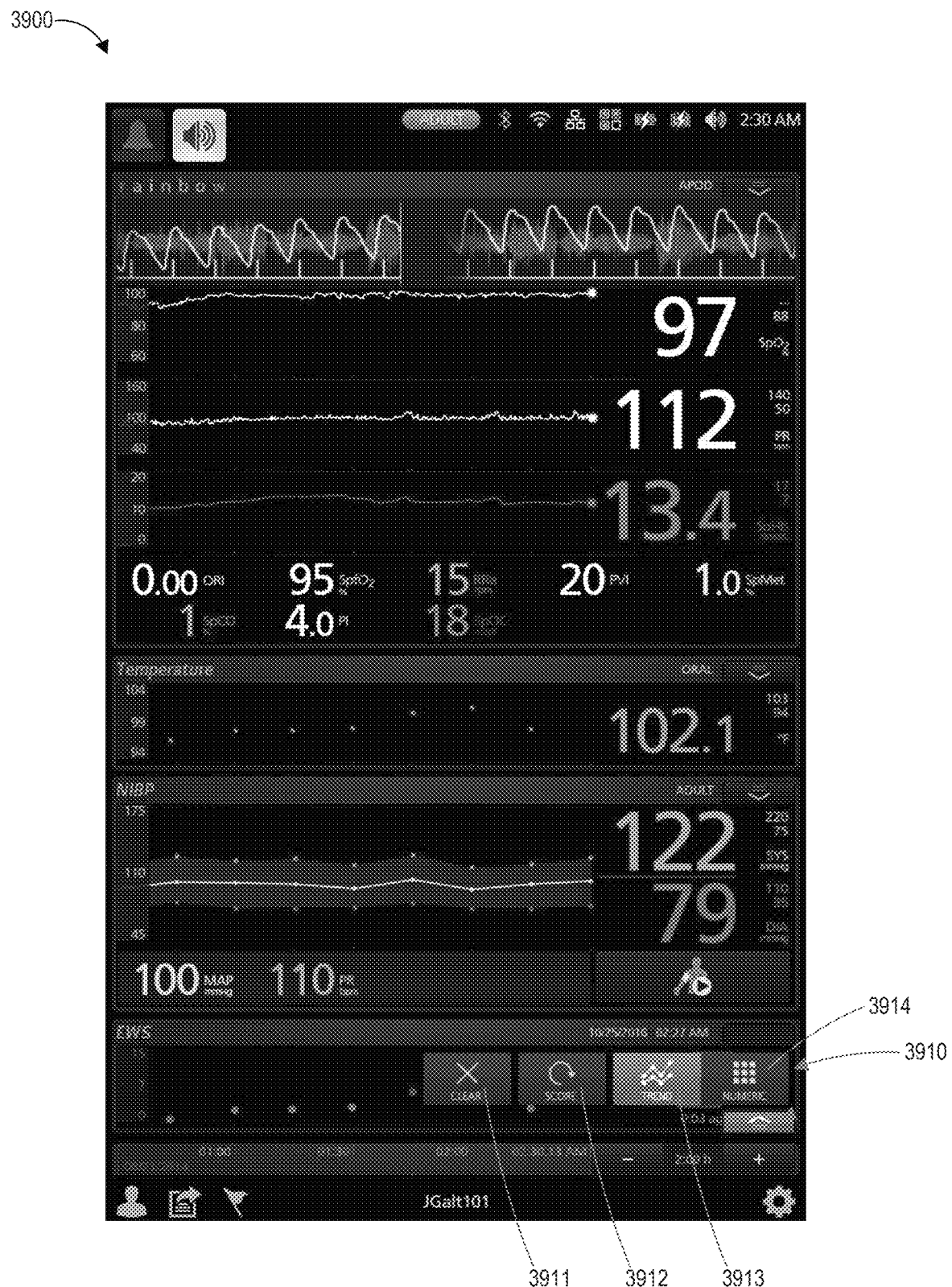

Turning to FIG. 39, another example patient monitor display 3900 is shown. The patient monitor display 3900 is an example display that may be output when the EWS menu button 3730 is selected (see FIG. 37). In the display 3900, an example EWS menu 3910 is shown as a result of that button press. The example EWS menu 3910 includes a plurality of buttons including a clear button 3911, a calculate button 3912, a trend view button 3913, and a numeric view button 3914. The clear button 3911 can have similar or the same functionality as the button 410 described above with respect to FIG. 4. Likewise, the calculate button 3912 can have the same or similar functionality as the button 420 described above with respect to FIG. 4. The trend view button 3913, when selected, can cause a trend view such as shown in FIG. 37 to be displayed in the EWS region 3720. In contrast, the numeric view button 3914, when selected, can cause a numeric view to be displayed in an EWS region such as the region 220 in FIG. 2A to depict contributor scores instead of a trend view. However, both a trend view and a numeric view of the EWS may be presented on the same display at the same time in other implementations.

Figure 40:
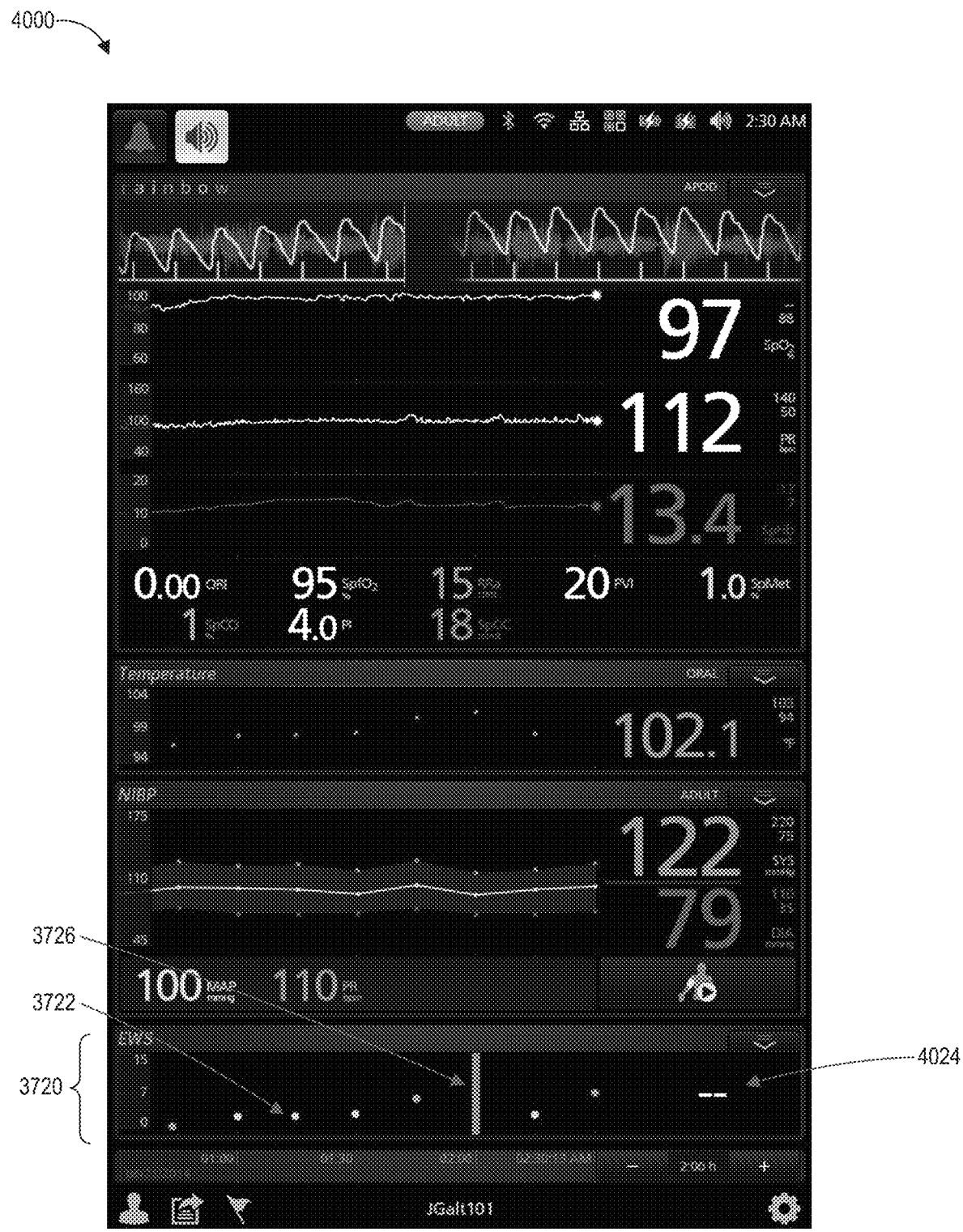

Turning to FIG. 40, another example patient monitor display 4000 is shown. The patient monitor display 4000 is similar to the display 3700 of FIG. 37, except that instead of a contributor score box 3724 being shown, a dash 4024 is shown in place of the EWS score. The dash 4024 indicates that a current EWS score has not been calculated or has recently been cleared. The dash 4024 may be displayed, for example, if the clear button 3911 of FIG. 39 has been selected. The patient monitor display 4000 is an example alternative view to the one shown in FIG. 5, where each of the contributor scores is also dashed out. Here, the trend 3722 continues to display even though the EWS score is dashed out. Alternatively, selecting the clear button 3911 can also clear the entire trend.

Figure 41:
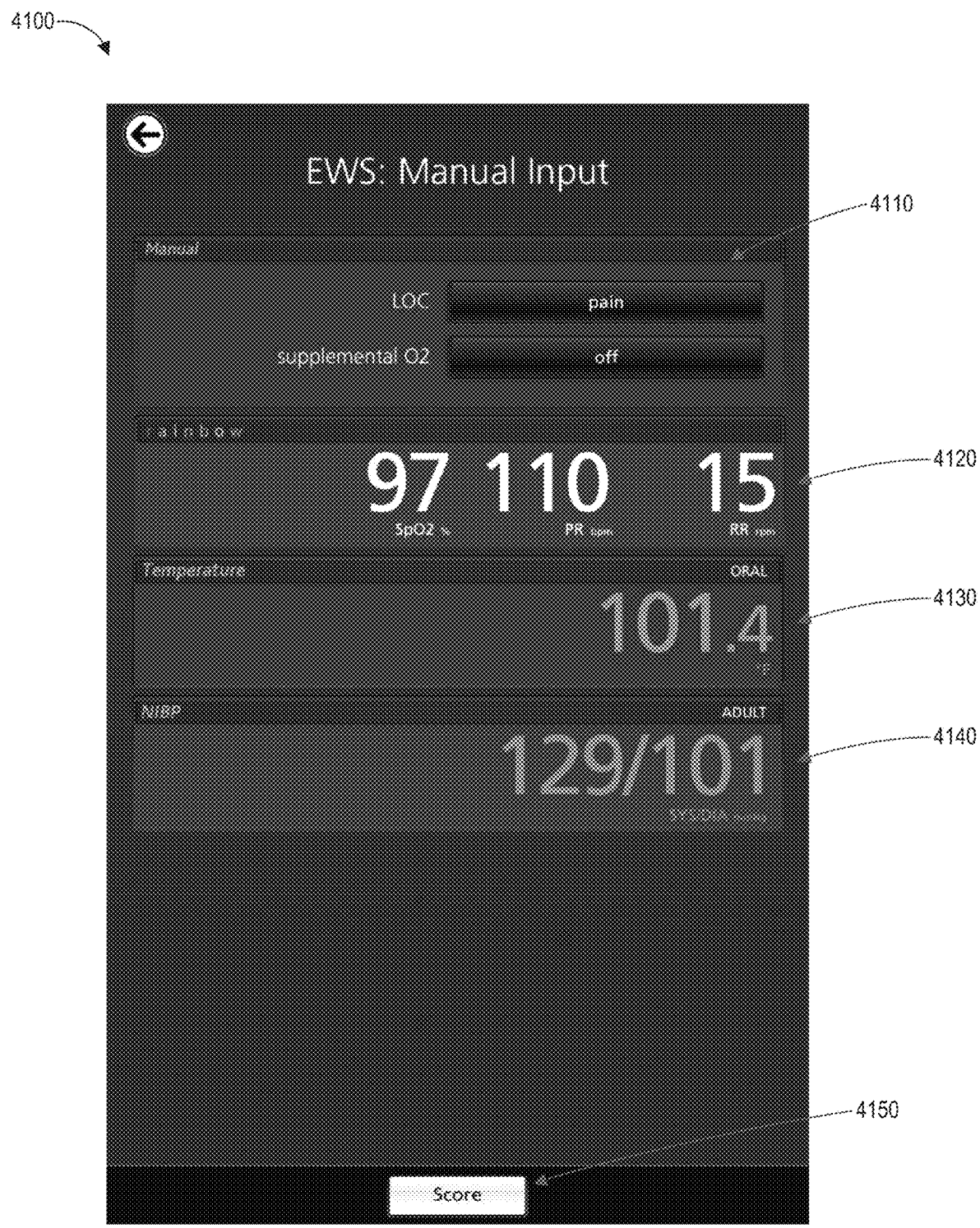
FIG. 41 depicts an example manual input menu.

Turning to FIG. 41, an example manual input menu 4100 is shown. The menu 4100 may be reached, for example, upon selecting the calculate button 3912 of FIG. 39. The manual input menu 4100 is another example version of the displays shown in FIGS. 7A, 9A, 9B, and 27. The menu 4100 includes example manual entry controls 4110 as well as automatically calculated parameters 4120, 4130 and 4140. The score button 4150 can be selected to calculate an early warning score. If the manual entry controls 4110 were not populated, the score button 4150 can be grayed out and thus not user selectable until the manual entry controls 4110 are populated.

Figure 42:
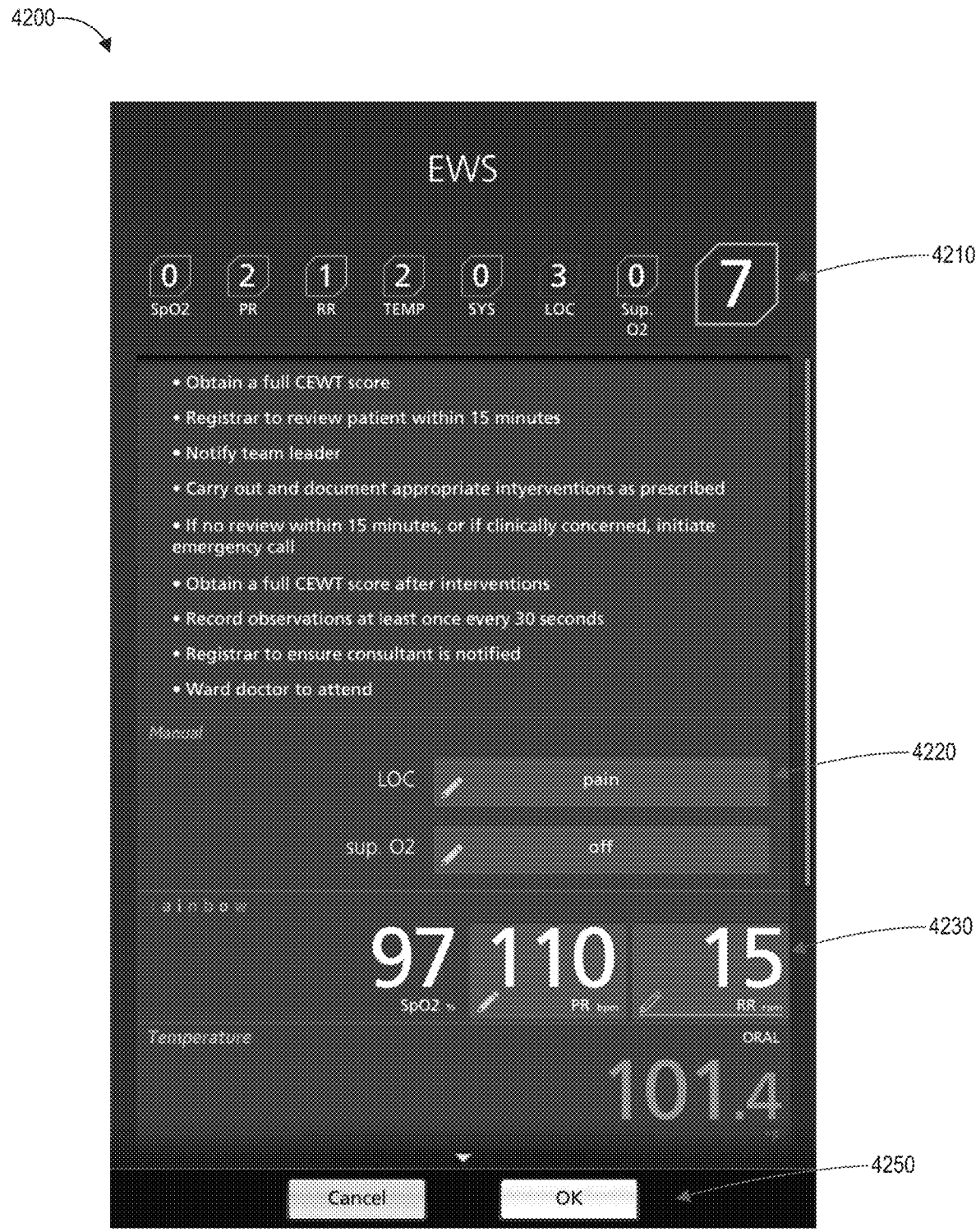
FIGS. 42-43 depict example review screens.

Turning to FIG. 42, an example review screen 4200 is shown. The review screen 4200 is similar to FIG. 27. At the top of the review screen 4200 are contributor scores and an EWS score 4210 with boxes surrounding the values in an example 3D format. Fields 4220 for adjusting manual parameters are provided, and fields 4230 for adjusting at least some calculated parameters or overwriting at least some calculated parameters are also provided. A button 4250 is also provided to confirm and update the EWS calculation. When the button 4250 is selected, the EWS and contributor scores 4210 can be saved to the patient monitor memory and/or sent to the EMR. The EWS and contributor scores 4210 can be saved to the memory of the monitor and then sent to the EMR when a network connection is established with the monitor. For example, the EWS and contributor scores 4210 can be automatically sent to the EMR if the patient monitor is already connected to the network. if the monitor is not already connected to the network, the patient monitor can save the EWS and contributor scores 4210 in a memory for subsequent transmission to the EMR once the patient monitor connects to the network (for example by coming into range of an access point associated with the network).

Figure 43:

Turning to FIG. 43, another example review screen 4300 is shown similar to the review screen 4200 of FIG. 42. In this review screen, the EWS is replaced with an E 4320 representing an emergency because one of the contributor scores 4310 is represented as an E indicating an emergency for the corresponding measured parameter. This feature is also described above with respect to FIG. 16. The review screen 4300 differs from FIG. 16 in a few respects, including that the boxes surrounding the contributor scores and the EWS score are shown as 3D boxes. In addition, the emergency "E's" are shaded with a particular color, which may be purple or some other vibrant color that can quickly attract the attention of a clinician. The E 4310 or 4320 may be flashing to further attract the clinician's attention. The color of the E contributor box and 4310 and the emergency EWS 4320 can be the same color as the vertical emergency bar 3726 of FIG. 37 (which can also flash to attract attention).

Figure 44:
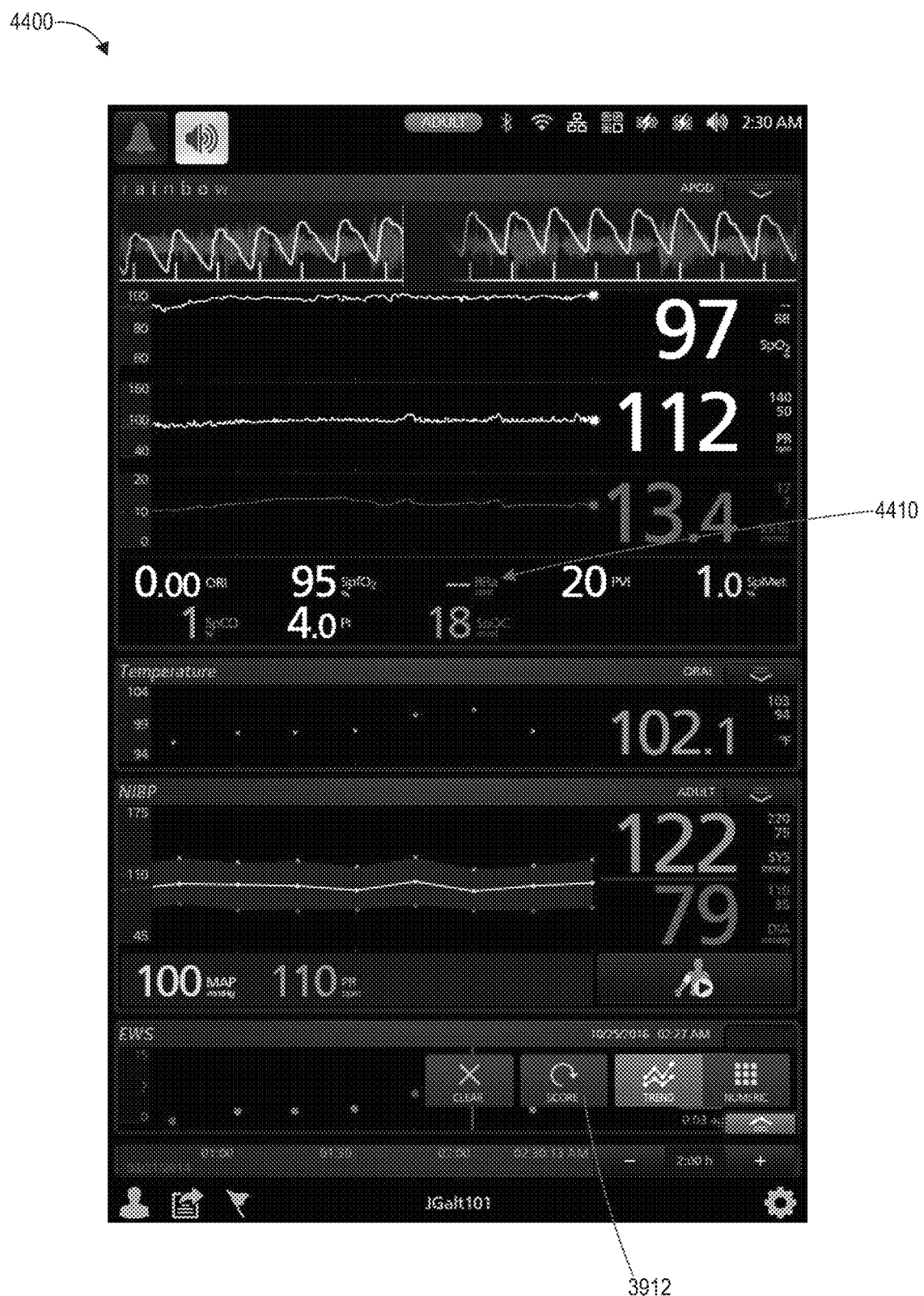
FIG. 44 depicts another patient monitor display.

Turning to FIG. 44, another example patient monitor display 4400 is shown, which is similar to the display 3900 of FIG. 39. In the patient monitor display 4400, one of the measurements 4410 is missing. In particular, respiratory rate from an acoustic sensor (RRa) is missing a reading. The measurement may be missing for any of a variety of factors. For instance, the sensor corresponding to the measurement 4410 that is missing may not be connected to the patient, or the measurement 4410 cannot be calculated due to a broken sensor, cable, low profusion, low signal quality, or interference noise, or the like. In this example, the score button 3912 can still be selected even if a parameter (such as RRa) that is part of the EWS is missing. However, subsequent calculation of the EWS may be prevented until a manual entry for the missing measurement 4410 is supplied. Alternatively, the EWS may nevertheless be calculated even though the measurement 4410 is missing.

Figure 45:
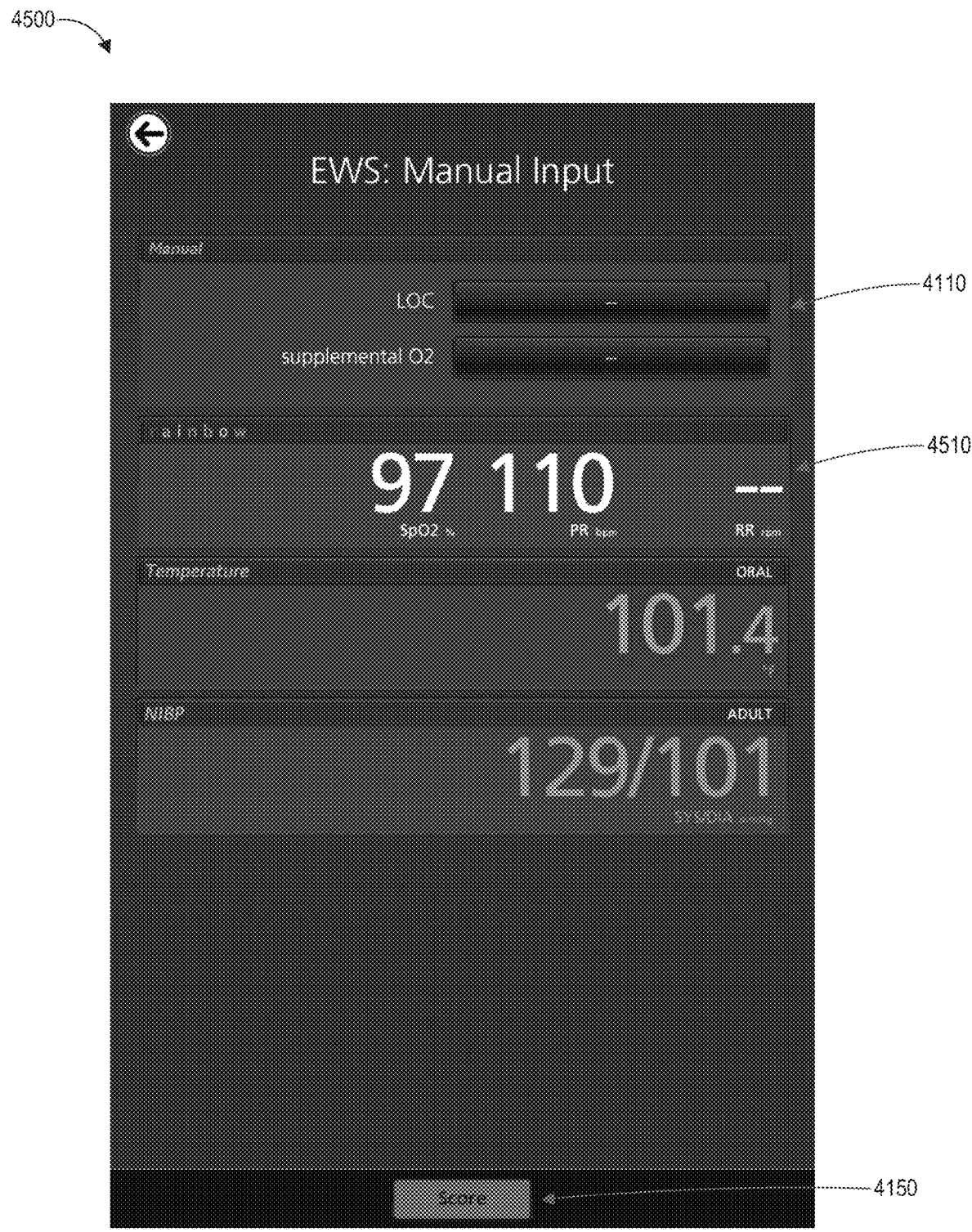
FIG. 45 depicts another example manual input screen.

Turning to FIG. 45, a manual input screen 4500 is shown, which is another example similar to the manual input screen 4100. The manual input screen 4500 may be reached by selecting the score button 3912 in FIG. 44. In this screen 4500, the manual entry controls 4110 have not yet been populated. Likewise, a missing measurement 4510 corresponding to the missing measurement 4410 of FIG. 44 is shown dashed out. The score button 4150 accordingly is greyed out and hence non-selectable until the manual entry controls 4110 and/or the missing measurement 4510 are populated. In one option, the manual entry controls 4110 can be populated, and then the score button 4150 may be user-selectable. Further, the missing reading 4510 can be supplied on the review screen shown in FIG. 46, reached after selecting the score button 4150.

Figure 46:
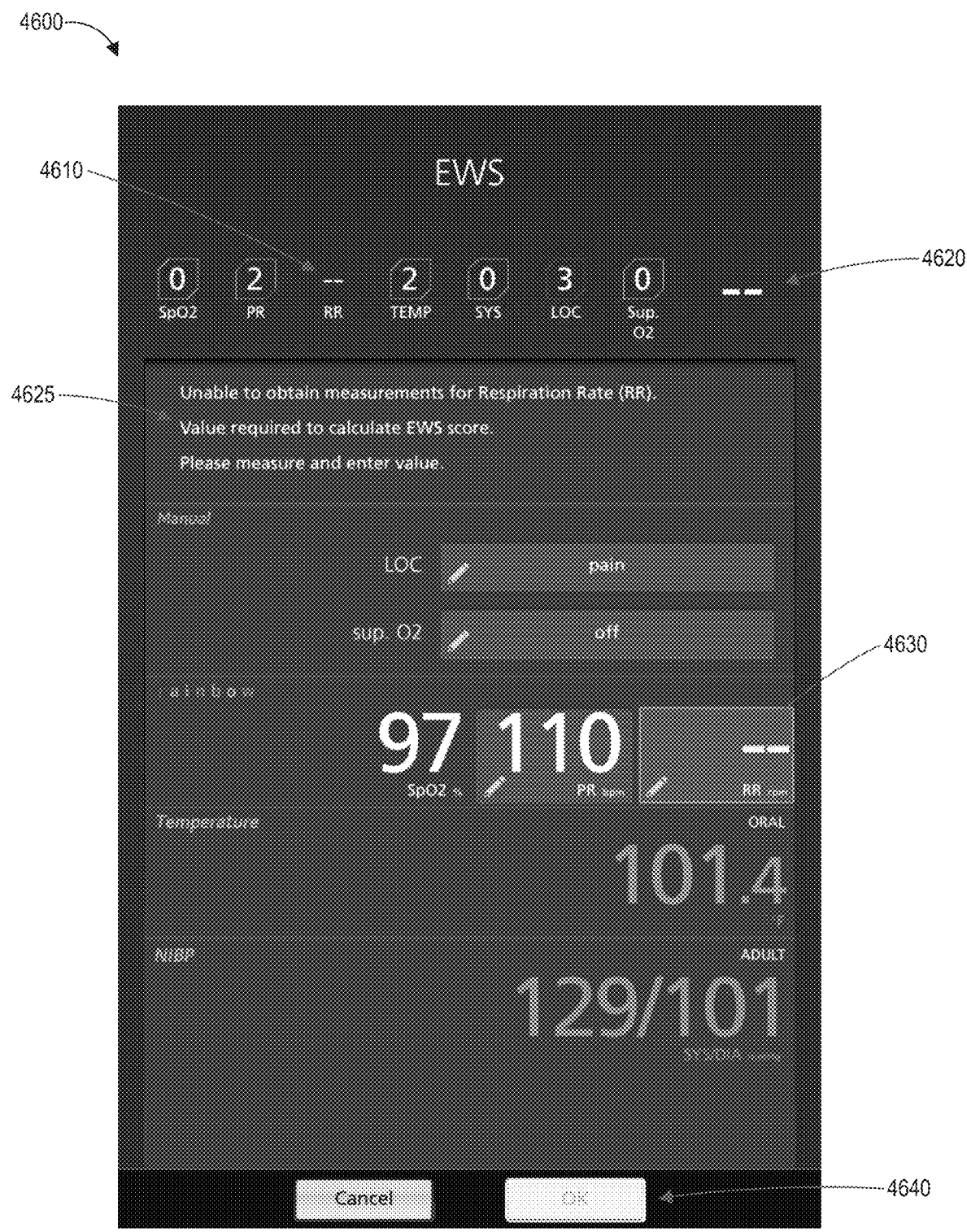
FIG. 46 depicts another example review screen.

Turning to FIG. 46, an example review screen 4600 is shown. In the review screen 4600, there is a missing contributor score dashed out (4610), and accordingly, a missing or blank EWS score 4620. An error message 4625 indicates that the patient monitor was unable to obtain measurements for respiration rate (RR), that the value is required to calculate EWS score (in this example), and that the clinician should measure and enter the value. Some parameters can be required to calculate EWS while others may not be. For example, vital signs may be required to calculate EWS while other parameters like weight or supplemental oxygen may not be required to calculate the EWS. FIG. 13 provides a contrasting example, where EWS can be calculated even when there are missing parameters in the contributor scores (in that example, temperature, capillary refill, and systolic blood pressure are missing contributor scores, yet EWS is calculated).

Figure 47:
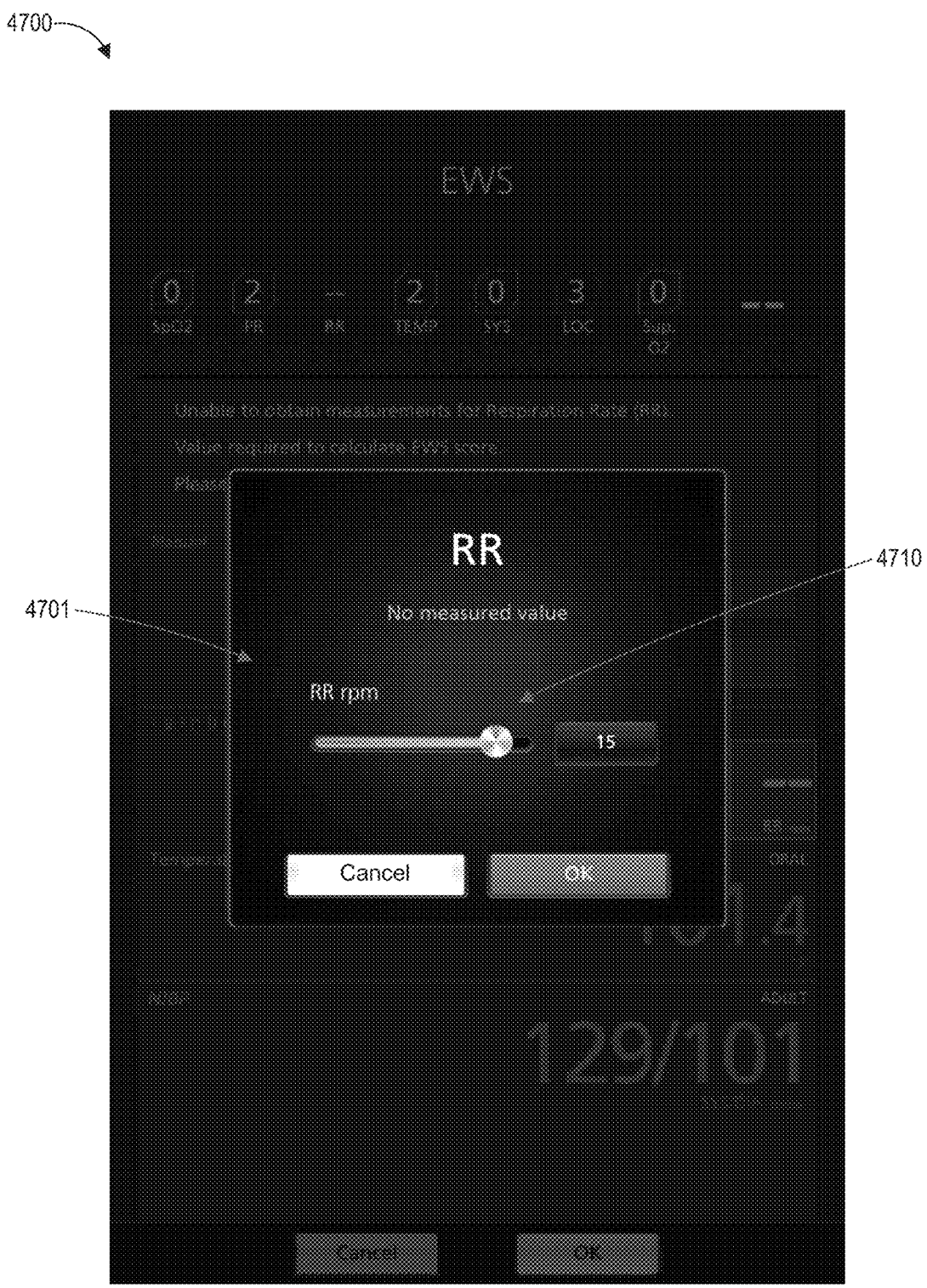
FIG. 47 depicts an example user interface with an edit result overlay.

Referring again to FIG. 46, a manual overwrite button 4630 is also provided, which the clinician can use to manually input the missing parameter measured manually (for example, by counting patient breaths) (see also FIG. 47). An okay button 4640 is provided but greyed out in this example until the missing parameter (here respiratory rate) is filled in. Once the parameter is filled in, then the button 4640 may become selectable to update the early warning score or to save the automatically updated early warning score to the memory and/or EMR.

Turning to FIG. 47, an example user interface 4700 is shown with an edit result overlay 4701. In the overlay 4701, a manual input slider 4710 is provided for respiratory rate, which when selected, can cause respiratory rate to be input into the review screen 4600 of FIG. 46. The overlay 4701 can be accessed by selecting the manual override button 4630 in FIG. 46.

Figure 48:
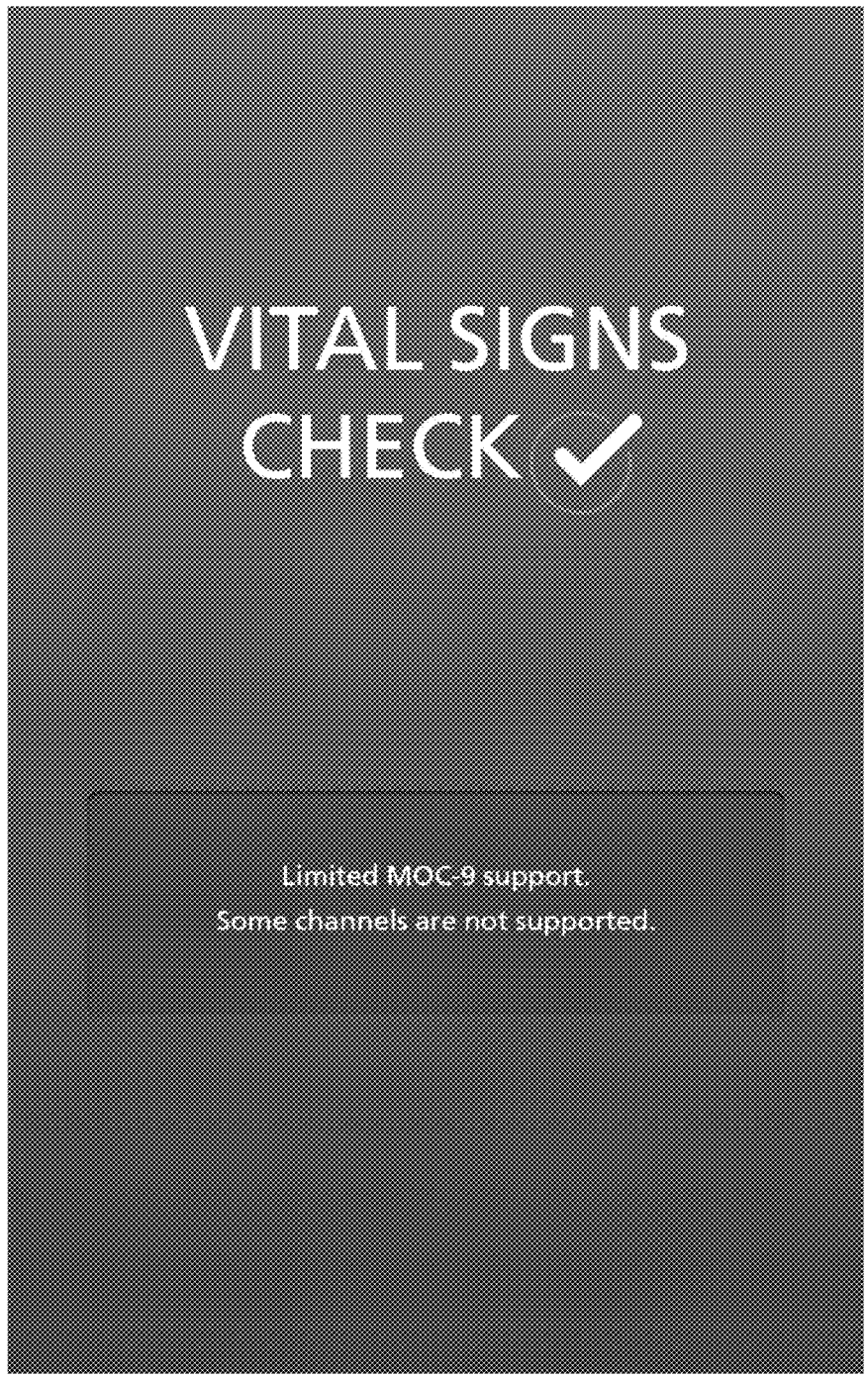
FIG. 48 depicts an example splash screen for an example vital signs check mode.
Figure 53:
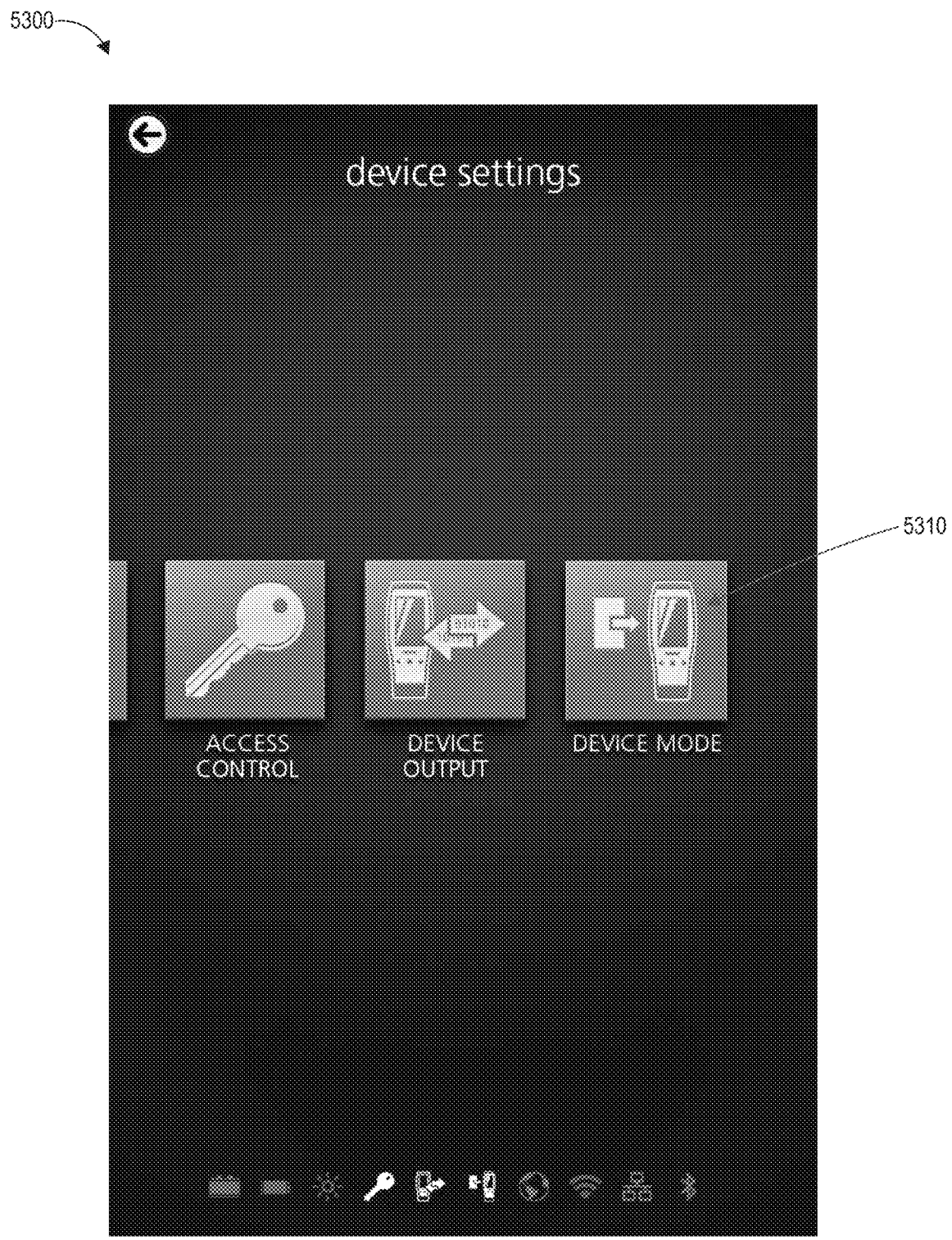
FIG. 53 depicts an example device settings menu.
Figure 54:
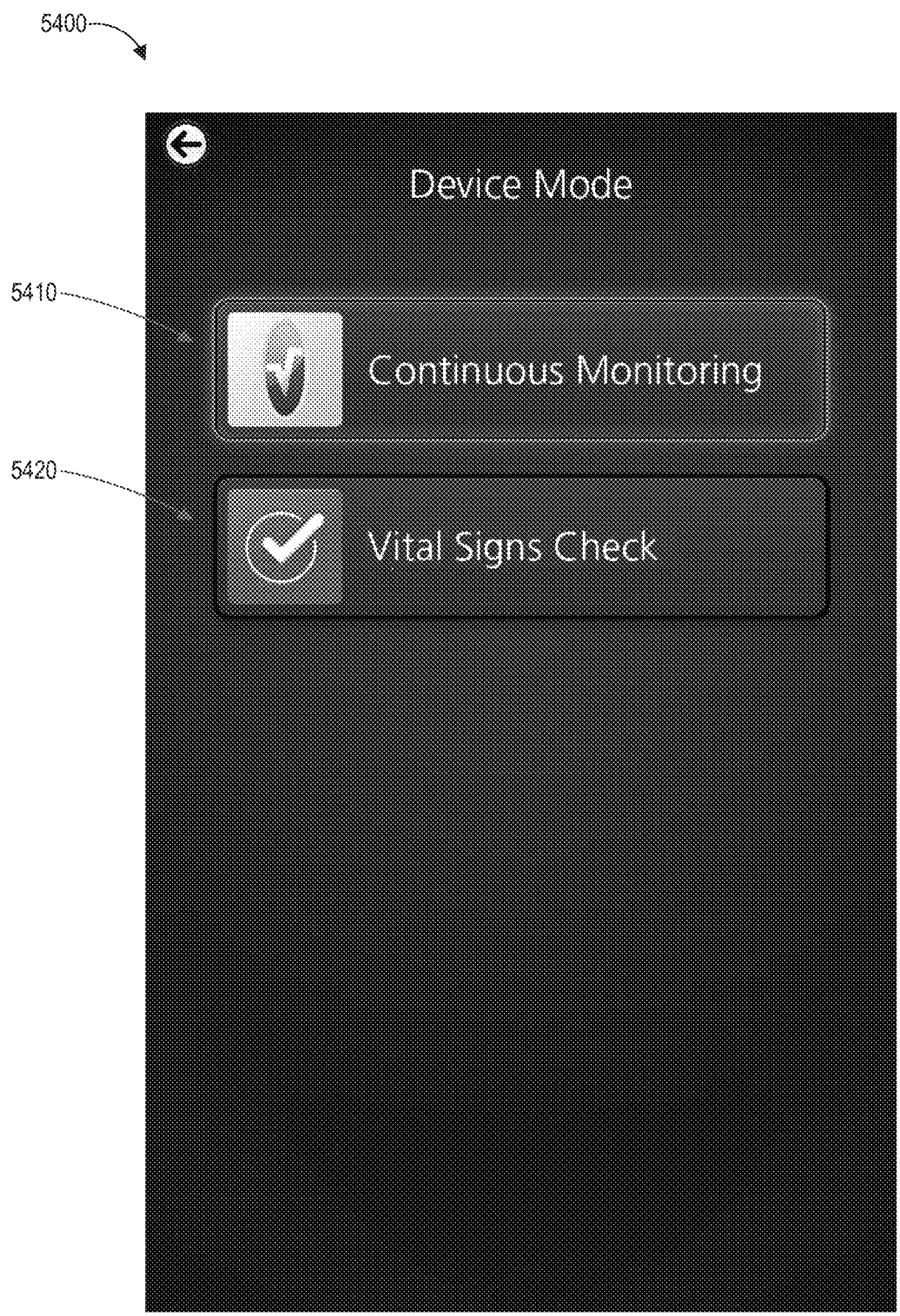
FIG. 54 depicts an example device mode menu.

Turning to FIG. 48, an example splash screen 4800 is shown indicating that the patient monitor is in vital signs check mode (FIGS. 53 through 54 described below illustrate example menus to enter this vital signs check mode). Vital signs check mode is another example mode that can be a hybrid of the continuous mode and spot check mode described above. In a continuous mode, a patient monitor can output changing parameters frequently as well as alarms. In spot check mode, the parameters may stop changing on the monitor display when a spot check measurement is taken. In vital signs check mode, if a spot check is initiated but a clinician waits too long on a spot check related screen to take some action (such as waiting to long to save the spot check measurements), the monitor may revert to a display of continuous measurements. Also, alarms may be triggered in vital signs check mode, for example, by physiological parameters exceeding safe limits. Further, during vital signs check mode, continuous monitoring may continue in the background even while the spot check is being performed on a spot check screen, which may result in an alarm triggering even during review of a spot check measurement.

Figure 49:
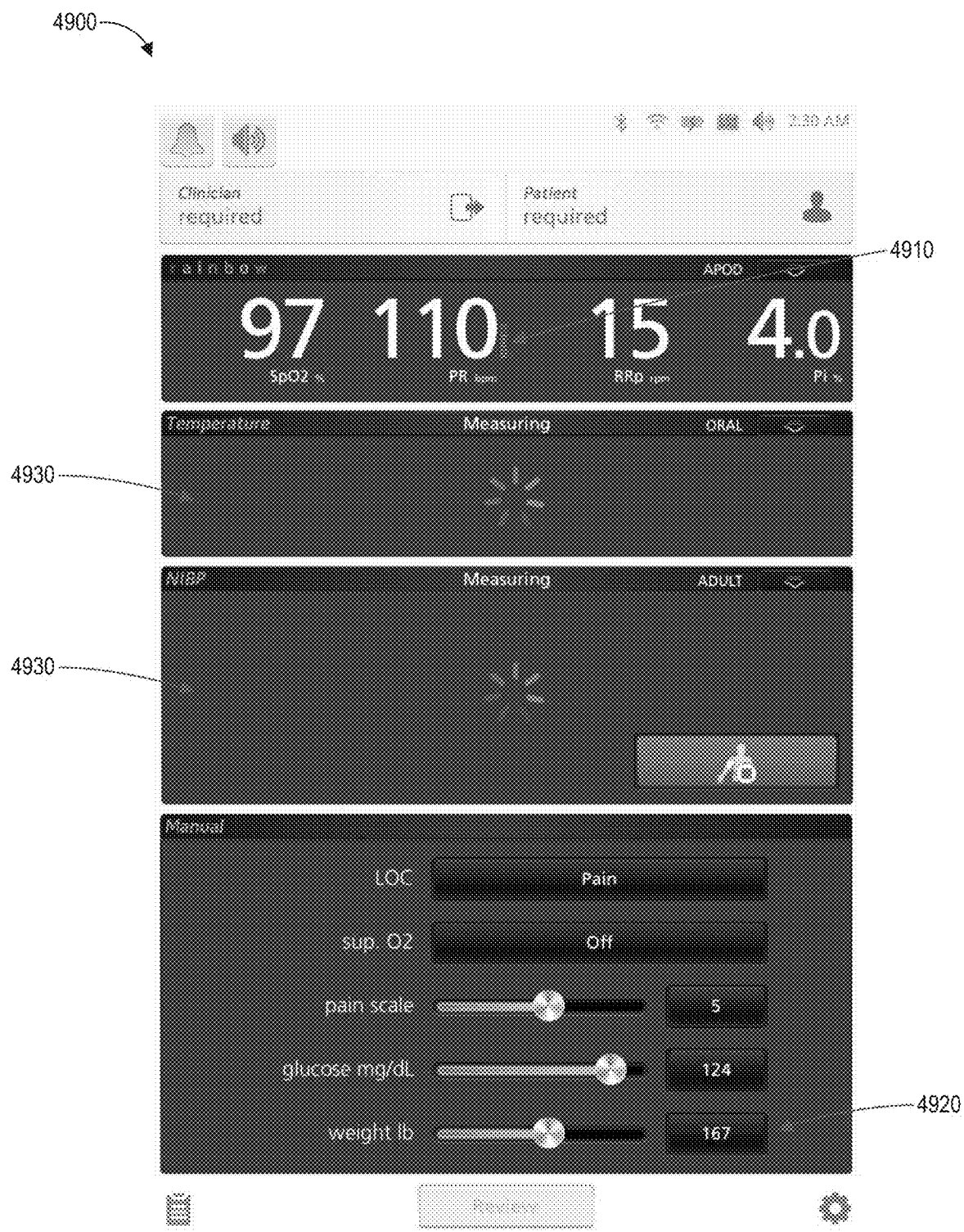
FIGS. 49-50 depict additional example measurement user interfaces.

Turning to FIG. 49, an example measurement user interface 4900 is shown similar to the user interface 2500 of FIG. 25. One difference in this interface 4900 is that a signal IQ indicator 4910 is shown next to the pulse rate measurement. The signal IQ indicator 4910 can indicate the quality of the optical sensor signal used to obtain the measurements shown at the top of the user interface 4900 (including SPO2 pulse rate, respiratory rate and PI). The quality of the sensor signal can reflect the confidence that the algorithm used to calculate the various parameters shown has in the quality of the sensor signal. A noisy or deformed signal, for instance, might be determined to have low signal quality and thus a low signal IQ.

In addition, measurement areas 4930 indicate that measurements are currently being taken from temperature and NIBP sensors, similar to FIG. 25. In addition to the manual entry parameters shown in FIG. 25 in area 2350, another example parameter, weight 4920, is shown being input into the user interface 4900 and is just another example of the many optional manual parameters that can be supplied to the patient monitor.

Figure 50:
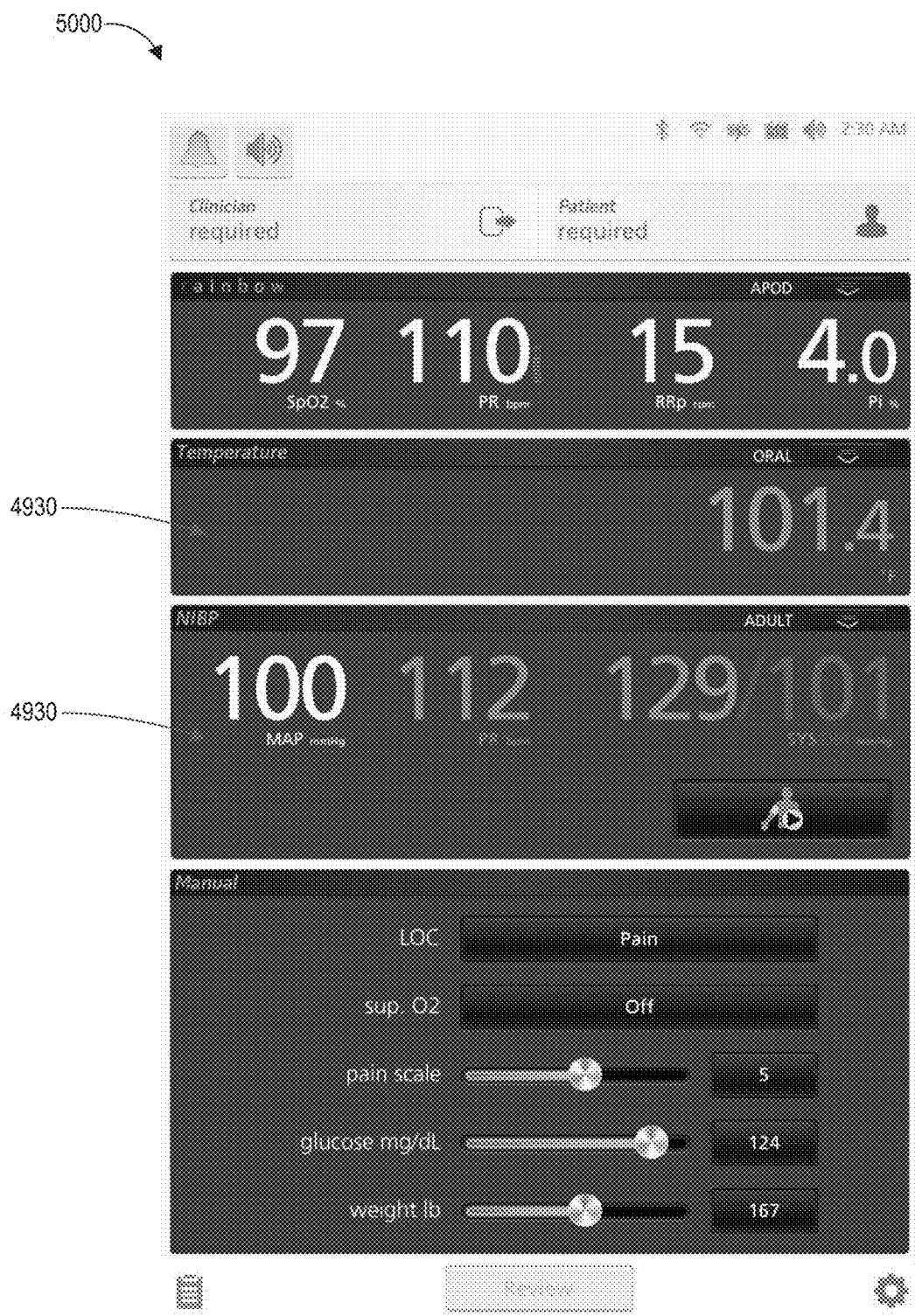

Turning to FIG. 50, an example measurement user interface 5000 is shown that may be reached after the measurement area 4930 of FIG. 49 is populated with measurements. FIG. 50 is similar to FIG. 26 except that FIG. 50 also includes the differences shown in FIG. 49.

Figure 51:
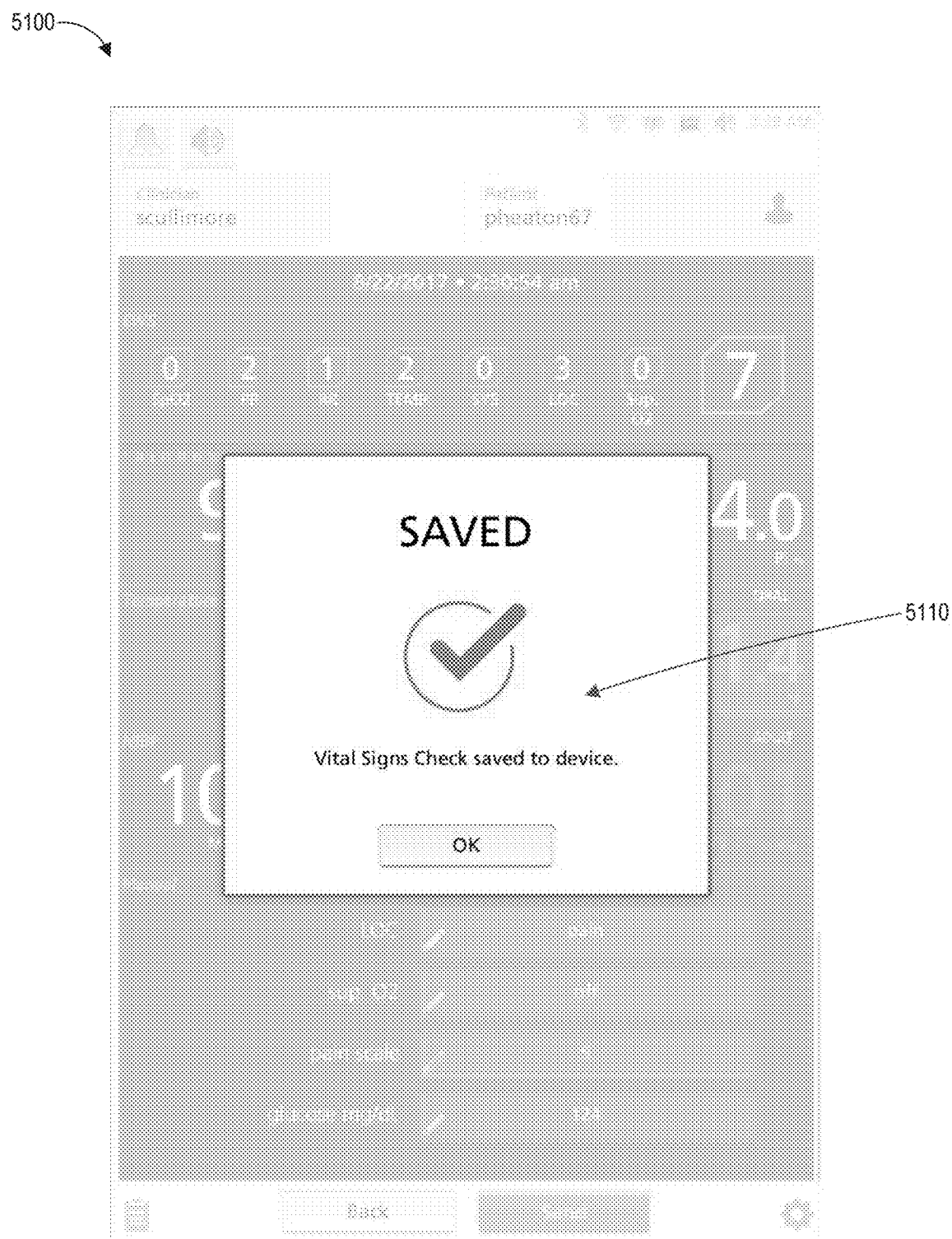
FIG. 51, depicts an example user interface with a vital signs check saved overlay.

Turning to FIG. 51, an example user interface 5100 is shown with a vital signs check saved overlay 5110. The overlay 5110 can indicate that the vital signs check has been saved to the patient monitor. As described above, the vital signs, including the EWS measurements and other parameter values, can be sent over a network to the EMR once the patient monitor is within range or otherwise connected to the network.

Figure 52:
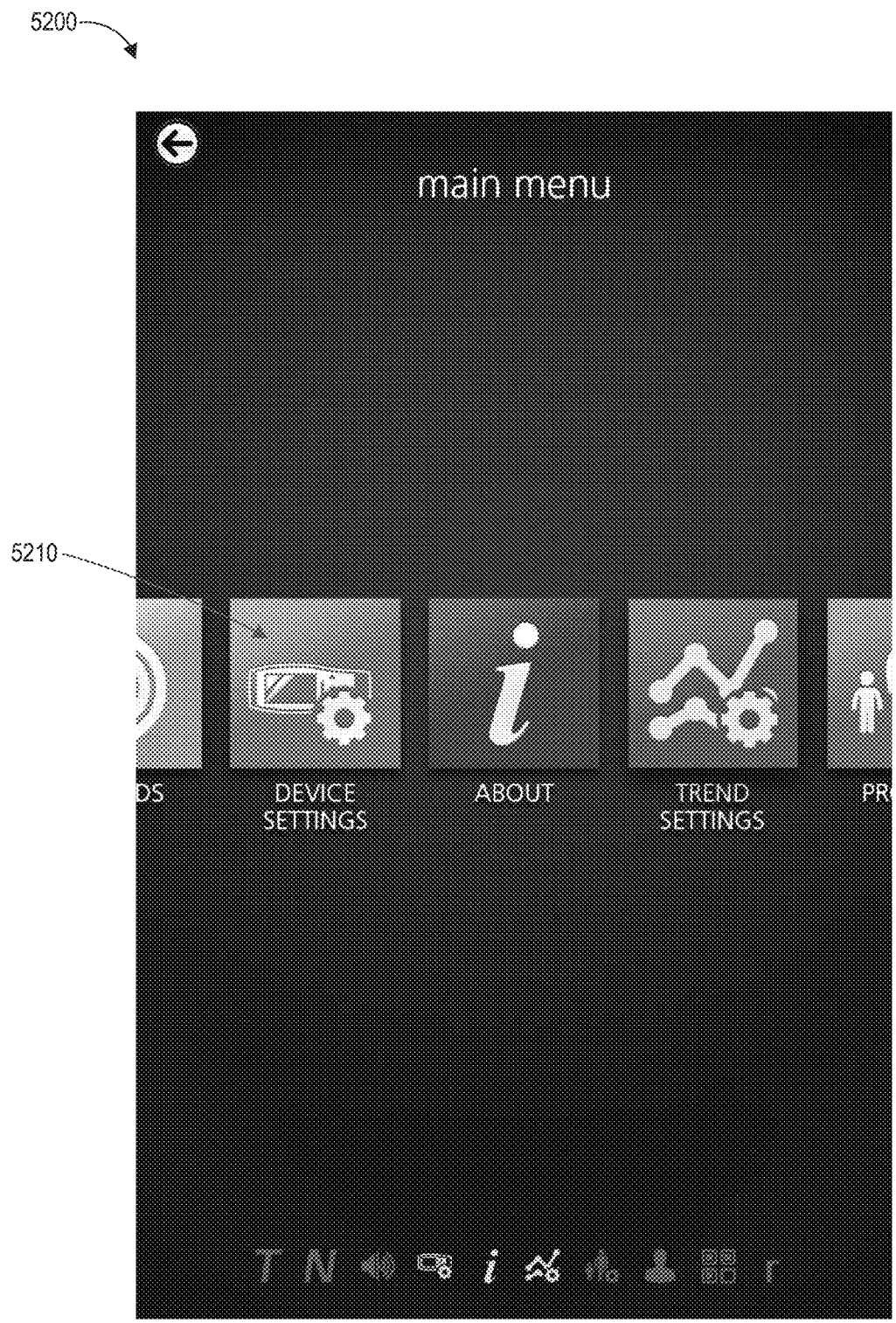
FIG. 52 depicts an example main menu user interface.

Turning to FIG. 52, an example main menu user interface 5200 is shown. The main menu user interface 5200 includes several example settings, including a device settings button 5210, which upon user selection can present the device settings menu 5300 of FIG. 53. In the device settings menu 5300, an example device mode button 5310 is provided, which when selected can output the device mode menu 5400 of FIG. 54. In the user interface 5400, a continuous mode button 5410 is provided as well as a vital signs check button 5420. Selection of the vital signs check button 5420 may lead to user interface 4800 of FIG. 48. Although not shown, a spot check mode may also be provided and may be user selectable in addition to or in place of the vital signs check mode.

Figure 55:
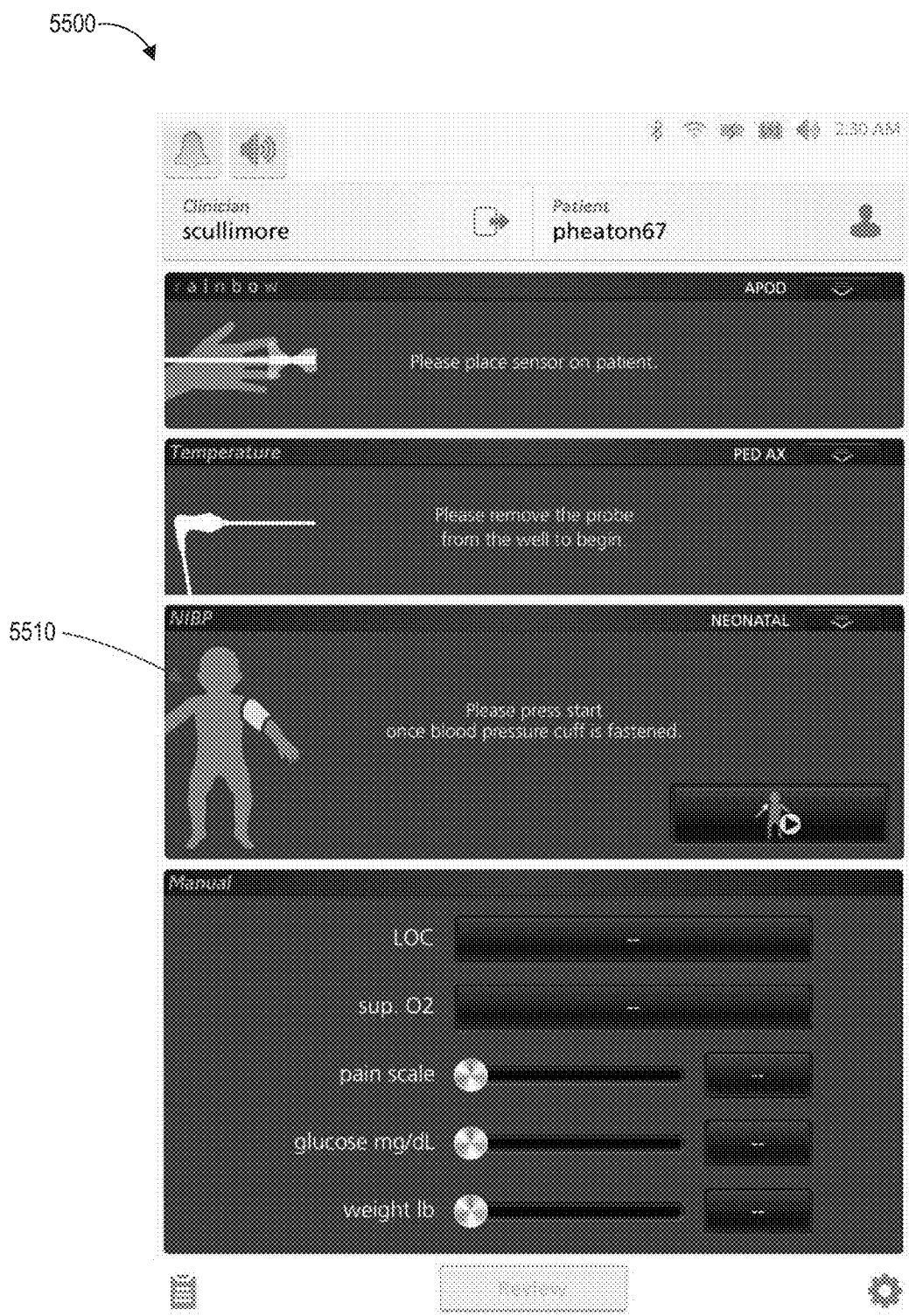
FIGS. 55-58 depict additional example measurement user interfaces.

Turning to FIG. 55, another example measurement user interface 5500 is shown, which is similar to the interfaces of FIG. 23. A difference between FIG. 55 and FIG. 23 is that an image 5510 of a neonate is shown in FIG. 55, whereas FIG. 23 depicts an adult. Displaying either a neonate or an adult image can visually remind a clinician that the patient monitor is in a neonate or adult monitoring mode. Without this reminder, the clinician may accidentally measure an adult with neonate settings or vice versa, which could lead to incorrect measurements or incorrect alarm limits.

Figure 56:
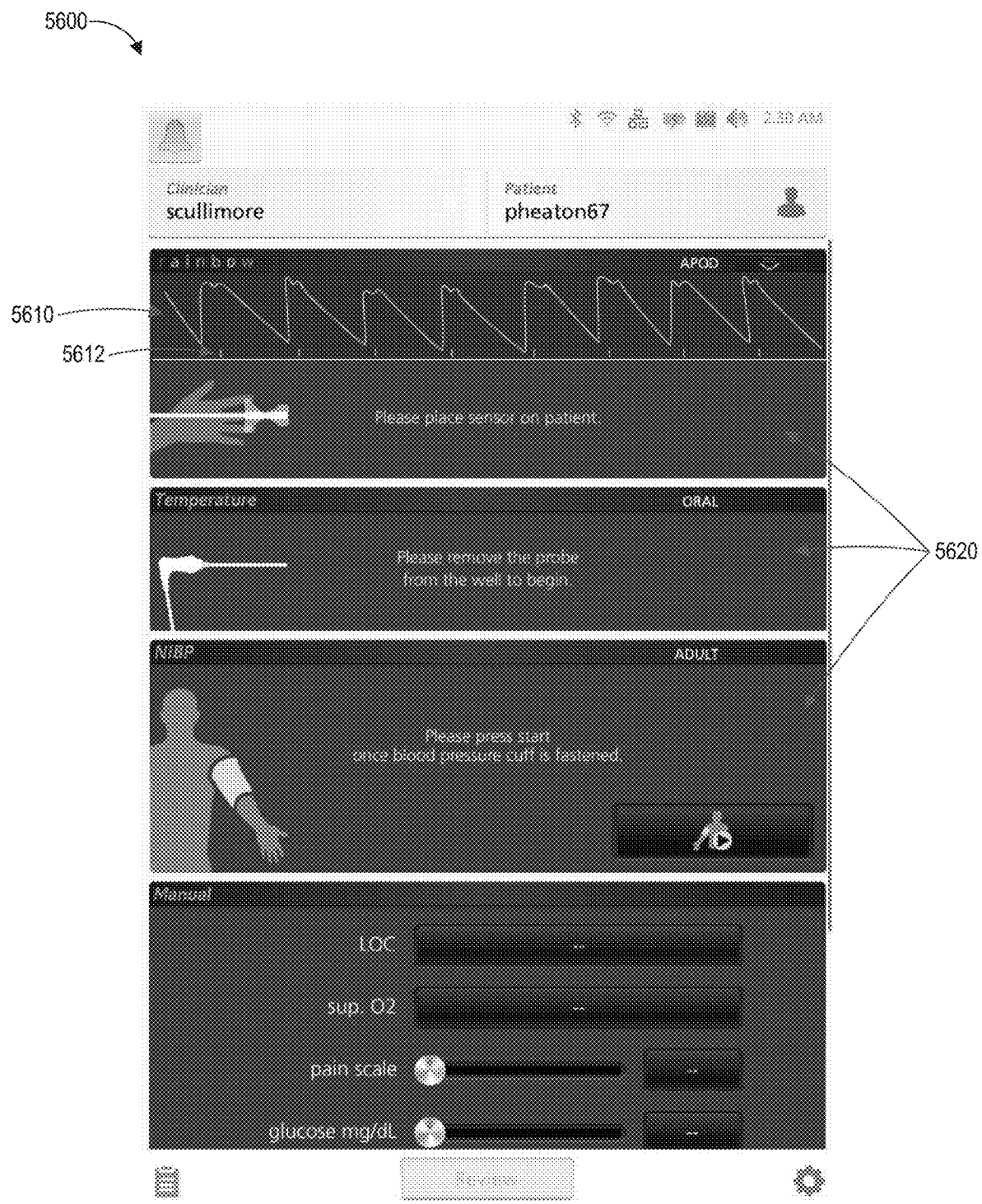

Turning to FIG. 56, another example measurement user interface 5600 is shown, which is similar to the interfaces of FIGS. 23 and 55. In the interface 5600 however, a plethysmograph or pleth waveform 5610 is provided. The waveform 5610 may be updated continuously or frequently while an optical sensor is reading data from a patient. A corresponding signal IQ indicator 5612 is shown underneath the pleth waveform 5610. The height of the bars in the signal IQ indicators 5612 can correspond to signal quality or confidence in the signal. Signal IQ is described in greater detail above. Although not shown, the pleth waveform 5610 may be superimposed with a respiration waveform if a respiration sensor of some kind is connected to the patient. The respiration waveform may also be on a separate area of the display than the pleth waveform 5610 so that they are not overlapping. In addition, as in FIG. 23, there are instructions 5620 to place various sensors on the patient to begin measurement.

Figure 57:
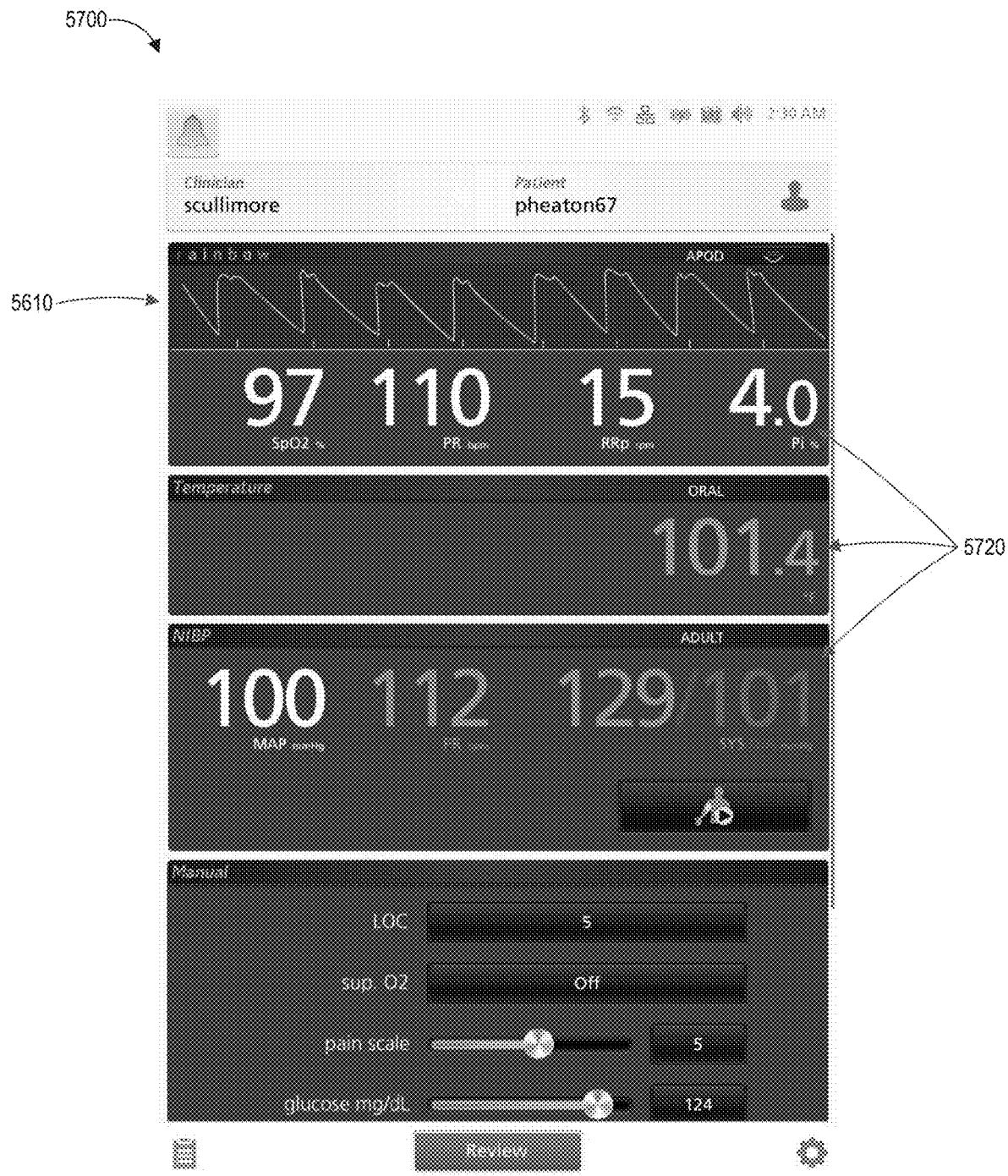

Turning to FIG. 57, another example measurement user interface 5700 is shown, which is similar to that shown in FIG. 26. The user interface 5700 includes measurements 5720 populated based on the sensors connected as instructed in FIG. 56.

Figure 58:
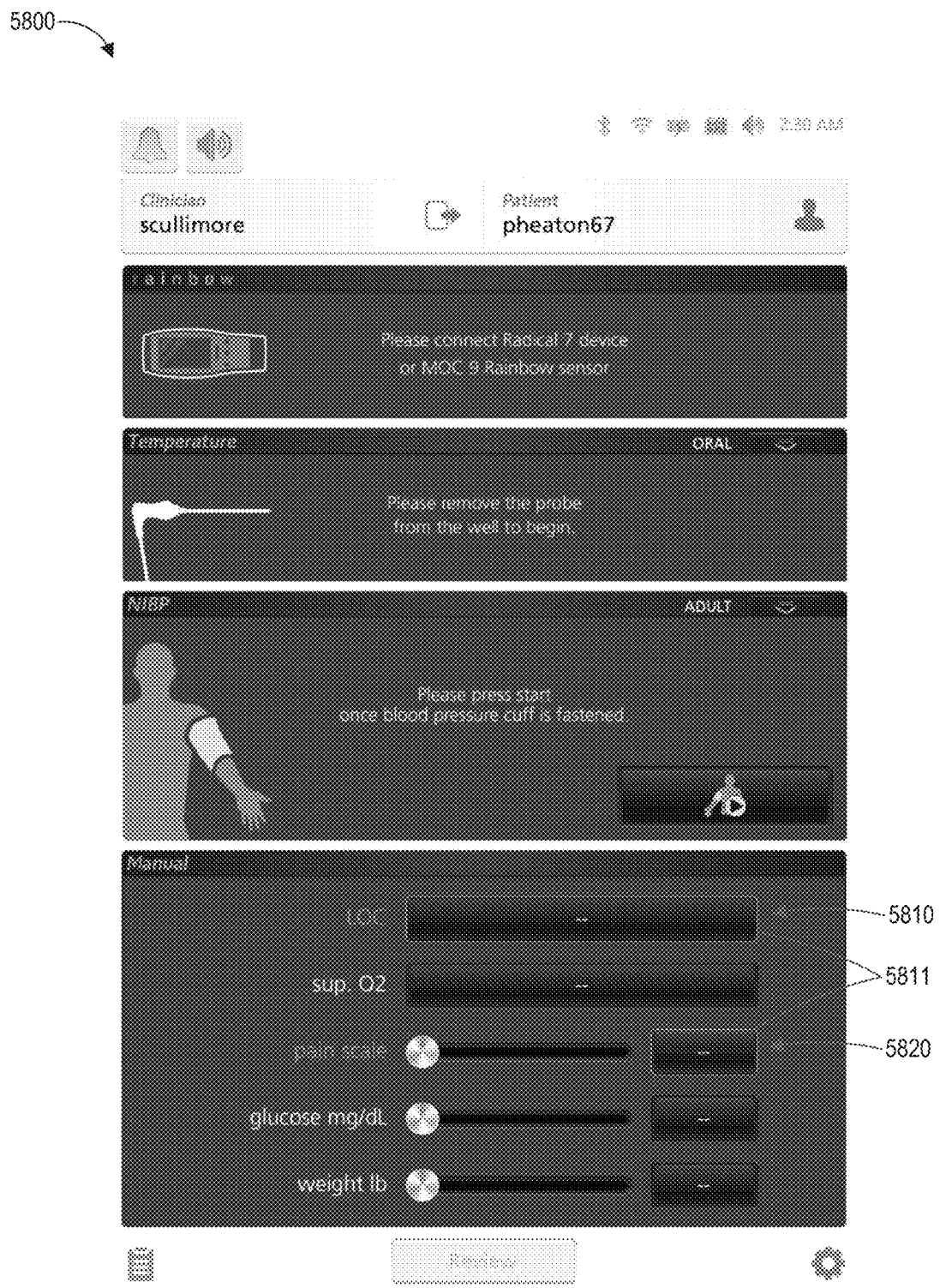

Turning to FIG. 58, another example measurement user interface 5800 is shown similar to the interfaces in FIGS. 55, 56, 23, and 24. However, surrounding fields 5810 and 5820 are bounding boxes 5811 that can indicate that certain parameters may be required for calculating an EWS measurement. For example, the bounding boxes 5811 (which may be boxes that have a light color around them or some other indication that sets them apart from other fields shown) can indicate that those particular parameters required for EWS measurement. However, having bounding boxes 5811 and required EWS measurement parameters can be optional.

Figure 59:
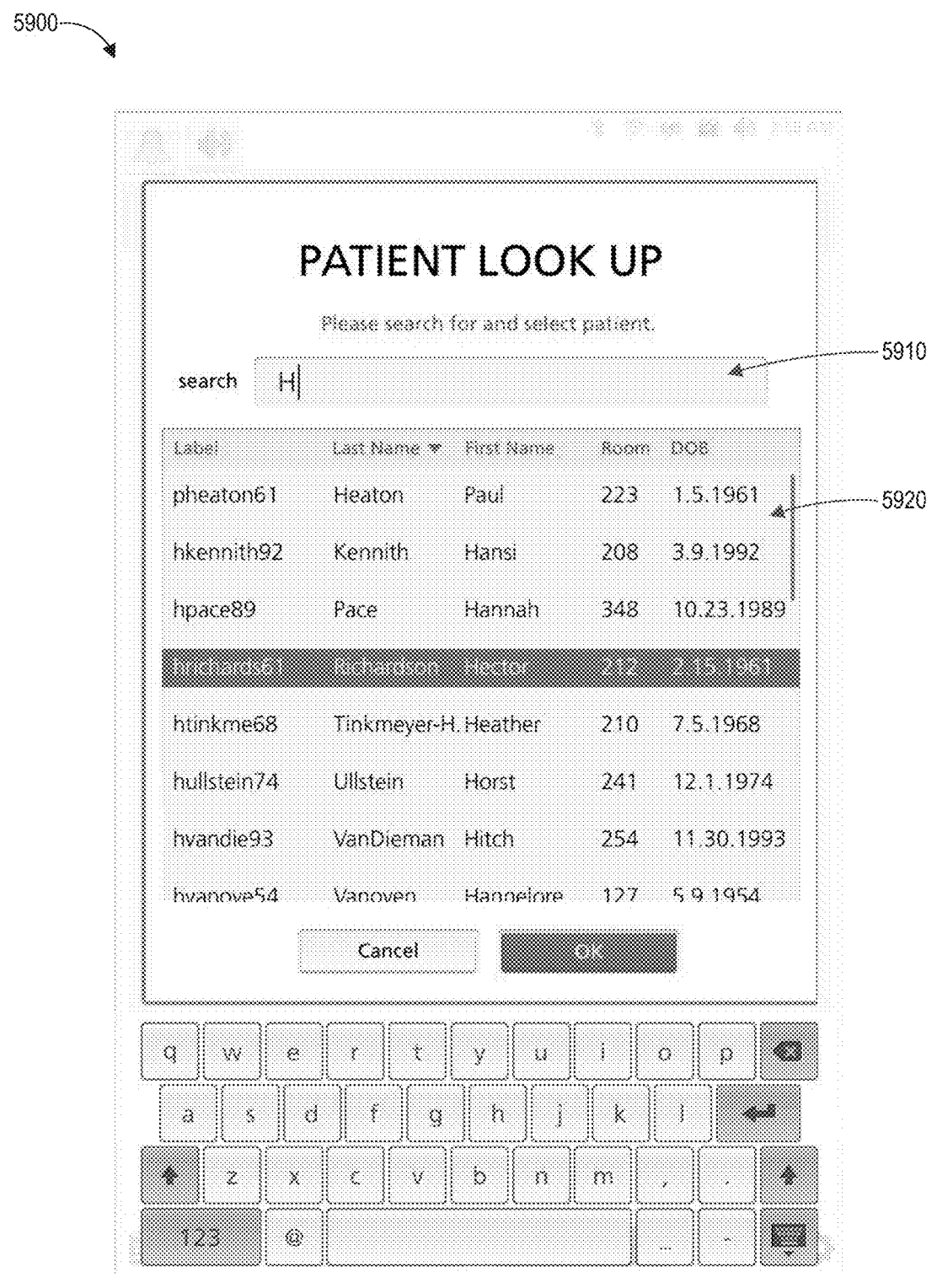

Turning to FIG. 59, an example patient lookup user interface 5900 is shown. As described above with respect to FIGS. 21 through 22, one way to admit a patient and a clinician to the patient monitor 100 is to scan a wrist bracelet of the patient and a badge of the clinician. The patient monitor can then perform an automatic lookup of the patient and clinician and admit or otherwise assign them to the patient monitor. As a result, any parameters and EWS scores calculated for a patient can be associated with the patient and the clinician in the EMR.

In some cases, however, it may not be possible or desirable to use scanning technology. Instead, the patient lookup user interface 5900 or a similar user interface may be used to look up the patient. As shown, a list of patients 5920 is provided, and a search box 5910 is provided to search for a particular patient. Once found, the patient can be selected from the list 5920 to admit them automatically to the patient monitor. A similar user interface like the one shown in FIG. 59 can be used to look up the clinician and admit the clinician to the patient monitor.

Figure 60:
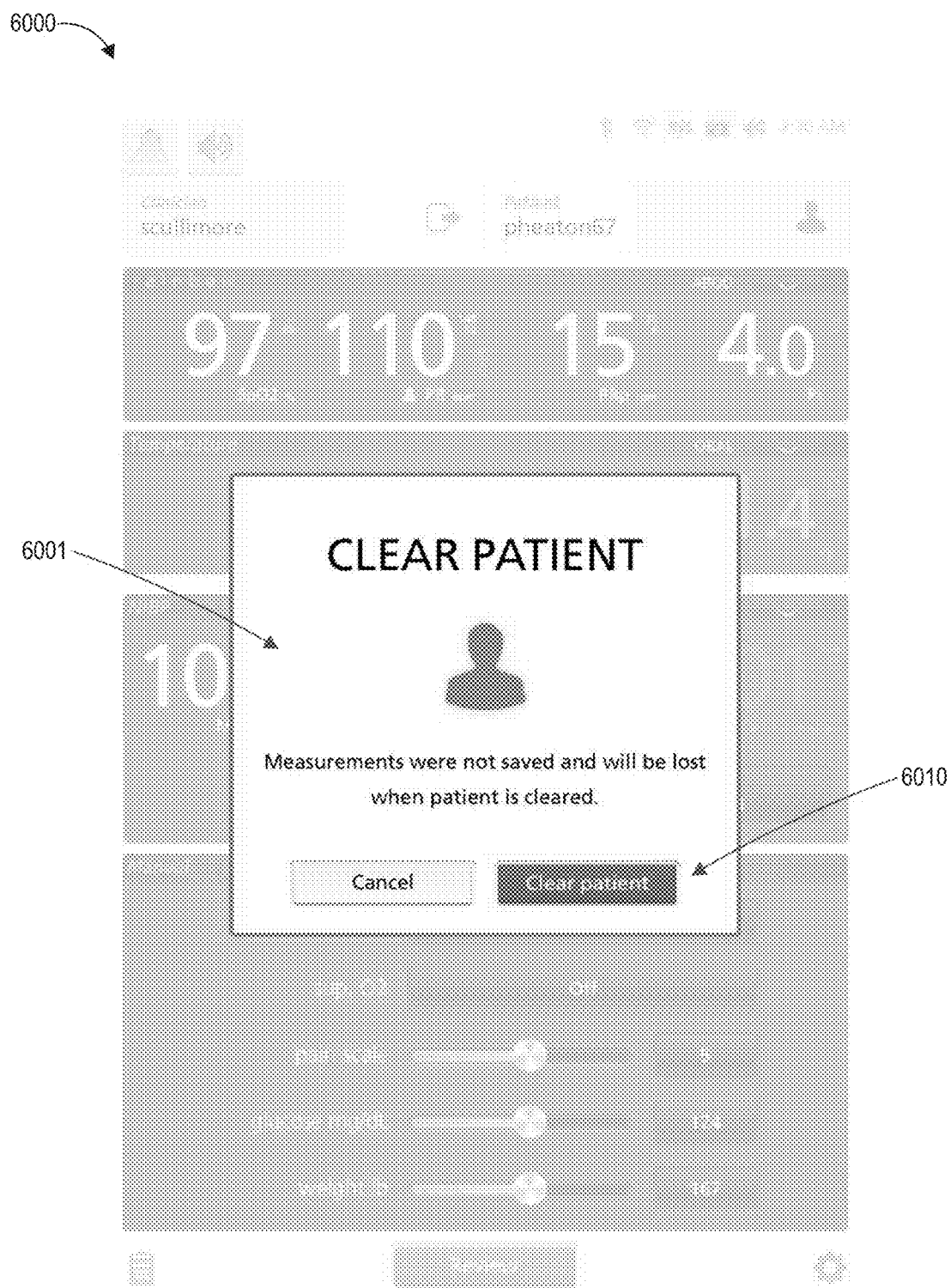
FIG. 60 depicts an example user interface with a clear patient data overlay.

Turning to FIG. 60, another example user interface 6000 is shown with a clear patient data overlay 6001. The overlay 6001 can be reached from any user interface described herein because the purpose of the overlay 6001 can be to clear patient data from the patient monitor. This patient data can be cleared by selecting a clear patient button 6010. Clearing the patient's data can enable the patient monitor to be used for another patient and may entail disassociating the current patient from the patient monitor in the memory of the patient monitor. Clearing the patient data may but need not clear the clinician admitted to the monitor. Clearing the patient data using the overlay 6001 may remove the patient's data from the display, but the patient monitor and/or the EMR may continue to store the patient's data.

Figure 61:
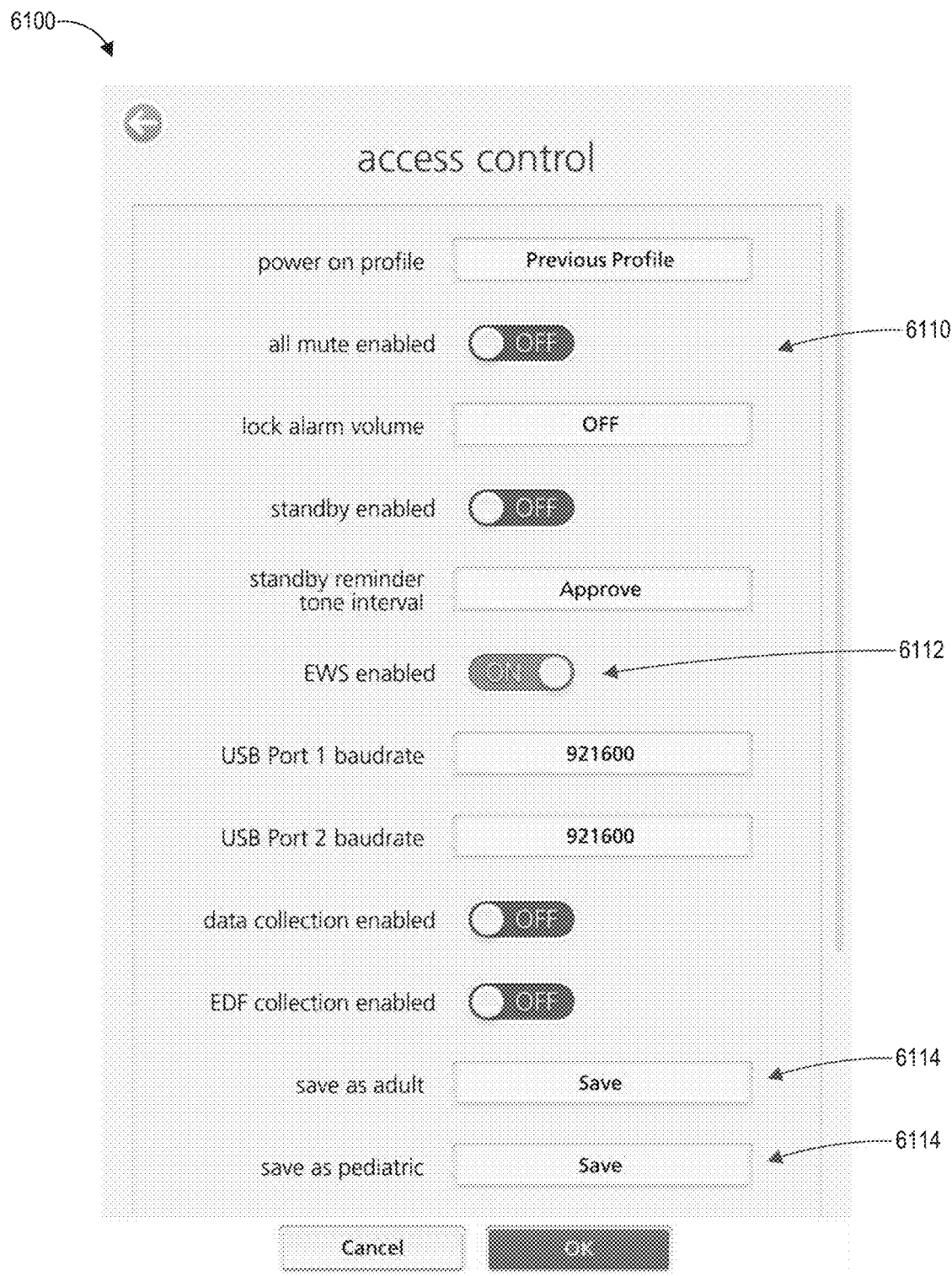
FIG. 61 depicts an example settings user interface.

Turning to FIG. 61, an example settings user interface 6100 is shown that may be output by the patient monitor. The example settings user interface 6100 includes a plurality of different settings for the patient monitor. For example, in "all mute enabled" setting 6110 is provided. Selecting the all mute enabled setting 6110 can cause all alarms to be muted at the patient monitor. Another example setting 6112 can enable EWS calculations or disable EWS calculations. The EWS feature is currently enabled in the depicted example user interface. Additional options 6114 can enable the device to be saved in an adult or pediatric mode so that different particular algorithms can be used by default at the patient monitor, whether adult or neonate.

Figure 62:
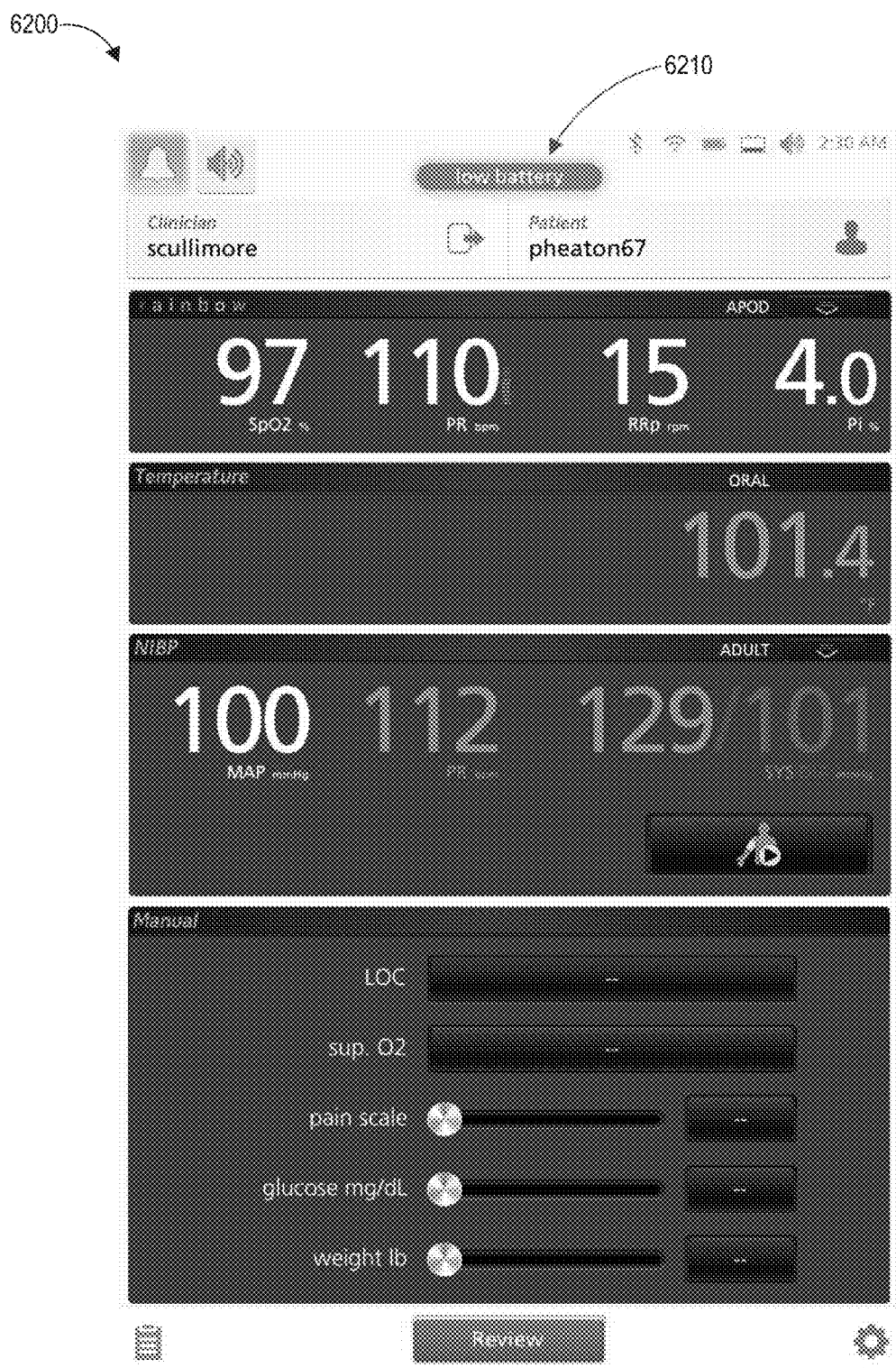
FIGS. 62-64 depict example alarm user interfaces.

Various alarm interfaces will now be described. Turning to FIG. 62, an example alarm user interface 6200 is provided similar to the user interface of FIG. 50. The user interface 6200 includes a low battery alarm 6210 at the top of the display, which can be output on any of the screens described herein but for example purposes is shown on the particular user interface shown.

Figure 63:
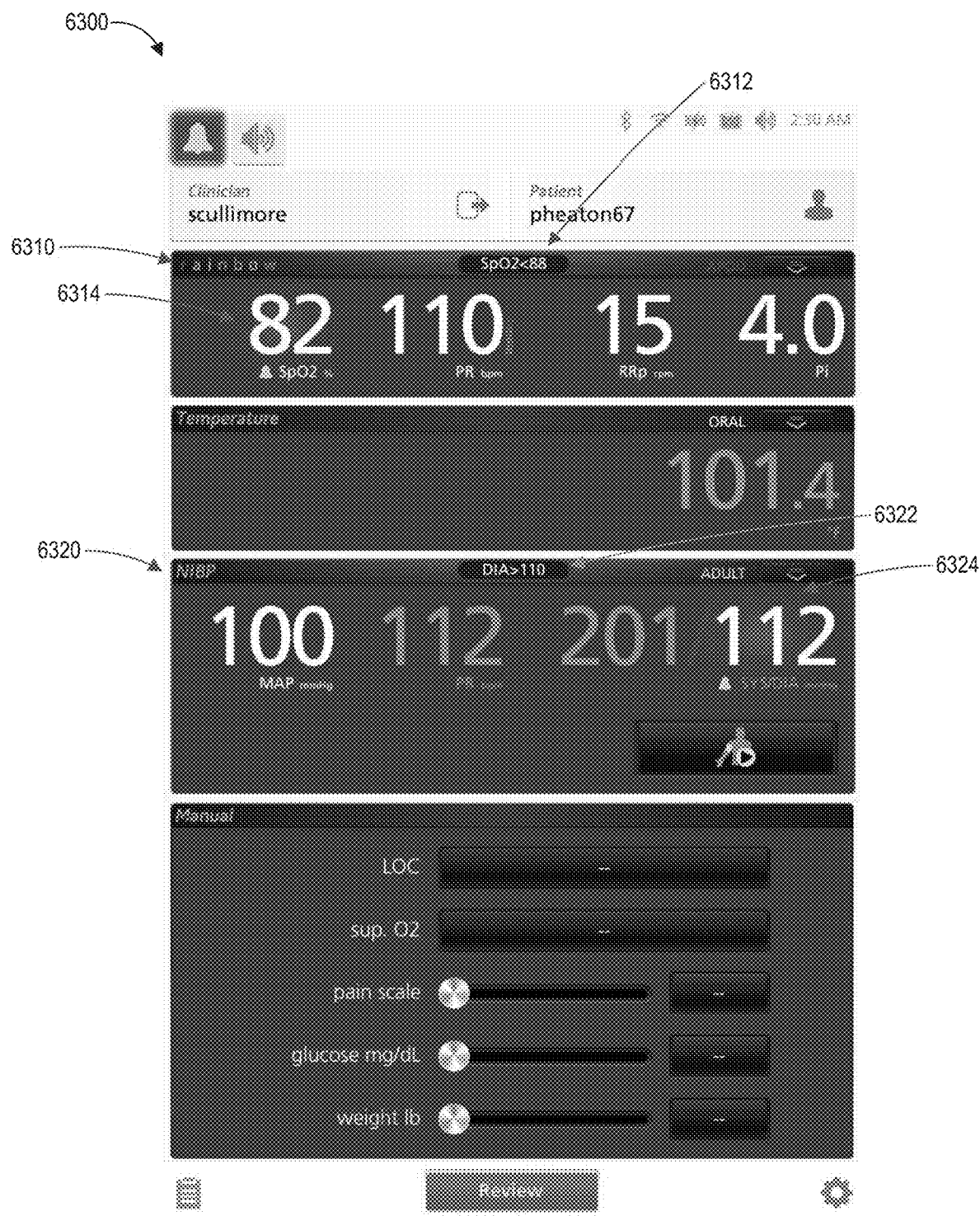

Turning to FIG. 63, another example alarm user interface 6300 is shown similar to that of FIGS. 50 and 62. It includes menu bars 6310 and 6320, both of which can depict alarm notifications for various parameters. The menu bar 6310 includes an alarm notification 6312 for the $SpO_2$ parameter, and the menu bar 6320 includes an alarm notification 6322 for a diastolic blood pressure parameter. In addition, a glow 6314 and a glow 6324 each depict glows behind the parameters that are alarming. The glow can be a colored mass of light, such as red colored behind the parameter of interest such as SPO2 or diastolic blood pressure. The glows can flash to further indicate the presence of an alarm.

Figure 64:
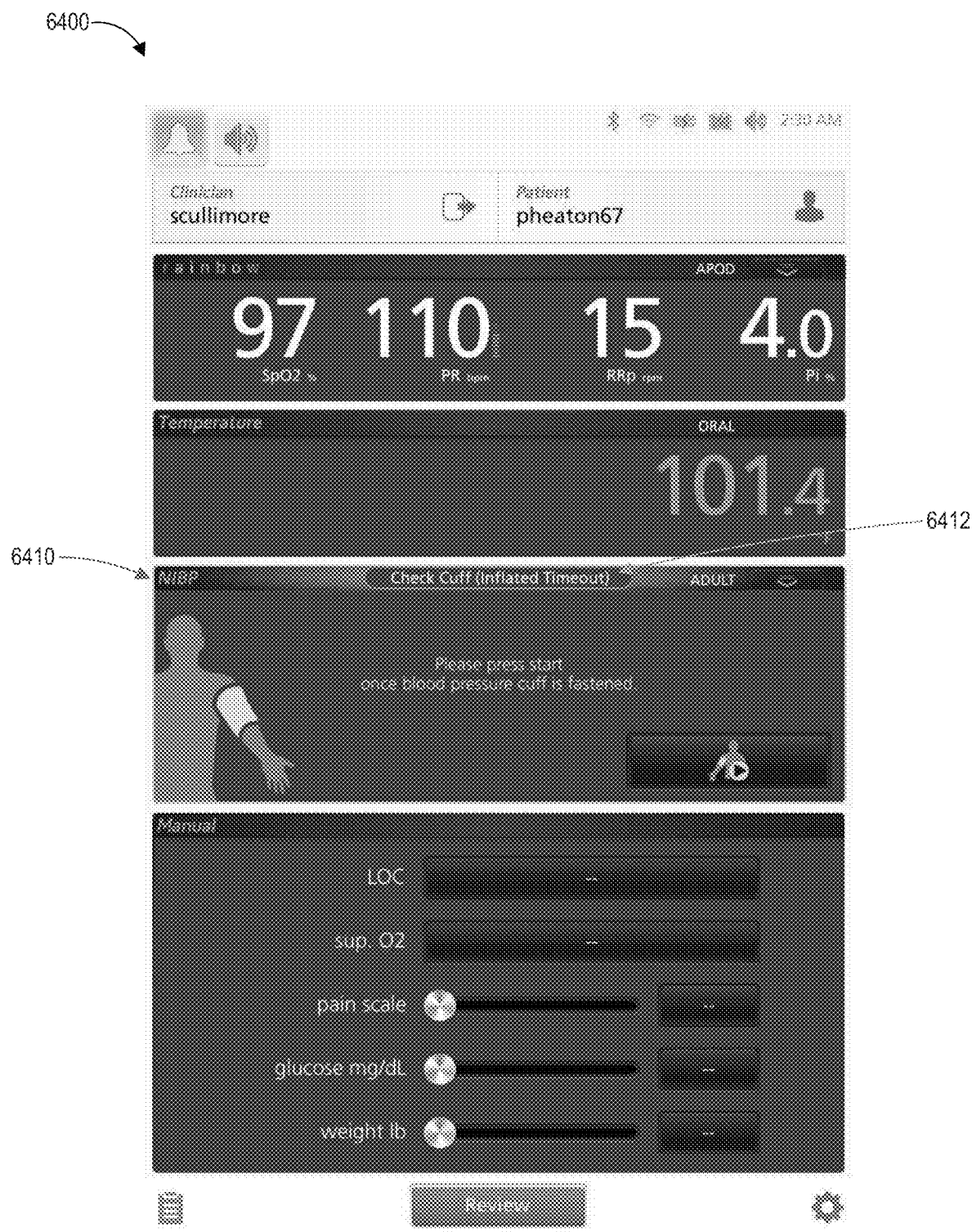

Turning to FIG. 64, another example alarm user interface 6400 is shown similar to the interfaces of FIGS. 50, 62, and 63, which includes a menu bar 6410 that depicts a check cuff inflated timeout alarm 6412. This timeout alarm can show that there is an error with the blood pressure cuff that should be checked.

Figure 65:
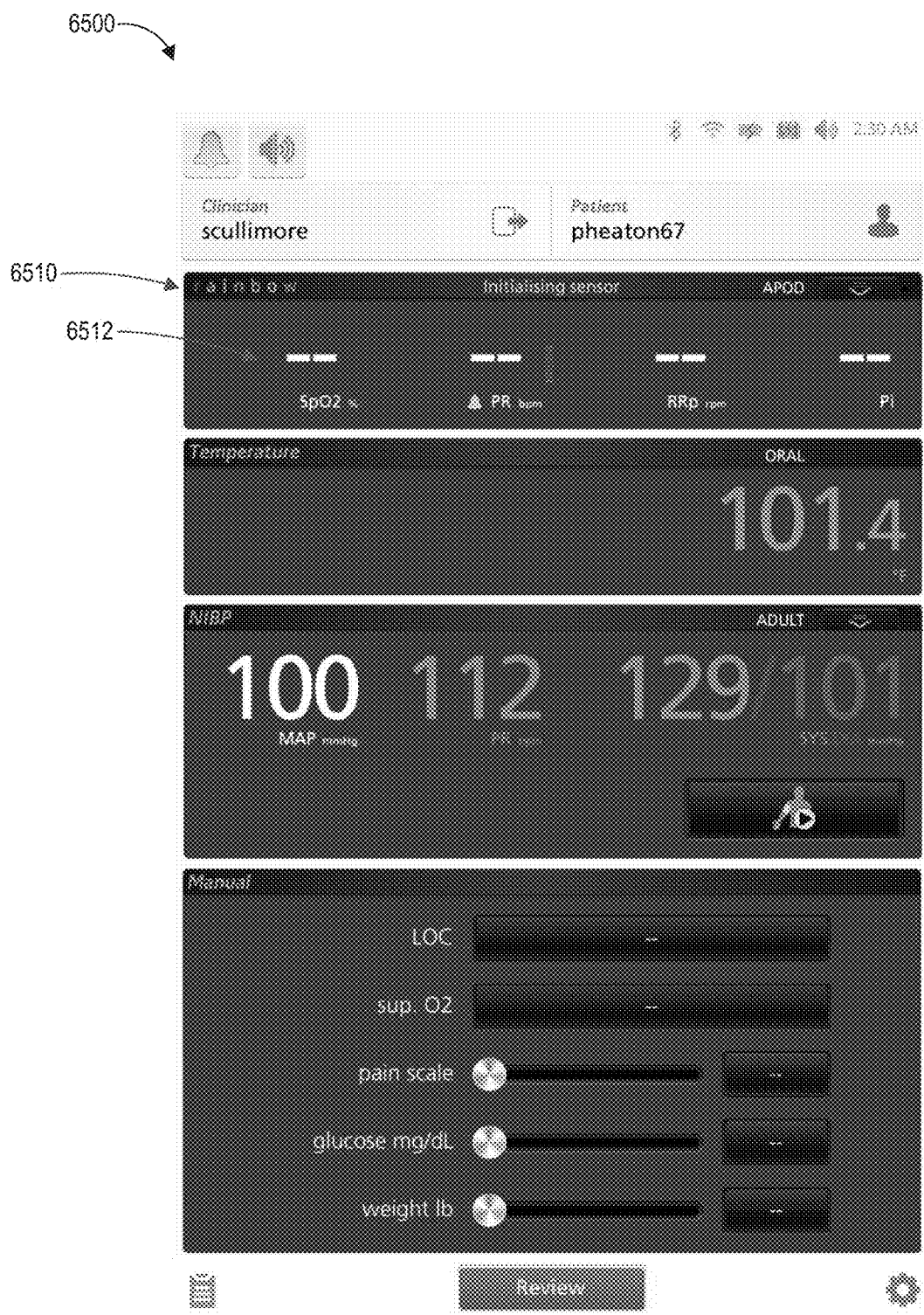
FIG. 65 depicts an example initialization user interface.

Turning to FIG. 65, another example initialization user interface 6500 is shown which is similar to the interfaces in FIGS. 50 and 62-64. A menu bar 6510 is shown that includes an initializing sensor indication 6511, and a blank sensor value 6512 are shown because the sensor has not yet been initialized.

Figure 66:
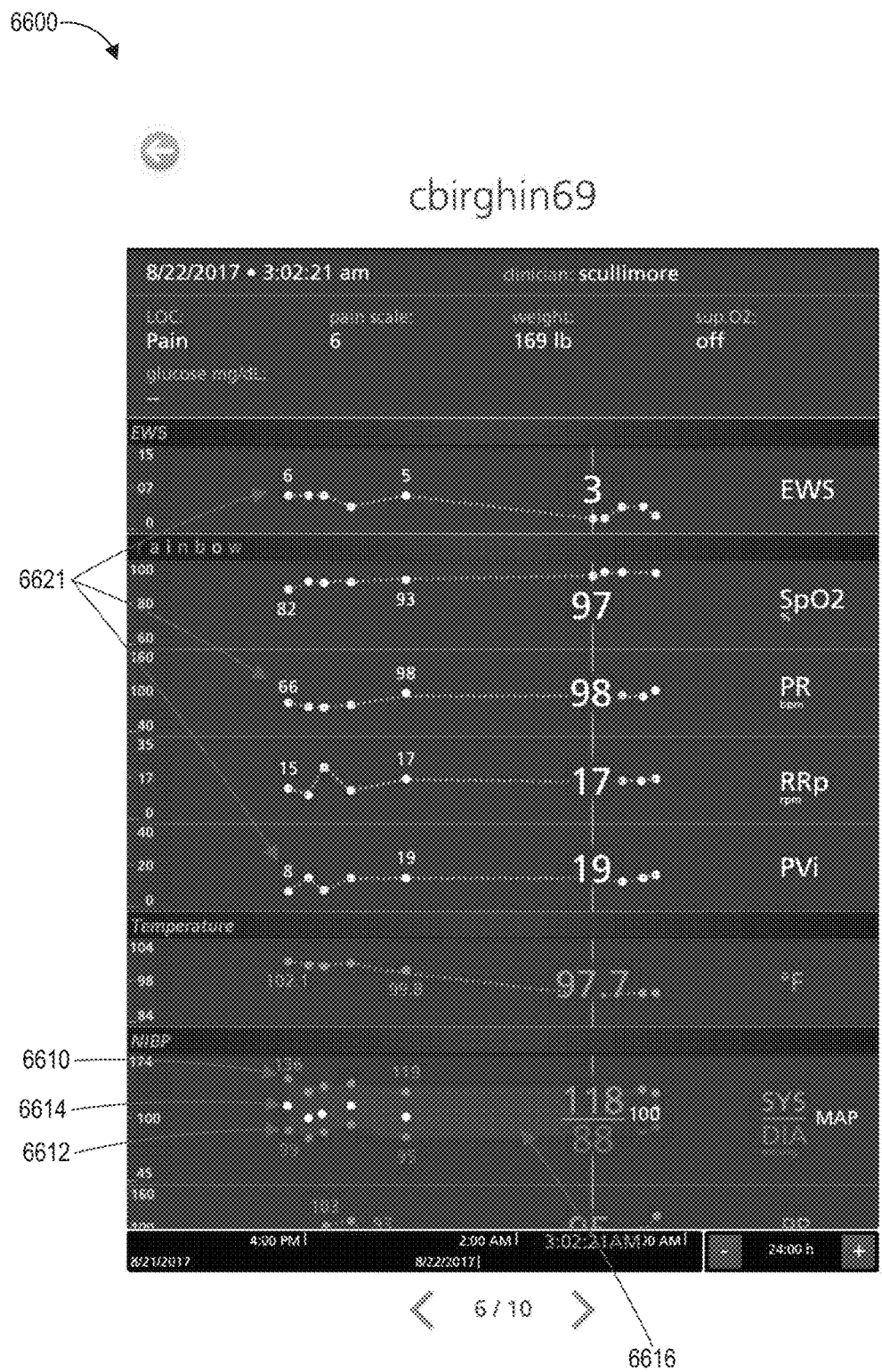
FIGS. 66-68 depict example trend user interfaces.

Turning to FIG. 66, an example trend user interface 6600 is shown. The example user interface 6600 is similar to the user interfaces of FIGS. 32-34 and includes trends 6621 similar to the trends 3221 of FIG. 32. For blood pressure, however, instead of including a trend as in FIGS. 32-34, a more robust set of data is displayed. This data includes points 6610 corresponding to systolic blood pressure points, points 6612 corresponding to diastolic blood pressure shown vertically below the points 6610. Between the points 6610 and 6612 are points 6614 which correspond to main arterial pressure (MAP). A green band 6616 is shown to indicate the difference between the systolic and diastolic pressures at various points. The color and shading of the band 6616 can be varied.

Figure 67:
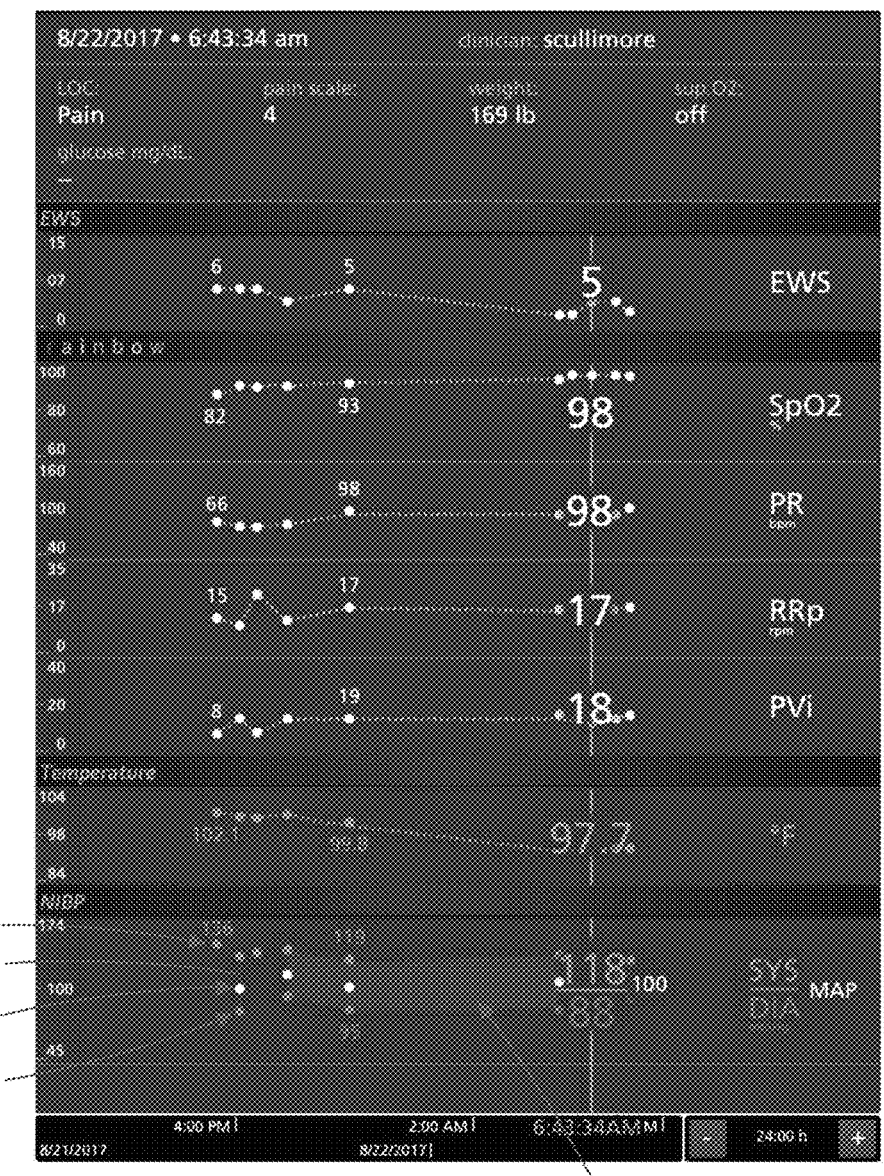

Turning to FIG. 67, another example trend user interface 6700 is shown. The user interface 6700 is similar to the user interface of FIG. 66, except that in this example, the blood pressure data is depicted differently. There are systolic points 6710 and diastolic points 6714 and mean arterial points 6712, just as in FIG. 66. In addition, a band 6716 is shown to indicate the difference between the systolic and diastolic points 6710, 6714. However, the band 6716 (which may be colored green or some other color or otherwise shaded) is shown for measurements that have both systolic and corresponding diastolic measurements directly beneath them. Other diastolic measurements or systolic measurements may be provided that do not have a corresponding systolic or diastolic measurement. As a result, example sole systolic measurements are shown without another corresponding measurement vertically below. When only one type of blood pressure measurement can be obtained (systolic or diastolic), main arterial pressure may not be calculated, and the band 6716 does not extend to those measurements. However, a line 6716 may be drawn between measurements that are disconnected from the band 6716 by virtue of a discontinuity with respect to systolic or diastolic measurements. The line 6716 can pass through a mean arterial pressure point 6712 as shown.

Figure 68:
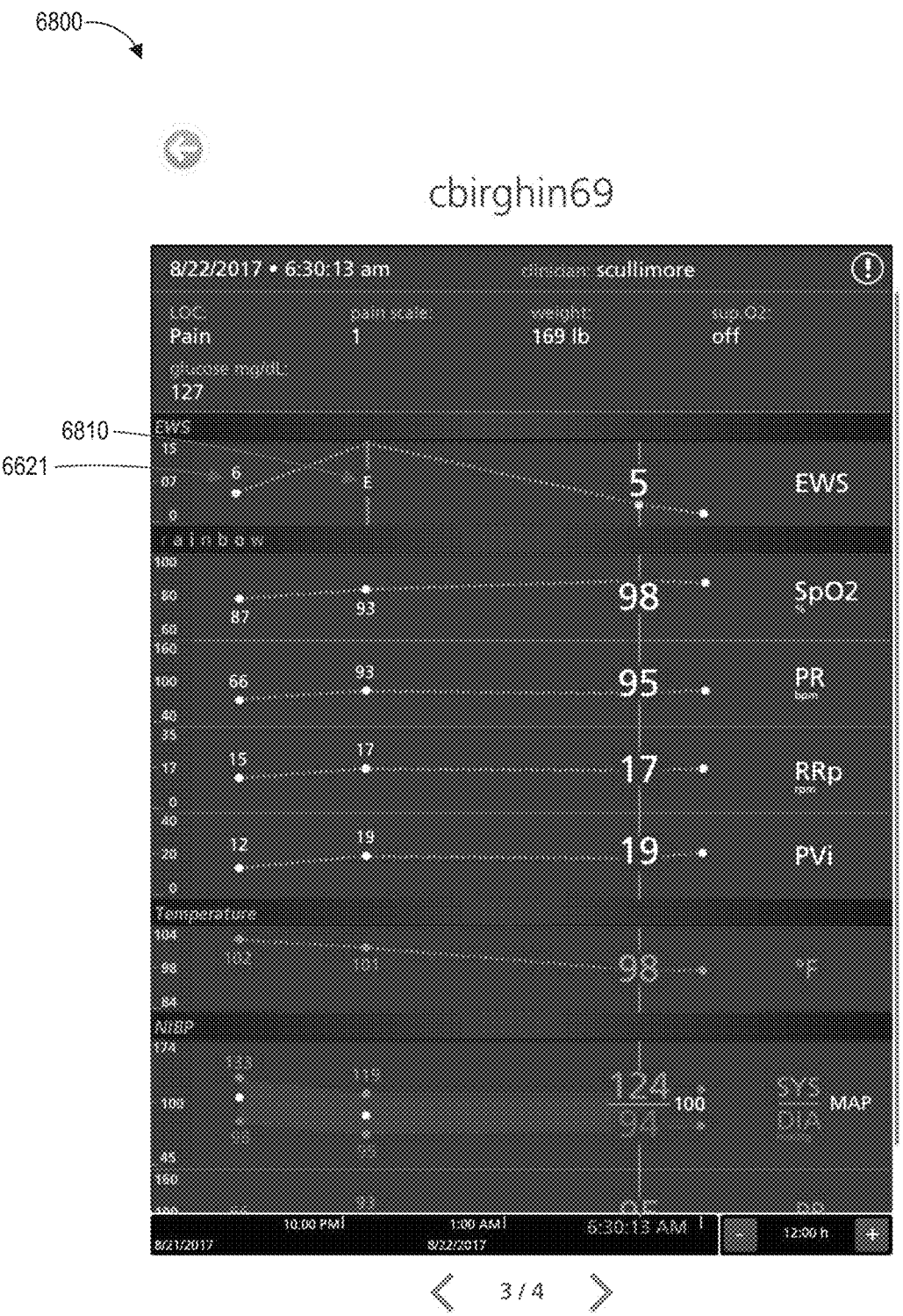

Turning to FIG. 68, another example trend interface 6800 is shown. The interface 6800 is similar to the interface of FIGS. 66 and 67 except that the user interface includes an emergency marker 6810 on the trend graph 6621 for the EWS score. Emergency marker 6810 is similar to the vertical emergency bar 3726 of FIG. 37 and is also a vertical emergency bar. However, the emergency marker 6810 includes an E superimposed thereon to indicate that an emergency occurred at that time. The E need not be superimposed on the marker 6810, or the E may be superimposed upon the vertical bar 3726 in FIG. 37. Many other variations are also possible.

Spot-Check Overview

Any of the features described above, including EWS features, spot-check features, and vital signs check features, can be combined with any of the additional optional features set forth below. Spot-check measurements, for instance, can involve applying a sensor or sensors for a period of time to a patient and obtaining signals from the sensors, which can be utilized to determine one or more of various measurements, such as one or more physiological parameters associated with an individual. In general, a spot-check system can employ a credit- or token-based scheme in which one or more credits can enable spot-check monitor and/or a sensor to make a single measurement of a group of predefined parameters. Expressed differently, a credit can, in effect, act as a voucher that can be exchanged for a group of measurements.

The number of spot-check credits, and thus the number of remaining or available spot-check system uses, associated with any given user, patient monitor, or sensor can be controlled or limited. For example, the number of spot-check credits can correspond to a service life of a sensor or patient monitor, which can be defined in terms of a permitted or estimated number of available uses or amount of usage time. In some cases, an available use (and/or a signal spot-check credit) can correspond to a single measurement of a group of predefined parameters and/or can correspond to receiving a single signal (for example, over a particular duration of time) from a spot-check sensor. Accordingly, the credits can advantageously provide a mechanism to inform users that a medical device, such as a sensor, has exceeded its designed service length. In addition or alternatively, the number of spot-check credits can correspond to a number of prescribed or recommended measurements. For example, the tokens can be provided to the patient by a physician based on a prescription. Still, in some cases, the spot-check credits can represent a quantum of currency, specifying a price per use or per unit time. Further, tokens can correspond to a subscription service.

A spot-check system can include a physiological monitor in communication with a sensor so as to perform spot-check measurements in conjunction with the sensor. The physiological monitor or the sensor can include a memory that stores a number of remaining spot-check credits. The monitor can read the number of remaining spot-check credits, and the monitor can be enabled to make a physiological measurement in conjunction with the sensor if the number of remaining spot-check credits is greater than a threshold (non-limiting example: zero). The number of spot-check credits can be decremented in response to a determination that a valid spot-check signal was received.

For various reasons, a signal from a spot-check device may be invalid and/or a measurement or parameter determined from a signal from a spot-check device may be invalid. It will be appreciated that throughout this specification reference is made to an invalid signal. In this sense it is to be understood that the term invalid signal can be broadly construed as any signal that is determined to be unreliable or inaccurate. Furthermore, in some cases, an invalid signal can be broadly construed as corresponding to an undesired measurement, irrespective of whether the signal was reliable or accurate. Example considerations in the determination of an invalid signal include, but are not limited to, the stability of the signal, the presence of interference on the signal, a signal Identification and Quality indicator ("signal IQ"), a comparison to previous or valid signal, a confidence of the signal, patient movement during the sensing of a sensor, the placement of the sensor, cancellation of a measurement, timing of a cancellation, a successive or duplicative measurement, or the like.

In some cases, the number of spot-check credits is not decremented in response to a determination that an invalid spot-check signal was received. In other words, despite taking receiving a signal, the spot-check system can effectively ignore or disregard it due to it invalidity. By determining whether a spot-check signal is valid or invalid, the spot-check system is advantageously improving patient monitoring.

System Overview

Figure 69:
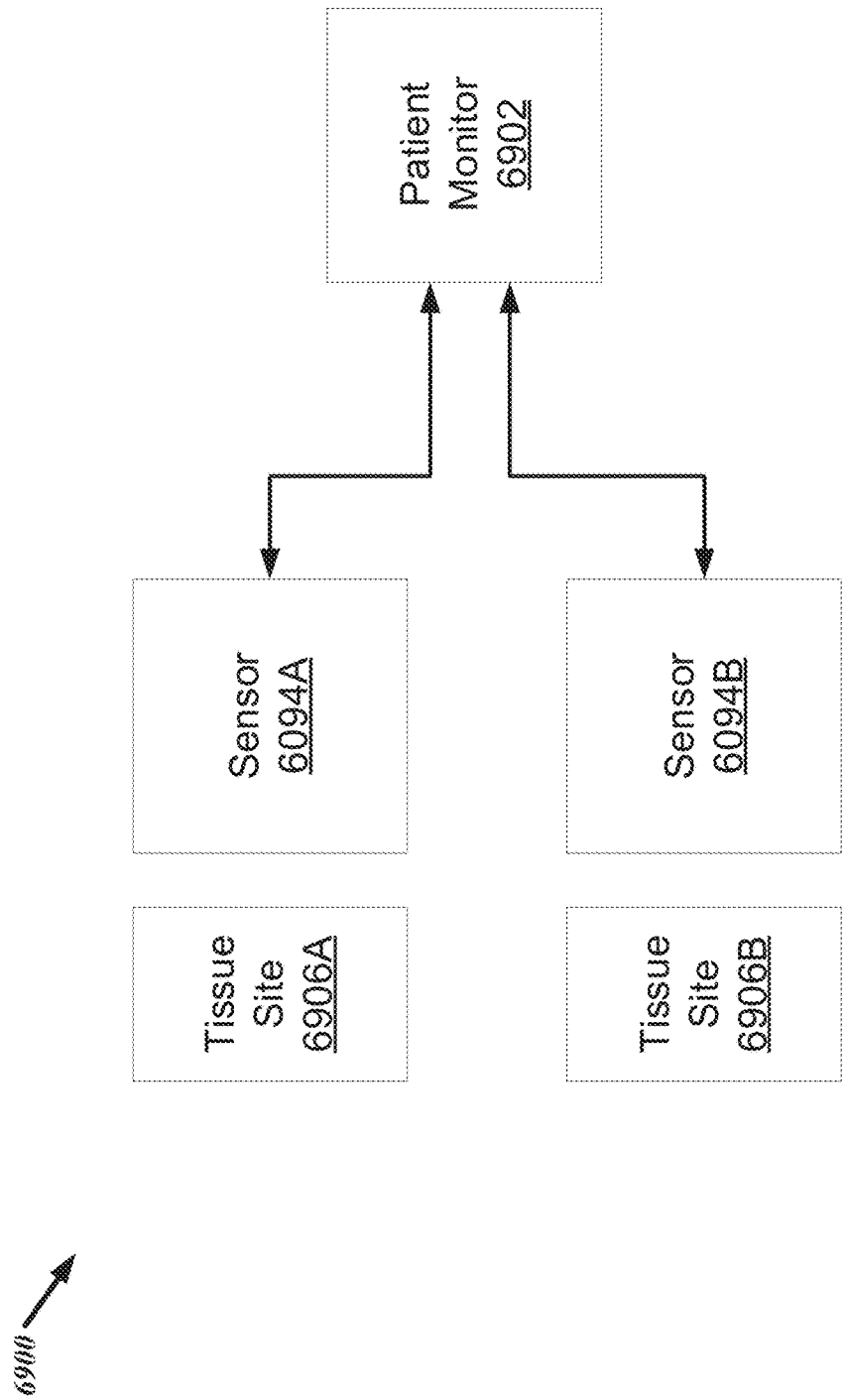
FIG. 69 illustrates an example spot-check monitor.

FIG. 69 illustrates an example spot-check system 6900 that includes a spot-check monitor 6902 and sensors 6904A, 6904B. The sensors 6904A, 6904B can be applied to patient tissue sites 6906A, 6906B, respectively, and generate one or more signals. The spot-check monitor 6902 can receive the one or more signals from the sensors 6904A, 6904B and can determine, based on the received signal(s), one or more measurements, such as one or more physiological parameters.

Each of the sensors 6904A, 6904B can include a combination of one or more various sensors. For example, the sensors 6904A, 6904B can include, but are not limited to, a spectrometer, a pulse oximetry device, a plethysmograph sensor, a pressure sensor, an electrocardiogram sensor, or acoustic sensor, among other sensors. The tissue sites 6906A, 6906B can include one or more of a finger, a nose, a limb, a head, an ear, a neck, an upper body, or a lower body.

The spot-check monitor 6902 can include a sensor interface and a processor. The spot-check monitor 6902 can receive a signal from one or more of the sensors 6904A, 6904B and can determine, based on the received signal, one or more physiological parameters, such as blood oxygen saturation (SpO2), pulse rate (PR), pulse rate variability (PRV), Perfusion Index (Pi), Total Hemoglobin (SpHb®), Oxygen Content (SpOC™), Pleth Variability Index (PVi®), Methemoglobin (SpMet®), Carboxyhemoglobin (SpCO®), Acoustic Respiration Rate (RRa®), a concentration of an analyte, pulse pressure variation (PPV), stroke volume (SV), stroke volume variation (SVV), mean arterial pressure (MAP), central venous pressure (CVP), Carboxyhemoglobin (HbCO), or Methemoglobin (HbMet), among other parameters.

System Structure

Figure 70:
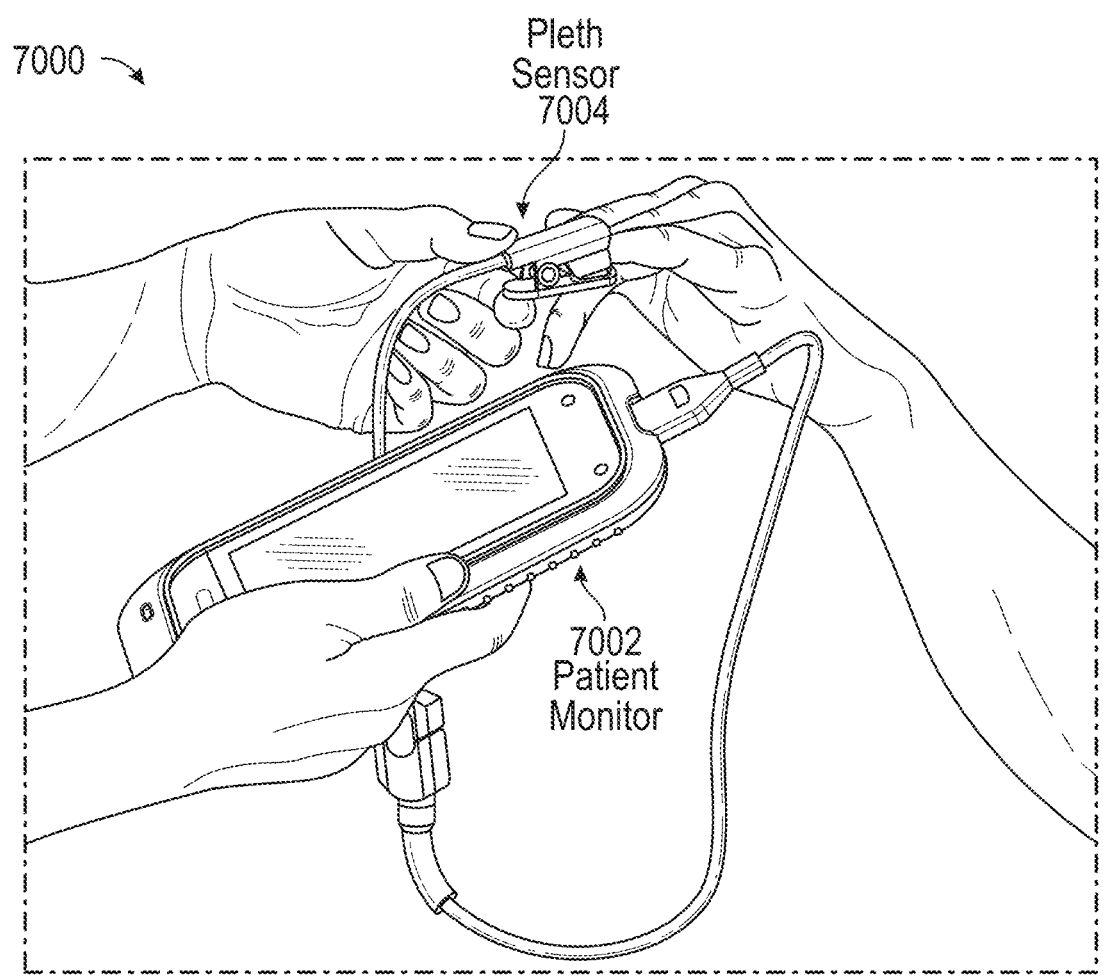
FIGS. 70, 71, 72A, 72B, 73A, and 73B illustrate additional example spot-check systems, which can be examples of the spot-check monitor of FIG. 69.
Figure 71:
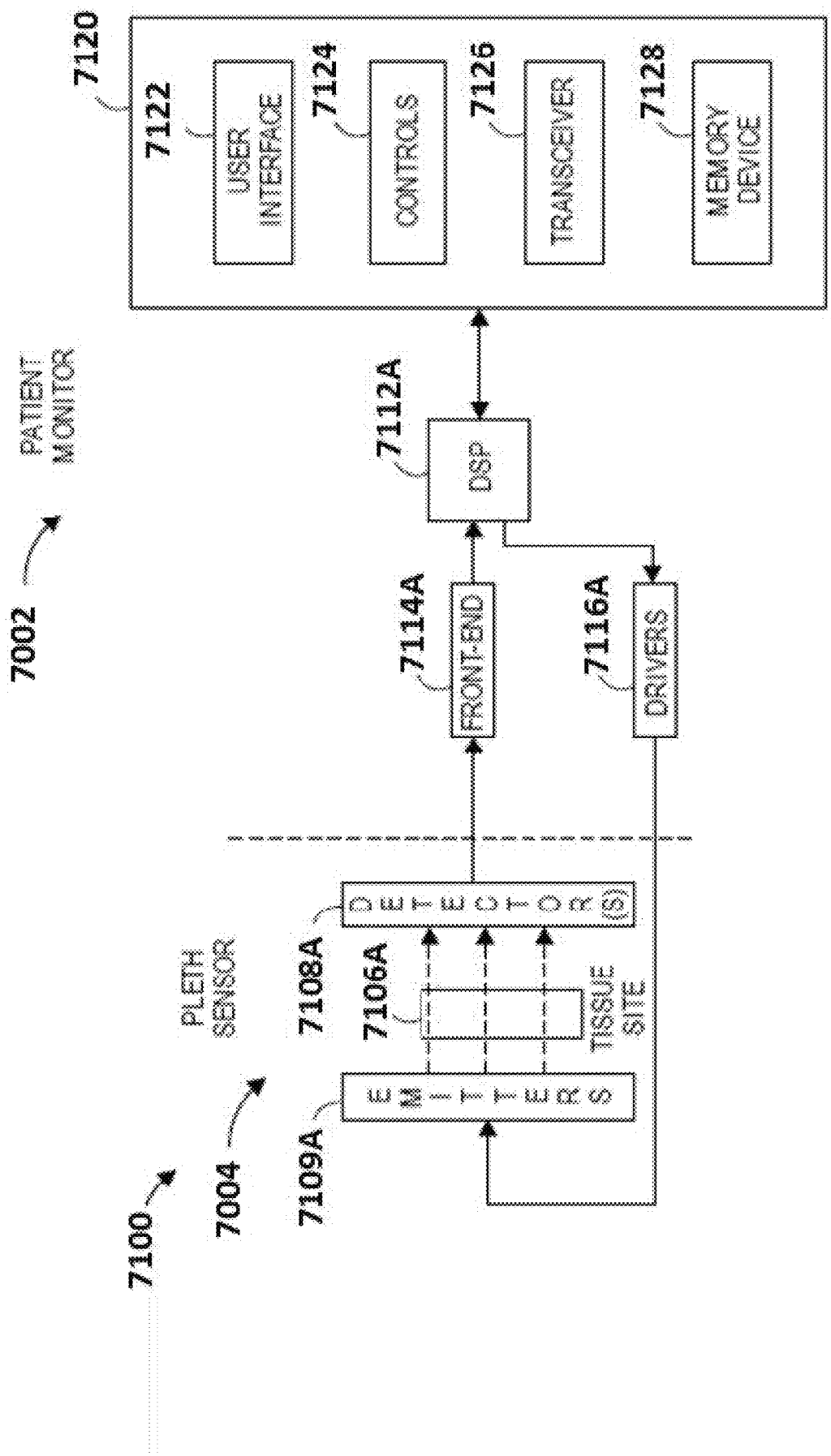

FIGS. 70-71 illustrate example spot-check systems 7000, 7100, which can be embodiments of the spot-check system 6900 of FIG. 69. The spot-check systems 7000, 7100 include a spot-check monitor 7002 and a pleth sensor 7004. The pleth sensor 7004 can be applied to tissue site 7106A of a patient, and used to detect changes in the patient's vascular system that are caused by the changes at the patient's heart. In these examples, the pleth sensor 7004 can be applied to a finger of the patient.

Referred to FIG. 71, the DSP 7112A can communicate via drivers 7116A with the pleth sensor 7004 and receive via a front-end 7114A one or more light intensity signals indicative of one or more physiological parameters of the patient. The drivers 7116A can convert digital control signals into analog drive signals capable of driving emitters 7109A to illuminate the tissue site 7106A. Detector(s) 7108A can, in turn, generate one or more composite analog light intensity signals responsive to light detected by the detector(s) 7108A after attenuation by the tissue site 7106A. The front-end 7114A can convert the one or more composite analog light intensity signals from the detector(s) 7108A into digital data and input the digital data into the DSP 7112A. The digital data from the front-end 7116A can be referred to herein as a plethysmograph waveform, plethysmograph, or pleth for short. The digital data from the front-end 7116A can have plethysmograph channels corresponding to individual emitter wavelengths, such as a red channel and an IR channel. The digital data from the front-end 7116A can be representative of a change in the absorption of particular wavelengths of light as a function of the changes in the tissue site 7106A resulting from pulsing blood.

The DSP 7112A can include one or more data or signal processors configured to execute one or more programs for determining physiological parameters from input data. The DSP 7112A can perform operations that include calculating and outputting one or more plethysmograph measures, such as PVI®. The operations performed by the DSP 7112A can be implemented in software, firmware or other form of code or instructions, or logic or other hardware, or a combination of the above.

The DSP 7112A can communicate with one or more input or output devices 7120. The one or more input or output devices 7120 can include a user interface 7122, controls 7124, a transceiver 7126, and a memory device 7128.

The user interface 7122 can include a numerical or graphical display that provides readouts of measures or parameters, trends and bar graphs of measures or parameters, visual indications that measures are, say, above a threshold, visual indicators like LEDs of various colors that signify measure magnitude, or device management interfaces, which can be generated by LEDs, LCDs, or CRTs, for example. The user interface 7122 can include an audible output device that provides readouts or audible indications that measures are, say, above a threshold. The user interface 7122 can include one or more input devices like a keypad, touch screen, pointing device, voice recognition device, and computer that can be used to supply control or configuration data, such as initialization settings, from the user interface 7122 to the instrument manager 7110. In some implementations, the user interface 7122 can be an interface for devices as well as users.

The controls 7124 can be outputs to medical equipment, such as drug administration devices, ventilators, or fluid IVs, so as to control the amount of administered drugs, ventilator settings, or the amount of infused fluids. In some implementations, the spot-check monitor 7002 can use the controls 7124 to automatically treat the patient. For example, controls 7124 can provide fluid to the patient, provide medication to the patient, turn on a fan to cool the patient, or adjust a temperature of a room to heat or cool the patient.

The transceiver 7126 via an antenna can transmit information about operation of the spot-check monitor 7002 to an electronic device or receive control or configuration data for operating the spot-check monitor 7002. The transceiver can, for example, communicate via a computer network or intermediary device or directly with the electronic device using electromagnetic radiation.

The memory device 7128 can be used to store information about operation of the spot-check monitor 7002. This information can, for example, include readouts of measures or parameters, trends and bar graphs of measures or parameters, visual indications or indicators.

Figure 72A:
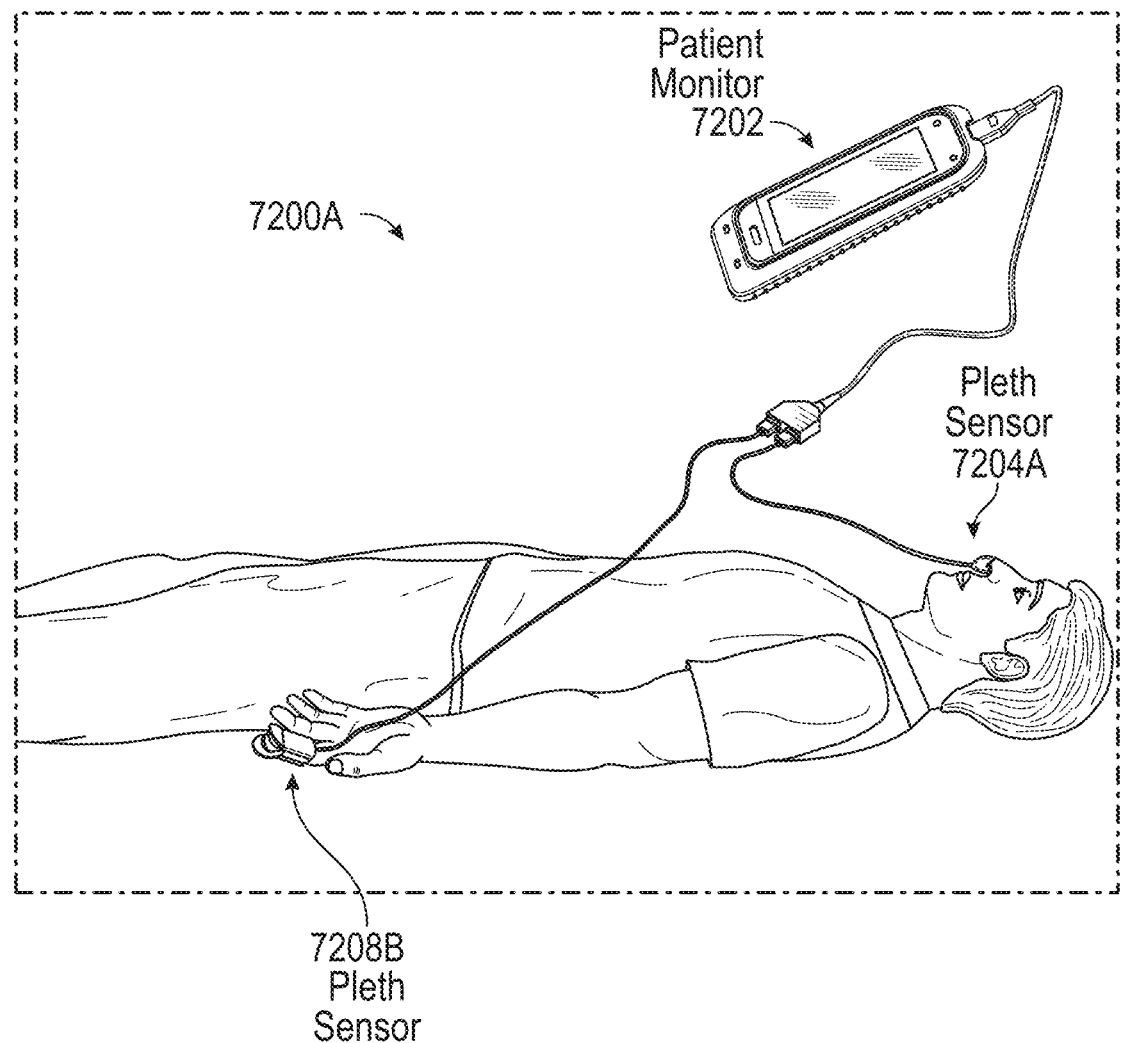
Figure 72B:
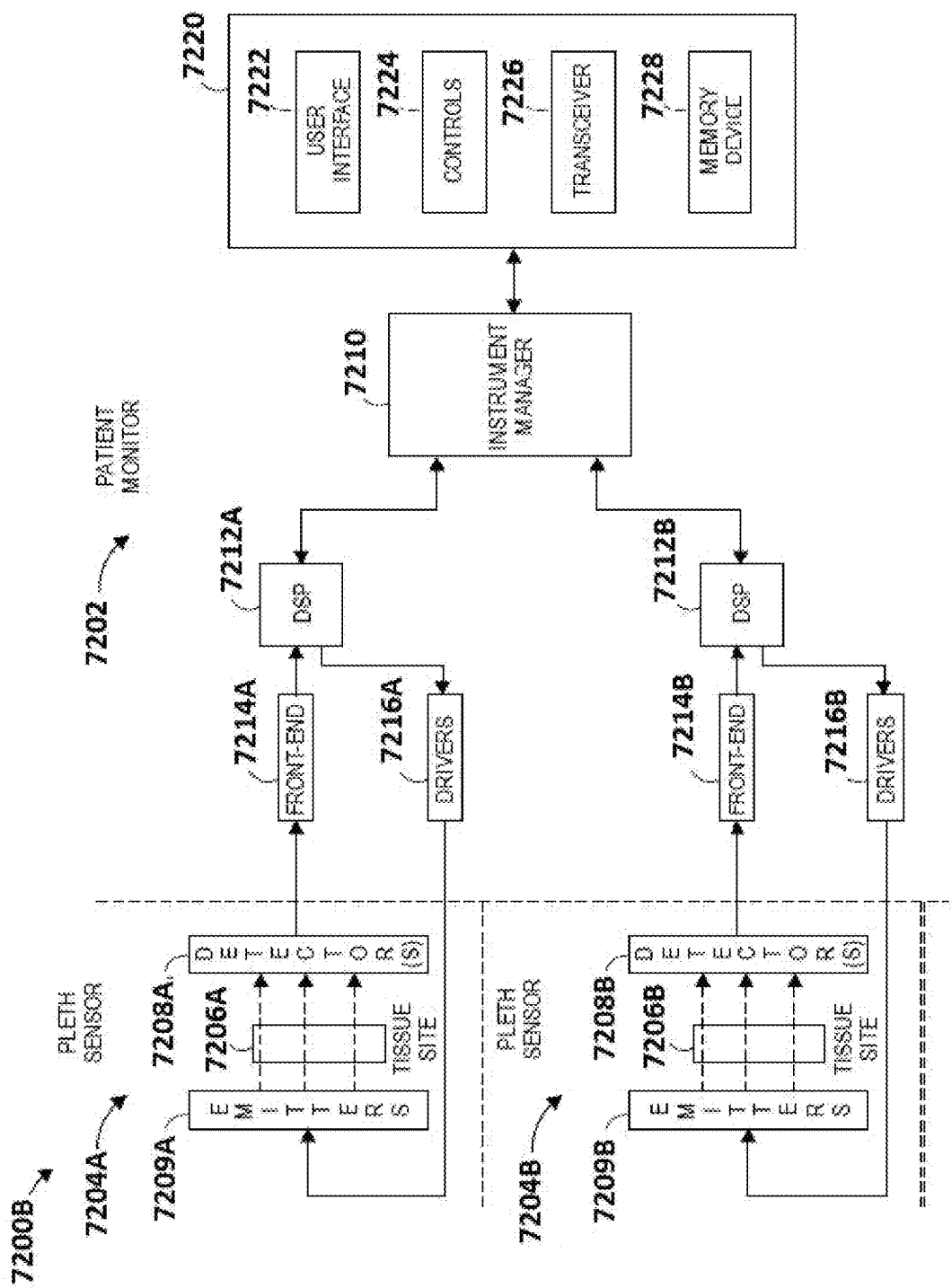

FIGS. 72A-72B illustrate example spot-check systems 7200A, 7200B, which can be embodiments of the spot-check system 6900 of FIG. 69. The spot-check systems 7200A, 7200B can include a spot-check monitor 7202, a pleth sensor 7204A, and a pleth sensor 7204B. The pleth sensor 7204A and the pleth sensor 7204B can be respectively detecting from tissue sites 7206A, 7206B of a patient, and can be used to detect changes in the patient's vascular system that are caused by the changes at the patient's heart. In the example of FIG. 72A, the spot-check system 7200A is depicted with the pleth sensor 7204A applied to a nose of the patient and the pleth sensor 7204B applied to a finger of the patient.

The spot-check monitor 7202 can include an instrument manager 7210 that monitors or controls the activity of the pleth sensor 7204A using DSP 7212A and the pleth sensor 7204B using DSP 7212B. The instrument manager 7210 can include a controller for managing operations of the instrument manager 7210.

Many of the components of the spot-check system 7200B can operate similarly to corresponding components of the spot-check system 7100. One or more input or output devices 7120, user interface 7122, controls 7124, transceiver 7126, and memory device 7128 can respectively operate similarly to one or more input or output devices 7220, user interface 7222, controls 7224, transceiver 7226, and memory device 7228 of the spot-check system 7200B. Additionally, the DSP 7112A, front-end 7114A, drivers 7116A, detector(s) 7108A, and emitters 7109A can respectively operate similarly to DSP 7212A, front-end 7214A, drivers 7216A, detector(s) 7208A, and emitters 7209A of the spot-check system 7200B. Moreover, the DSP 7112A, front-end 7114A, drivers 7116A, detector(s) 7108A, and emitters 7109A can respectively operate similarly to DSP 7212B, front-end 7214B, drivers 7216B, detector(s) 7208B, and emitters 7209B of the spot-check system 7200B.

Figure 73A:
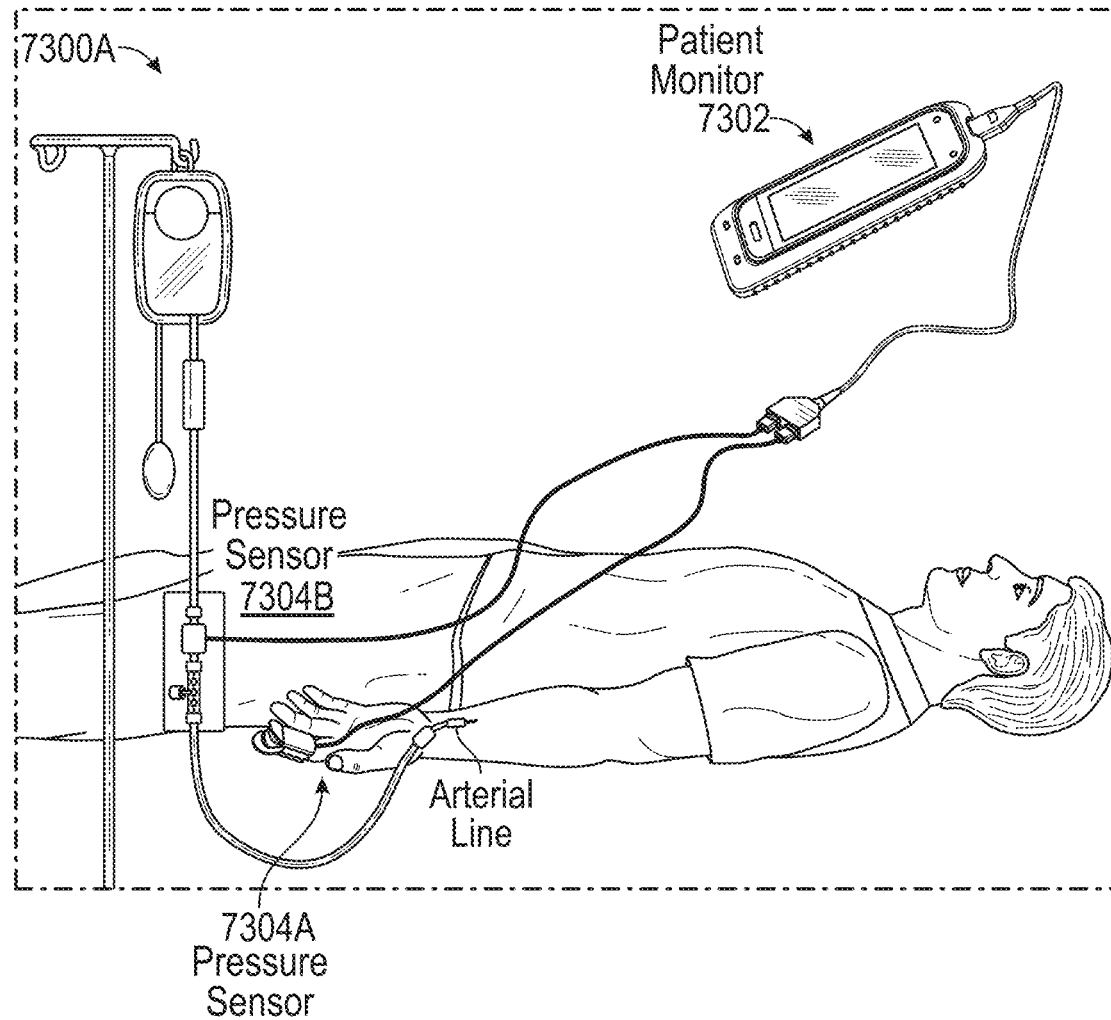
Figure 73B:
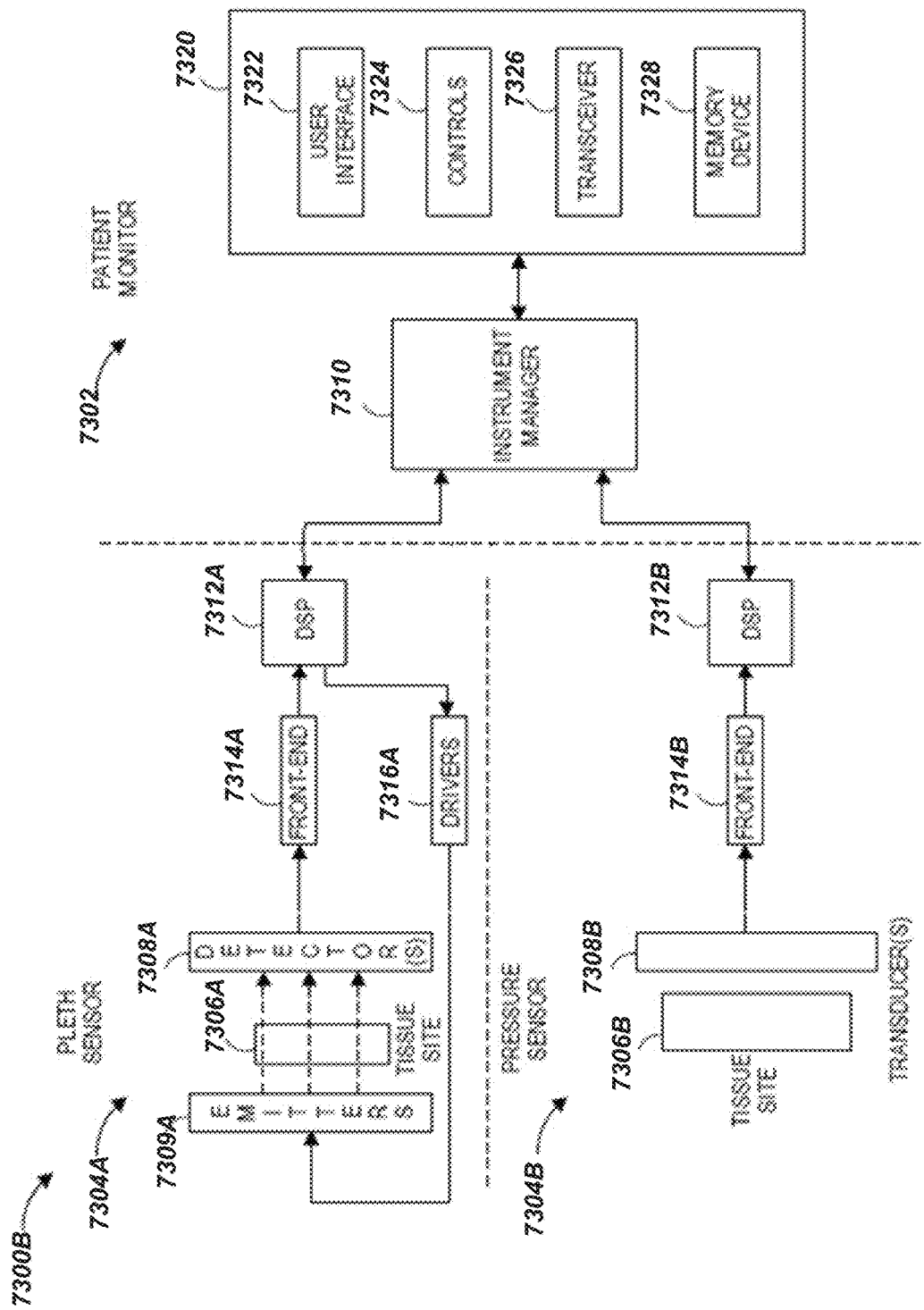

FIGS. 73A-73B illustrate example spot-check systems 7300A, 7300B, which can be embodiments of the spot-check system 6900 of FIG. 69. The spot-check systems 7300A, 7300B can include a spot-check monitor 7302, a pleth sensor 7304A, and a pressure sensor 7304B. The pleth sensor 7304A and the pressure sensor 7304B can be respectively applied to tissue sites 7306A, 7306B of a patient. In the example of FIG. 73A, the spot-check system 7300A is depicted with the pleth sensor 7304A applied to a finger of the patient and the pressure sensor 7304B detecting from an artery of the patient.

The DSP 7312B can receive via a front-end 7314B one or more pressure signals from transducer(s) 7308B of the pressure sensor 7304B. The transducer(s) 7308B can generate the one or more pressure signals responsive to detected pressure, such as pulse pressure, at the tissue site 7306B. The front-end 7314B can, in turn, filter or pre-process the one or more pressure signals and convert the one or more pressure signals into digital data for input into the DSP 7312B. The digital data from the front-end 7314B can be referred to herein as a pressure waveform.

The DSP 7312B can include one or more data or signal processors configured to execute one or more programs for determining physiological parameters from input data. The DSP 7312B can perform operations that include calculating and outputting one or more pressure measures, such as PPV. The operations performed by the DSP 7312B can be implemented in software, firmware or other form of code or instructions, or logic or other hardware, or a combination of the above.

Many of the components of the spot-check system 7300B can operate similarly to corresponding components of the spot-check system 7100. One or more input or output devices 7120, user interface 7122, controls 7124, transceiver 7126, and memory device 7128 can respectively operate similarly to one or more input or output devices 7320, user interface 7322, controls 7324, transceiver 7326, and memory device 7328 of the spot-check system 7300B. Additionally, the DSP 7112A, front-end 7114A, drivers 7116A, detector(s) 7108A, and emitters 7109A can respectively operate similarly to DSP 7312A, front-end 7314A, drivers 7316A, detector(s) 7308A, and emitters 7309A of the spot-check system 7100. Moreover, the instrument manager 7210 can operate similarly to instrument manager 7310 of the spot-check system 7300B.

As illustrated in FIG. 73B, one or more of the components related to signal acquisition and processing (for example, front end 7314A, drivers 7316A, front-end 7314B, DSP 7112A, DSP 7112B, etc.) can be incorporated into a connecting cable, the sensor itself, or are otherwise closer to the sensor site. As such, in some embodiments, of the spot-check system 6900 can include a spot-check monitor which includes primarily the input or output devices 7120, 7220, 7320 and the instrument manager 7210, 7310 (if appropriate). By reducing the number of components included in the spot-check monitor 6902, 7002, 7202, 7302, the monitor can, in some instances, be smaller in size and/or more portable, which can be more convenient for home or "spot-check" use.

Although not illustrated in FIGS. 69, 70, 71, 72A, 72B, 73A, and 73B the spot-check monitors 6902, 7002, 7202, 7302 or cables connecting the spot-check monitors 6902, 7002, 7202, 7302 to the sensors can further include one or more outputs that supply the signal(s) from one or more of the sensors to one or more other electronic devices for further processing. As one example, the signal(s) from one or more of the sensors can be output in parallel by one or more of the sensors or the cables that couple the one or more sensors to the spot-check monitors 6902, 7002, 7202, 7302. In another example, the spot-check monitors 6902, 7002, 7202, 7302 can include one or more outputs for outputting copy(ies) of the signal(s) from one or more of the sensors. In some instances, the copy(ies) of the signal(s) may be adjusted relative to the original(s) with filtering, scaling, or other changing prior to being provided to the one or more other electric devices.

One or more of the components relating to signal acquisition and/or processing can be incorporated into one or more connecting cables, the sensors themselves, or are otherwise closer to the sensor sites. As such, the patient monitor can include primarily the input or output devices and an instrument manager (if appropriate). In addition, some of the components are illustrated as separate units but can be combined. For instance, front end can be combined into one or more front ends, drivers can be combined into one or more drives, can be combined into one or more DSPs, etc. By reducing the number of components included in the patient monitor, the monitor can be smaller in size and/or more portable, which can be more convenient for home or "spot check" use.

Invalid Signal

As described herein, for various reasons, a signal received from a spot-check device, such as a sensor, may be invalid. That is, the signal generated by the sensor and/or a measurement using the signal is unreliable, inaccurate, or otherwise undesired. When implementing a credit- or token-based scheme in which one or more credits can enable the spot-check monitor and/or a sensor to make a single measurement, it can be undesirable or objectionable to exchange or charge a credit for these invalid signals or measurements. Accordingly, in some cases, the spot-check system can perform various checks on the signal received from the sensor to determine whether the signal should be deemed valid or invalid. If determined to be an invalid signal, in some cases, the spot-check system can be configured not to charge a credit for that invalid measurement. Put a different way, the spot-check system can be configured not to decrement the number of available spot-check uses in response to a determination that a spot-check signal was invalid.

In some instances, the spot-check monitor can determine the validity of a signal using one or more techniques, which may be referred to herein as a series of checks or tests that the spot-check monitor can perform on the signal to assess its validity. The spot-check monitor can suitably arbitrate between the techniques, or use multiple techniques. Based on one or more determinations, the spot-check monitor can prioritize (or weight) some techniques over other techniques. For example, if the spot-check monitor determines or perceives a technique to be inaccurate or unreliable, the spot-check monitor can give that technique little or no weight. Similarly, if the spot-check monitor determines or perceives a technique to be accurate or very reliable, the spot-check monitor can heavily weight that technique high or even use that technique for the sole determination.

The spot-check monitor can assess a Signal IQ of the signal to determine whether the signal was valid or invalid. Signal IQ is a Signal Identification and Quality indicator of the Masimo pulse oximetry waveform data, and can directly relate to SpO2 and/or pulse rate data, among other physiological data. The spot-check monitor can analyze an incoming signal and remove noise or motion components to measure arterial oxygen saturation and pulse rate using one or more algorithms. In some cases, the Signal IQ can be representative of the relative confidence if these algorithms, which can represent the degree of success the algorithm had in finding and extracting a signal based upon its particular specialty. A Signal IQ check can become a particularly effective assessment during motion, low perfusion or environmental interference, such as when the pleth can be completely obscured by artifact. In some cases, a low Signal IQ results in a determination that the signal was invalid. In contrast, a high Signal IQ can result in a determination that the signal was valid.

The spot-check monitor can additionally or alternatively assess the signal using various other checks. For example, the spot-check monitor can compare or analyze the signal to calculate, derive or determine an accuracy or a confidence value of a signal. For example, the spot-check monitor can compare the signal to a previously determined or model signals. The accuracy or confidence level determination can be based at least in part on how close the comparison to the other signals are. For example, if the signal satisfies a threshold corresponding to the previous or model measurement then the monitor can determine that the signal was valid. In contrast, if the signal does not satisfy a threshold corresponding to the previous or model measurement then the monitor can determine that the signal was invalid.

Furthermore, the monitor can calculate one or more parameters from the received signal and can compare the calculated parameters to previously calculated or known parameters to determine the validity of the signal. For example, if a pressure measure determined from a received signal changed a small amount as compared to a model pressure measure, the spot-check monitor can determine that the change in the pressure measure may be due partly, largely, or entirely to vascular tonal change (e.g., expansion and contraction of the patient's vascular system). Accordingly, the spot-check monitor can determine that the pressure measure is invalid and therefore the signal is invalid. As described herein, the spot-check monitor can track, record, or communicate that an invalid signal was received. In addition, in some embodiments, the spot-check monitor can determine, based on a determined reason for the invalid signal, whether the invalid signal was the fault (or primarily the fault) of the patient's actions, carelessness, movement, placement of the measuring device, etc. In some instances (such as when the patient caused an inaccurate signal), although the signal may be determined to be invalid, the spot-check monitor does not count the measurement as an invalid signal. Instead, the signal is considered a valid signal.

Other checks by the spot-check monitor can include determining if the sensor exhibited a not properly attached condition, patient movement detection, or poor positioning of the sensor detection. For example, if the spot-check monitor determines that the sensor was not positioned correctly or the patient moved more than a threshold amount during the sensing by the sensor, the monitor can determine that the signal was invalid. Furthermore, the spot-check monitor can assess one or more of a signal stability or a signal strength against a threshold to determine if the signal is valid or invalid Canceling or Removing a Receive Signal or Calculated Measurement In some cases, an individual may be able to cancel or stop a measurement from either being taken or calculated, even after the sensing has been initiated. For example the user may have accidentally selected or started the sensing by the sensor. Alternatively, the user may have initially desired to calculate a measurement, but, for one reason or another (for instance, an emergency, a phone call, etc.), the user may want to cancel.

In these situations, the spot-check monitor can receive the user's cancellation request, and, in response, can stop the calculation of the measurement and/or be configured to ignore the signal received from the sensor. In some cases, even if a valid signal was received by the monitor, if it was subsequently or concurrently cancelled, the signal can be deemed invalid. Further, despite receiving a valid signal, because the signal is deemed invalid, the spot-check system can configured not to decrement the available number of credits.

However, in some cases, if a valid signal was received, a credit decremented despite a user's attempt to cancel the measurement. For example, a user may have reached a maximum number of canceled measurements. Alternatively, the user may have been too late in attempting to cancel the measurement. For example, the spot-check monitor may disallow the cancellation of measurements after a certain period of time has passed between the start of the sensing by the sensor.

In some cases, a user may be able to cancel or remove a previously recorded measurement that was calculated from a valid signal. For example, the user may have accidentally or unknowingly taken successive measurements of the same parameter. Although the monitor most likely received successive valid signals, successive calculations of the same measurement may be not helpful or desirable. Thus, at least one of a set of successive valid signals may be deemed invalid, despite its accuracy, reliability, or otherwise valid nature. For example, a certain parameter may not change dramatically over time. Thus, the spot-check monitor can permit a user to delete a successive measurement from the records kept by the spot-check monitor, despite it being a valid measurement. In some instances, the spot-check monitor can itself track and assess the timestamp of signals and can delete, or otherwise fail to record an otherwise valid measurement corresponding to those signals, for example, based at least on the time stamp of the signal.

Other circumstances which the spot-check monitor can be configured to ignore a valid signal can include, but are not limited to, a power outage, a child playing with the machine, an emergency during the measurement process, etc. The spot-check monitor can be configured to permit a user to delete or otherwise remove a certain number of recorded measurements corresponding to valid signals, or add back a certain number of spot-check credits. For example, a number of "redo" measurements can be associated with an individual, and can correspond to how familiar the individual is with the spot-check monitor. For example, the number of "redo" measurements can provide the patient with a buffer when learning to use the spot-check monitor.

Spot-Check Credits

The number of spot-check credits, and thus the number of remaining or available spot-check system uses, associated with any given user, patient monitor, or sensor can be controlled or limited. For example, the number of spot-check credits can correspond to a service life of a sensor or patient monitor, which can be defined in terms of a permitted or estimated number of available uses or amount of usage time. In addition or alternatively, the number of spot-check credits can correspond to a number of prescribed or recommended uses that result in a valid signal. Still, in some cases, the spot-check credits can represent a quantum of currency, specifying a price per use or per unit time, or a subscription service.

The physiological monitor or the sensor can include a memory that stores a number of remaining spot-check credits. The monitor can read the number of remaining spot-check credits, and the monitor can be enabled to make a physiological measurement in conjunction with the sensor signal if the number of remaining spot-check credits is greater than a threshold (non-limiting example: zero). The number of spot-check credits can be decremented in response to a determination that a valid spot-check signal was received. In contrast, the number of spot-check credits is not decremented in response to a determination that an invalid spot-check signal was received. In other words, despite receiving a signal and using the sensor, the spot-check system can effectively ignore or disregard the invalid signal.

In various aspects, the spot-check system can be configured to perform a measurement only when a number of available uses is greater than a threshold. Accordingly, the number of token available to an individual can control the capabilities of the patient monitoring device. That is, if no tokens are available, the spot-check monitoring device can be configured not to calculate measurement and/or the sensor can be configured not to be used, unless, for example, new tokens are made available. For example, one or more elements of the spot-check system, such as a spot-check monitor or a sensor, can store an indication of a number of available or remaining uses (or tokens). Based on a determination that a number of available uses satisfies a threshold, the spot-check monitor can be configured to receive a signal from the sensor, and a number of number of available uses can be decremented. In contrast, based on a determination that a number of available uses does not satisfy the threshold, the spot-check system can be configured not to calculate a measurement or receive a signal from a sensor. However, in some cases, the spot-check system can be configured receive a signal or calculate a measurement in spite of a determination that a number of available uses does not satisfy the threshold.

As described herein, the spot-check system can advantageously be configured to assess the validity of a particular signal to determine whether a valid or invalid signal was received. Based on a determination that a valid signal was received, the number of available uses can be decremented. In contrast, based on a determination that an invalid signal was received, the number of available uses can remain the same. In other words, despite using the sensor and/or monitor, the spot-check system can ignore an invalid signal or not count the use towards a patient's quota associated with the number of credits and/or available uses.

In some cases, the spot-check system can provide feedback to the user, indicating why a signal was invalid and/or suggestions to improve the signal. In some cases, the number of available uses can be decremented despite a determination of an invalid signal. For example, a user may be given a limited number of passes corresponding to invalid signal, each pass permitting the user to disregard an invalid signal. The spot-check system can track a number of invalid signal. If the number of invalid signal satisfies a threshold corresponding to the permitted number of passes corresponding to the invalid signal, the spot-check system can count the invalid signal as a valid signal and decrement the number of available uses.

Example Spot-Check Monitor

Figure 74:
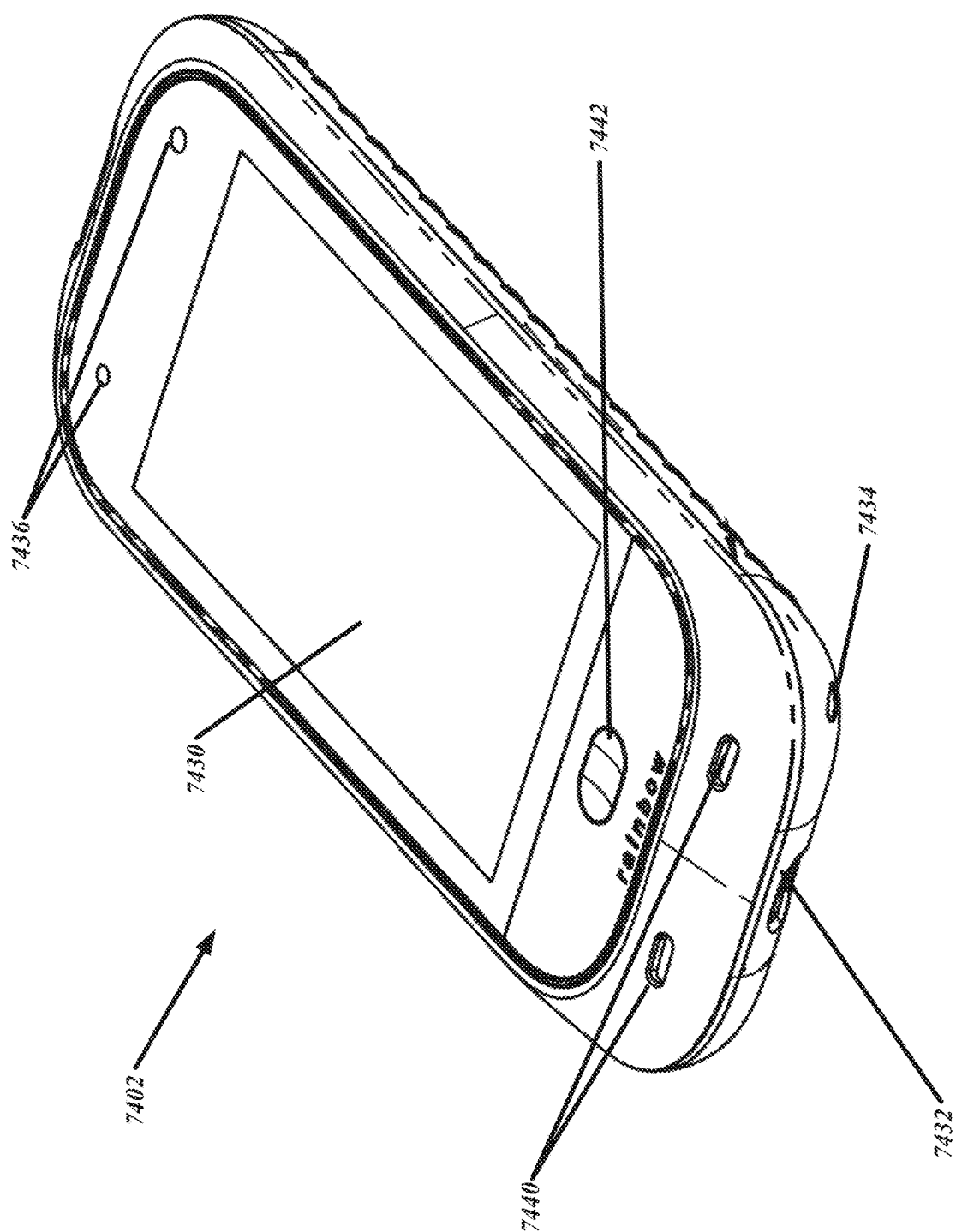
FIG. 74 illustrates a perspective view of an example spot-check monitor, which can be examples of the spot-check monitor of FIG. 69.
Figure 75:
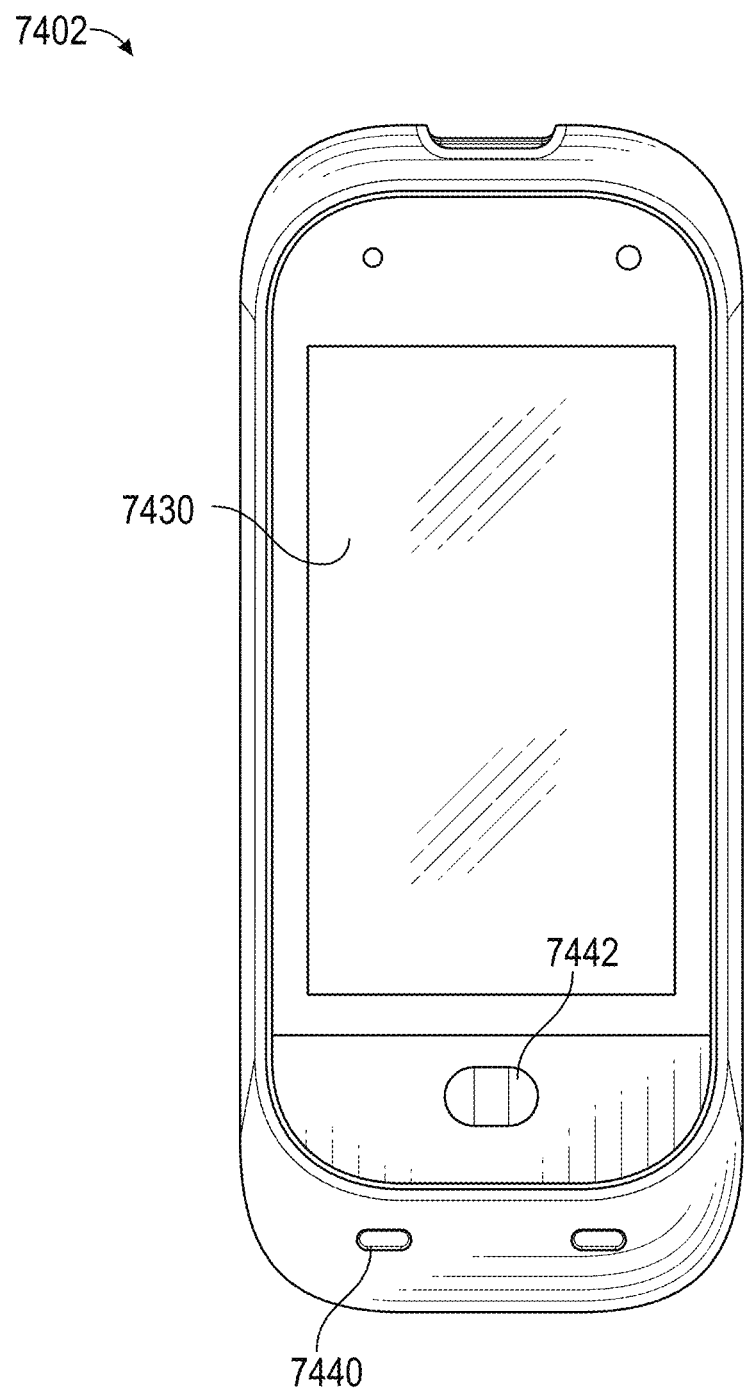
FIGS. 75, 76, 77, 78, 79, and 80 respectively illustrate front, back, first side, second side, top, and bottom views of the portable spot-check monitor of FIG. 74.
Figure 76:
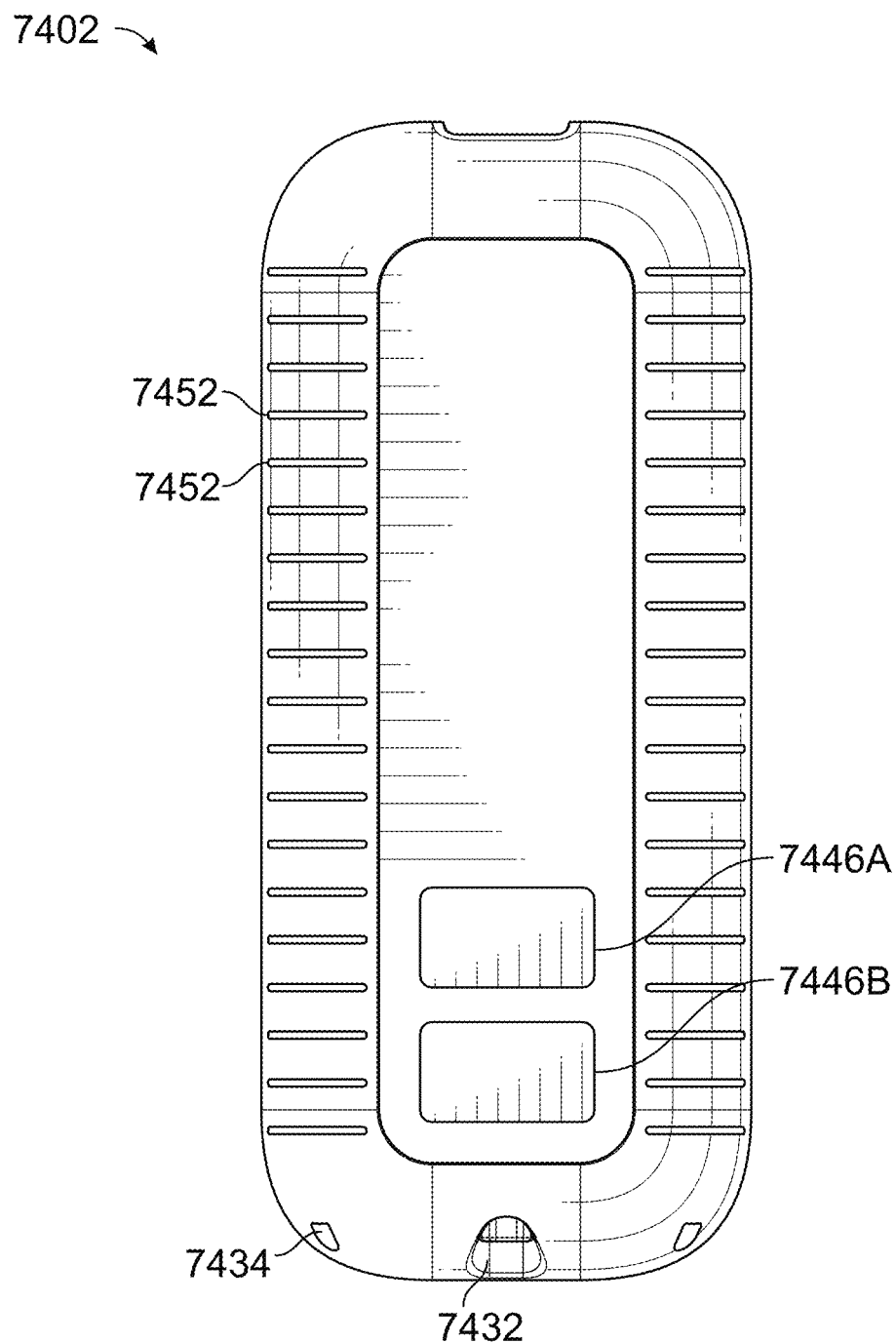
Figure 77:
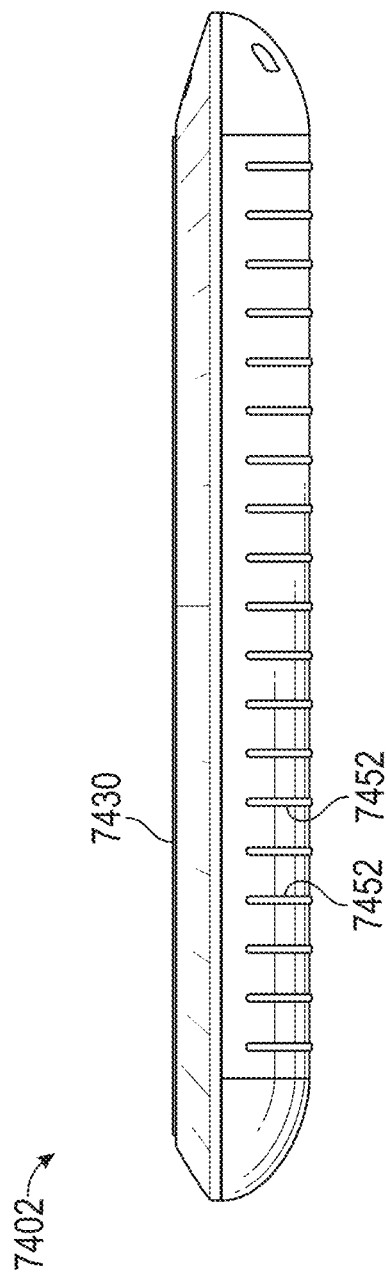
Figure 78:
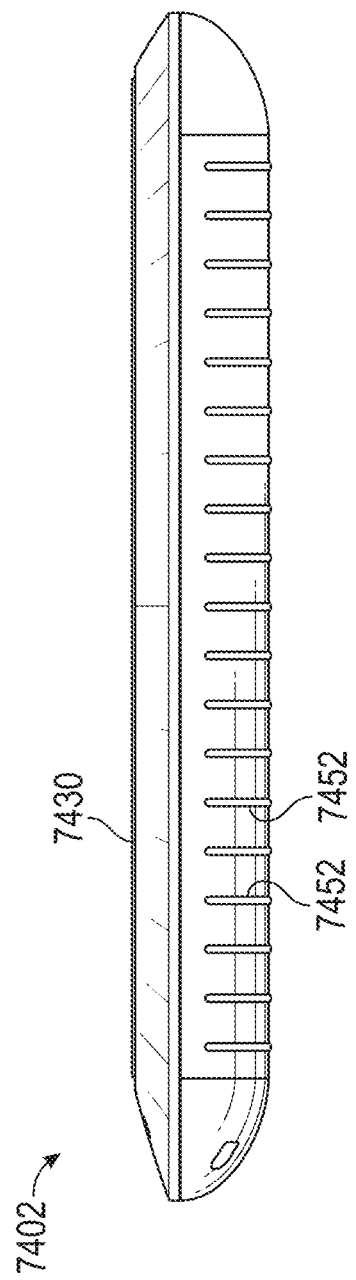
Figure 79:
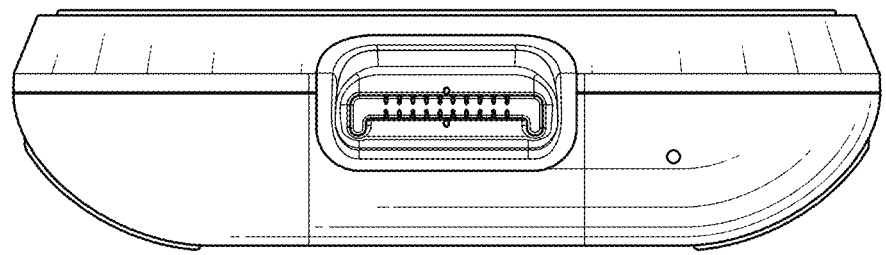
Figure 80:
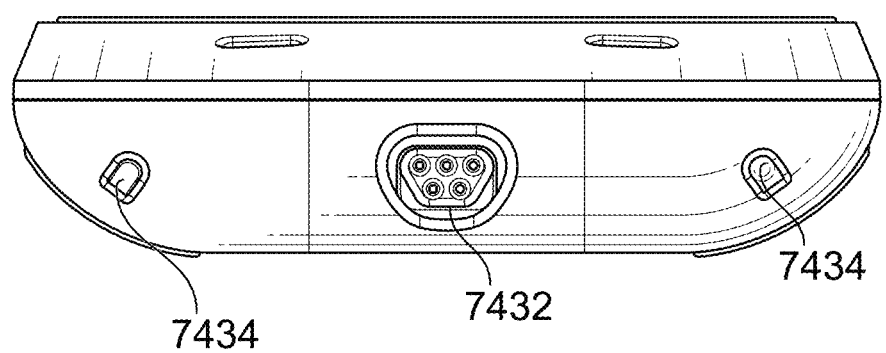
Figure 81:
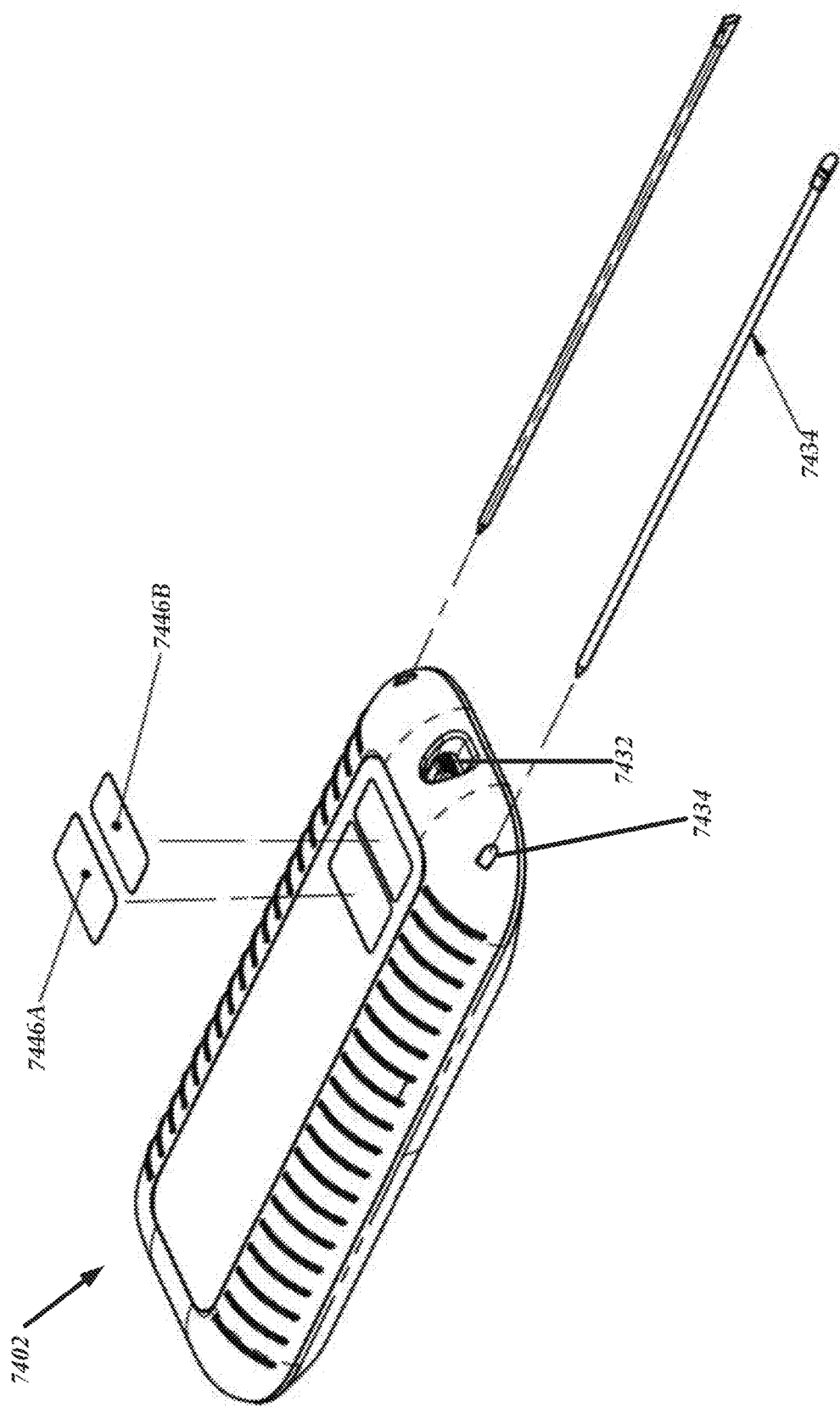
FIG. 81 illustrates an exploded view of stylus insertion in the portable spot-check monitor of FIG. 74.

FIG. 74 illustrates a perspective view of an example spot-check monitor 7402, which can be embodiment of the spot-check monitor 6902 of FIG. 69. FIGS. 75-80 respectively illustrate front, back, first side, second side, top, and bottom views of the spot-check monitor of FIG. 74. As illustrated, the spot-check monitor 7402 includes a display 7430, an audio input component 7440, an audio output component 7436, a pointing/selecting device 7442, a plurality of grips 7452, and one or more labels 7446A, 7446B. In addition, the spot-check monitor 7402 includes a port 7432 for connecting to a sensor and/or charging, as well as a removable stylus 7434. FIG. 81 illustrates an exploded view of stylus and spot-check monitor.

The display 7430 can be a numerical or graphical display that provides readouts of measures or parameters, trends and bar graphs of measures or parameters, visual indications that measures are, say, above a threshold, visual indicators like LEDs of various colors that signify measure magnitude, or device management interfaces, which can be generated by LEDs, LCDs, or CRTs, for example. In addition, the display 7430 can provide readouts of a history of one or more measurements. For instance, the display 7430 can show a complete, recent, or selected history of valid or invalid measurements. In addition, the display 7430 can provide readouts of a total number of measurements, a number of invalid signals, a number of valid signals, or a remaining number of available uses of the sensor or monitor over a selectable time period. In some embodiments, the display 7430 can include a touch screen that can be used to supply control or configuration data, such as initialization settings, select a measurement, or cancel a measurement.

The user interface can include an audible output device 7436 that provides readouts or audible indications that measures are, say, above a threshold. The user interface can further include one or more input devices like a keypad, touch screen 7430, pointing device 7442, voice recognition device 7440, and computer. In some implementations, the user interface can be an interface for devices as well as users.

Valid Measurement Determination

Figure 82:
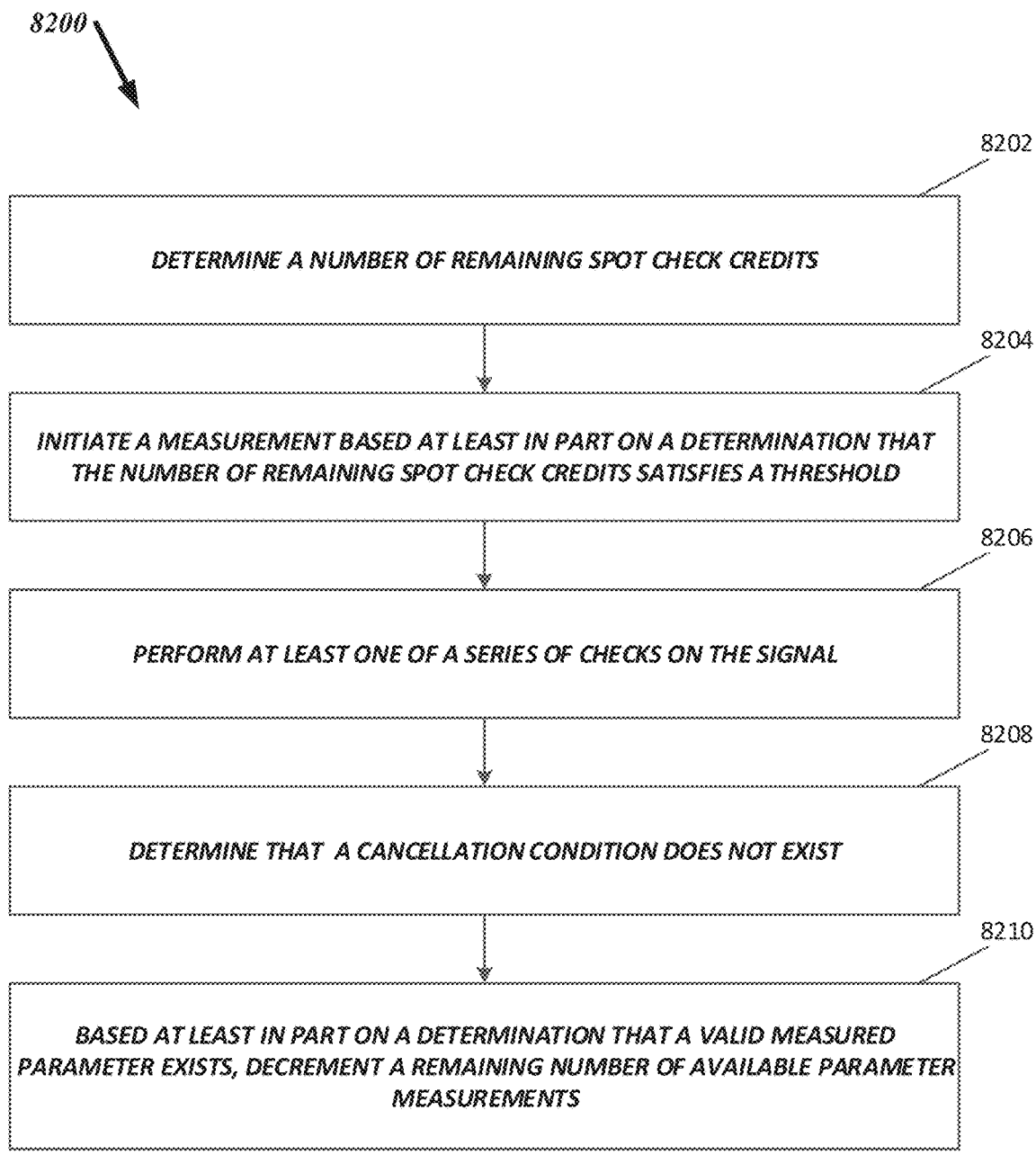
FIG. 82 illustrates an example method of determining a whether a valid measurement was performed on the patient.

FIG. 82 illustrates a method 8200 of determining the validity of a measurement taken by a spot-check system. The method may be implemented by the various components of the spot-check system 6900. For convenience, the method 8200 is described in the context of the spot-check system 6900 but may instead be implemented by other spot-check systems not shown. The method 8200 provides one example approach by which the spot-check monitor 6902 can determine a whether a valid signal was received.

At block 8202, the process 8200 can read or determine a number of remaining spot-check credits. For example, a spot-check system can employ a credit- or token-based scheme in which one or more spot-check credits can enable a spot-check monitor and/or a sensor to make a single measurement of a group of predefined parameters, which can correspond to receiving a single signal from a spot-check sensor. The spot-check monitor or the sensor can include a memory that stores the number of remaining spot-check credits. The monitor can read the number of remaining spot-check credits, and the system can be enabled to make the measurement of the group of predefined parameters using a single signal from a sensor if the number of remaining spot-check credits is greater than a threshold (non-limiting example: zero).

At block 8202, the process can initiate the sensing of a spot-check sensor based at least in part on a determination that the number of remaining spot-check credits satisfies a threshold. In some cases the threshold can be zero while in other cases the threshold may be higher. If the number of remaining spot-check credits does not satisfy the threshold, the process 8200 can be configured not to allow the sensor to begin sensing. In addition or alternatively, the process 8200 can present to the user a request to purchase additional credits.

At block 8204, the process 8200 receives a signal from which the monitor can calculate a group of predefined parameters from a sensor coupled to a patient. As described herein, the sensor can include a combination of one or more of a spectrometer, a pulse oximetry device, a plethysmograph sensor, a pressure sensor, an electrocardiogram sensor, or acoustic sensor, among other sensors.

At block 8206, the process 8200 can perform one or more of a series of checks on received signal to assess a validity of the received signal. For example, the spot-check monitor can suitably arbitrate between the checks, or use multiple checks. Based on one or more determinations, the spot-check monitor can prioritize (or weight) some checks over other checks. For example, if the spot-check monitor determines or perceives a check to be inaccurate or unreliable, the spot-check monitor can give that check little or no weight. Similarly, if the spot-check monitor determines or perceives a check to be accurate or very reliable, the spot-check monitor can heavily weight that check high or even use that check for the sole determination.

As described herein, the checks can include, but are not limited to, an assessment of Signal IQ, a comparison to a previously determined or model signal, a determination if the sensor exhibited a not properly attached condition, patient movement detection, or poor positioning of the sensor detection. Further, the one or more checks can include any of the accuracy, quality, patient, or sensor determinations as described herein. Non-limiting examples of the plurality of checks include: determining if the signal satisfies a threshold signal strength; determining if the signal corresponds to a previously valid signal, determining if the signal includes signal interference, determining if the sensor exhibited a not properly attached condition, determining if the patient satisfied a movement threshold, and determining a confidence value associated with the signal and determining whether the confidence value satisfies a confidence threshold.

At block 8208, the process 8200 can determine whether a valid cancellation exists. In some case, an individual may be able to cancel or stop a measurement. For instance, the user may have accidentally selected or started a measurement. Alternatively, the user may have initially desired the measurement, but, for one reason or another (for instance, an emergency, a phone call, etc.), the user may want to cancel.

In these situations, the spot-check monitor can receive the user's cancellation request, and, in response, can treat a received signal as an invalid signal. In some cases, the signal was received, but the measurement calculation was subsequently or concurrently cancelled. In cases such as these, despite receiving a valid signal, the spot-check system can treat the signal as an invalid signal.

At block 8210, based at least in part on a determination that a valid spot-check measurement was performed, the spot-check monitor can decrement a remaining number of available credits, which is sometimes referred to herein as a remaining number of available uses of the sensor and/or monitor. For example, a spot-check credit can enable a spot-check monitor to make a single measurement of a group of predefined parameters, which can correspond to receiving a single signal from a spot-check sensor. In some cases, the spot-check monitor and/or sensor can store the number of valid signals received and/or the number of uses remaining.

FURTHER EXAMPLES

Various example features can be found in the following clauses, which can be implemented together with any combination of the features described above:

Clause 1: A pulse oximetry monitor configured to perform a spot-check measurement of a physiological parameter, the monitor comprising:

a driver circuit that drives one or more emitters of an optical sensor at multiple wavelengths of light to cause the one or more emitters to transmit the multiple wavelengths of light through body tissue of a patient;

a hardware processor in communication with the sensor, the hardware processor configured to:

determine a number of remaining spot-check credits;

based at least in part on a determination that the number of spot-check credits satisfies a threshold, initiate a spot-check measurement by obtaining a signal from the optical sensor;

compute the spot-check measurement based on the signal;

assess a validity of the spot-check measurement;

based at least in part on a determination that the spot-check measurement is valid, update the number of remaining spot-check credits; and output the spot-check measurement to a display of the pulse oximetry monitor.

Clause 2: The monitor of clause 1, wherein the spot-check measurement is an oxygen saturation measurement or a hemoglobin measurement.

Clause 3: The monitor of any of the preceding clauses, wherein the number of remaining spot-check credits are stored in memory of the sensor, and wherein to determine the number of remaining spot-check credits is configured to read from the sensor.

Clause 4: The monitor of any of the preceding clauses, wherein to assess the validity of the spot-check measurement, the processor is configured to assess a validity of the signal obtained from the optical sensor.

Clause 5: The monitor of any of the preceding clauses, wherein to assess the validity of the signal the processor is configured to assess a quality of the signal.

Clause 6: The monitor of any of the preceding clauses, wherein the processor is configured to determine the that spot-check signal is valid based at least in part on a determination that the signal quality of the signal satisfied a signal quality threshold for a least a threshold portion of a time window during which the measurement was taken.

Clause 7: The monitor of any of the preceding clauses, wherein the quality of the signal is based at least in part on a combination of one or more of a signal IQ, a signal stability, or a signal strength of the signal obtained from the optical sensor.

Clause 8: The monitor of any of the preceding clauses, wherein the quality of the signal is based at least in part on a combination of one or more of a position or location of the optical sensor during the measurement or an identified amount of patient movement during the measurement.

Clause 9: The monitor of any of the preceding clauses, wherein to assess the validity of the spot-check measurement, the processor is further configured to compare the measurement to an expected or previously determined measurement.

Clause 10: The monitor of any of the preceding clauses, wherein the processor is configured to determine that the spot-check signal is valid based at least in part on a determination that the measurement matches or is within a threshold of the expected or previously determined measurement.

Clause 11: The monitor of any of the preceding clauses, wherein to assess the validity of the signal measurement, the processor is further configured to determine that a cancellation condition does not exist.

Clause 12: The monitor of any of the preceding clauses, wherein the processors is configured to determine the number of remaining spot-check credits in response to a request to initiate the spot-check measurement.

Clause 13: The monitor of any of the preceding clauses, wherein, responsive to a determination that the number of remaining spot-check credits does not satisfy the threshold, the processor is further configured to output an indication of an insufficient number of remaining spot-checks to the display.

Clause 14: The monitor of any of the preceding clauses, wherein the hardware processor is further configured to compute the spot-check measurement upon either detecting that the physiological sensor has been disconnected from the patient or upon detecting that the clinician has selected a display input requesting the spot-check measurement.

Clause 15: The monitor of any of the preceding clauses, wherein the hardware processor is further configured to compute an early warning score based on contributor scores derived from the spot-check measurement and a plurality of other physiological parameter measurements, and output in a single region of the display the early warning score together with the contributor scores or a trend of prior early warning scores.

Clause 16: A method of performing a spot-check measurement of a physiological parameter, the method comprising:
  under control of a hardware processor of a patient monitor,
    determining a number of remaining spot-check credits associated with a physiological sensor configured to be used to measure a physiological parameter of a patient;
    based at least in part on a determination that the number of spot-check credits satisfies a threshold, initiating a spot-check measurement in conjunction with a sensor;
    receiving a signal indicative of the spot-check measurement from the physiological sensor;
    computing the spot-check measurement based on the signal;
    assessing a validity of the spot-check measurement;
    based at least in part on a determination that the measurement is valid, updating the number of remaining spot-check credits; and
    outputting the spot-check measurement for presentation to a clinician.

Clause 17: The method of clause 16, wherein the number of remaining spot-check credits are stored in memory of the sensor, and said determining the number of remaining spot-check credits comprises reading the number of remaining from the sensor memory.

Clause 18: The method of any of the preceding clauses, wherein said assessing the validity of the spot-check measurement comprises assessing a validity of the signal obtained from the optical sensor.

Clause 19: The method of any of the preceding clauses, said assessing the validity of the signal comprises assessing a quality of the signal.

Clause 20: The method of any of the preceding clauses, wherein the determination that the spot-check signal is valid is based at least in part on a determination that the signal quality of the signal satisfied a signal quality threshold for a least a threshold portion of a time window during which the measurement was taken.

Clause 21: The method of any of the preceding clauses, wherein the quality of the signal is based at least in part on a combination of one or more of a signal IQ, a signal stability, or a signal strength of the signal obtained from the optical sensor.

Clause 22: The method of any of the preceding clauses, wherein the quality of the signal is based at least in part on a combination of one or more of a position or location of the optical sensor during the measurement or an identified amount of patient movement during the measurement.

Clause 23: The method of any of the preceding clauses, wherein said assessing the validity of the spot-check measurement comprises comparing the measurement to an expected or previously determined measurement.

Clause 24: The method of any of the preceding clauses, further comprising determining that the spot-check measurement is valid based at least in part on a determination that the measurement matches or is within a threshold of the expected or previously determined measurement.

Clause 25: The method of any of the preceding clauses, wherein said assessing the validity of the spot-check measurement, comprises determining that a cancellation condition does not exist.

Clause 26: The method of any of the preceding clauses, further comprising determining the number of remaining spot-check credits in response to a request to initiate the spot-check measurement.

Clause 27: The method of any of the preceding clauses, further comprising responsive to a determination that the number of remaining spot-check credits does not satisfy the threshold, causing a display to display an indication of an insufficient number of remaining spot-checks.

Clause 28: A medical device configured to receive a physiological signal from a physiological sensor coupled with a patient and to perform a spot-check measurement based on the physiological signal, the medical device comprising:
  a circuit board comprising circuitry configured to receive the physiological signal either from a cable connected to the physiological sensor or wirelessly from the physiological sensor;
  a display in electrical communication with the circuit board;
  a speaker in electrical communication with the circuit board;
  a memory device in electrical communication with the circuit board, the memory device comprising executable instructions stored thereon; and
  a processor in electrical communication with the circuit board, the processor configured to implement the executable instructions so as to:
    measure a plurality of physiological parameter values from the physiological signal;
    output the physiological parameter values to the display;
    detect that the physiological sensor has been disconnected from the patient;
    select a currently-displayed one of the physiological parameter values as the spot-check measurement upon detecting that the physiological sensor has been disconnected from the patient;
    freeze the currently-displayed one of the physiological parameter values on the display; and
    output audio of the spot-check measurement to the speaker.

Clause 29: The medical device of clause 28, wherein the processor is further configured to lock the medical device in spot-check mode so that continuous measurements are not able to be calculated by the medical device when in the spot-check mode.

Clause 30: The medical device of any of the preceding clauses, wherein the processor is further configured to select a plurality of additional spot-check measurements and to output a graph of the spot-check measurement and the additional spot-check measurements on the display, the graph representing a trend of the spot-check measurement and the additional spot-check measurements.

Clause 31: The medical device of any of the preceding clauses, wherein the processor is further configured to cause the display to output a user interface control together with the spot-check measurement, the user interface control selectable by a user to permit a user to overwrite the spot-check measurement with a manual measurement.

Clause 32: The medical device of any of the preceding clauses, wherein the processor is further configured to measure a second plurality of physiological parameter values from the physiological signal;

select one of the second plurality of physiological parameter values as a second spot-check measurement upon said detecting that the physiological signal has been disconnected from the patient;

output audio of the second spot-check measurement to the speaker; and output the second spot-check measurement to the display.

Clause 33: The medical device of any of the preceding clauses, wherein the processor is further configured to:

calculate a contributor score for each of the spot-check measurement and the second spot-check measurement;

derive an early warning score at least in part from the contributor scores; and output the contributor scores and the early warning score together in a group on the display, apart from the spot-check measurement and the second spot-check measurement.

Clause 34: The medical device of any of the preceding clauses, wherein the contributor scores are depicted together in a single row or a single column.

Clause 35: The medical device of any of the preceding clauses, wherein the contributor scores are depicted together in two rows, a first row and a second row, and wherein the first row is offset from the second row.

Clause 36: The medical device of any of the preceding clauses, wherein each of the contributor scores is associated with an indicator having a color representing the severity level.

Clause 37: The medical device of any of the preceding clauses, further comprising outputting a trend graph of the early warning score and subsequent early warning scores over time.

Clause 38: The medical device of any of the preceding clauses, wherein the trend graph comprises colored dots to indicate severity of the early warning score and subsequent early warning scores.

Clause 39: The medical device of any of the preceding clauses, wherein the trend graph comprises an emergency bar indicator.

Clause 40: A method for using a medical device to perform a spot-check measurement, the method comprising:

by a medical device comprising electronic hardware:

receiving a physiological signal from a sensor coupled with a patient;

measuring, from the physiological signal, a plurality of first values of a first physiological parameter and a plurality of second values of a second physiological parameter;

detecting that the sensor has been disconnected from the patient or that a clinician has selected a display input requesting spot-check measurements;

selecting one of the first values and one of the second values as the spot-check measurements upon either detecting that the physiological sensor has been disconnected from the patient or upon detecting that the clinician has selected the display input requesting the spot-check measurements; and outputting the spot-check measurements audibly or to a display.

Clause 41: The method of clause 40, further comprising outputting a review screen on the display comprising functionality that permits the clinician to adjust one or both of the spot-check measurements.

Clause 42: The method of any of the preceding clauses, further comprising outputting a list of the spot-check measurements for the patient, each of the spot-check measurements selectable by a clinician.

Clause 43: The method of any of the preceding clauses, further comprising outputting a trend graph of the spot-check measurements in response to selection of one of the spot-check measurements by the clinician.

Clause 44: The method of any of the preceding clauses, further comprising reverting to a continuous-mode output of the first and second physiological parameters after a timeout period.

Clause 45: The method of any of the preceding clauses, further comprising, in response to said detecting that the sensor has been disconnected from the patient or that a clinician has selected an input requesting spot-check measurements, calculating an early warning score based at least in part on the spot-check measurements, and outputting the early warning score to the display.

Clause 46: The method of any of the preceding clauses, further comprising outputting a trend graph of the early warning score over time.

Clause 47: The method of any of the preceding clauses, further comprising, prior to said receiving, outputting an option to place the medical device in spot-check mode;

receiving a selection of the option to place the medical device in the spot-check mode; and subsequent to receiving the selection of the option, rebooting the medical device in spot-check mode and not permitting continuous monitoring.

Clause 48: A pulse oximetry monitor configured to assess a validity of a signal obtained from a sensor, the monitor comprising:

a driver circuit that drives one or more emitters of an optical sensor at multiple wavelengths of light to cause the one or more emitters to transmit the multiple wavelengths of light through body tissue of a patient;

a hardware processor in communication with the optical sensor, the hardware processor configured to:

determine a number of remaining spot-check credits;

based at least in part on a determination that the number of spot-check credits satisfies a threshold, obtain a signal from the optical sensor;

assess a validity of the signal; and based at least in part on a determination that the signal is valid, update the number of remaining spot-check credits.

Clause 49: A pulse oximetry monitor and/or system configured to perform a spot-check measurement of a physiological parameter as shown and/or described in the drawings or foregoing description.

Clause 50: A method for using a medical device to perform a spot-check measurement, the method comprising one or more steps or features of the drawings or foregoing description.

Terminology

Many other variations than those described herein can be apparent from this disclosure. For example, depending on the embodiment, certain acts, events, or functions of any of the algorithms described herein can be performed in a different sequence, can be added, merged, or left out altogether (for example, not all described acts or events can be necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

Not necessarily all such advantages are achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as may be taught or suggested herein.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality can be implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a hardware processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A hardware processor can be a microprocessor, but in the alternative, the processor can be a controller, microcontroller, or state machine, combinations of the same, or the like. A processor can include electrical circuitry or digital logic circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, are generally intended to convey that certain embodiments include, while other embodiments do not include, certain features, elements and/or states. Thus, such conditional language is not generally intended to imply that features, elements and/or states are in any way may required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" mechanism one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, can be otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments may require at least one of X, at least one of Y, or at least one of Z to each be present.

Unless otherwise explicitly stated, articles such as "a" or "an" should generally be interpreted to include one or more described items. Accordingly, phrases such as "a device configured to" is intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it is understood that various omissions, substitutions, and changes in the form and details of the devices or algorithms illustrated can be made without departing from the spirit of the disclosure. As is recognized, certain embodiments of the inventions described herein can be embodied within a form that does not provide all of the features and benefits set forth herein, as some features can be used or practiced separately from others.

What is claimed is:

1. A pulse oximetry monitor configured to perform a spot-check measurement of a physiological parameter, the monitor comprising:

a driver circuit that drives one or more emitters of a physiological sensor at multiple wavelengths of light to cause the one or more emitters to transmit the multiple wavelengths of light through body tissue of a patient;

a hardware processor in communication with the physiological sensor, the hardware processor configured to:
   determine a number of remaining spot-check credits;
   in response to a determination that the number of remaining spot-check credits satisfies a threshold, enable selection of a spot-check measurement;
   measure, from a physiological signal, a plurality of values of a physiological parameter;
   upon detecting that the physiological sensor has been detached from the patient, select one of the plurality of values as the spot-check measurement;
   assess a validity of the spot-check measurement;
   based at least in part on a determination that the spot-check measurement is valid, update the number of remaining spot-check credits; and
   output the spot-check measurement audibly or to a display.

2. The monitor of claim 1, wherein to assess the validity of the spot-check measurement the hardware processor is configured to assess a quality of the physiological signal based at least in part on at least one of a signal IQ, a signal stability, or a signal strength of the physiological signal.

3. The monitor of claim 1, wherein the hardware processor is further configured to determine that spot-check measurement is valid based at least in part on a determination that a signal quality of the physiological signal satisfies a signal quality threshold.

4. The monitor of claim 1, wherein the hardware processor is further configured to compute an early warning score based on contributor scores derived from the spot-check measurement and a plurality of other physiological parameter measurements, and output in a single region of the display the early warning score together with the contributor scores or a trend of prior early warning scores.

5. The monitor of claim 1, wherein the selected value of the plurality of values corresponds to a most recently measured value of the plurality of values.

6. The monitor of claim 1, wherein the display is configured to display only one value of the plurality of values at a time, wherein to select the one of the plurality of values as the spot-check measurement, the hardware processor is configured to freeze a currently-displayed one of the plurality of values on the display, wherein the currently-displayed one of the plurality of values is the selected one of the plurality of values.

7. The monitor of claim 1, wherein the hardware processor is further configured to lock the monitor in spot-check mode so that continuous measurements are not able to be calculated by the hardware processor.

8. A method of performing a spot-check measurement of a physiological parameter, the method comprising:
   under control of a hardware processor of a patient monitor,
      determining a number of remaining spot-check credits;
      in response to a determination that the remaining number of spot-check credits satisfies a threshold, enabling selection of a spot-check measurement;
      measuring, from a physiological signal received from a physiological sensor, a plurality of values of a physiological parameter;
      upon detecting that the physiological sensor has detached from a patient, selecting one of the plurality of values as the spot-check measurement;
      assessing a validity of the spot-check measurement;
      based at least in part on a determination that the spot-check measurement is valid, updating the number of remaining spot-check credits; and
      outputting the spot-check measurement audibly or for presentation on a display.

9. The method of claim 8, said assessing the validity of the spot-check measurement comprises assessing a quality of the physiological signal received from the physiological sensor.

10. The method of claim 8, wherein said assessing the validity of the spot-check measurement comprises comparing the spot-check measurement to an expected or previously determined value of the physiological parameter.

11. The method of claim 8, wherein said assessing the validity of the spot-check measurement comprises determining that a cancellation condition does not exist.

12. The method of claim 8, further comprising determining the number of remaining spot-check credits in response to a request to initiate the spot-check measurement.

13. The method of claim 8, wherein the selected value of the plurality of values corresponds to a most recently measured value of the plurality of values.

14. The method of claim 8, wherein the display is configured to display only one value of the plurality of values at a time, wherein selecting the one of the plurality of values as the spot-check measurement comprises selecting a currently-displayed one of the plurality of values on the display.

15. The method of claim 8, further comprising locking the patient monitor in spot-check mode so that continuous measurements are not able to be calculated by the hardware processor.

* * * * *